US008614309B2

(12) United States Patent
Feinstein et al.

(10) Patent No.: US 8,614,309 B2
(45) Date of Patent: Dec. 24, 2013

(54) DOUBLE-STRANDED RNA DIRECTED TO CASP2 AND METHODS OF USE THEREOF

(75) Inventors: Elena Feinstein, Rehovot (IL); Huseyin Aygun, Frankfurt am Main (DE); Rami Skaliter, Nes Ziona (IL); Hagar Kalinski, Rishon-le-Zion (IL); Igor Mett, Rehovot (IL); James McSwiggen, Boulder, CO (US); Leonid Beigelman, San Mateo, CA (US)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 12/733,998

(22) PCT Filed: Sep. 4, 2008

(86) PCT No.: PCT/IL2008/001197
§ 371 (c)(1),
(2), (4) Date: Jan. 18, 2011

(87) PCT Pub. No.: WO2009/044392
PCT Pub. Date: Apr. 9, 2009

(65) Prior Publication Data
US 2011/0112168 A1 May 12, 2011

Related U.S. Application Data

(60) Provisional application No. 60/997,576, filed on Oct. 3, 2007, provisional application No. 61/000,664, filed on Oct. 25, 2007, provisional application No. 61/003,535, filed on Nov. 15, 2007, provisional application No. 61/010,040, filed on Jan. 4, 2008, provisional application No. 61/128,519, filed on May 22, 2008, provisional application No. 61/134,638, filed on Jul. 10, 2008, provisional application No. 61/189,035, filed on Aug. 15, 2008.

(51) Int. Cl.
*C07H 21/04* (2006.01)
(52) U.S. Cl.
USPC ......... 536/24.5; 536/24.31; 536/24.1; 514/44
(58) Field of Classification Search
None
See application file for complete search history.

(56) References Cited

U.S. PATENT DOCUMENTS

| | | | |
|---|---|---|---|
| 5,753,789 A | 5/1998 | Chu et al. | |
| 5,874,277 A | 2/1999 | Shintani et al. | |
| 5,891,683 A | 4/1999 | Usman et al. | |
| 5,898,031 A | 4/1999 | Crooke | |
| 5,929,042 A | 7/1999 | Troy et al. | |
| 5,998,203 A | 12/1999 | Matulic-Adamic et al. | |
| 6,107,094 A | 8/2000 | Crooke | |
| 6,117,657 A | 9/2000 | Usman et al. | |
| 6,235,886 B1 | 5/2001 | Manoharan et al. | |
| 6,251,666 B1 | 6/2001 | Beigelman | |
| 6,268,490 B1 | 7/2001 | Imanishi et al. | |
| 6,506,559 B1 | 1/2003 | Fire | |
| 6,586,238 B1 | 7/2003 | Matulic-Adamic et al. | |
| 6,602,858 B2 | 8/2003 | Beigelman | |
| 7,056,704 B2 | 6/2006 | Tuschl et al. | |
| 7,078,196 B2 | 7/2006 | Tuschl et al. | |
| 7,335,765 B2 | 2/2008 | Kaneko et al. | |
| 7,452,987 B2 | 11/2008 | Giese et al. | |
| 7,629,456 B2 | 12/2009 | Lange et al. | |
| 7,812,002 B2 | 10/2010 | Feinstein | |
| 7,893,245 B2 | 2/2011 | Giese et al. | |
| 8,090,542 B2 | 1/2012 | Khvorova et al. | |
| 8,097,710 B2 | 1/2012 | Baulcombe et al. | |
| 2003/0027783 A1 | 2/2003 | Zernicka-Goetz et al. | |
| 2003/0108923 A1 | 6/2003 | Tuschl et al. | |
| 2004/0192626 A1 | 9/2004 | McSwiggen et al. | |
| 2004/0229266 A1 | 11/2004 | Tuschl et al. | |
| 2004/0265839 A1 | 12/2004 | Mello et al. | |
| 2005/0004064 A1 | 1/2005 | Tei et al. | |
| 2005/0020525 A1 | 1/2005 | McSwiggen et al. | |
| 2005/0037988 A1 | 2/2005 | Zamore et al. | |
| 2005/0080246 A1 | 4/2005 | Allerson et al. | |
| 2005/0181382 A1 | 8/2005 | Zamore et al. | |
| 2005/0223427 A1 | 10/2005 | Leake et al. | |
| 2005/0233342 A1 | 10/2005 | Manoharan et al. | |
| 2005/0255487 A1 | 11/2005 | Khvorova et al. | |
| 2006/0058266 A1 | 3/2006 | Manoharan et al. | |
| 2006/0069056 A1 | 3/2006 | Feinstein et al. | |

(Continued)

FOREIGN PATENT DOCUMENTS

EP 0540742 A1 5/1993
WO WO 99/14226 3/1999

(Continued)

OTHER PUBLICATIONS

International Search Report issued by the International Searching Authority (ISA/US) on Mar. 30, 2009 in connection with International Application No. PCT/IL08/01197.
Written Opinion issued by the International Searching Authority (ISA/US) on Mar. 30, 2009 in connection with International Application No. PCT/IL08/01197.
International Preliminary Report on Patentability issued by the International Searching Authority (ISA/US) on Apr. 7, 2010 in connection with International Application No. PCT/IL08/01197.

(Continued)

*Primary Examiner* — Kimberly Chong
(74) *Attorney, Agent, or Firm* — John P. White; Cooper & Dunham LLP

(57) ABSTRACT

The invention relates to siRNA compounds possessing novel sequences and structural motifs which down-regulate the expression of specific human genes. The invention also relates to pharmaceutical compositions comprising such compounds and a pharmaceutically acceptable carrier. The present invention also provides a method of treating and/or preventing the incidence or severity of various diseases or conditions associated with the genes and/or symptoms associated with such diseases or conditions comprising administering to a subject in need of treatment for such disease or condition and/or symptom the compound or the pharmaceutical composition in a therapeutically effective dose so as to thereby treat the subject.

34 Claims, 79 Drawing Sheets

(56) References Cited

U.S. PATENT DOCUMENTS

| | | | |
|---|---|---|---|
| 2006/0172965 A1 | 8/2006 | Shepard et al. |
| 2006/0217329 A1 | 9/2006 | Feinstein et al. |
| 2006/0241072 A1 | 10/2006 | Baker |
| 2007/0031844 A1 | 2/2007 | Khvorova et al. |
| 2007/0032441 A1 | 2/2007 | McSwiggen et al. |
| 2007/0039072 A1 | 2/2007 | Khvorova et al. |
| 2007/0185047 A1 | 8/2007 | Bhat et al. |
| 2008/0311051 A1 | 12/2008 | Chauvier et al. |
| 2009/0162365 A1 | 6/2009 | Feinstein et al. |

FOREIGN PATENT DOCUMENTS

| | | |
|---|---|---|
| WO | WO 00/44895 | 8/2000 |
| WO | WO 00/44914 | 8/2000 |
| WO | WO 01/68836 | 9/2001 |
| WO | WO 02/24720 | 3/2002 |
| WO | WO 02/055693 | 7/2002 |
| WO | WO 03/039523 | 5/2003 |
| WO | WO 03/064621 | 8/2003 |
| WO | WO 03/070918 | 8/2003 |
| WO | WO 03/074654 | 9/2003 |
| WO | WO 2004/103389 | 12/2004 |
| WO | WO 2005/013886 | 2/2005 |
| WO | WO 2005/110464 A3 | 11/2005 |
| WO | WO 2007/087451 | 8/2007 |
| WO | WO 2007/091269 A3 | 8/2007 |
| WO | WO 2009/044392 A2 | 4/2009 |

OTHER PUBLICATIONS

Amarzguioui et al., (2003) "Tolerance for Mutations and Chemical Modifications in a siRNA". Nucleic Acids Research, 31(2):589-95.
Barik, (2005) "Silence of the Transcripts; RNA Interference in Medicine". Mol. Med 2005, 83:764-773.
Bass, (2001) "The Short Answer". Nature 411:428-29.
Braasch et al., (2003) "RNA Interference in Mammalian Cells by Chemically-Modified RNA". Biochemistry, 42:7967-7975.
Caplen et al., (2001) "Specific Inhibition of Gene Expression by Small Double-Stranded RNAs in Invertebrate Vertebrate Systems". Proc. Natl. Acad. Sci., 98(17):9742-47.
Chakraborty, (2007) "Potentiality of Small Interfering RNAs-(siRNA) as Recent Therapeutic Targets for Gene-Silencing". Current Drug Targets, 8(3):469-82.
Chiu et al., (2002) "RNAi in Human Cells: Basic Structural and Functions Features of Small Interfering RNA". Molecular Cell, vol. 19, pp. 549-561.
Chiu et al., (2003) "siRNA Function in RNAi: a Chemical Modification Analysis". RNA, 9(9):1034-48.
Czauderna et al., (2003) "Structural Variations and Stabilising Modifications of Synthetic siRNAs in Mammalian Cells". Nucleic Acids Research, 31(11):2705-16.
Damha et al., (1991) "Oligonucleotides Containing Unnatural L-2'-deoxyribose". Tetrahedron Letters 32(23):2573-76.
Damha et al., (1994) "Antisense L/D-Oligodeoxynucleotide Chimeras: Nuclease Stability, Base-Pairing Properties, and Activity at Directing Ribonuclease H". Biochem 33:7877-7885.
Elbashir et al., (2001) "RNA Interference is Mediated by 21-and 22-nucleotide RNAs". Genes & Development, 15:188-200.
Elbashir et al., (2001) "Functional Anatomy of siRNAs for Mediating Efficient RNAi in Drosophila Melanogaster Embryo Lysate". EMBO Journal, 20 (23):6877-88.
Elbashir et al., (2001) "Duplexes of 21-nucleotide Mediated RNA Interference in Cultured Mammalian Cells". Nature, 411:494-498.
Elmen et al., (2005) "Locked nucleic acid (LNA) mediated improvements in siRNA stability and functionality". NAR, 33(1):439-47.
Fire et al., (1998) "Potent and Specific Genetic Interference by Double-Stranded RNA in Caenorhabditis Elegans". Nature, vol. 391:806-811.
Garbesi et al., (1993) "L-DNAs as Potential Antimessenger Oligonucleotides: A Reassessment". Nuc. Acids Res., 21(18)4159-65.

Holen et al., (2002) "Positional Effects of Short Interfering RNAs Targeting the Human Coagulation Trigger Tissue Factor". NAR, 30(8):1757-66.
Kawakimi et al., (2005) "Thermodynamic Analysis of Duplex Formation of Heterochiral DNA with L-deoxyadenosine". Analyt. Sci., Feb. 2005 (21):77-82.
Kim et al., (2007) "Superior Structure Stability and Selectivity of Hairpin Nucleic Acid Probes with an L-DNA Stem". Nuc. Acids Res., 35(21):7279-7287.
Mahato et al., (2005) "Modulation of Gene Expression by Antisense and Antigene Oligadeoxynucleotides and Small Interfering RNA". Expert Opinion on Drug Delivery, 2(1):3-28.
McManus et al., (2002) "Gene Silencing in Mammals by Small Interfering RNAs". Nature Reviews Genetics, 3:737-747.
Mucke, (2007) "New ocular therapeutics: A view from the patenting perspective". IDrugs 10(1):37-41.
Prakash et al., (2005) "Positional Effect of Chemical Modifications on Short Interference RNA Activity in Mammalian Cells". J. Med Chem., 48(13):4247-53.
Scherer and Rossi (2004) "Therapeutic Applications of RNA Interferences: Recent Advances in siRNA Design". Advances in Genetics, 22:1-21.
Singh et al., (2001) Cell-specific caspase expression by different neuronal phenotypes in transient retinal ischemia. J Neurochem. 77(2):466-75.
Sioud et al., (2004) "Potential Design Rules and Enzymatic Synthesis of siRNAs" Methods in Molec Biol., 252:457-468.
Tolentino et al., (2004) "Intravitreal injection of vascular endothelial growth factor small interfering RNA inhibits growth and leakage in a nonhuman primate, laser-induced model of choroidal neovascularization". Retina. 24(4) :660.
Ui-Tei et al., (2006) "Essential Notes Regarding the Design of Functional siRNAs for Efficient Mammalian RNAi". J Biomed Biotechnol, 2006:65052.
Ui-Tei et al., (2008) "DNA-modified siRNA-dependent Gene Silencing with Reduced Off-target Effect is Induced through a Pathway Parallel to that for siRNA-mediated RNA Interference". Proc 2008 Micro-NanoMechatronics and Human Science (MHS2008), 339-345.
Ui-Tei et al., (2008) "Functional Dissection of siRNA Sequence by Systematic DNA Substitution: Modified siRNA with a DNA Seed Arm is a Powerful Tool for Mammalian Gene Silencing with Significantly Reduced Off-target Effect". Nucleic Acids Research, 36(7):2136-51.
Urata et al., (1992) "Synthesis and Properties of Mirror-image DNA". Nucleic Acids Research 20(13)3325-3332.
Wang et al., (2005) Endotoxemic acute renal failure is attenuated in caspase-1-deficient mice AJP: Renal Physiology, 288(5) :F997-F1004.
Zamore et al., (2000) "RNAi: Double-Stranded RNA Directs the ATP-Dependent Cleavage of mRNA at 21 to 23 Nucleotide Intervals". Cell, 101:25-33.
International Search Report mailed Oct. 7, 2008 in connection with International Application PCT/IL2007/001278 (WO 2008/050329).
International Preliminary Report on Patentability issued Apr. 28, 2009 including Written Opinion mailed Oct. 7, 2008 in connection with International Patent Application PCT/IL2007/001278 (WO2008/050329).
International Search Report mailed Dec. 12, 2008 in connection with International Patent Application PCT/IL2008/000248 (WO 2007/091269).
International Preliminary Report on Patentability issued Jan. 19, 2010 including Written Opinion mailed Nov. 10, 2008 in connection with International Patent Application PCT/IL2008/000248 (WO 2008/104978).
International Search Report mailed Apr. 14, 2010 in connection with International Patent Application PCT/US2009/061570 (WO 2010/048352).
International Preliminary Report on Patentability issued Apr. 26, 2011 including Written Opinion in connection with International Patent Application PCT/US2009/061570 (WO 2010/048352).

(56) References Cited

OTHER PUBLICATIONS

Amendment filed Nov. 25, 2009 in response to Restriction Requirement issued Jul. 27, 2009 in connection with U.S. Appl. No. 11/978,089 (US 2009/0162365).
Non-final Office Action issued Jul. 26, 2010 in connection with U.S. Appl. No. 11/978,089 (US 2009/0162365).
Amendment filed Jan. 26, 2011 in response to Non-final Office Action issued Jul. 26, 2010 in connection with U.S. Appl. No. 11/978,089 (US 2009/0162365).
Final Office Action issued Mar. 14, 2011 in connection with U.S. Appl. No. 11/978,089 (US 2009/0162365).
Amendment filed Jan. 19, 2012 in response to Final Office Action issued Mar. 14, 2012 in connection with U.S. Appl. No 11/978,089 (US 2009/0162365).
Extended European Search Report and Opinion issued Jan. 9, 2011 in connection with EP 11170912.7 (Divisional application of EPO National Phase application of PCT/IL2007/001278).
Supplementary European Search Report and Opinion issued Dec. 6, 2011 in connection with EP 08808012.2 (EPO National Phase application of PCT/IL2008/001197).
Claims filed May 20, 2011 upon entry to EP National Phase of PCT/US2009/061570 (in claim 1, sense strand SEQ ID No. 9015 and antisense strand SEQ ID No. 9516, are identical to SEQ ID No. 140 and SEQ ID No. 139 respectively, in the instant application).
Rule 161/162 Communication issued Jun. 1, 2011 in connection with EP 09748890.2 (EPO National Phase application of PCT/US2009/061570).
Response filed Dec. 9, 2011 to the Rule 161/162 Communication issued Jun. 1, 2011 in connection with EP 09748890.2(EPO National Phase application of PCT/US2009/061570).
Examination Report issued Mar. 27, 2012 in connection with EP 09748890.2 (EPO National Phase application of PCT/US2009/061570).
English translation of First Office Action issued Sep. 1, 2011 in connection with CN 200880110087.0 (Chinese National Phase application of PCT/IL2008/001197).
English translation of response and claims filed Mar. 16, 2012 to First Office Action issued Sep. 1, 2011 in connection with CN 200880110087.0 (Chinese National Phase application of PCT/IL2008/001197).
English translation of voluntary claim amendment filed Sep. 1, 2011 with Request for Examination in connection with RU 2010113514 (Russian National Phase application of PCT/IL2008/001197).
English translation of Official Action issued Feb. 9, 2012 in connection with RU 2010113514 (Russian National Phase application of PCT/IL2008/001197).
Second preliminary amendment in response to notification of missing requirements under 35 U.S.C. §371, filed May 17, 2011 in connection with U.S. Appl. No. 13/062,161 (US 2011/0229557) (In claim 74, sense strand SEQ ID No. 9015 and antisense strand SEQ ID No. 9516, are identical to SEQ IDd No. 140 and SEQ ID No. 139 respectively in the instant application).
English Translation of Office Action dated Jul. 12, 2012, issued in connection with Chinese Application No. 200880110087.0.
Response to Supplementary European Search Report and Opinion, issued in connection with European Patent Application No. 088080122 on Dec. 6, 2011.
Claims filed with Response to Supplementary European Search Report and Opinion, issued in connection with European Patent Application No. 08808012.2 on Dec. 6, 2011.
Office Action issued on Nov. 20, 2012, in connection with European Patent Application No. 08808012.2.
Response to Extended European Search Report, issued in connection with European Patent Application No. 11170912.7 on Sep. 1, 2011.
Claims filed with Response to Extended European Search Report, issued in connection with European Patent Application No. 11170912.7 on Sep. 1, 2011.
Office Action issued Aug. 1, 2012, in connection with European Patent Application No. 11170912.7.
Office Action issued Jan. 8, 2013, in connection with U.S. Appl. No. 13/062,161.
Response to Office Action issued Jan. 8, 2013, in connection with U.S. Appl. No. 13/062,161.
English Translation of Response filed no earlier than Jun. 11, 2012, to Office Action issued on Feb. 9, 2012 in connection with Russian Patent Application No. 2010113514.
English Translation of Office Action issued on Jul. 27, 2012, in connection with Russian Patent Application No. 2010113514.
English Translation of Response filed no earlier than Sep. 23, 2012, to Office Action issued on Jul. 27, 2012 in connection with Russian Patent Application No. 2010113514.

Figure 1A

| # | | Sequence | SEQ ID |
|---|---|---|---|
| #1 | S1.<br>As1. | 5'-gaagaaaa555ccgcaaaa-3'<br>5'-u5uugcggaaauuuucuuc-3' | SEQ ID NO: 87179<br>SEQ ID NO: 87180 |
| #2 | S1.<br>As2. | 5'-gaagaaaa555ccgcaaaa-3'<br>5'-uuuugcggaaauuu57557-3' | SEQ ID NO: 87179<br>SEQ ID NO: 87180 |
| #3 | S1.<br>As3. | 5'-gaagaaaa555ccgcaaaa-3'<br>5'-55uugcggaaauuuucuuc-3' | SEQ ID NO: 87179<br>SEQ ID NO: 87180 |
| #4 | S2.<br>As1. | 5'-86686aaauuuccgcaaaa-3'<br>5'-u5uugcggaaauuuucuuc-3' | SEQ ID NO: 87179<br>SEQ ID NO: 87180 |
| #5 | S2.<br>As2. | 5'-86686aaauuuccgcaaaa-3'<br>5'-uuuugcggaaauuu57557-3' | SEQ ID NO: 87179<br>SEQ ID NO: 87180 |
| #6 | S2.<br>As3. | 5'-86686aaauuuccgcaaaa-3'<br>5'-55uugcggaaauuuucuuc-3' | SEQ ID NO: 87179<br>SEQ ID NO: 87180 |
| #7 | S3.<br>As1. | 5'-8668666655uccgcaaaa-3'<br>5'-u5uugcggaaauuuucuuc-3' | SEQ ID NO: 87179<br>SEQ ID NO: 87180 |
| #8 | S3.<br>As2. | 5'-8668666655uccgcaaaa-3'<br>5'-uuuugcggaaauuu57557-3' | SEQ ID NO: 87179<br>SEQ ID NO: 87180 |
| #9 | S3.<br>As3. | 5'-8668666655uccgcaaaa-3'<br>5'-55uugcggaaauuuucuuc-3' | SEQ ID NO: 87179<br>SEQ ID NO: 87180 |
| #10 | S4.<br>As1. | 5'-8668666655577gcaaaa-3'<br>5'-u5uugcggaaauuuucuuc-3' | SEQ ID NO: 87179<br>SEQ ID NO: 87180 |
| #11 | S4.<br>As2. | 5'-8668666655577gcaaaa-3'<br>5'-uuuugcggaaauuu57557-3' | SEQ ID NO: 87179<br>SEQ ID NO: 87180 |
| #12 | S4.<br>As3. | 5'-8668666655577gcaaaa-3'<br>5'-55uugcggaaauuuucuuc-3' | SEQ ID NO: 87179<br>SEQ ID NO: 87180 |

Figure 2

| Duplex # | Strand | Sequence (5' -> 3') | SEQ ID No. |
|---|---|---|---|
| 4 | SEN | 5' <u>GAAGAA</u>GAAAAUUUCCGCAAAAA 3' | SEQ ID NO: 87183 |
|  | AS | 5' U<u>U</u>UUUGCGGAAAUUUUCUUCUUC 3' | SEQ ID NO: 87184 |
| 5 | SEN | 5' <u>GAAGAA</u>GAAAAUUUCCGCAAAAA 3' | SEQ ID NO: 87183 |
|  | AS | 5' UUUUUGCGGAAAUUUUCUUCUUC 3' | SEQ ID NO: 87184 |
| 6 | SEN | 5' <u>GAAGA</u>AGAAAAUUUCCGCAAAAA 3' | SEQ ID NO: 87183 |
|  | AS | 5' <u>UU</u>UUUGCGGAAAUUUUCUUCUUC 3' | SEQ ID NO: 87184 |
| 8 | SEN | 5' <u>GAAGAAGAAA</u>AUUUCCGCAAAAA 3' | SEQ ID NO: 87183 |
|  | AS | 5' UUUUUGCGGAAAUUUUCUUCUUC 3' | SEQ ID NO: 87184 |
| 11 | SEN | 5' <u>GAAGAAGAAAUU</u>CCGCAAAAA 3' | SEQ ID NO: 87183 |
|  | AS | 5' UUUUUGCGGAAAUUUUCUUCUUC 3' | SEQ ID NO: 87184 |
| 2 | SEN | 5' GAAGAAGAAA<u>AUU</u>CCGCAAAAA 3' | SEQ ID NO: 87183 |
|  | AS | 5' UUUUUGCGGAAAUUUUCUUCUUC 3' | SEQ ID NO: 87184 |

Figure 3A

| | | | |
|---|---|---|---|
| 4+19 | Sense | 5'-CCUUGCACUCCUGAAUUUUAUCA-3' | SEQ ID NO: 267 |
| | AS | 5'-UGAUAAAAUUCAGGAGUGCAAGG-3' | SEQ ID NO: 268 |
| 3+19+1 | Sense | 5'-CUUGCACUCCUGAAUUUUAUCAA-3' | SEQ ID NO: 269 |
| | AS | 5'-UUGAUAAAAUUCAGGAGUGCAAG-3' | SEQ ID NO: 270 |
| 2+19+2 | Sense | 5'-UUGCACUCCUGAAUUUUAUCAAA-3' | SEQ ID NO: 271 |
| | AS | 5'-UUUGAUAAAAUUCAGGAGUGCAA-3' | SEQ ID NO: 272 |
| 1+19+3 | Sense | 5'-UGCACUCCUGAAUUUUAUCAAAC-3' | SEQ ID NO: 273 |
| | AS | 5'-GUUUGAUAAAAUUCAGGAGUGCA-3' | SEQ ID NO: 274 |
| 19+4 | Sense | 5'-GCACUCCUGAAUUUUAUCAAACA-3' | SEQ ID NO: 275 |
| | AS | 5'-UGUUUGAUAAAAUUCAGGAGUGC-3' | SEQ ID NO: 276 |

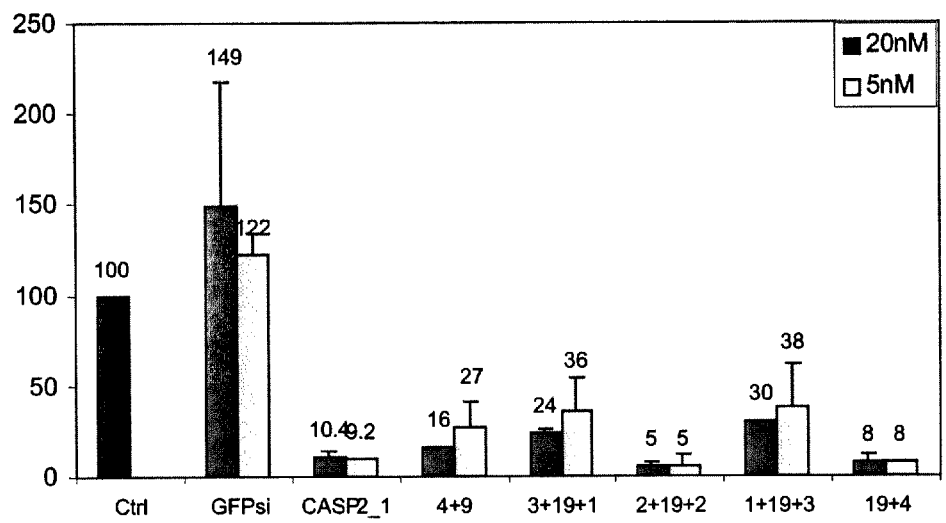

| 4+19 | Sense | 5'-CCUUGCACUCCUGAAUUUUAUCA -3' | SEQ ID NO: 267 |
|---|---|---|---|
| | AS | 5'-UGAUAAAAUUCAGGAGUGC AAGG-3' | SEQ ID NO: 268 |
| 3+19+1 | Sense | 5'-CUUGCACUCCUGAAUUUUAUCA A-3' | SEQ ID NO: 269 |
| | AS | 5'-UUGAUAAAAUUCAGGAGUGC AAG-3' | SEQ ID NO: 270 |
| 2+19+2 | Sense | 5'-UUGCACUCCUGAAUUUUAUCA AA-3' | SEQ ID NO: 271 |
| | AS | 5'-UUUGAUAAAAUUCAGGAGUGC AA-3' | SEQ ID NO: 272 |
| 1+19+3 | Sense | 5'-UGCACUCCUGAAUUUUAUCA AAC-3' | SEQ ID NO: 273 |
| | AS | 5'-GUUUGAUAAAAUUCAGGAGUGC A-3' | SEQ ID NO: 274 |
| 19+4 | Sense | 5'-GCACUCCUGAAUUUUAUCA AACA-3' | SEQ ID NO: 275 |
| | AS | 5'-UGUUUGAUAAAAUUCAGGAGUGC -3' | SEQ ID NO: 276 |

Figure 5B

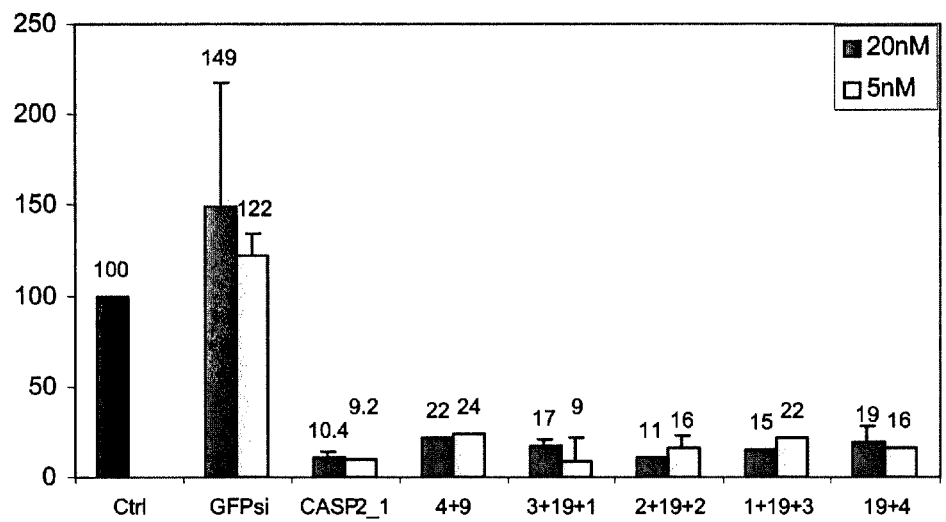

Figure 6A

|   | 5' ⟶ 3' | |
|---|---|---|
| #1 | 3prime1QM5-s  GAAGAAAAUUUCCGCA666-dT | SEQ ID NO: 87185 |
|    | 3prime1QM5-as UUUUGCGGAAAUUUUC557-dT | SEQ ID NO: 87186 |
| #2 | 3prime2QM5-s  866GAAAAUUUCCGCAAAA-dT | SEQ ID NO: 87185 |
|    | 3prime1QM5-as UUUUGCGGAAAUUUUC557-dT | SEQ ID NO: 87186 |
| #3 | 3prime3QM5-s  866GAAAAUUUCCGCA666-dT | SEQ ID NO: 87185 |
|    | 3prime1QM5-as UUUUGCGGAAAUUUUC557-dT | SEQ ID NO: 87186 |
| #4 | QM5-s 5' GAAGAAAAUUUCGCGCAAA 3' | SEQ ID NO: 87179 |
|    | 3prime1QM5-as UUUUGCGGAAAUUUUC557-dT | SEQ ID NO: 87186 |
| #5 | 3prime1QM5-s  GAAGAAAAUUUCCGCA666-dT | SEQ ID NO: 87185 |
|    | 3prime2QM5-as 555UGCGGAAAUUUUCUUC-dT | SEQ ID NO: 87186 |

|   | 5' ⟶ 3' | |
|---|---|---|
| #6 | 3prime2QM5-s  866GAAAAUUUCCGCAAAA-dT | SEQ ID NO: 87185 |
|    | 3prime2QM5-as 555UGCGGAAAUUUUCUUC-dT | SEQ ID NO: 87186 |
| #7 | 3prime3QM5-s  866GAAAAUUUCCGCA666-dT | SEQ ID NO: 87185 |
|    | 3prime2QM5-as 555UGCGGAAAUUUUCUUC-dT | SEQ ID NO: 87186 |
| #8 | QM5-s 5' GAAGAAAAUUUCGCGCAAA 3' | SEQ ID NO: 87179 |
|    | 3prime2QM5-as 555UGCGGAAAUUUUCUUC-dT | SEQ ID NO: 87186 |
| #9 | 3prime1QM5-s  GAAGAAAAUUUCCGCA666-dT | SEQ ID NO: 87185 |
|    | 3prime3QM5-as 555UGCGGAAAUUUUC557-dT | SEQ ID NO: 87186 |
| #10 | 3prime1QM5-s  GAAGAAAAUUUCCGCA666-dT | SEQ ID NO: 87185 |
|     | QM5-as 5' UUUUGCGGAAAUUUUCUUC 3' | SEQ ID NO: 87180 |

Figure 7A

| #1 | 1 CASP2_4 S/<br>1CASP2_4 AS | S-5'- GCCAGAAUGUGGAACUC*C*U*dT-3'<br>AS-5'- AGGAGUUCCACAUUCUG*G*C*dT-3' | SEQ ID NO: 87187<br>SEQ ID NO: 87188 |
|---|---|---|---|
| #2 | 2 CASP2_4 S/<br>1CASP2_4 AS | S-5'- G*C*C*AGAAUGUGGAACUCCUdT-3'<br>AS-5'- AGGAGUUCCACAUUCUG*G*C*dT-3' | SEQ ID NO: 87187<br>SEQ ID NO: 87188 |
| #3 | 1 CASP2_4 S/<br>1CASP2_4 AS<br>(BLUNT) | S-5'- GCCAGAAUGUGGAACUC*C*U*-3'<br>AS-5'- AGGAGUUCCACAUUCUG*G*C-3' | SEQ ID NO: 139<br>SEQ ID NO: 140 |
| #4 | 2 CASP2_4 S/<br>1CASP2_4 AS<br>(BLUNT) | S-5'- G*C*C*AGAAUGUGGAACUCCU-3'<br>AS-5'- AGGAGUUCCACAUUCUG*G*C-3' | SEQ ID NO: 139<br>SEQ ID NO: 140 |

Figure 7B

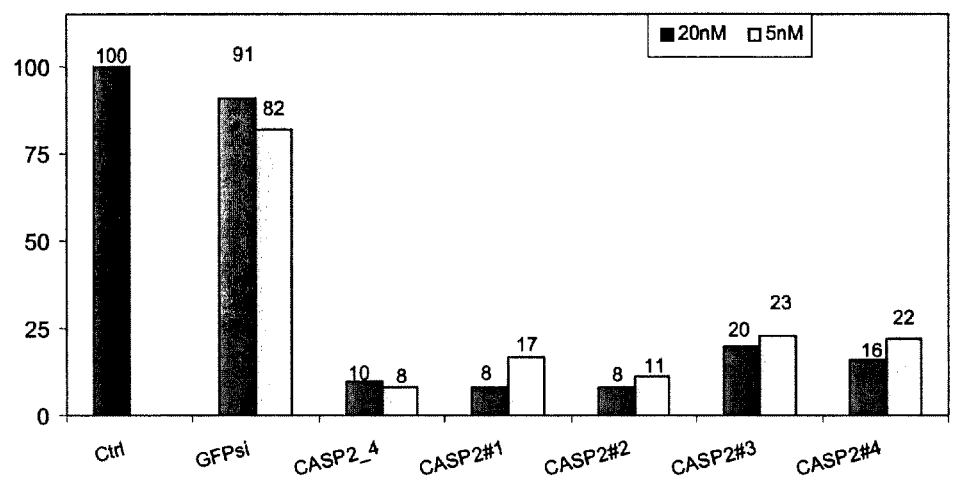

Figure 8A

| #1 | 1 DDIT4_2 S/<br>1 DDIT4_2 AS | S-5'- UACUGUAGCAUGAAACA*A*A*dT-3'<br>AS-5'- UUUGUUUCAUGCUACAG*U*A*dT-3' | SEQ ID NO: 87189<br>SEQ ID NO: 87190 |
|---|---|---|---|
| #2 | 2 DDIT4_2 S/<br>1 DDIT4_2 AS | S-5'- U*A*C*UGUAGCAUGAAACAAAdT-3'<br>AS-5'- UUUGUUUCAUGCUACAG*U*A*dT-3' | SEQ ID NO: 87189<br>SEQ ID NO: 87190 |
| #3 | 1 DDIT4_2 S/<br>1 DDIT4_2 AS<br>(BLUNT) | S-5'- UACUGUAGCAUGAAACA*A*A-3'<br>AS-5'- UUUGUUUCAUGCUACAG*U*A-3' | SEQ ID NO: 87191<br>SEQ ID NO: 87192 |
| #4 | 2 DDIT4_2 S/<br>1 DDIT4_2 AS<br>(BLUNT) | S-5'- U*A*C*UGUAGCAUGAAACAAA-3'<br>AS-5'- UUUGUUUCAUGCUACAG*U*A-3' | SEQ ID NO: 87191<br>SEQ ID NO: 87192 |

Figure 8B

| #1 | 1 QM5 S/<br>1 QM5 AS | S-5'- GAAGAAAAUUUCCGCAA*A*A*dT-3'<br>AS-5'- UUUUGCGGAAAUUUUCU*U*C*dT-3' | SEQ ID NO: 87185<br>SEQ ID NO: 87186 |
|---|---|---|---|
| #2 | 2 QM5 S/<br>1 QM5 AS | S-5'- G*A*A*GAAAAUUUCCGCAAAAdT-3'<br>AS-5'- UUUUGCGGAAAUUUUCU*U*C*dT-3' | SEQ ID NO: 87185<br>SEQ ID NO: 87186 |
| #3 | 1 QM5 S/<br>1 QM5 AS<br>(BLUNT) | S-5'- GAAGAAAAUUUCCGCAA*A*A-3'<br>AS-5'- UUUUGCGGAAAUUUUCU*U*C-3' | SEQ ID NO: 87179<br>SEQ ID NO: 87180 |
| #4 | 2 QM5 S/<br>1 QM5 AS<br>(BLUNT) | S-5'- G*A*A*GAAAAUUUCCGCAAAA-3'<br>AS-5'- UUUUGCGGAAAUUUUCU*U*C-3' | SEQ ID NO: 87179<br>SEQ ID NO: 87180 |

Figure 9A

| | | |
|---|---|---|
| #3-dT | S-5'-GAAGAAAAUUUCCGC AAAAdT-3' | SEQ ID NO: 87185 |
| | AS-5'-UUUUGCGGAAAUUUUCU *U*C*dT-3' | SEQ ID NO: 87186 |
| #3-Blunt | S-5'-GAAGAAAAUUUCCGC AAAA-3' | SEQ ID NO: 87179 |
| | AS-5'-UUUUGCGGAAAUUUUCU *U*C-3' | SEQ ID NO: 87180 |
| #4-dT | S-5'-GAAGAAAAU UUCCGCAA *A*A*dT-3' | SEQ ID NO: 87185 |
| | AS-5'-U<u>U</u>UUGCGGAAAUUUUCU *U*C*dT-3' | SEQ ID NO: 87186 |
| #4-Blunt | S-5'-GAAGAAAAU UUCCGCAA *A*A-3' | SEQ ID NO: 87179 |
| | AS-5'-U<u>U</u>UUGCGGAAAUUUUCU *U*C-3' | SEQ ID NO: 87180 |
| #5-dT | S-5'-GAAGAAAAU UUCCGCAA *A*A*dT-3' | SEQ ID NO: 87185 |
| | AS-5'-U<u>U</u>UUGCGGAAAUUUUCU *U*C*dT-3' | SEQ ID NO: 87186 |
| #5-Blunt | S-5'-GAAGAAAAU UUCCGCAA *A*A-3' | SEQ ID NO: 87179 |
| | AS-5'-U<u>U</u>UUGCGGAAAUUUUCU *U*C-3' | SEQ ID NO: 87180 |
| #6-dT | S-5'-G*A*A*GAAAAU UUCCGCAA *A*A*dT-3' | SEQ ID NO: 87185 |
| | AS-5'-UUUUGCGGAAAUUUUC UUCdT-3' | SEQ ID NO: 87186 |
| #6-Blunt | S-5'-G*A*A*GAAAAU UUCCGCAA *A*A-3' | SEQ ID NO: 87179 |
| | AS-5'-UUUUGCGGAAAUUUUC UUC-3' | SEQ ID NO: 87180 |
| #7-dT | S-5'-G*A*A*GAAAAUUUCCGCAA *A*A*dT-3' | SEQ ID NO: 87185 |
| | AS-5'-UUUUGCGGAAAUUUUC UUCdT-3' | SEQ ID NO: 87186 |
| #7-Blunt | S-5'-G*A*A*GAAAAUUUCCGCAA *A*A-3' | SEQ ID NO: 87179 |
| | AS-5'-UUUUGCGGAAAUUUUC UUC-3' | SEQ ID NO: 87180 |
| #8-dT | S-5'-G*A*A*GAAAAU UUCCGCAA *A*A*dT-3' | SEQ ID NO: 87185 |
| | AS-5'-UUUUGCGGAAAUUUUC UUCdT-3' | SEQ ID NO: 87186 |
| #8-Blunt | S-5'-G*A*A*GAAAAU UUCCGCAA *A*A-3' | SEQ ID NO: 87179 |
| | AS-5'-UUUUGCGGAAAUUUUC UUC-3' | SEQ ID NO: 87180 |

Figure 9B

| | | |
|---|---|---|
| #9-dT | S-5'-GAAGAAAAU UUCCGCAA *A*A*dT-3' | SEQ ID NO: 87185 |
| | AS-5'-UUUUGCGGAAAUUUUC UUCdT-3' | SEQ ID NO: 87186 |
| # 9-Blunt | S-5'-GAAGAAAAU UUCCGCAA *A*A-3' | SEQ ID NO: 87179 |
| | AS-5'-UUUUGCGGAAAUUUUC UUC-3' | SEQ ID NO: 87180 |
| #10-dT | S-5'-GAAGAAAAUUUCCGCAA *A*A*dT-3' | SEQ ID NO: 87185 |
| | AS-5'-UUUUGCGGAAAUUUUCUUCdT-3' | SEQ ID NO: 87186 |
| # 10-Blunt | S-5'-GAAGAAAAUUUCCGCAA *A*A-3' | SEQ ID NO: 87179 |
| | AS-5'-UUUUGCGGAAAUUUUCUUC-3' | SEQ ID NO: 87180 |
| #11-dT | S-5'-G*A*A*GAAAAU UUCCGCAAAAdT-3' | SEQ ID NO: 87185 |
| | AS-5'-UUUUGCGGAAAUUUUCUUCdT-3' | SEQ ID NO: 87186 |
| # 11-Blunt | S-5'-G*A*A*GAAAAU UUCCGCAAAA-3' | SEQ ID NO: 87179 |
| | AS-5'-UUUUGCGGAAAUUUUCUUC-3' | SEQ ID NO: 87180 |
| #12-dT | S-5'-GAAGAAAAUUUCCGCA AAAdT-3' | SEQ ID NO: 87185 |
| | AS-5'-UUUUGCGGAAAUUUUCUUCdT-3' | SEQ ID NO: 87186 |
| # 12-Blunt | S-5'-GAAGAAAAUUUCCGCA AAA-3' | SEQ ID NO: 87179 |
| | AS-5'-UUUUGCGGAAAUUUUCUUC-3' | SEQ ID NO: 87180 |
| #13-dT | S-5'-GAAGAAAAUUUCCGCAAAAdT-3' | SEQ ID NO: 87185 |
| | AS-5'-UUUUGCGGAAAUUUUCUUCdT-3' | SEQ ID NO: 87186 |
| # 13-Blunt | S-5'-GAAGAAAAUUUCCGCAAAA-3' | SEQ ID NO: 87179 |
| | AS-5'-UUUUGCGGAAAUUUUCUUC-3' | SEQ ID NO: 87180 |

Figure 10A

| Dup.# | Strand | Sequence (5' -> 3') | SEQ ID No. |
|---|---|---|---|
| 1 | SEN | 5' GAAGAAGAAAAUUUCCGCAA*A*A*A 3' | SEQ ID NO: 87183 |
|   | AS  | 5' UUUUUGCGGAAAUUUUCUUC*U*U*C 3' | SEQ ID NO: 87184 |
| 2 | SEN | 5' G*A*A*GAAGAAAAUUUCCGCAAAAA 3' | SEQ ID NO: 87183 |
|   | AS  | 5' UUUUUGCGGAAAUUUUCUUC*U*U*C 3' | SEQ ID NO: 87184 |
| 3 | SEN | 5' G*A*A*GAAGAAAAUUUCCGCAA*A*A*A 3' | SEQ ID NO: 87183 |
|   | AS  | 5' UUUUUGCGGAAAUUUUCUUC*U*U*C 3' | SEQ ID NO: 87184 |
| 1alt | SEN | 5' GAAGAAGAAAAUUUCCGCAA*A*A*A 3'' | SEQ ID NO: 87183 |
|      | AS  | 5' <u>UUUUUGCGGAAAUUUUCUUCUUC</u> 3' | SEQ ID NO: 87184 |
| 2alt | SEN | 5' G*A*A*GAAGAAAAUUUCCGCAAAAA 3' | SEQ ID NO: 87183 |
|      | AS  | 5' <u>UUUUUGCGGAAAUUUUCUUCUUC</u> 3' | SEQ ID NO: 87184 |
| 3alt | SEN | 5' G*A*A*GAAGAAAAUUUCCGCAA*A*A*A 3' | SEQ ID NO: 87183 |
|      | AS  | 5' <u>UUUUUGCGGAAAUUUUCUUCUUC</u> 3' | SEQ ID NO: 87184 |

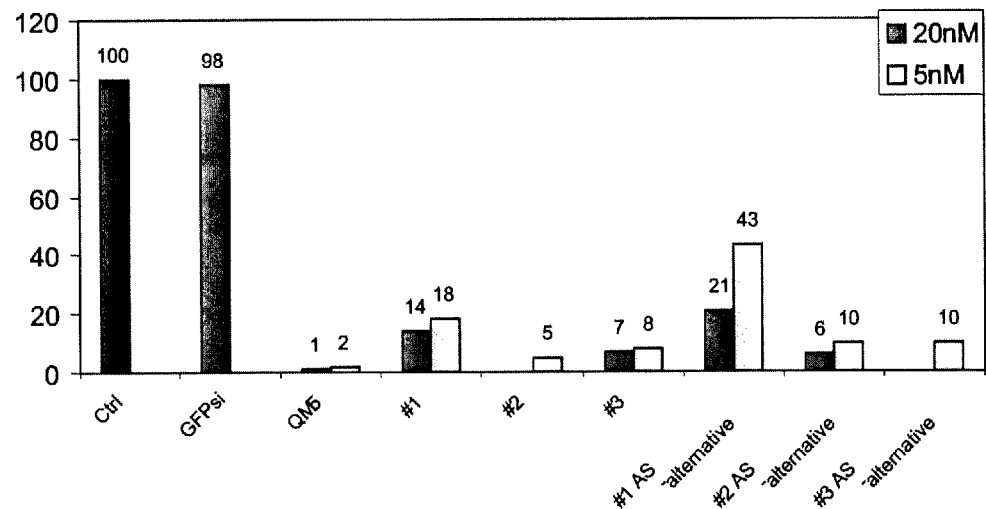

| 4+19 | Sense | 5'-C*C*U*UGCACUCCUGAAUUUUAUCA-3' | SEQ ID NO: 267 |
|---|---|---|---|
| | AS | 5'-UGAUAAAAUUCAGGAGUGCAAGG-3' | SEQ ID NO: 268 |
| 3+19+1 | Sense | 5'-C*U*U*GCACUCCUGAAUUUUAUCAA-3' | SEQ ID NO: 269 |
| | AS | 5'-UUGAUAAAAUUCAGGAGUGCAAG-3' | SEQ ID NO: 270 |
| 2+19+2 | Sense | 5'-U*U*G*CACUCCUGAAUUUUAUCAAA-3' | SEQ ID NO: 271 |
| | AS | 5'-UUUGAUAAAAUUCAGGAGUGCAA-3' | SEQ ID NO: 272 |
| 1+19+3 | Sense | 5'-U*G*C*ACUCCUGAAUUUUAUCAAAC-3' | SEQ ID NO: 273 |
| | AS | 5'-GUUUGAUAAAAUUCAGGAGUGCA-3' | SEQ ID NO: 274 |
| 19+4 | Sense | 5'-G*C*A*CUCCUGAAUUUUAUCAAACA-3' | SEQ ID NO: 275 |
| | AS | 5'-UGUUUGAUAAAAUUCAGGAGUGC-3' | SEQ ID NO: 276 |

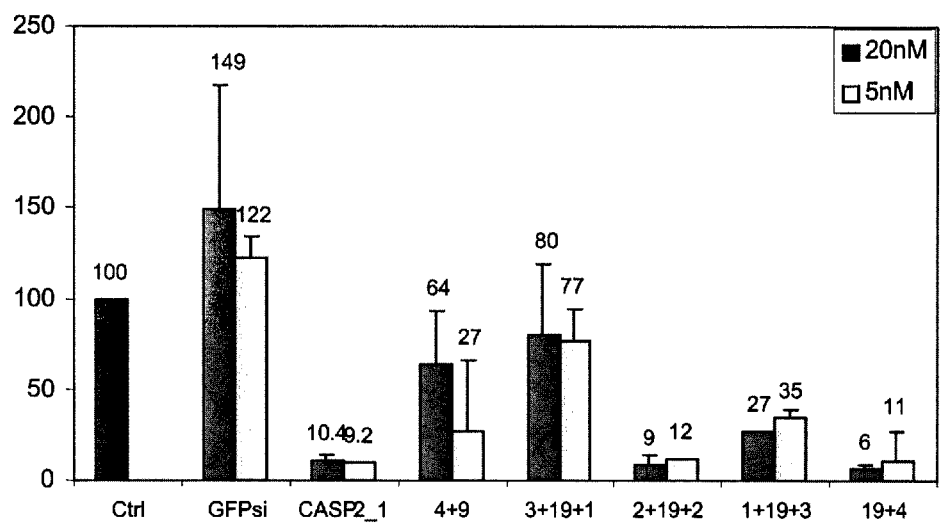

| 4+19 | Sense | 5'-C*C*U*UGCACUCCUGAAUUUUAUCA-3' | SEQ ID NO: 267 |
|---|---|---|---|
|  | AS | 5'-UGAUAAAAUUCAGGAGUGCAA*G*G-3' | SEQ ID NO: 268 |
| 3+19+1 | Sense | 5'-C*U*UGCACUCCUGAAUUUUAUCAA-3' | SEQ ID NO: 269 |
|  | AS | 5'-UUGAUAAAAUUCAGGAGUGCA*A*G-3' | SEQ ID NO: 270 |
| 2+19+2 | Sense | 5'-U*U*G*CACUCCUGAAUUUUAUCAAA-3' | SEQ ID NO: 271 |
|  | AS | 5'-UUUGAUAAAAUUCAGGAGUGC*A*A-3' | SEQ ID NO: 272 |
| 1+19+3 | Sense | 5'-U*G*C*ACUCCUGAAUUUUAUCAAAC-3' | SEQ ID NO: 273 |
|  | AS | 5'-GUUUGAUAAAAUUCAGGAGUG*C*A-3' | SEQ ID NO: 274 |
| 19+4 | Sense | 5'-G*C*A*CUCCUGAAUUUUAUCAAACA-3' | SEQ ID NO: 275 |
|  | AS | 5'-UGUUUGAUAAAAUUCAGGAGU*G*C-3' | SEQ ID NO: 276 |

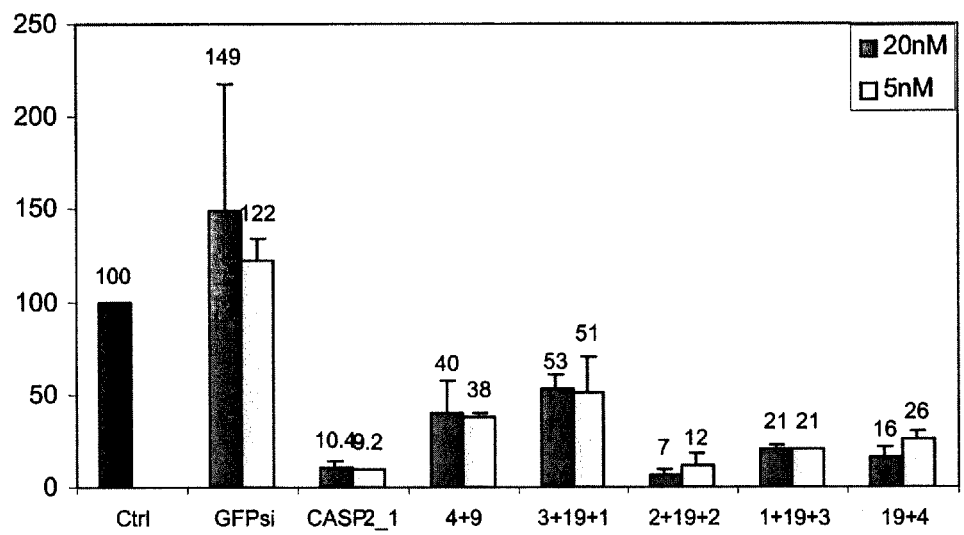

| No | siRNA-duplex name | Mirror nucleotide siRNA structures underlined characters =mirror nucs | SEQ ID No. |
|---|---|---|---|
| 1 | Sp4QM5-S/Sp4QM5-AS | S-5'-GAAGAAAAUUUCCGCAA<u>AA</u>-dT- 3' | SEQ ID NO: 87185 |
| | | AS-3'-dT-<u>C</u>UUCUUUUAAAGGCGUUUU- 5' | SEQ ID NO: 87186 |
| 2 | Sp5QM5-S/Sp4QM5-AS | S-5'-<u>GA</u>AGAAAAUUUCCGCAAAAA-dT- 3' | SEQ ID NO: 87185 |
| | | AS-3'-dT-<u>C</u>UUCUUUUAAAGGCGUUUU- 5' | SEQ ID NO: 87186 |
| 3 | Sp6QM5-S/Sp4QM5-AS | S-5'-<u>GA</u>AGAAAAUUUCCGCAA<u>AA</u>-dT- 3' | SEQ ID NO: 87185 |
| | | AS-3'-dT-<u>C</u>UUCUUUUAAAGGCGUUUU- 5' | SEQ ID NO: 87186 |
| 4 | QM5-S/Sp4QM5-AS | S-5'-GAAGAAAAUUUCCGCAAAAA-dT- 3' | SEQ ID NO: 87185 |
| | | AS-3'-dT-<u>C</u>UUCUUUUAAAGGCGUUUU- 5' | SEQ ID NO: 87186 |
| 5 | Sp4QM5-S/Sp5QM5-AS | S-5'-GAAGAAAAUUUCCGCAA<u>AA</u>-dT- 3' | SEQ ID NO: 87185 |
| | | AS-3'-dT-CUUCUUUUAAAGGCGUUU<u>T</u>- 5' | SEQ ID NO: 87193 |
| 6 | Sp5QM5-S/Sp5QM5-AS | S-5'-<u>GA</u>AGAAAAUUUCCGCAAAAA-dT- 3' | SEQ ID NO: 87185 |
| | | AS-3'-dT-CUUCUUUUAAAGGCGUUU<u>T</u>- 5' | SEQ ID NO: 87193 |
| 7 | Sp6QM5-S/Sp5QM5-AS | S-5'-<u>GA</u>AGAAAAUUUCCGCAA<u>AA</u>-dT- 3' | SEQ ID NO: 87185 |
| | | AS-3'-dT-<u>C</u>UUCUUUUAAAGGCGUUU<u>T</u>- 5' | SEQ ID NO: 87193 |
| 8 | QM5-S/Sp5QM5-AS | S-5'-GAAGAAAAUUUCCGCAAAAA-dT- 3' | SEQ ID NO: 87185 |
| | | AS-3'-dT-CUUCUUUUAAAGGCGUUU<u>T</u>- 5' | SEQ ID NO: 87193 |
| 9 | Sp4QM5-S/Sp6QM5-AS | S-5'-GAAGAAAAUUUCCGCAA<u>AA</u>-dT- 3' | SEQ ID NO: 87185 |
| | | AS-3'-dT-<u>C</u>UUCUUUUAAAGGCGUUU<u>T</u>- 5' | SEQ ID NO: 87193 |
| 10 | Sp4QM5-S/QM5-AS | S-5'-GAAGAAAAUUUCCGCAA<u>AA</u>-dT- 3' | SEQ ID NO: 87185 |
| | | AS-3'-dT-CUUCUUUUAAAGGCGUUUU- 5' | SEQ ID NO: 87186 |
| 11 | Sp5QM5-S/Sp6QM5-AS | S-5'-<u>GA</u>AGAAAAUUUCCGCAAAAA-dT- 3' | SEQ ID NO: 87185 |
| | | AS-3'-dT-<u>C</u>UUCUUUUAAAGGCGUUU<u>T</u>- 5' | SEQ ID NO: 87193 |
| 12 | Sp5QM5-S/QM5-AS | S-5'-<u>GA</u>AGAAAAUUUCCGCAAAAA-dT- 3' | SEQ ID NO: 87185 |
| | | AS-3'-dT-CUUCUUUUAAAGGCGUUUU- 5' | SEQ ID NO: 87186 |
| 13 | Sp6QM5-S/Sp6QM5-AS | S-5'-<u>GA</u>AGAAAAUUUCCGCAA<u>AA</u>-dT- 3' | SEQ ID NO: 87185 |
| | | AS-3'-dT-<u>C</u>UUCUUUUAAAGGCGUUU<u>T</u>- 5' | SEQ ID NO: 87193 |
| 14 | QM5-S/Sp6QM5-AS | S-5'-GAAGAAAAUUUCCGCAAAAA-dT- 3' | SEQ ID NO: 87185 |
| | | AS-3'-dT-<u>C</u>UUCUUUUAAAGGCGUUU<u>T</u>- 5' | SEQ ID NO: 87193 |
| 15 | Sp6QM5-S/QM5-AS | S-5'-<u>GA</u>AGAAAAUUUCCGCAA<u>AA</u>-dT- 3' | SEQ ID NO: 87185 |
| | | AS-3'-dT-<u>C</u>UUCUUUUAAAGGCGUUUU- 5' | SEQ ID NO: 87186 |

Figure 13C
L-DNA structure
| | |
|---|---|
| S 5'- GAAGAAAAUUUCCGCA<u>666</u>-dT-3' | SEQ ID NO: 87185 |
| AS 5'- UUUUGCGGAAAUUUUC<u>557</u>-dT-3' | SEQ ID NO: 87186 |
<u>5</u>: L-thymidine
<u>6</u>: L-deoxyadenosine
<u>7</u>: L-deoxycytidine
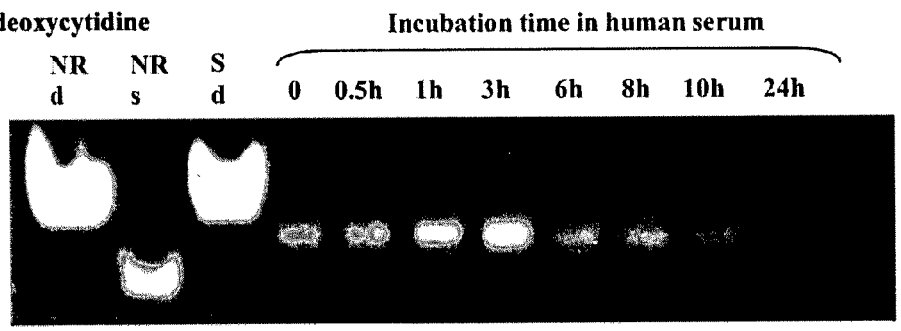
Figure 13D
IC50 = 0.23 nM           IC50 = 0.09 nM
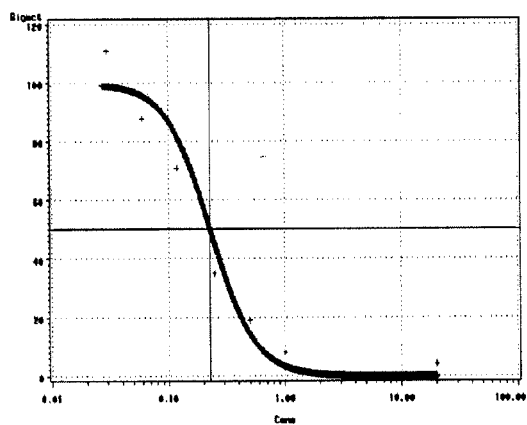 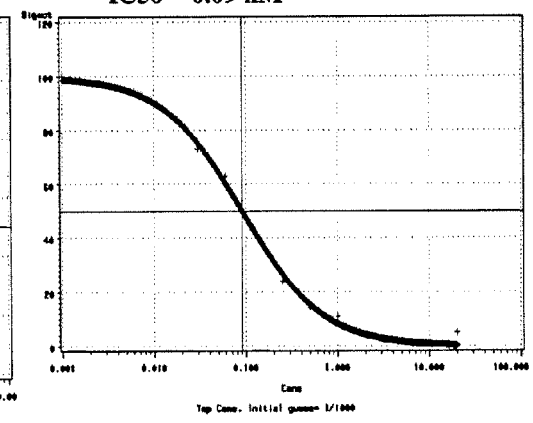
S-5'-XmXmXmXmXmXmXmXmXmX    S-5'-XXXXXXXXXXXXXXXXXXXLL-3'
AS-3'-mXmXmXmXmXmXmXmXmXm    AS-3' LXXXXXXXXXXXXXXXXXXX
m – 2'O-Me
L – L-RNA

Figure 14A

| No | LNA siRNA-duplex name | LNA siRNA structures | SEQ ID No. |
|---|---|---|---|
|  |  | underlined characters =LNA nucs |  |
| 1 | LNA1QM5-S/LNA1QM5-AS | S-5'-GAAGAAAAUUUCCGCA<u>AAA</u>-dT-3' | SEQ ID NO: 87185 |
|  |  | AS-3'-dT-<u>CUU</u>CUUUUAAAGGCGUUUU-5' | SEQ ID NO: 87186 |
| 2 | LNA2QM5-S/LNA1QM5-AS | S-5'-<u>GAA</u>GAAAAUUUCCGCAAAA-dT-3' | SEQ ID NO: 87185 |
|  |  | AS-3'-dT-<u>CUU</u>CUUUUAAAGGCGUUUU-5' | SEQ ID NO: 87186 |
| 3 | LNA3QM5-S/LNA1QM5-AS | S-5'-<u>GAA</u>GAAAAUUUCCGCA<u>AAA</u>-dT-3' | SEQ ID NO: 87185 |
|  |  | AS-3'-dT-<u>CUU</u>CUUUUAAAGGCGUUUU-5' | SEQ ID NO: 87186 |
| 4 | QM5-S/LNA1QM5-AS | S-5'-GAAGAAAAUUUCCGCAAAA-3' | SEQ ID NO: 87179 |
|  |  | AS-3'-dT-<u>CUU</u>CUUUUAAAGGCGUUUU-5' | SEQ ID NO: 87186 |
| 5 | LNA1QM5-S/LNA2QM5-AS | S-5'-GAAGAAAAUUUCCGCA<u>AAA</u>-dT-3' | SEQ ID NO: 87185 |
|  |  | AS-3'-dT-CUUCUUUUAAAGGCG<u>UUU</u>-5' | SEQ ID NO: 87186 |
| 6 | LNA2QM5-S/LNA2QM5-AS | S-5'-<u>GAA</u>GAAAAUUUCCGCAAAA-dT-3' | SEQ ID NO: 87185 |
|  |  | AS-3'-dT-CUUCUUUUAAAGGCG<u>UUU</u>-5' | SEQ ID NO: 87186 |
| 7 | LNA3QM5-S/LNA2QM5-AS | S-5'-<u>GAA</u>GAAAAUUUCCGCA<u>AAA</u>-dT-3' | SEQ ID NO: 87185 |
|  |  | AS-3'-dT-CUUCUUUUAAAGGCG<u>UUU</u>-5' | SEQ ID NO: 87186 |
| 8 | QM5-S/LNA2QM5-AS | S-5'-GAAGAAAAUUUCCGCAAAA-3' | SEQ ID NO: 87179 |
|  |  | AS-3'-dT-CUUCUUUUAAAGGCG<u>UUU</u>-5' | SEQ ID NO: 87186 |
| 9 | LNA1QM5-S/LNA3QM5-AS | S-5'-GAAGAAAAUUUCCGCA<u>AAA</u>-dT-3' | SEQ ID NO: 87185 |
|  |  | AS-3'-dT-<u>CUU</u>CUUUUAAAGGCG<u>UUU</u>-5' | SEQ ID NO: 87186 |
| 10 | LNA1QM5-S/QM5-AS | S-5'-GAAGAAAAUUUCCGCA<u>AAA</u>-dT-3' | SEQ ID NO: 87185 |
|  |  | AS-3'-CUUCUUUUAAAGGCGUUUU-5' | SEQ ID NO: 87180 |
| 11 | LNA2QM5-S/LNA3QM5-AS | S-5'-<u>GAA</u>GAAAAUUUCCGCAAAA-dT-3' | SEQ ID NO: 87185 |
|  |  | AS-3'-dT-<u>CUU</u>CUUUUAAAGGCG<u>UUU</u>-5' | SEQ ID NO: 87186 |
| 12 | LNA2QM5-S/QM5-AS | S-5'-<u>GAA</u>GAAAAUUUCCGCAAAA-dT-3' | SEQ ID NO: 87185 |
|  |  | AS-3'-CUUCUUUUAAAGGCGUUUU-5' | SEQ ID NO: 87180 |
| 13 | LNA3QM5-S/LNA3QM5-AS | S-5'-<u>GAA</u>GAAAAUUUCCGCA<u>AAA</u>-dT-3' | SEQ ID NO: 87185 |
|  |  | AS-3'-dT-<u>CUU</u>CUUUUAAAGGCG<u>UUU</u>-5' | SEQ ID NO: 87186 |
| 14 | QM5-S/LNA3QM5-AS | S-5'-GAAGAAAAUUUCCGCAAAA-3' | SEQ ID NO: 87179 |
|  |  | AS-3'-dT-<u>CUU</u>CUUUUAAAGGCG<u>UUU</u>-5' | SEQ ID NO: 87186 |
| 15 | LNA3QM5-S/QM5-AS | S-5'-<u>GAA</u>GAAAAUUUCCGCA<u>AAA</u>-dT-3' | SEQ ID NO: 87185 |
|  |  | AS-3'-CUUCUUUUAAAGGCGUUUU-5' | SEQ ID NO: 87180 |
| 16 | QM5-S/QM5-AS (positive control) | S-5'-GAAGAAAAUUUCCGCAAAA-3' | SEQ ID NO: 87179 |
|  |  | AS-3'-CUUCUUUUAAAGGCGUUUU-5' | SEQ ID NO: 87180 |

Tandem siRNA molecule

S-5'  agagcgagaugaucuggaadTsdTuuagagaagaucuacguguuadTsdT3'
(SEQ ID NO:87194)

A-3'dTsdTucucgcucuacuagaccuudTsdT   ucucuucuagaugcacaau         5'
(SEQ ID NO:87195)                   (SEQ ID NO:87196)

Figure 17A

| duplex No | siRNA-duplex name | Bold underlined N = 2'Ome  Small case italicized = 2'-5'bond plus 3'Ome | Activity 20nM- % target gene post KD | SEQ ID No. |
|---|---|---|---|---|
| 1 | 3'Ome-1QM5-as/ 3'Ome-1-QM5-s | S-5'-GAAGAAAAUUUCCGCAaaA-3' |  | SEQ ID NO:87179 |
|   |   | AS-5'-UUUUGCGGAAAUUUUCuuC- 3' |  | SEQ ID NO:87180 |
| 2 | 3'Ome-1QM5-as/ 3'Ome-2-QM5-s | S-5'-*gaa*GAAAAUUUCCGCAAAA-3' | 35; 17 | SEQ ID NO:87179 |
|   |   | AS-5'-UUUUGCGGAAAUUUUCuuC- 3' |  | SEQ ID NO:87180 |
| 3 | 3'Ome-1QM5-as/ QM5-s | S-5'- GAAGAAAAUUUCCGCAAAA- 3' | 57 | SEQ ID NO:87179 |
|   |   | AS-5'-UUUUGCGGAAAUUUUCuuC- 3' |  | SEQ ID NO:87180 |
| 4 | 3'Ome-2-QM5-as/ 3'Ome-1-QM5-s | S-5'-GAAGAAAAUUUCCGCAaaA-3' | 100 | SEQ ID NO:87179 |
|   |   | AS-5'-uuuUGCGGAAAUUUUCUUC- 3' |  | SEQ ID NO:87180 |
| 5 | 3'Ome-2-QM5-as/ 3'Ome-2-QM5-s | S-5'-*gaa*GAAAAUUUCCGCAAAA-3' | 100 | SEQ ID NO:87179 |
|   |   | AS-5'-uuuUGCGGAAAUUUUCUUC- 3' |  | SEQ ID NO:87180 |
| 6 | 3'Ome-2-QM5-as/ QM5-s | S-5'- GAAGAAAAUUUCCGCAAAA- 3' | 100 | SEQ ID NO:87179 |
|   |   | AS-5'-uuuUGCGGAAAUUUUCUUC- 3' |  | SEQ ID NO:87180 |
| 7 | QM5as/ 3'Ome-1-QM5-s | S-5'-GAAGAAAAUUUCCGCAaaA-3' | 26 (5nM); 13 | SEQ ID NO:87179 |
|   |   | AS-5'-UUUUGCGGAAAUUUUCUUC- 3' |  | SEQ ID NO:87180 |
| 8 | QM5as/ 3'Ome-2-QM5-s | S-5'-*gaa*GAAAAUUUCCGCAAAA-3' | 16; 16 | SEQ ID NO:87179 |
|   |   | AS-5'-UUUUGCGGAAAUUUUCUUC- 3' |  | SEQ ID NO:87180 |

Figure 17B

| siRNA-duplex No | siRNA-duplex name | *Italicized small case=P-Ethoxy-dN;* <u>N</u> = 2'-Ome | Activity at 20nM-% target gene KD | SEQ ID No. |
|---|---|---|---|---|
| 1 | Y1QM5-as/ Y1QM5-s | S-5'-GAAGAAAAUUUCCGCA*aaa*-dT-3' | 55 (5nM) | SEQ ID NO:87185 |
| | | AS-5'-UUUUGCGGAAAUUUUC*uuc*-dT-3' | | SEQ ID NO:87186 |
| 2 | Y1QM5-as/ Y2QM5-s | S-5'-*gaa*GAAAAUUUCCGCAAAA-dT-3' | 100 | SEQ ID NO:87185 |
| | | AS-5'-UUUUGCGGAAAUUUUC*uuc*-dT-3' | | SEQ ID NO:87186 |
| 3 | Y1QM5-as/ QM5-s | S-5'-GAA<u>GAAAAUUUCCGCAAAA</u>- 3' | 38 | SEQ ID NO:87179 |
| | | AS-5'-UUUUGCGGAAAUUUUC*uuc*-dT-3' | | SEQ ID NO:87186 |
| 4 | Y2QM5-as/ Y1QM5-s | S-5'-GAAGAAAAUUUCCGCA*aaa*-dT-3' | 87 | SEQ ID NO:87185 |
| | | AS-5'-*uuu*UGCGGAAAUUUUCUUC-dT-3' | | SEQ ID NO:87186 |
| 5 | Y2QM5-as/ Y2QM5-s | S-5'-*gaa*GAAAAUUUCCGCAAAA-dT-3' | 100 | SEQ ID NO:87185 |
| | | AS-5'-*uuu*UGCGGAAAUUUUCUUC-dT-3' | | SEQ ID NO:87186 |
| 6 | Y2QM5-as/ QM5-s | S-5'-GAA<u>GAAAAUUUCCGCAAAA</u>- 3' | 100 | SEQ ID NO:87179 |
| | | AS-5'-*uuu*UGCGGAAAUUUUCUUC-dT-3' | | SEQ ID NO:87186 |
| 7 | QM5-as/ Y1QM5-s | S-5'-GAAGAAAAUUUCCGCA*aaa*-dT-3' | 27 (5nM) | SEQ ID NO:87185 |
| | | AS-3'-<u>CUUCUUUUAAAGGCGUUUU</u>- 5' | | SEQ ID NO:87180 |
| 8 | QM5-as/ Y2QM5-s | S-5'-*gaa*GAAAAUUUCCGCAAAA-dT-3' | 19 | SEQ ID NO:87185 |
| | | AS-3'-<u>CUUCUUUUAAAGGCGUUUU</u>- 5' | | SEQ ID NO:87180 |

Figure 17C

| siRNA-duplex No | siRNA-duplex name | *ITALICS CAPITAL* = 2'-5'-nucs; n=LNA; N - 2'-Ome *italics small* - L-DNA | 3'-end Pi | Activity at 20nM-% target gene KD (residual) | SEQ ID No. |
|---|---|---|---|---|---|
| 4 | CASP2_4_DS_1 | gccAGAAUGUGGAACU*CCU* | y | 11 (8) | SEQ ID NO:139 |
| | | *AGGAGUUCCACAUUCUGGC* | y | | SEQ ID NO:140 |
| 5 | CASP2_4_DS_2 | gccAGAAUGUGGAACU*CCU* | y | 10 (8) | SEQ ID NO:139 |
| | | *AGGAGUUCCACAUUCUGGC* | y | | SEQ ID NO:140 |
| 4 | CASP2_4_S-2-5-Pi-3'/ CASP2_4_AS-Pi | GCCAGAAUGUGGAACU*CCU* | y | 6 | SEQ ID NO:139 |
| | | *AGGAGUUCCACAUUCUGGC* | y | | SEQ ID NO:140 |
| 1 | CASP2_4_S1/ CASP2_4_AS_alt | GCCAGAAUGUGGAACU*CCU* | y-2' | 11 | SEQ ID NO:139 |
| | | *AGGAGUUCCACAUUCUGGC* | y | | SEQ ID NO:140 |
| 2 | CASP2_4_S2/ CASP2_4_AS_alt | GCCAGAAUGUGGAACU*CCU* | y-2' | 17 | SEQ ID NO:139 |
| | | *AGGAGUUCCACAUUCUGGC* | y | | SEQ ID NO:140 |
| 5 | CASP2_4_S5/ CASP2_4_AS_alt | GCCAGAAUGUGGAACUC*cu* | y | 3 | SEQ ID NO:139 |
| | | *AGGAGUUCCACAUUCUGGC* | y | | SEQ ID NO:140 |
| 6 | CASP2_4_S6/ CASP2_4_AS_alt | GCCAGAAUGUGGAACUC*Cu* | y | 6 | SEQ ID NO:139 |
| | | *AGGAGUUCCACAUUCUGGC* | y | | SEQ ID NO:140 |
| 7 | CASP2_4_S7/ CASP2_4_AS_alt | GCCAGAAUGUGGAACU*ccu* | y | 10 | SEQ ID NO:139 |
| | | *AGGAGUUCCACAUUCUGGC* | y | | SEQ ID NO:140 |
| 8 | CASP2_4_S8/ CASP2_4_AS_alt | GCCAGAAUGUGGAACUC*cu* | y | 4 | SEQ ID NO:139 |
| | | *AGGAGUUCCACAUUCUGGC* | y | | SEQ ID NO:140 |
| 9 | CASP2_4_S9/ CASP2_4_AS_alt | GCCAGAAUGUGGAACUCC*u* | y | 8 | SEQ ID NO:139 |
| | | *AGGAGUUCCACAUUCUGGC* | y | | SEQ ID NO:140 |
| 10 | CASP2_4_S10/ CASP2_4_AS_alt | GCCAGAAUGUGGAACUC*cu* | y | 7 | SEQ ID NO:139 |
| | | *AGGAGUUCCACAUUCUGGC* | y | | SEQ ID NO:140 |
| 11 | CASP2_4_S11/ CASP2_4_AS_alt | GCCAGAAUGUGGAACUCC*cU* | y | 6 | SEQ ID NO:139 |
| | | *AGGAGUUCCACAUUCUGGC* | y | | SEQ ID NO:140 |
| 12 | CASP2_4_S12/ CASP2_4_AS_alt | GCCAGAAUGUGGAACU*Cc*U | y | 18 | SEQ ID NO:139 |
| | | *AGGAGUUCCACAUUCUGGC* | y | | SEQ ID NO:140 |
| 3 | CASP2_4_S3/ CASP2_4_AS_alt | GCCAGAAUGUGGAACU*CCU* | y | 17 | SEQ ID NO:139 |
| | | *AGGAGUUCCACAUUCUGGC* | y | | SEQ ID NO:140 |

Figure 18

| Strand name | 19-mer - Sense - (5'>3') | |
|---|---|---|
| CASP2_4-S-dn1 | GCCAGAAUGUG*GAACTCCT* | SEQ ID NO:87201 |
| CASP2_4-S-dn2 | GCCAGAAUGUGG*AACTCCT* | SEQ ID NO:87202 |
| CASP2_4-S-dn3 | GCCAGAAUGUGGA*ACTCCT* | SEQ ID NO:87203 |
| CASP2_4-S-dn4 | *GCCAGA*AUGUGGAACUCCU | SEQ ID NO:87204 |
| CASP2_4-S-dn5 | *GCCAGA*AUGUGGA*ACTCCT* | SEQ ID NO:87205 |
| CASP2_4-S-dn6 | *GCCAG*AAUGUGGA*ACTCCT* | SEQ ID NO:87206 |

| Strand name | 19-mer-Antisense (5'>3') | |
|---|---|---|
| CASP2_4-AS-dn1 | *AGGAGTTC*CACAUUCUGGC | SEQ ID NO:87207 |
| CASP2_4-AS-dn2 | *AGGAGTT*CCACAUUCUGGC | SEQ ID NO:87208 |
| CASP2_4-AS-dn3 | *AGGAGT*UCCACAUUCUGGC | SEQ ID NO:87209 |
| CASP2_4-AS-dn4 | *AGGAG*UUCCACAUUCUGGC | SEQ ID NO:87210 |
| CASP2_4-AS-dn5 | *AGGAG*UUCCACAUU*CTGGC* | SEQ ID NO:87211 |
| CASP2_4-AS-dn6 | 6g8a8u5c7a7a5u7u8g7 | SEQ ID NO:140 |

Figure 19A

| Strand sequence 5'>3' | Strand | SEQ ID No. |
|---|---|---|
| Gc̲CAGAAUGUGGAACUCc̲U | Sense | SEQ ID NO: 139 |
| AGGAGUUCCACAUUCUGGC | AS | SEQ ID NO: 140 |
| | | |
| GcCAGAAUGUGGAACUc̲cU | Sense | SEQ ID NO: 139 |
| A̲G̲G̲A̲G̲U̲U̲C̲C̲A̲C̲A̲U̲U̲C̲U̲G̲G̲C̲ | AS | SEQ ID NO: 140 |
| Legend | | |
| n̲ = L-DNA | | |
| N̲ - 2'-OMe ribonucleotide | | |

Figure 19B

| Sense Strand (N'y); 19-mer (5'>3') | SEQ ID No. |
|---|---|
| Gc̲CAGAAUGUGGAACUc̲cU | SEQ ID NO: 139 |
| Gc̲ c̲AGAAUGUGGAACUc̲cU | SEQ ID NO: 139 |
| Gc̲CAGAAUGUGGAACUCc̲U | SEQ ID NO: 139 |
| Gc̲ c̲AGAAUGUGGAACUCc̲U | SEQ ID NO: 139 |
| Lc-GCCAGAAUGUGGAACUc̲cU | SEQ ID NO: 139 |
| Lc-GCCAGAAUGUGGAACUc̲cU | SEQ ID NO: 139 |
| Lc-GCCAGAAUGUGGAACUCc̲U | SEQ ID NO: 139 |
| Lc-GCCAGAAUGUGGAACUCc̲U | SEQ ID NO: 139 |
| ab-GCCAGAAUGUGGAACUc̲cU | SEQ ID NO: 139 |
| ab-GCCAGAAUGUGGAACUc̲cU | SEQ ID NO: 139 |
| ab-GCCAGAAUGUGGAACUCc̲U | SEQ ID NO: 139 |
| ab-GCCAGAAUGUGGAACUCc̲U | SEQ ID NO: 139 |
| AS Strand (N)x; 19-mer (5'>3') | |
| AGGAGUUCCACAUUCUGGC | SEQ ID NO: 140 |
| A̲GGA̲G̲UUC̲CA̲CA̲UUC̲UG̲GC̲ | SEQ ID NO: 140 |
| A̲G̲G̲A̲G̲U̲U̲C̲C̲A̲C̲A̲U̲U̲C̲U̲G̲G̲C̲ | SEQ ID NO: 140 |
| Legend | | n̲ = L-DNA (L-deoxyribocytidine)
N̲ - 2'-OMe ribonucleotide
Lc- L-Deoxy cytidine 5'-overhang
ab- Abasic 2'deoxyribo moiety

Figure 19C

| OLIGO NAME | SEQUENCE (5' -> 3') | SEQ ID No. |
|---|---|---|
| CASP2_4_S1 | 5' GCCAGAAUGUGGAAdCUC_cA | SEQ ID NO:87212 |
| CASP2_4_S2 | 5' GCCAGAAUGUGGAAdC_cC_cA | SEQ ID NO:87213 |
| CASP2_4_S3 | 5' I GCCAGAAUGUGGAAdCUC_cA | SEQ ID NO:87212 |
| CASP2_4_S4 | 5' _c GCCAGAAUGUGGAAdCUC_cA | SEQ ID NO:87212 |
| CASP2_4_S5 | 5' C6-GCCAGAAUGUGGAAdCUC_cA | SEQ ID NO:87212 |
| CASP2_4_S6 | 5' C6-GCCAGAAUGUGGAAdC_cC_cA | SEQ ID NO:87213 |
| CASP2_4_S7 | 5' G_cCAGAAUGUGGAAdCUC_cA | SEQ ID NO:87212 |
| CASP2_4_S8 | 5' G_cCAGAAUGUGGAAdC_cC_cA | SEQ ID NO:87213 |
| | | |
| CASP2_4_AS1 | 5' AGGAGUUCCACAUUCUGGC | SEQ ID NO:140 |
| CASP2_4_AS2 | 5' AG_gAGUU_cCA_cAUUCUGG_c | SEQ ID NO:140 |

| _n_ = L-DNA (L-deoxyribonucleotide) |
|---|
| N - 2'-OMe ribonucleotide |
| dN- 2'deoxynucleotide |
| I- INVERTED Abasic 2'deoxyribo moiety |
| C6- C6 imino Pi |

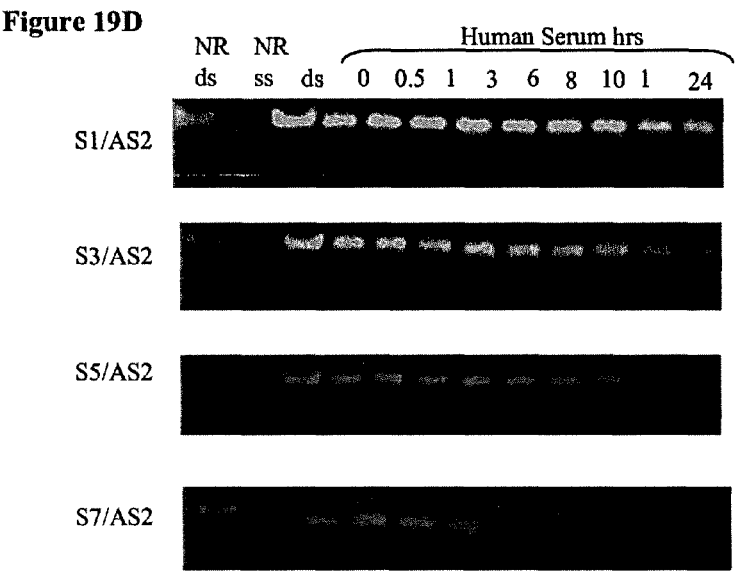

| DUPLEX motifs (5' > 3') SEN/AS | 3'end P1 | Activity at 20nM % target gene KD (= residual target gene activity) | SEQ ID NO. |
|---|---|---|---|
| GAAGGATCTTCGGAATGAT<br>ATCATTCCGAAGATCCTTC | Y<br>Y | 1.7 | SEQ ID NO:87139<br>SEQ ID NO:87140 |
| GAAGGATCTTCGGAATGAT<br>ATCATTCCGAAGATCCTTC | N<br>Y | 2.1 | SEQ ID NO:87139<br>SEQ ID NO:87140 |
| GAAGGATCTTCGGAATG*A*T<br>ATCATTCCGAAGATCCTTC | N<br>Y | 3.4 | SEQ ID NO:87139<br>SEQ ID NO:87140 |
| GAAGGATCTTCGGAATG*A*T<br>ATCATTCCGAAGATCCTTC | Y<br>Y | 3.2 | SEQ ID NO:87139<br>SEQ ID NO:87140 |
| GAAGGATCTTCGGAATG*A*T<br>ATCATTCCGAAGATCCTTC | Y 2'<br>Y | 3.2 | SEQ ID NO:87139<br>SEQ ID NO:87140 |
| GAAGGATCTTCGGAATGat<br>ATCATTCCGAAGATCCTTC | Y<br>Y | 2.2 | SEQ ID NO:87139<br>SEQ ID NO:87140 |
| GAAGGATCTTCGGAATGat<br>ATCATTCCGAAGATCCTTC | N<br>Y | 2.5 | SEQ ID NO:87139<br>SEQ ID NO:87140 |
| GAAGGATCTTCGGAATGAT<br>ATCATTCCGAAGATCCTTC | Y<br>N | 3 | SEQ ID NO:87139<br>SEQ ID NO:87140 |
| GAAGGATCTTCGGAATGAT<br>ATCATTCCGAAGATCCTTC | N<br>N | 6 | SEQ ID NO:87139<br>SEQ ID NO:87140 |
| GAAGGATCTTCGGAATG*A*T<br>ATCATTCCGAAGATCCTTC | N<br>N | 8 | SEQ ID NO:87139<br>SEQ ID NO:87140 |
| GAAGGATCTTCGGAATG*A*T<br>ATCATTCCGAAGATCCTTC | Y<br>N | 4 | SEQ ID NO:87139<br>SEQ ID NO:87140 |
| GAAGGATCTTCGGAATG*A*T<br>ATCATTCCGAAGATCCTTC | Y 2'<br>N | 5 | SEQ ID NO:87139<br>SEQ ID NO:87140 |
| GAAGGATCTTCGGAATGat<br>ATCATTCCGAAGATCCTTC | Y<br>N | 4 | SEQ ID NO:87139<br>SEQ ID NO:87140 |
| GAAGGATCTTCGGAATGat<br>ATCATTCCGAAGATCCTTC | N<br>N | 4 | SEQ ID NO:87139<br>SEQ ID NO:87140 |

*Note: T in the above table corresponds to U in the Sequence Listing originally filed

Figure 20

Legend

| |
|---|
| Underlined N- 2'OMe ribonucleotide |
| ab - abasic pseudonucleotide |
| I - inverted abasic pseudonucleotide |
| *Italicized 5N= 5-OMe DNA* |
| White capital N - LNA |
| *italicized small case underlined* : L-DNA |
| ~~strikethrough - mismatches~~ |

Figure 20A

| Name | Set1-Sense strands(5'>3') | SEQ ID No. |
|---|---|---|
| CASP2_4_S1 | 5'-GCCAGAAUGUGGAACUC<u>c</u>U (19) | SEQ ID NO: 139 |
| CASP2_4_S2 | 5'-GCCAGAAUGUGGAACU<u>cc</u>U (19) | SEQ ID NO: 139 |
| CASP2_4_S3 | 5'-*5G* CCAGAAUGUGGAACUCcU (19) | SEQ ID NO: 139 |
| CASP2_4_S4 | 5'-*5G* CCAGAAUGUGGAACU<u>*Cc*</u>U (19) | SEQ ID NO: 139 |
| CASP2_4_S5 | 5'-I-GCCAGAAUGUGGAACUC<u>c</u>U (20) | SEQ ID NO: 139 |
| CASP2_4_S6 | 5'-I-GCCAGAAUGUGGAACU<u>cc</u>U (20) | SEQ ID NO: 139 |
| Name | Set1- AS strands (5'-3') | |
| CASP2_4_AS1 | 5'- A<u>GG</u>Aab<u>UU</u>CCACA<u>U</u>U<u>CU</u>GG<u>C</u> (19) | SEQ ID NO: 140 |
| CASP2_4_AS2 | 5'- A<u>GG</u>AGab<u>U</u>CCACA<u>U</u>U<u>CU</u>GG<u>C</u> (19) | SEQ ID NO: 140 |
| CASP2_4_AS3 | 5'- A<u>GG</u>AG<u>U</u>UCCACA<u>U</u>UabGG<u>C</u> (19) | SEQ ID NO: 140 |
| CASP2_4_AS4 | 5'- A<u>GG</u>AG<u>UU</u>CCACA<u>U</u>ab<u>CU</u>GG<u>C</u> (19) | SEQ ID NO: 140 |
| CASP2_4_ASx | 5'- A<u>GG</u>AG<u>UU</u>CCACAUUab<u>U</u>GGC (19) | SEQ ID NO: 140 |
| CASP2_4_ASy | 5'- A<u>GG</u>Aab<u>UU</u>CCACA<u>U</u>UCUGGC (19) | SEQ ID NO: 140 |

Figure 20B

| Name | Set2-Sense strands(5'>3') | SEQ ID No. |
|---|---|---|
| CASP2_4_S7 | 5'-I CCAGAAUGUGGAACabababab (19) | SEQ ID NO: 139 |
| CASP2_4_S8 | 5'-5G CAGAAUGUGGAAabababab (19) | SEQ ID NO: 139 |
| CASP2_4_S9 | 5'-I abCAGAAUGUGGAACUababab (19) | SEQ ID NO: 139 |
| CASP2_4_S10 | 5'-I ababAGAAUGUGGAACUCabab (19) | SEQ ID NO: 139 |
| CASP2_4_S11 | 5'-I abababGAAUGUGGAACUCCab (19) | SEQ ID NO: 139 |
| CASP2_4_S12 | 5'-I ababababAAUGUGGAACUCCU (19) | SEQ ID NO: 139 |
| CASP2_4_S13 | 5'-5G CCAGAAUGUGGAAababababab(19) | SEQ ID NO: 139 |
| CASP2_4_S14 | 5'-IG abababAAUGUGGAACUCCU (19) | SEQ ID NO: 139 |
| Name | Set2- AS strands (5'-3') | |
| CASP2_4_AS5 | 5'- AGGAGUUCCACAUUCUGGC (19) | SEQ ID NO: 140 |
| CASP2_4_AS6 | 5'- AGGAGUUCCACAUUCUGGC (19) | SEQ ID NO: 140 |

Figure 20C

| Name | Set3-duplex sequences (5'>3') | SEQ ID No. |
|---|---|---|
| CASP2_4_S15 | 5'-I GCCAGAAUGUGGAAUUCcU (20) | a SEQ ID NO:139 |
| CASP2_4_AS7 | 5'- AGGAAUUCCACAUUCUGGC (19) | d SEQ ID NO:140 |
| CASP2_4_S16 | 5'-I GCCAGAAUGUGGAAUUCcU (20) | a SEQ ID NO:139 |
| CASP2_4_AS7 | 5'- AGGAAUUCCACAUUCUGGC (19) | d SEQ ID NO:140 |
| CASP2_4_S17 | 5'-I GCCAGAAUGUGGACUCcU (20) | b SEQ ID NO:139 |
| CASP2_4_AS8 | 5'- AGGAGUCCACAUUCUGGC (19) | e SEQ ID NO:140 |
| CASP2_4_S18 | 5'-I GCCAGAAUGUGGACUCcU (20) | b SEQ ID NO:139 |
| CASP2_4_AS8 | 5'- AGGAGUCCACAUUCUGGC (19) | e SEQ ID NO:140 |
| CASP2_4_S19 | 5'-I GCCAGAUGUGGAACUCcU (20) | c SEQ ID NO:139 |
| CASP2_4_AS9 | 5'- AGGAGUUCCACAUCUGGC (19) | f SEQ ID NO:140 |
| CASP2_4_S20 | 5'-I GCCAGAUGUGGAACUCcU (20) | c SEQ ID NO:139 |
| CASP2_4_AS9 | 5'- AGGAGUUCCACAUCUGGC (19) | f SEQ ID NO:140 |

Figure 20D

| Oligo Name | Set4- SEN strands (5'>3') | SEQ ID No. |
|---|---|---|
| CASP2_4_S1 | 5'-GCCAGAAUGUGGAACUCcU (19) | SEQ ID NO: 139 |
| CASP2_4_S2 | 5'-GCCAGAAUGUGGAACUccU (19) | SEQ ID NO: 139 |
| CASP2_4_S3 | 5'-5G CCAGAAUGUGGAACUCcU (19) | SEQ ID NO: 139 |
| CASP2_4_S4 | 5'-5G CCAGAAUGUGGAACUccU (19) | SEQ ID NO: 139 |
| CASP2_4_S5 | 5'-I GCCAGAAUGUGGAACUCcU (20) | SEQ ID NO: 139 |
| CASP2_4_S6 | 5'-I GCCAGAAUGUGGAACUccU (20) | SEQ ID NO: 139 |

| Oligo Name | Set4- AS strands (5'-3') | |
|---|---|---|
| CASP2_4_AS10 | 5'- AGGAabUUCCACAUUCUGGC (19) | SEQ ID NO: 140 |
| CASP2_4_AS11 | 5'- AGGAGbaUCCACAUUCUGGC (19) | SEQ ID NO: 140 |
| CASP2_4_AS12 | 5'- AGGAGUUCCACAUUabUGGC (19) | SEQ ID NO: 140 |
| CASP2_4_AS13 | 5'- AGGAGUUCCACAUabCUGGC (19) | SEQ ID NO: 140 |
| CASP2_4_AS14 | 5'- AGGAabUUCCACAUUCUGGC (19) | SEQ ID NO: 140 |
| CASP2_4_AS15 | 5'- AGGAabUUCCACAUUCUGGC (19) | SEQ ID NO: 140 |
| CASP2_4_AS16 | 5'- AGGAGUUCCACAUUabUGGC (19) | SEQ ID NO: 140 |
| CASP2_4_AS17 | 5'- AGGAGUUCCACAUUabUGGC (19) | SEQ ID NO: 140 |

Figure 20E

| Oligo Name | Set5-Sense strands(5'>3')<br>Same sense strands as in SET1 | SEQ ID No. |
|---|---|---|
| CASP2_4_S1 | 5'-GCCAGAAUGUGGAACUC<u>c</u>U (19) | SEQ ID NO:139 |
| CASP2_4_S2 | 5'-GCCAGAAUGUGGAACU<u>cc</u>U (19) | SEQ ID NO:139 |
| CASP2_4_S3 | 5'-5G CCAGAAUGUGGAACUC<u>c</u>U (19) | SEQ ID NO:139 |
| CASP2_4_S4 | 5'-5G CCAGAAUGUGGAACU<u>cc</u>U (19) | SEQ ID NO:139 |
| CASP2_4_S5 | 5'-I GCCAGAAUGUGGAACUC<u>c</u>U (20) | SEQ ID NO:139 |
| CASP2_4_S6 | 5'-I GCCAGAAUGUGGAACU<u>cc</u>U (20) | SEQ ID NO:139 |

| Oligo Name | Set5- AS strands (5'-3') | SEQ ID No. |
|---|---|---|
| CASP2_4_AS18 | 5'- A<u>GGAGU</u>ab<u>CC</u>AC<u>AUUC</u>U<u>GGC</u> (19) | SEQ ID NO:140 |
| CASP2_4_AS19 | 5'- A<u>GGAGUU</u>ab<u>C</u>AC<u>AUUC</u>U<u>GGC</u> (19) | SEQ ID NO:140 |
| CASP2_4_AS20 | 5'- A<u>GGAGUUC</u>ab<u>AC</u>AU<u>UC</u>U<u>GGC</u> (19) | SEQ ID NO:140 |
| CASP2_4_AS21 | 5'- A<u>GGAGUUCC</u>ab<u>C</u>AU<u>UC</u>U<u>GGC</u> (19) | SEQ ID NO:140 |
| CASP2_4_AS22 | 5'- A<u>GGAGUUCCA</u>ab<u>AUUCUGGC</u> (19) | SEQ ID NO:140 |
| CASP2_4_AS23 | 5'- A<u>GGAGUUCCAC</u>ab<u>UUCUGGC</u> (19) | SEQ ID NO:140 |
| CASP2_4_AS24 | 5'- A<u>GGAGUUC</u>C<u>AC</u>Aab<u>UCUGGC</u> (19) | SEQ ID NO:140 |

Figure 20F

| Oligo Name | Set6-Sense strand(5'>3') | SEQ ID No. |
|---|---|---|
| CASP2_4_S0 | 5'-GCCAGAAUGUGGAACUCCU (19) | SEQ ID NO:139 |

| Oligo Name | Set6- AS strands (5'-3') | SEQ ID No. |
|---|---|---|
| CASP2_4_AS0 | 5'- AGGAGUUCCACAUUCUGGC (19) | SEQ ID NO:140 |
| CASP2_4_AS1 | 5'- AGGAabUUCCACAUUCUGGC (19) | SEQ ID NO:140 |
| CASP2_4_AS2 | 5'- AGGAGabUCCACAUUCUGGC (19) | SEQ ID NO:140 |
| CASP2_4_AS3 | 5'- AGGAGUUCCACAUUabUGGC (19) | SEQ ID NO:140 |
| CASP2_4_AS4 | 5'- AGGAGUUCCACAUabCUGGC (19) | SEQ ID NO:140 |
| CASP2_4_AS18 | 5'- AGGAGUabCCACAUUCUGGC (19) | SEQ ID NO:140 |
| CASP2_4_AS19 | 5'- AGGAGUUabCACAUUCUGGC (19) | SEQ ID NO:140 |
| CASP2_4_AS20 | 5'- AGGAGUUCabACAUUCUGGC (19) | SEQ ID NO:140 |
| CASP2_4_AS21 | 5'- AGGAGUUCCabCAUUCUGGC (19) | SEQ ID NO:140 |
| CASP2_4_AS22 | 5'- AGGAGUUCCAabAUUCUGGC (19) | SEQ ID NO:140 |
| CASP2_4_AS23 | 5'- AGGAGUUCCACabUUCUGGC (19) | SEQ ID NO:140 |
| CASP2_4_AS24 | 5'- AGGAGUUCCACAabUCUGGC (19) | SEQ ID NO:140 |

Figure 20G

| Oligo Name | Set7-Sense strands(5'>3') | SEQ ID No. |
|---|---|---|
| CASP2_4_S1 | 5'-GCCAGAAUGUGGAACUCcU (19) | SEQ ID NO:139 |
| CASP2_4_S2 | 5'-GCCAGAAUGUGGAACUccU (19) | SEQ ID NO:139 |
| CASP2_4_S3 | 5'-5G CCAGAAUGUGGAACUCcU (19) | SEQ ID NO:139 |
| CASP2_4_S4 | 5'-5G CCAGAAUGUGGAACUccU (19) | SEQ ID NO:139 |
| CASP2_4_S5 | 5'-I GCCAGAAUGUGGAACUCcU (20) | SEQ ID NO:139 |
| CASP2_4_S6 | 5'-I GCCAGAAUGUGGAACUccU (20) | SEQ ID NO:139 |

| Oligo Name | Set7- AS strand (5'-3') | SEQ ID No. |
|---|---|---|
| CASP2_4_AS0 | 5'- AGGAGUUCCACAUUCUGGC (19) | SEQ ID NO:140 |

Figure 21

| Monomer name/ alias | Structure | Base pairing capability | Availability/ supplier | Citations/references |
|---|---|---|---|---|
| 6 des amino adenosine/ Nebularine | Nebularine | 1H bond could be possible | Chem Genes ANP-7601 | |
| 4-Me-indole | 4-Methylindole | None | Glen Research 10-1045-90 | |
| 3-nitropyrrole | 3-nitropyrrole | None | Glen Research 10-1043-90 | |
| 5-nitroindole | 5-Nitroindole | None | Glen Research 10-1044-90 | |
| Ds | dS | None | Glen Res 10-1521-90 | http://www.glenresearch.com/GlenReports/GR20-11.html or Hirao Nature Methids, 2006,3729-35 |
| Pa | dP | None | Glen Res10-1523-90 | http://www.glenresearch.com/GlenReports/GR20-11.html or Hirao Nature Methids, 2006,3729-35 |
| N3-Me ribo U | N3-Me-riboU | Probably none due to steric hindrance of Me group | Chem Genes ANP-7451 | |

Figure 21 cont.

| Monomer name/ alias | Structure | Base pairing capability | Availability/ supplier | Citations/references |
|---|---|---|---|---|
| N3-Me riboT | 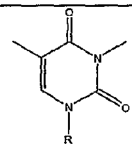 | Probably none due to steric hindrance of Me group | Chem Genes ANP-7461 | |
| N3-Me dC | | Probably none due to steric hindrance of Me group | Chem Genes ANP3851 | |
| N3-Me-dT | 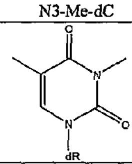 | Probably none due to steric hindrance of Me group | Chem Genes ANP3856 | Nature 419,178, 2002 |
| N1-Me-dG | 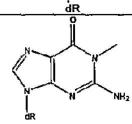 | Probably none due to steric hindrance of Me group | Chem Genes ANP6122 | Nature 419,178, 2002 |
| N1-Me-dA | 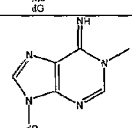 | Probably none due to steric hindrance of Me group | Chem Genes ANP-6121 | Nature 419,178, 2002 |
| N3-ethyl-dC | 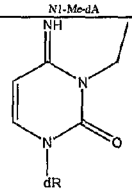 | Probably none due to steric hindrance of Me group | Chem Genes ANP3856 | Nature 419,178, 2002 BBA ,823,111,1985 NAR ,20,6471,1992 |
| N3-Me dC | | Probably none due to steric hindrance of Et group | Chem Genes ANP3851 | Nature 419,178, 2002 BBA ,823,111,1985 NAR ,20,6471,1992 |

FIG. 23

| ID | Sense | AntiSense | Activity at 20nM (% of control) | IC50 (nM) | Stability in hum-serum |
|---|---|---|---|---|---|
| Q-001 | rG;rA;rG;rA;rA;rA;rA;rU;rU;rC;rG;rC;rA;LdA;LdA;LdA;dT$ (SEQ ID No. 87185) | rU;rU;rU;rU;rG;rC;rG;rA;rA;rU;rU;rU;rU;rC;LdT;LdT;LdC;dT$ (SEQ ID No. 87186) | 100 | | 10 |
| Q-002 | LdG;LdA;LdA;rG;rA;rA;rA;rA;rU;rU;rC;rG;rC;rA;rA;rA;rA;dT$ (SEQ ID No. 87185) | rU;rU;rU;rU;rG;rC;rG;rA;rA;rU;rU;rU;rU;rC;LdT;LdC;dT$ (SEQ ID No. 87186) | 100 | | |
| Q-003 | LdG;LdA;LdA;rG;rA;rA;rA;rA;rU;rU;rC;rG;rC;rA;LdA;LdA;LdA;dT$ (SEQ ID No. 87185) | rU;rU;rU;rU;rG;rC;rG;rA;rA;rU;rU;rU;rU;rC;LdT;LdC;dT$ (SEQ ID No. 87186) | 100 | | |
| Q-004 | rG;mA;rA;mG;rA;mA;rA;mA;rU;mU;rU;mC;rC;mG;rC;mA;rA;mA;rA$ (SEQ ID No. 87179) | rU;rU;rU;rU;rG;rC;rG;rA;rA;rU;rU;rU;rU;rC;rU;rU;rC;dT$ (SEQ ID No. 87186) | 100 | | |
| Q-005 | rG;rA;rA;rG;rA;rA;rA;rA;rU;rU;rC;rG;rC;rA;LdA;LdA;LdA;dT$ (SEQ ID No. 87185) | LdT;LdT;LdT;LdT;rU;rG;rC;rG;rA;rA;rU;rU;rU;rU;rC;rU;rC;dT$ (SEQ ID No. 87186) | 89 | | |
| Q-006 | LdG;LdA;LdA;rG;rA;rA;rA;rA;rU;rU;rC;rG;rC;rA;rA;rA;rA;dT (SEQ ID No. 87185) | LdT;LdT;LdT;LdT;rU;rG;rC;rG;rA;rA;rU;rU;rU;rU;rC;rU;rC;dT$ (SEQ ID No. 87186) | 84 | | |
| Q-007 | LdG;LdA;LdA;rG;rA;rA;rA;rA;rU;rU;rC;rG;rC;rA;LdA;LdA;LdA;dT (SEQ ID No. 87185) | LdT;LdT;LdT;LdT;rU;rG;rC;rG;rA;rA;rU;rU;rU;rU;rC;rU;rU;rC;dT$ (SEQ ID No. 87186) | 100 | | |
| Q-008 | rG;mA;rA;mG;rA;mA;rA;mA;rU;mU;rU;mC;rC;mG;rC;mA;rA;mA;rA$ (SEQ ID No. 87179) | LdT;LdT;LdT;LdT;rU;rG;rC;rG;rA;rA;rU;rU;rU;rU;rC;LdT;LdT;LdC;dT (SEQ ID No. 87186) | 92 | | |
| Q-009 | rG;rA;rA;rG;rA;rA;rA;rA;rU;rU;rC;rG;rC;rA;LdA;LdA;LdA;dT (SEQ ID No. 87185) | mU;rU;mU;rU;mG;rU;mG;rC;mG;rA;mA;rA;mA;rU;mU;rU;mU;rC;mU;rU;mC;dT$ (SEQ ID No. 87186) | 17 | | 3 |
| Q-010 | LdG;LdA;LdA;rG;rA;rA;rA;rA;rU;rU;rC;rG;rC;rA;rA;rA;rA;dT (SEQ ID No. 87185) | LdT;LdT;LdT;LdT;rU;rG;rC;rG;rA;rA;rU;rU;rU;rU;rC;LdT;LdT;LdC;dT$ (SEQ ID No. 87186) | 100 | | |
| Q-011 | LdG;LdA;LdA;rG;rA;rA;rA;rA;rU;rU;rC;rG;rC;rA;rA;rA;rA;dT (SEQ ID No. 87185) | mU;rU;mU;rU;mG;rU;mG;rC;mG;rA;mA;rA;mA;rU;mU;rU;mU;rC;mU;rU;mC;dT$ (SEQ ID No. 87186) | 74 | | |
| Q-012 | LdG;LdA;LdA;rG;rA;rA;rA;rA;rU;rU;rC;rG;rC;rA;LdA;LdA;LdA;dT (SEQ ID No. 87185) | mU;rU;mU;rU;mG;rU;mG;rC;mG;rA;mA;rA;mA;rU;mU;rU;mU;rC;mU;rU;mC;dT$ (SEQ ID No. 87186) | 100 | | |
| Q-013 | LdG;LdA;LdA;rG;rA;rA;rA;rA;rU;rU;rC;rG;rC;rA;LdA;LdA;LdA;dT (SEQ ID No. 87185) | LdT;LdT;LdT;LdT;rU;rG;rC;rG;rA;rA;rU;rU;rU;rU;rC;LdT;LdT;LdC;dT (SEQ ID No. 87186) | 74 | | |
| Q-014 | LdG;LdA;LdA;rG;rA;rA;rA;rA;rU;rU;rC;rG;rC;rA;LdA;LdA;LdA;dT (SEQ ID No. 87185) | mU;rU;mU;rU;mG;rU;mG;rC;mG;rA;mA;rA;mA;rU;mU;rU;mU;rC;mU;rU;mC;dT$ (SEQ ID No. 87186) | 82 | | |
| Q-015 | rG;mA;rA;mG;rA;mA;rA;mA;rU;mU;rU;mC;rC;mG;rC;mA;rA;mA;rA$ (SEQ ID No. 87179) | LdT;LdT;LdT;LdT;rU;rG;rC;rG;rA;rA;rU;rU;rU;rU;rC;LdT;LdT;LdC;dT (SEQ ID No. 87186) | 25 | | 0 |
| Q-016 | rG;rA;rA;rG;rA;rA;rA;rA;rU;rU;rC;rG;rC;rA;rA;rA;rA (SEQ ID No. 87179) | rU;mU;rU;mU;rG;rC;rG;rA;rA;rU;rU;rU;rU;rC;rU;rU;rC (SEQ ID No. 87180) | 100 | | |
| Q-017 | rG;rA;rA;rG;rA;rA;rA;rA;rU;rU;rC;rG;rC;rA;rA;rA;rA (SEQ ID No. 87179) | rU;rU;rU;rU;rG;rC;rG;rA;rG;rA;rA;rU;rU;rU;rU;rC;mU;mU;mC (SEQ ID No. 87180) | 12 | | 24 |
| Q-018 | rG;rA;rA;rG;rA;rA;rA;rA;rU;rU;rC;rG;rC;rA;rA;rA;rA (SEQ ID No. 87179) | mU;rU;rU;rU;rG;rC;rG;rA;rG;rA;rA;rU;rU;rU;rU;rC;mU;mU;mC (SEQ ID No. 87180) | 40 | | 24 |

FIG. 23 Continued

| ID | Sense | AntiSense | Activity at 20nM (% of control) | IC50 (nM) | Stability in human serum |
|---|---|---|---|---|---|
| Q-019 | mG;mA;mA;mG;mA;rA;A;rA;rU;rU;rC;rG;rU;rC;rC;rA;rA;rA (SEQ ID No. 87179) | rU;mU;rU;rG;rC;rG;rA;rA;rA;rU;rU;rU;rU;rU;rC;rU;rU;rC (SEQ ID No. 87180) | 10 | | |
| Q-020 | mG;mA;mA;mG;mA;rA;A;rA;rU;rU;rC;rG;rU;rC;rC;rA;rA;rA (SEQ ID No. 87179) | rU;rU;rU;rG;rC;rG;rA;rA;rA;rU;rU;rU;mU;mC;mU;mC (SEQ ID No. 87180) | 13 | 0.977 | |
| Q-021 | mG;mA;mA;mG;mA;rA;rA;rA;rU;rU;rC;rG;rU;rC;rC;rA;rA;rA (SEQ ID No. 87179) | mU;mU;rU;rG;rC;rG;rA;rA;rA;rU;rU;rU;rU;rU;rC (SEQ ID No. 87180) | 16 | | |
| Q-022 | mG;mA;mA;mG;mA;mA;mA;mA;rU;rU;rC;rG;rU;rC;rC;rA;rA;rA (SEQ ID No. 87179) | rU;rU;rU;rG;rC;rG;rA;rA;rA;rU;rU;rU;mU;mC;mU;mC (SEQ ID No. 87180) | 40 | | |
| Q-023 | mG;mA;mA;mG;mA;mA;mA;mA;mA;mA;rU;rC;rG;rU;rC;rC;rA;rA;rA (SEQ ID No. 87179) | rU;rU;rU;rG;rC;rG;rA;rA;rA;rU;rU;rU;mU;mC;mU;mC (SEQ ID No. 87180) | 14 | 0.913 | |
| Q-024 | mG;mA;mA;mG;mA;mA;mA;mA;mA;mA;rU;rC;rG;rU;rC;rC;rA;rA;rA (SEQ ID No. 87179) | mU;mU;rU;rG;rC;rG;rA;rA;rA;rU;rU;rU;rU;rU;rC (SEQ ID No. 87180) | 52 | | |
| Q-025 | mG;mA;mA;mG;mA;mA;mA;mA;mA;mU;mU;mC;rG;rU;rC;rC;rA;rA;rA (SEQ ID No. 87179) | rU;rU;rU;rG;rC;rG;rA;rA;rA;rU;rU;rU;mU;mC;mU;mC (SEQ ID No. 87180) | 35 | | |
| Q-026 | mG;mA;mA;mG;mA;mA;mA;mA;mA;mU;mU;mC;mC;rG;rU;rC;rC;rA;rA;rA (SEQ ID No. 87179) | mU;mU;rU;rG;rC;rG;rA;rA;rA;rU;rU;rU;mU;mC;mU;mC (SEQ ID No. 87180) | 11 | 0.871 | |
| Q-027 | mG;mA;mA;mG;mA;mA;mA;mA;mA;mU;mU;mC;mC;mC;rG;rU;rC;rA;rA;rA (SEQ ID No. 87179) | mU;mU;rU;rG;rC;rG;rA;rA;rA;rU;rU;rU;rU;rU;rC (SEQ ID No. 87180) | 44 | | |
| Q-028 | rG;rA;rA;rG;rA;rA;rA;rA;rU;rU;rC;rG;rU;rC;rC;rA;rA2p;rA2p;dT$ (SEQ ID No. 87185) | rU;rU;rU;rG;rC;rG;rA;rA;rA;rU;rU;rU;rU;rU;rC;rU2p;rC2p;dT$ (SEQ ID No. 87186) | 6 | | 16 |
| Q-029 | rG2p;rA2p;rA2p;rG;rA;rA;rA;rA;rU;rU;rC;rG;rU;rC;rC;rA;rA;rA;dT$ (SEQ ID No. 87185) | rU;rU;rU;rG;rC;rG;rA;rA;rA;rU;rU;rU;rU;rU;rC;rU2p;rC2p;dT$ (SEQ ID No. 87186) | 3 | | 6 |
| Q-030 | rG2p;rA2p;rA2p;rG;rA;rA;rA;rA;rU;rU;rC;rG;rU;rC;rC;rA;rA2p;rA2p;rA2p;dT$ (SEQ ID No. 87185) | rU;rU;rU;rG;rC;rG;rA;rA;rA;rU;rU;rU;rU;rU;rC;rU2p;rC2p;dT$ (SEQ ID No. 87186) | 9 | | 3 |
| Q-031 | rG;rA;rA;rG;rA;rA;rA;rA;rU;rU;rC;rG;rU;rC;rC;rA;rA;rA;dT (SEQ ID No. 87185)$ | rU;rU;rU;rG;rC;rG;rA;rA;rA;rU;rU;rU;rU;rU;rC;rU2p;rC2p;dT$ (SEQ ID No. 87186) | 20 | | |
| Q-032 | rG;rA;rA;rG;rA;rA;rA;rA;rU;rU;rC;rG;rU;rC;rC;rA;rA2p;rA2p;dT$ (SEQ ID No. 87185) | rU2p;rU2p;rU2p;rG;rC;rG;rA;rA;rA;rU;rU;rU;rU;rU;rC;rU;rU;rC;dT$ (SEQ ID No. 87186) | 100 | | |
| Q-033 | rG2p;rA2p;rA2p;rG;rA;rA;rA;rA;rU;rU;rC;rG;rU;rC;rC;rA;rA;rA;dT$ (SEQ ID No. 87185) | rU2p;rU2p;rU2p;rG;rC;rG;rA;rA;rA;rU;rU;rU;rU;rU;rC;rU;rU;rC;dT$ (SEQ ID No. 87186) | 100 | | |
| Q-034 | rG2p;rA2p;rA2p;rG;rA;rA;rA;rA;rU;rU;rC;rG;rU;rC;rC;rA;rA2p;rA2p;dT$ (SEQ ID No. 87185) | rU2p;rU2p;rU2p;rG;rC;rG;rA;rA;rA;rU;rU;rU;rU;rU;rC;rU;rU;rC;dT$ (SEQ ID No. 87186) | 100 | | |
| Q-035 | rG;rA;rA;rG;rA;rA;rA;rA;rU;rU;rC;rG;rU;rC;rC;rA;rA;rA;dT$ (SEQ ID No. 87185) | rU2p;rU2p;rU2p;rG;rC;rG;rA;rA;rA;rU;rU;rU;rU;rU;rC;rU;rU;rC;dT$ (SEQ ID No. 87186) | 54 | | |
| Q-036 | rG;rA;rA;rG;rA;rA;rA;rA;rU;rU;rC;rG;rU;rC;rC;rA;rA2p;rA2p;dT$ (SEQ ID No. 87185) | rU2p;rU2p;rU2p;rG;rC;rG;rA;rA;rA;rU;rU;rU;rU;rU;rC;rU2p;rC2p;dT$ (SEQ ID No. 87186) | 100 | | |

FIG. 23 Continued

| ID | Sense | AntiSense | Activity at 20nM (% of control) | IC50 (nM) | Stability in human serum |
|---|---|---|---|---|---|
| Q-037 | rG;rA;rA;rG;rA;rA;rU;rU;rG;rC;rC;rG;rC;rA;rA2p;rA2p; dT$ (SEQ ID No. 87185) | mU;rU;mU;rU;mG;rG;mC;rC;mG;rG;mA;rA;mA;rU;mU;rU;mU;rU;mC; dT$ (SEQ ID No. 87186) | 10 | 0.41 | 8 |
| Q-038 | rG2p;rU2p;rA2p;rG;rA;rA;rU;rU;rG;rC;rC;rG;rC;rA;rA;rA; dT$ (SEQ ID No. 87185) | rU2p;rU2p;rU2p;rU;rU;rG;rG;rC;rC;rG;rG;rA;rA;rU;rU2p;rU2p;rC 2p;dT$ (SEQ ID No. 87186) | 70 | | |
| Q-039 | rG2p;rA2p;rA2p;rG;rA;rA;rU;rU;rG;rC;rC;rG;rC;rA;rA;rA; dT$ (SEQ ID No. 87185) | mU;mU;mU;rU;mU;rG;rG;mC;mG;rG;mA;rA;mA;rU;mU;rU;mU;mC$ (SEQ ID No. 87180) | 2 | | 8-10 |
| Q-040 | rG2p;rA2p;rA2p;rG;rA;rA;rA;rU;rU;rG;rC;rC;rG;rC;rA;rA2 p;rA2p;dT$ (SEQ ID No. 87185) | rU2p;rU2p;rU2p;rU;rU;rG;rG;rC;rG;rG;rA;rA;rA;rU;rU2p;rU2p;rC 2p;dT$ (SEQ ID No. 87186) | 100 | | |
| Q-041 | rG;rA;rG;rA;rA;rA;rU;rU;rG;rC;rC;rG;rC;rA;rA;rA;dT$ (SEQ ID No. 87185) | rU2p;rU2p;rU2p;rU;rG;rC;rG;rG;rA;rA;rA;rU;rU;rU2p;rU2p;rC 2p;dT$ (SEQ ID No. 87186) | 100 | | |
| Q-042 | rG2p;rA2p;rG;rA;rA;rA;rU;rU;rC;rC;rG;rC;rA;rA2p;rA2p;rA2 p;A2p;dT$ (SEQ ID No. 87185) | mU;rU;mU;rU;mG;rC;mG;rG;mA;rA;mA;rU;mU;rU;mU;rU;mC$ (SEQ ID No. 87180) | 15 | | 10-24 |
| Q-043 | rG;mA;rA;mG;rA;mA;rU;mU;rC;mC;rC;mG;rC;mA;rA;mA;r A;rA;dT$ (SEQ ID No. 87185) | mU;rU;mU;rU;mU;rG;mG;rC;mG;rG;mA;rA;mA;rU;mU;rU;mU;rU;mC$ (SEQ ID No. 87180) | 1 | | |
| Q-044 | rG;mG;rA;mA;rG;mA;rA;mA;rU;mU;rC;mC;rC;mG;rC;mG;r C;mA;rA;mA;rA (SEQ ID No. 87181) | mU;rG;mU;rU;mG;rG;mC;rC;mG;rG;mA;rA;mA;rU;mU;rU;mU;rU;mC;r U;mU;rC;mC (SEQ ID No. 87182) | 7 | 0.29 | 24 |
| Q-045 | rG;mG;rA;mA;rG;mA;rA;mA;rU;mU;rC;mC;rC;mG;rC;mG;r C;mA;rA;mA;rA (SEQ ID No. 87181) | mU;rU;mU;rU;mU;rG;mC;rG;mG;rA;mA;rA;mU;rU;mU;rU;mU;rU;mU;r C;mU;rU;mC (SEQ ID No. 87182) | 100 | | |
| Q-046 | rG;mA;rA;mG;rA;mA;rA;mU;rU;mC;rC;mG;rC;mA;rA;mC;r A;mA;rA;mA;rA (SEQ ID No. 87183) | mU;rU;mU;rU;mU;rG;mC;rG;mG;rA;mA;rA;mU;rU;mU;rU;mU;rU;mU;r U;mU;rC;mC (SEQ ID No. 87184) | 5 | | |
| Q-047 | rG;mA;rA;mG;rA;mA;rA;mU;rU;mC;rC;mG;rC;mA;rA;mC;r A;mA;rA;mA;rA (SEQ ID No. 87183) | mU;rU;mU;rU;mU;rU;mU;rG;mC;rG;mG;rA;mA;rA;mU;rU;mU;rU;mU;r C;mU;rU;mC (SEQ ID No. 87184) | 5 | 0.386 | 24 |
| Q-048 | rG;rA;rG;rA;rA;rA;rU;rU;rC;rC;rG;rC;rA;inaA;inaA;inaA; T$ (SEQ ID No. 87185) | rU;rU;rU;rU;rU;rG;rC;rG;rA;rA;rA;rU;rU;rU;rC;inaT;inaC;dT$ (SEQ ID No. 87186) | 69 | | |
| Q-049 | inaG;inaA;inaA;rG;rA;rA;rA;rU;rU;rC;rC;rG;rC;rA;rA;rA;rA;d T$ (SEQ ID No. 87185) | rU;rU;rU;rU;rU;rG;rC;rG;rA;rA;rA;rU;rU;rU;rC;inaT;inaC;dT$ (SEQ ID No. 87186) | 66 | | |
| Q-050 | inaG;inaA;inaA;rG;rA;rA;rA;rU;rU;rC;rC;rG;rC;rA;inaA; inaA;dT$ (SEQ ID No. 87179) | rU;rU;rU;rU;rU;rG;rC;rG;rA;rA;rA;rU;rU;rU;rC;inaT;inaC;dT$ (SEQ ID No. 87186) | 51 | | |
| Q-051 | rG;mA;rA;mG;rA;mA;rA;mA;rU;mU;rC;mC;rG;mG;rC;mA;rA;mA;r A$ (SEQ ID No. 87179) | rU;rU;rU;rU;rU;rG;rC;rG;rA;rA;rA;rU;rU;rU;rC;inaT;inaC;dT$ (SEQ ID No. 87186) | 51 | | |
| Q-052 | rG;rA;rG;rA;rA;rA;rU;rU;rC;rC;rG;rC;rA;inaA;inaA;inaA; T$ (SEQ ID No. 87185) | inaT;inaT;inaT;rU;rG;rC;rG;rA;rA;rA;rU;rU;rU;rU;rC;rU;rC;dT$ (SEQ ID No. 87186) | 68 | | |
| Q-053 | inaG;inaA;inaA;rG;rA;rA;rA;rU;rU;rC;rC;rG;rC;rA;rA;rA;rA;d T$ (SEQ ID No. 87185) | inaT;inaT;inaT;rU;rG;rC;rG;rA;rA;rA;rU;rU;rU;rU;rC;rU;rC;dT$ (SEQ ID No. 87186) | 80 | | |
| Q-054 | inaG;inaA;inaA;rG;rA;rA;rA;rU;rU;rC;rC;rG;rC;rA;inaA;inaA; inaA;dT$ (SEQ ID No. 87185) | inaT;inaT;inaT;rU;rG;rC;rG;rA;rA;rA;rU;rU;rU;rU;rC;rU;rC;dT$ (SEQ ID No. 87186) | 69 | | |

FIG. 23 Continued

| ID | Sense | AntiSense | Activity at 20nM (% of control) | IC50 (nM) | Stability in human serum |
|---|---|---|---|---|---|
| Q-055 | rG;mA;rA;mG;rA;mA;rA;mA;rU;mU;rC;mC;rG;mC;mA;rA;mA;rA$ (SEQ ID No. 87179) | lnaT;lnaT;lnaT;rU;rG;rC;rG;rA;rA;rA;rU;rU;rU;rC;rU;rU;rC;dT$ (SEQ ID No. 87186) | 64 | | |
| Q-056 | rG;rA;rA;rG;rA;rA;rA;rA;rU;rU;rC;rC;rG;rC;rA;lnaA;lnaA;lnaA;dT$ (SEQ ID No. 87185) | lnaT;lnaT;lnaT;rU;rG;rC;rG;rA;rA;rA;rU;rU;rU;rC;lnaT;lnaT;lnaC;dT$ (SEQ ID No. 87186) | 56 | | |
| Q-057 | rG;rA;rA;rG;rA;rA;rA;rA;rU;rU;rC;rC;rG;rC;rA;lnaA;lnaA;lnaA;dT$ (SEQ ID No. 87185) | mU;rU;mU;rU;mG;rC;mG;rA;mA;rA;mA;rU;mU;rU;mU;rC;mU;rU;mC$ (SEQ ID No. 87180) | 4 | 0.23 | 0 |
| Q-058 | lnaG;lnaA;lnaA;rG;rA;rA;rA;rA;rU;rU;rC;rC;rG;rC;rA;rA;rA;rA;dT$ (SEQ ID No. 87186) | lnaT;lnaT;lnaT;rU;rG;rC;rG;rA;rA;rA;rU;rU;rU;rC;lnaT;lnaT;lnaC;dT$ (SEQ ID No. 87186) | 62 | | |
| Q-059 | lnaG;lnaA;lnaA;rG;rA;rA;rA;rA;rU;rU;rC;rC;rG;rC;rA;rA;rA;rA;dT$ (SEQ ID No. 87186) | mU;rU;mU;rU;mG;rC;mG;rA;mA;rA;mA;rU;mU;rU;mU;rC;mU;rU;mC$ (SEQ ID No. 87180) | 9,4 | 0.18 | 0 |
| Q-060 | lnaG;lnaA;lnaA;rG;rA;rA;rA;rA;rU;rU;rC;rC;rG;rC;rA;lnaA;lnaA;lnaA;dT$ (SEQ ID No. 87185) | lnaT;lnaT;lnaT;rU;rG;rC;rG;rA;rA;rA;rU;rU;rU;rC;lnaT;lnaT;lnaC;dT$ (SEQ ID No. 87186) | 51 | | |
| Q-061 | rG;mA;rA;mG;rA;mA;rA;mA;rU;mU;rC;mC;rG;mC;rA;mA;rA;mA;rA$ (SEQ ID No. 87179) | lnaT;lnaT;lnaT;rU;rG;rC;rG;rA;rA;rA;rU;rU;rU;rC;lnaT;lnaT;lnaC;dT$ (SEQ ID No. 87186) | 55 | | |
| Q-062 | lnaG;lnaA;lnaA;rG;rA;rA;rA;rA;rU;rU;rC;rC;rG;rC;rA;lnaA;lnaA;lnaA;dT$ (SEQ ID No. 87185) | mU;rU;mU;rU;mG;rC;mG;rA;mA;rA;mA;rU;mU;rU;mU;rC;mU;rU;mC$ (SEQ ID No. 87180) | 2 | 0.22 | 0 |
| Q-063 | LdG;LdA;rA;rG;rA;rA;rA;rA;rU;rU;rC;rC;rG;rC;rA;rA;LdA;LdA;dT$ (SEQ ID No. 87185) | rU;rU;rU;rU;rG;rC;rG;rA;rA;rA;rU;rU;rU;rC;rU;rU;LdC;dT$ (SEQ ID No. 87186) | 14,5 | 0.091 | 10 |
| Q-064 | LdG;LdA;rA;rG;rA;rA;rA;rA;rU;rU;rC;rC;rG;rC;rA;rA;LdA;LdA;dT$ (SEQ ID No. 87185) | rU;rU;rU;rU;rG;rC;rG;rA;rA;rA;rU;rU;rU;rC;rU;rU;LdC;dT$ (SEQ ID No. 87186) | 10 | | 1 |
| Q-065 | LdG;LdA;rA;rG;rA;rA;rA;rA;rU;rU;rC;rC;rG;rC;rA;rA;LdA;LdA;dT$ (SEQ ID No. 87185) | rU;rU;rU;rU;rG;rC;rG;rA;rA;rA;rU;rU;rU;rC;rU;rU;LdC;dT$ (SEQ ID No. 87186) | 16 | | 0 |
| Q-066 | rG;rA;rA;rG;rA;rA;rA;rA;rU;rU;rC;rC;rG;rC;rA;rA;rA;rA;dT$ (SEQ ID No. 87186) | rU;rU;rU;rU;rG;rC;rG;rA;rA;rA;rU;rU;rU;rC;rU;rU;LdC;dT$ (SEQ ID No. 87186) | 54 | | |
| Q-067 | rG;rA;rA;rG;rA;rA;rA;rA;rU;rU;rC;rC;rG;rC;rA;rA;LdA;LdA;dT$ (SEQ ID No. 87185) | LdT;rU;rU;rU;rG;rC;rG;rA;rA;rA;rU;rU;rU;rC;rU;rU;rC;dT$ (SEQ ID No. 87186) | 24 | | |
| Q-068 | LdG;LdA;rA;rG;rA;rA;rA;rA;rU;rU;rC;rC;rG;rC;rA;rA;rA;rA;dT$ (SEQ ID No. 87186) | LdT;rU;rU;rU;rG;rC;rG;rA;rA;rA;rU;rU;rU;rC;rU;rU;rC;dT$ (SEQ ID No. 87186) | 30 | | |
| Q-069 | LdG;LdA;rA;rG;rA;rA;rA;rA;rU;rU;rC;rC;rG;rC;rA;rA;LdA;LdA;dT$ (SEQ ID No. 87185) | LdT;rU;rU;rU;rG;rC;rG;rA;rA;rA;rU;rU;rU;rC;rU;rU;rC;dT$ (SEQ ID No. 87186) | 47 | | |
| Q-070 | rG;rA;rA;rG;rA;rA;rA;rA;rU;rU;rC;rC;rG;rC;rA;rA;rA;rA;dT$ (SEQ ID No. 87186) | LdT;rU;rU;rU;rG;rC;rG;rA;rA;rA;rU;rU;rU;rC;rU;rU;rC;dT$ (SEQ ID No. 87186) | 32 | | |
| Q-071 | rG;rA;rA;rG;rA;rA;rA;rA;rU;rU;rC;rC;rG;rC;rA;rA;LdA;LdA;dT$ (SEQ ID No. 87185) | LdT;rU;rU;rU;rG;rC;rG;rA;rA;rA;rU;rU;rU;rC;rU;rU;LdC;dT$ | 67 | | |
| Q-072 | rG;rA;rA;rG;rA;rA;rA;rA;rU;rU;rC;rC;rG;rC;rA;rA;LdA;LdA;dT$ (SEQ ID No. 87185) | rU;rU;rU;rU;rG;rC;rG;rA;rA;rA;rU;rU;rU;rC;rU;rU;rC;dT$ (SEQ ID No. 87186) | 7,1 | | 3 |

FIG. 23 Continued

| ID | Sense | AntiSense | Activity at 20nM (% of control) | IC50 (nM) | Stability in human serum |
|---|---|---|---|---|---|
| Q-073 | LdG;LdA;rA;rG;rA;rA;rU;rU;rC;rG;rG;rC;rA;rA;rA;rA;dT$ (SEQ ID No. 87185) | LdT;rU;rU;rU;rG;rC;rG;rA;rA;rU;rU;rC;rU;rU;rC;rU;rU;LdC;dT$ (SEQ ID No. 87186) | 66 | | |
| Q-074 | LdG;LdA;rA;rG;rA;rA;rA;rU;rU;rC;rG;rG;rC;rA;rA;rA;rA;dT$ (SEQ ID No. 87185) | rU;rU;rU;rU;rG;rC;rG;rA;rA;rU;rU;rC;rU;rU;rC;rU;rU;rC;dT$ (SEQ ID No. 87186) | 6 | | 0 |
| Q-075 | LdG;LdA;rA;rG;rA;rA;rU;rU;rC;rG;rG;rC;rA;rA;LdA;LdA;dT$ (SEQ ID No. 87185) | LdT;rU;rU;rU;rG;rC;rG;rA;rA;rU;rU;rC;rU;rU;rC;rU;rU;LdC;dT$ (SEQ ID No. 87186) | 77 | | |
| Q-076 | rG;rA;rA;rG;rC;rA;rA;rU;rU;rC;rG;rG;rC;rG;rC;rA;rA;rA;rA;dT$ (SEQ ID No. 87185) | LdT;rU;rU;rU;rG;rC;rG;rA;rA;rU;rU;rC;rU;rU;LdC;dT$ (SEQ ID No. 87186) | 63 | | |
| Q-077 | LdG;LdA;rA;rG;rA;rA;rU;rU;rC;rG;rG;rC;rA;rA;LdA;LdA;dT$ (SEQ ID No. 87185) | rU;rU;rU;rU;rG;rC;rG;rA;rA;rU;rU;rC;rU;rU;rC;rU;rU;rC;dT$ (SEQ ID No. 87186) | 11 | | 0 |
| Q-078 | mG;mA;mA;mG;mA;rG;rA;rA;rA;rU;rU;rC;rG;rC;rA;rA;rA;rA (SEQ ID No. 87183) | rU;mU;rU;rU;rG;rC;rG;rA;rA;rU;rU;rC;rU;rU;rC;rU;rU;rC (SEQ ID No. 87184) | 5 | | 0 |
| Q-079 | mG;mA;mA;mG;mA;rG;rA;rA;rA;rU;rU;rC;rG;rC;rA;rA;rA;rA (SEQ ID No. 87183) | rU;rU;rU;rU;rG;rC;rG;rA;rA;rU;rU;rC;rU;rU;rC;rU;mU;mC;mU;m U;mC (SEQ ID No. 87184) | 7 | | |
| Q-080 | mG;mA;mA;mG;mA;rG;rA;rA;rA;rU;rU;rC;rG;rC;rA;rA;rA;rA (SEQ ID No. 87183) | mU;mU;rU;rU;rG;rC;rG;rA;rA;rU;rU;rC;rU;rU;rC;rU;rU;rC;rU;r C (SEQ ID No. 87184) | 4 | | |
| Q-081 | mG;mA;mA;mG;mA;mA;mG;mA;mA;rA;rU;rA;rU;rC;rG;rC;rA;rC;rG;rC;rA;rA;rA;rA (SEQ ID No. 87183) | rU;rU;rU;rU;rG;rC;rG;rA;rA;rU;rU;rC;rU;rU;rC;rU;rU;rC;mU;m U;mC (SEQ ID No. 87184) | 5 | | 0 |
| Q-082 | mG;mA;mA;mG;mA;mA;mG;mA;mA;mA;mU;mU;rC;rG;rC;rG;rC;rA;rA;rA;rA;rA (SEQ ID No. 87183) | rU;rU;rU;rU;rG;rC;rG;rA;rA;rU;rU;rC;rU;rU;rC;rU;rU;rC;mU;m U;mC (SEQ ID No. 87184) | 11 | | |
| Q-083 | rG;rA;rA;rG;rA;rG;rA;rA;rA;mA;mA;mU;rU;rC;rG;rC;rG;rC;rA;rA;r A;rA;rA (SEQ ID No. 87183) | rU;rU;rU;rU;rG;rC;rG;rA;rA;rU;rU;rC;rU;rU;rC;rU;rU;rC;mU;m U;mC (SEQ ID No. 87184) | 24 | | |
| Q-084 | rG;rA;rA;rG;rA;rA;rA;rA;rU;rA;rU;rC;rG;rC;rG;rC;rA;rA;rA2p;rA2p (SEQ ID No. 87183) | rU;rU;rU;rU;rG;rC;rG;rA;rA;rU;rU;rC;rU;rU;rC;rU;rU;rC;rU2p;rU2 p;rC2p (SEQ ID No. 87184) | 14 | | 0 |
| Q-085 | rG2p;rA2p;rA2p;rA2p;rG;rA;rA;rA;rU;rU;rC;rG;rC;rG;rC;rA;rA;rA;rA (SEQ ID No. 87183) | rU;rU;rU;rU;rG;rC;rG;rA;rA;rU;rU;rC;rU;rU;rC;rU2p;rU2p;rC2 p;rC2p (SEQ ID No. 87184) | 1 | | |
| Q-086 | rG2p;rA2p;rA2p;rA2p;rG;rA;rA;rA;rU;rU;rC;rG;rC;rG;rC;rA;rA;rA;rA (SEQ ID No. 87183) | rU;rU;rU;rU;rG;rC;rG;rA;rA;rU;rU;rC;rU;rU;rC;rU;rU;rC;rU2p;rU 2p;rC2p (SEQ ID No. 87184) | 7 | | |
| Q-087 | rC;mC;rU;mU;rG;mC;rA;mC;rU;mC;rC;mU;mG;mA;rA;mU;rU;mU (SEQ ID No. 87185) | mU;rG;mA;rU;mA;rA;mA;rA;mA;rA;mU;rU;mC;rA;mG;rG;mA;rG;mA;rG;mC;mC;rU (SEQ ID No. 87184) | 16 | | |
| Q-088 | rC;mU;rU;mU;rG;rC;mA;rC;mU;rC;mC;rU;mG;rA;mA;rU;mU;rU (SEQ ID No. 87185) | mU;rU;mG;rA;mU;rA;mA;rA;mA;rA;mU;rU;mC;rA;mG;rG;mA;rG;mC;mC (SEQ ID No. 87184) | 23 | | |
| Q-089 | rU;mU;rU;mG;mC;mA;rC;mU;rC;mC;rU;rG;mA;rA;rU;rU;rU;rA;mU (SEQ ID No. 87185) | mU;rU;mU;rG;mA;rU;mA;rA;rA;mA;rA;mU;rU;mC;rA;mG;rG;mA;rG;mA;rG;mU;r G;mC;rA;mA (SEQ ID No. 87184) | 7 | | |
| Q-090 | rU;mG;rC;mA;rC;mU;rC;mC;rU;mG;rA;mA;rU;rU;rU;rA;rA;rU;mU;rA;mU (SEQ ID No. 87185) | mG;rU;mU;rU;mG;rA;mU;rA;rA;mA;rA;mA;rU;rU;mC;mA;rG;rG;mA;rG;rC;mA;mU (SEQ ID No. 87184) | 30 | | |

FIG. 23 Continued

| ID | Sense | AntiSense | Activity at 20nM (% of control) | IC50 (nM) | Stability in human serum |
|---|---|---|---|---|---|
| Q-091 | rG;mC;rA;mC;rU;mC;rC;mU;rG;mA;rA;mU;rU;mA;rU;mC; rA;mA;rA;mC;rA (SEQ ID No. 275) | mU;rG;mU;rU;mU;rG;mA;rU;mA;rA;mA;rA;mU;mC;rA;mG;rG;mA;r G;mU;rG;mC (SEQ ID No. 276) | 10 | | |
| Q-092 | rC2p;rC2p;rU;rG;rC;rU;rC;rC;rU;rU;rU;rU;rU;rU;rU;rU; rA;rU;rC;rA (SEQ ID No. 267) | mU;rG;mA;rU;mA;rA;mU;mC;rA;mG;rG;mA;rG;mU;rG;mC;r A;mA;rG;mG (SEQ ID No. 268) | 43 | | |
| Q-093 | rC2p;rU2p;rU2p;rG;rC;rA;rC;rU;rC;rC;rU;rU;rU;rU;rA; rU;rC;rA;rA (SEQ ID No. 269) | mU;rU;mG;rA;mA;rA;mA;mU;rC;mA;rG;mG;rA;mG;rU;mG;r C;mA;rA;mG (SEQ ID No. 270) | 52 | | |
| Q-094 | rU2p;rU2p;rG2p;rC;rA;rC;rU;rC;rC;rU;rU;rU;rU;rA;rU; rC;rA;rA;rA (SEQ ID No. 271) | mU;rU;mU;rG;mA;rU;mA;rA;rA;rA;rA;mU;rC;rA;mG;rA;rG;mU;r G;mC;rA;mA (SEQ ID No. 272) | 13 | | 0 |
| Q-095 | rU2p;rG2p;rC;rA;rC;rU;rC;rC;rU;rG;rA;rA;rA;rU;rU;rC; rA;rA;rC (SEQ ID No. 273) | mG;rU;mU;rG;rA;mU;rA;mA;rA;rA;mA;rU;mU;rC;mA;rG;rA;mG;r U;mG;rC;mA (SEQ ID No. 274) | 27 | | |
| Q-096 | rG2p;rC2p;rA2p;rC;rU;rC;rC;rU;rG;rA;rU;rA;rA;rU;rU; rA;rA;rC;rA (SEQ ID No. 275) | mU;rU;mU;rU;mA;rU;mA;rU;mA;rA;rU;mC;rA;mG;rG;mA;r G;mU;rG;mC (SEQ ID No. 276) | 4 | | |
| Q-097 | mC;mC;mU;mG;rC;rA;rC;rU;rC;rC;rU;rG;rA;rU;rA;rA; rU;rU;rA;rA (SEQ ID No. 267) | mU;rU;mG;rA;mU;mA;rA;rU;rU;mC;rA;mG;rG;mA;rG;mU;rG;r A;mA;rA;mG (SEQ ID No. 268) | 31 | | |
| Q-098 | mC;mU;mU;mG;mC;mA;rC;rU;rC;rC;rU;rG;rA;rU;rA;rU; rC;rA;rA (SEQ ID No. 269) | mU;rU;mG;rA;mA;rA;mA;mU;rC;mA;rG;mG;rA;rG;rU;mG;r C;mA;rA;mG (SEQ ID No. 270) | 25 | | |
| Q-099 | mU;rU;mU;mG;mC;mA;rC;rU;rC;rC;rU;rA;rA;rU;rA;rU; C;rA;rA;rU (SEQ ID No. 271) | mU;rU;mU;rG;mA;rU;mA;rA;rU;rU;mC;rA;mU;rU;rC;mA;rG;mU;r G;mC;rA;mA (SEQ ID No. 272) | 9 | | |
| Q-100 | mU;rU;mU;mU;mC;mA;rC;rU;rC;rC;rU;rG;rA;rA;rU;rC;r A;rU;rA;rC (SEQ ID No. 273) | mG;rU;mU;rG;rA;mU;rG;rA;mA;rA;mA;rU;mU;rC;mA;rG;mU;r U;mG;rC;mA (SEQ ID No. 274) | 24 | | |
| Q-101 | mG;rC;mA;mC;mU;rC;rC;rU;rG;rA;rU;rA;rA;rU;rU;rA;rC;rA (SEQ ID No. 275) | mU;rG;mU;rU;mU;rG;mA;rU;mA;rA;mA;rA;rA;mA;rU;mC;rA;mG;rG;mA;r G;mU;rG;mC (SEQ ID No. 276) | 17 | | |
| Q-102 | mC;mC;mU;mU;mG;rC;rA;rC;rU;rC;rC;rU;rG;rA;rU;rA; A;rU;rC;rA (SEQ ID No. 267) | rU;mG;rA;rU;rG;rA;rA;rA;rA;rU;rA;rA;rU;rU;rC;rA;rG;rG;rA;rG;rU;rG;r G (SEQ ID No. 268) | 22 | | |
| Q-103 | mC;mU;mU;mG;mC;rA;rC;rU;rC;rC;rU;rG;rA;rU;rA;rA;r U;rC;rA;rA (SEQ ID No. 269) | rU;mU;rG;rA;rU;rA;rA;rA;rA;rU;rA;rU;rC;rA;rG;rC;rA;rG;rC;rA;rG (SEQ ID No. 270) | 20 | | |
| Q-104 | mU;mU;mG;mC;mA;rC;rU;rC;rC;rU;rG;rA;rU;rA;rA;rU; C;rA;rA;rA (SEQ ID No. 271) | rU;mU;rU;rG;rU;rU;rA;rA;rU;rU;rA;rU;rU;rC;rA;rG;rC;rA;rG;rC;rG;rU;rA (SEQ ID No. 272) | 10 | | |
| Q-105 | mU;mG;mC;mA;mC;rU;rC;rC;rU;rG;rA;rU;rA;rA;rU;rU; A;rA;rC;rA (SEQ ID No. 273) | rG;mU;rU;rU;rG;rU;rU;rA;rU;rA;rU;rC;rA;rG;rA;rG;rA;rG;rU;rG;rC; A (SEQ ID No. 274) | 15 | | |
| Q-106 | mG;mC;mA;mC;mU;mC;rC;rU;rG;rA;rU;rA;rA;rU;rA;rA;r A;rA;rC;rA (SEQ ID No. 275) | rU;mG;rU;rU;rU;rG;rU;rG;rA;rU;rU;rA;rA;rU;rU;rC;rA;rG;rC;rA;rG;rU;rG;r C (SEQ ID No. 276) | 19 | | |
| Q-107 | rC2p;rC2p;rU2p;rG;rC;rA;rC;rU;rC;rC;rU;rG;rA;rA;rU;rU; rA;rU;rC;rA (SEQ ID No. 267) | rU;rG;rA;rU;rA;rA;rU;rU;rC;rA;rG;rG;rA;rG;rU;rG;rC;rA2p;rG2 p;rG2p (SEQ ID No. 268) | 28 | | |
| Q-108 | rC2p;rU2p;rU2p;rG;rC;rA;rC;rU;rC;rC;rU;rG;rA;rU;rU; rU;rU;rA;rA (SEQ ID No. 269) | rU;rU;rG;rU;rU;rU;rA;rU;rC;rA;rG;rC;rG;rA;rG;rU;rG;rC;rA2p;rA2 p;rG2p (SEQ ID No. 270) | 47 | | |

FIG. 23 Continued

| ID | Sense | AntiSense | Activity at 20nM (% of control) | IC50 (nM) | Stability in human serum |
|---|---|---|---|---|---|
| Q-109 | rU2p;rU2p;rG2p;rC;rA;rC;rU;rC;rC;rU;rG;rA;rA;rA;rU;rU;rU;rU;rA;rU; rC;rA;rA;rA (SEQ ID No. 271) | rU;rU;rU;rG;rA;rU;rA;rU;rA;rA;rA;rU;rU;rC;rA;rG;rG;rA;rG;rC2p;rA2 p;rA2p (SEQ ID No. 272) | 9 | | |
| Q-110 | rU2p;rG2p;rC2p;rA;rC;rU;rC;rC;rU;rG;rA;rA;rA;rU;rU;rU;rU;rA;rU;rC; rA;rA;rA;rC (SEQ ID No. 273) | rG;rU;rU;rU;rG;rA;rU;rA;rU;rA;rA;rA;rU;rU;rC;rA;rG;rG;rA;rG;rU;rG2p;rC2 p;rA2p (SEQ ID No. 274) | 22 | | |
| Q-111 | rG2p;rC2p;rA2p;rC;rU;rC;rC;rU;rG;rA;rA;rA;rU;rU;rU;rU;rA;rU;rC;rA; rA;rA;rC;rA (SEQ ID No. 275) | rU;rG;rU;rU;rU;rG;rA;rU;rA;rU;rA;rA;rA;rU;rU;rC;rA;rG;rG;rA;rG;rU2p;rG2 p;rC2p (SEQ ID No. 276) | 20 | | |
| Q-112 | rG;rA;rG;rA;rA;rG;rA;rA;rA;rU;rU;rU;rC;rG;rC;rG;rA;rA;rU;rA2p ;rA2p;rA2p (SEQ ID No. 87183) | mU;rU;mU;rU;mU;rG;mG;rA;mA;rA;mU;rU;mC;rU;mU;r C;mU;rU;mC (SEQ ID No. 87184) | 21 | | |
| Q-113 | rG2p;rA2p;rA2p;rG;rA;rA;rG;rA;rA;rA;rU;rU;rU;rC;rC;rG;rC;rA; rA;rA;rA;rA (SEQ ID No. 87183) | mU;rU;mU;rU;mU;rG;mC;rG;mG;rA;mA;rA;mU;rU;mC;rU;mU;r C;mU;rU;mC (SEQ ID No. 87184) | 6 | 1.2 | 24 |
| Q-114 | rG2p;rA2p;rA2p;rG;rA;rA;rG;rA;rA;rA;rU;rU;rU;rC;rC;rG;rC;rA;rA; rA;rA2p;rA2p (SEQ ID No. 87183) | mU;rU;mU;rU;mU;rG;mC;rG;mG;rA;mA;rA;mU;rU;mC;rU;mU;r C;mU;rU;mC (SEQ ID No. 87184) | 1 | 4.556 | 24 |
| Q-115 | rG;rA;rA;rG;rA;rA;rA;rU;rU;rC;rC;rG;rC;rA;rA2p;rA2p;rA2p (SEQ ID No. 87179) | rU;rU;rU;rG;rC;rG;rA;rU;rU;rU;rC;rU;rU;rC;rU2p;rU2p;rC2p (SEQ ID No. 87180) | 56 | | 8 |
| Q-116 | rG2p;rA2p;rA2p;rG;rA;rA;rA;rU;rU;rC;rC;rG;rC;rA;rA;rA;rA (SEQ ID No. 87179) | rU;rU;rU;rG;rC;rG;rA;rU;rU;rU;rC;rU;rU;rC;rU2p;rU2p;rC2p (SEQ ID No. 87180) | 30 | | 0 |
| Q-117 | rU;rA;rC;rU;rG;rU;rU;rA;rA;rA;rA;rU;rA;rA;rU;rC;rA;rA2p;rA2p; dT$ (SEQ ID No. 87189) | rU;rU;rU;rU;rG;rU;rU;rU;rU;rA;rC;rA;rG;rU2p;rA2p;dT$ (SEQ ID No. 87190) | 41 | | |
| Q-118 | rU2p;rA2p;rC2p;rU;rG;rU;rU;rA;rA;rA;rA;rU;rA;rA;rU;rC;rA;rA;rA; dT$ (SEQ ID No. 87189) | rU;rU;rU;rU;rG;rU;rU;rU;rU;rA;rC;rA;rG;rU2p;rA2p;dT$ (SEQ ID No. 87190) | 75 | | |
| Q-119 | rU;rA;rC;rU;rG;rU;rU;rA;rA;rA;rA;rU;rA;rA;rU;rC;rA;rA2p;rA2p dT$ (SEQ ID No. 87191) | rU;rU;rU;rU;rA;rU;rU;rU;rU;rA;rC;rA;rG;rU2p;rA2p (SEQ ID No. 87192) | 36 | | 0 |
| Q-120 | rU2p;rA2p;rC2p;rU;rG;rU;rU;rA;rA;rA;rA;rU;rA;rA;rC;rA;rA;rA dT$ (SEQ ID No. 87191) | rU;rU;rU;rU;rA;rU;rU;rU;rU;rA;rC;rA;rG;rU2p;rA2p (SEQ ID No. 87192) | 77 | | 0 |
| Q-121 | rG;rC;rC;rA;rG;rA;rA;rU;rU;rG;rA;rA;rA;rU;rC2p;rC2p;rU2p; dT$ (SEQ ID No. 139) | rA;rG;rG;rA;rU;rU;rU;rC;rA;rA;rU;rU;rU;rU;rG;rG2p;rC2p;dT$ (SEQ ID No. 140) | 8 | | 0 |
| Q-122 | rG2p;rC2p;rC2p;rA;rG;rA;rA;rU;rU;rG;rA;rA;rA;rU;rC;rC;rU; dT$ (SEQ ID No. 139) | rA;rG;rG;rA;rU;rU;rU;rC;rA;rA;rU;rU;rU;rU;rG;rG2p;rC2p;dT$ (SEQ ID No. 140) | 8 | | |
| Q-123 | rG;rC;rC;rA;rG;rA;rA;rU;rU;rG;rA;rA;rA;rU;rC;rC;rU;rC2p;rU2p (SEQ ID No. 139) | rA;rG;rG;rA;rU;rU;rU;rC;rA;rA;rU;rU;rU;rU;rG;rG2p;rC2p (SEQ ID No. 140) | 10 | 0.932 | 24 |
| Q-124 | rG2p;rC2p;rC2p;rA;rG;rA;rA;rU;rU;rG;rA;rA;rA;rU;rC;rC;rU (SEQ ID No. 139) | rA;rG;rG;rA;rU;rU;rU;rC;rA;rA;rU;rU;rU;rU;rG;rG2p;rC2p (SEQ ID No. 140) | 16 | 1.7 | 10 |
| Q-125 | mG;mA;mA;mG;rA;rA;rA;rU;rU;rC;rG;rC;mA;mA;mA;mA;mA ;dT$ (SEQ ID No. 87185) | rU;rU;rU;rU;rG;rC;rG;rA;rA;rU;rU;rU;rC;rU2p;rU2p;rC2p;dT$ (SEQ ID No. 87186) | 3 | | |
| Q-126 | mG;mA;mA;mG;rA;rA;rA;rU;rU;rC;rC;rG;rA;rA;rA;rA;mA;mA (SEQ ID No. 87179) | rU;rU;rU;rU;rG;rC;rG;rA;rU;rU;rU;rC;rU;rU;rC;rU2p;rU2p;rC2p (SEQ ID No. 87180) | 26 | | |

FIG. 23 Continued

| ID | Sense | AntiSense | Activity at 20nM (% of control) | IC50 (aM) | Stability in human serum |
|---|---|---|---|---|---|
| Q-127 | rG;rA;rG;rA;rA;rA;rU;mU;rU;rC;rC;rA;rA2p;rA2p;rA2p;dT$ (SEQ ID No. 87185) | rU;mU;rU;rU;rG;rC;rG;rA;rG;rA;rA;rU;rU;rC;rU2p;rU2p;C2p;dT$ (SEQ ID No. 87186) | 58 | | |
| Q-128 | rG;rA;rG;rA;rG;rA;rA;rA;rU;mU;rU;rC;rC;rA;rA2p;rA2p;rA2p;dT$ (SEQ ID No. 87179) | rU;mU;rU;rU;rG;rC;rG;rA;rG;rA;rA;rU;rU;rC;rU2p;rU2p;rC2p (SEQ ID No. 87186) | 100 | | |
| Q-129 | rG2p;rA2p;rA2p;rG;rA;rA;rA;rU;mU;rU;rC;rC;rA;rA2p;rA2p;dT$ (SEQ ID No. 87185) | mU;mU;rU;rU;rG;rC;rG;rA;rG;rA;rA;rU;rU;rC;mU;mU;mC;dT$ (SEQ ID No. 87186) | 100 | | |
| Q-130 | rG2p;rA2p;rA2p;rG;rA;rA;rA;rU;mU;rU;rC;rC;rA;rA2p;rA2p;rA2p (SEQ ID No. 87179) | mU;mU;rU;rU;rG;rC;rG;rA;rG;rA;rA;rU;rU;rC;mU;mU;mC (SEQ ID No. 87180) | 75 | | |
| Q-131 | rG2p;rA2p;rA2p;rA;rA;rA;rA;rU;rU;rU;rC;rC;rC;rA;rA2p;rA2p;dT$ (SEQ ID No. 87185) | mU;mU;rU;rU;rG;rC;rG;rA;rG;rA;rA;rU;rU;rC;mU;mU;mC;dT$ (SEQ ID No. 87186) | 100 | | |
| Q-132 | rG2p;rA2p;rA2p;rG;rA;rA;rA;rU;rU;rU;rC;rC;rA;rA2p;rA2p;rA2p (SEQ ID No. 87179) | mU;mU;rU;rU;rG;rC;rG;rA;rG;rA;rA;rU;rU;rC;mU;mU;mC (SEQ ID No. 87180) | 70 | | |
| Q-133 | rG2p;rA2p;rA2p;rG;rA;rA;rA;rU;mU;rU;rC;rC;rA;rA2p;rA2p;dT$ (SEQ ID No. 87185) | rU;rU;rU;rU;rG;rC;rG;rA;rA;rU;rU;rC;mU;mU;mC;dT$ (SEQ ID No. 87186) | 38 | | |
| Q-134 | rG2p;rA2p;rA2p;rG;rA;rA;rA;rU;mU;rU;rC;rC;rA;rA2p;rA2p;rA2p (SEQ ID No. 87179) | rU;rU;rU;rU;rG;rC;rG;rA;rG;rA;rA;rU;rU;rC;mU;mU;mC (SEQ ID No. 87180) | 29 | | |
| Q-135 | rG;rA;rA;rG;rA;rA;rA;rU;mU;rU;rC;rC;rA;rA2p;rA2p;rA2p;dT$ (SEQ ID No. 87185) | rU;rU;rU;rU;rG;rC;rG;rA;rG;rA;rA;rU;rU;rC;mU;mU;mC;dT$ (SEQ ID No. 87186) | 27 | | |
| Q-136 | rG;rA;rA;rG;rA;rA;rA;rU;mU;rU;rC;rC;rA;rA2p;rA2p;rA2p (SEQ ID No. 87179) | rU;rU;rU;rU;rG;rC;rG;rA;rG;rA;rA;rU;rU;rC;mU;mU;mC (SEQ ID No. 87180) | 15 | | |
| Q-137 | rG;rA;rA;rG;rA;rA;rA;rU;rU;rU;rC;rC;rG;rA;rA2p;rA2p;dT$ (SEQ ID No. 87185) | mU;rU;mU;rU;mG;rC;mG;rA;mA;rA;mA;rU;mU;rU;mC;mU;dT$ (SEQ ID No. 87186) | 6 | | |
| Q-138 | rG;rA;rA;rG;rA;rA;rA;rU;rU;rU;rC;rC;rG;rA;rA2p;rA2p (SEQ ID No. 87179) | mU;rU;mU;rU;mG;rC;mG;rA;mA;rA;mA;rU;mU;rU;mC;mU;mC (SEQ ID No. 87180) | 6 | 0.408 | 24 |
| Q-139 | rG2p;rA2p;rA;rG;rA;rA;rA;rU;rU;rU;rC;rC;rG;rA;rA;rA (SEQ ID No. 87179) | mU;rU;mU;rU;mG;rC;mG;rA;mA;rA;mA;rU;mU;rU;mC;mU;mC (SEQ ID No. 87180) | 6 | | |
| Q-140 | rG2p;rA2p;rA2p;rA;rA;rA;rU;rU;rU;rC;rC;rG;rA;rA;rA (SEQ ID No. 87179) | mU;rU;mU;rU;mG;rC;mG;rA;mA;rA;mA;rU;mU;rU;mC;mU;mC; (SEQ ID No. 87180) | 3 | | |
| Q-141 | rG;rA;rA;rG;rA;rA;rA;rU;rU;rU;rC;rC;rG;rA;mA;mA;mA;dT$ (SEQ ID No. 87185) | mU;rU;mU;rU;mG;rC;mG;rA;mA;rA;mA;rU;mU;rU;mC;mU;dT$ (SEQ ID No. 87186) | 1 | | 10 |
| Q-142 | rG;rA;rA;rG;rA;rA;rA;rU;rU;rU;rC;rG;rG;rA;rA;mA;mA (SEQ ID No. 87179) | mU;rU;mU;rU;mG;rC;mG;rA;mA;rA;mA;rU;mU;rU;mC;mU;mC (SEQ ID No. 87180) | 1 | | |
| Q-143 | mG;mA;mA;mG;rA;rA;rA;rU;rU;rU;rC;rC;rG;rA;rA;rA;dT$ (SEQ ID No. 87185) | mU;rU;mU;rU;mG;rC;mG;rA;mA;rA;mA;rU;mU;rU;mC;mU;mC; (SEQ ID No. 87186) | 4 | | 10 |
| Q-144 | mG;mA;mA;mG;rA;rA;rA;rU;rU;rU;rC;rC;rG;rA;rA;rA (SEQ ID No. 87179) | mU;rU;mU;rU;mG;rC;mG;rA;mA;rA;mA;rU;mU;rU;mC;mU;mC (SEQ ID No. 87180) | 4 | | 24 |

FIG. 23 Continued

| ID | Sense | AntiSense | Activity at 20nM (% of control) | IC50 (nM) | Stability in ham-serum |
|---|---|---|---|---|---|
| Q-145 | rG;rA;rG;rA;rA;rA;rA;rU;rU;rC;rC;rG;rC;rA;rA;rA;rA;dT$ (SEQ ID No. 87185) | p;rU;rU;mU;rU;mG;rC;mG;mA;rA;mA;rU;mU;rU;mU;rC;mU;rU;m C$ (SEQ ID No. 87180) | 12 | | 24 |
| Q-146 | mG;mA;mA;mG;mA;mA;mA;mA;mU;mU;mC;mC;rG;rC;rA;rA;rA;rA;dT$ (SEQ ID No. 87185) | p;rU;rU;rU;rU;rG;rC;rG;rA;rA;rU;rU;rU;rU;mC;mU;mC;dT$ (SEQ ID No. 87186) | 41 | | |
| Q-147 | rG;rA;rG;rA;rA;rA;rA;rU;rU;rC;rC;rG;rC;rA;rA2p;rA2p;rA2p; dT$ (SEQ ID No. 87185) | p;rU;rU;rU;rU;rG;rC;rG;rA;rA;rU;rU;rU;rU;rC;rU2p;rC2p;dT $ (SEQ ID No. 87186) | 29 | | |
| Q-148 | rG;rA;rA;rG;rA;rA;rA;rU;rU;rC;rG;rC;rA;rA2p;rA2p;rA2p; dT$ (SEQ ID No. 87185) | rU2p;rU2p;rU;rG;rC;rG;rA;rA;rU;rU;rU;rU;rC;rU;rC;dT$ (SEQ ID No. 87186) | 88 | | |
| Q-149 | rG2p;rA2p;rA2p;rA;rA;rA;rU;rU;rC;rC;rG;rC;rA;rA;rA;rA; dT$ (SEQ ID No. 87185) | rU2p;rU2p;rU;rG;rC;rG;rA;rA;rU;rU;rU;rU;rC;rU;rC;dT$ (SEQ ID No. 87186) | 91 | | |
| Q-150 | lnaA;lnaC;rU;rC;rA;rG;rA;rC;rU;rU;rC;rA;rG2p;rC2 p;rU2p (SEQ ID No. 87214) | mA;rG;mC;rU;mG;rU;mC;rC;mA;rA;mG;rU;mC;rU;mG;rA;mG;rG;mU (SEQ ID No. 87215) | 62 | | 8 |
| Q-151 | lnaA;lnaC;rU;rC;rA;rG;rA;rC;rU;rU;rC;rA;rG2p;rC2 p;rU2p (SEQ ID No. 87214) | rA;rG;rC;rU;rG;rU;rC;rC;rA;rA;rG;rU;rC;rU;rG;rA;rG;rG;rU (SEQ ID No. 87215) | 51 | | 8 |
| Q-152 | lnaA;lnaC;rU;rC;rA;rG;rA;rC;rU;rU;rC;rA;rG2p;rC2 p;rU2p (SEQ ID No. 87214) | mA;mG;rC;rU;rG;rU;rC;rC;rA;rA;rG;rU;rC;rU;rG;rA;rG;rG;rU (SEQ ID No. 87215) | 61 | | 8 |
| Q-153 | lnaG;lnaC;lnaC;rU;rC;rA;rG;rA;rC;rU;rU;rC;rA;rG2p;rC2 p;rU2p (SEQ ID No. 139) | mA;rG;mG;rA;mG;rU;rG;rA;mC;rA;mC;rA;mU;rC;rU;rU;mG;rG;mC (SEQ ID No. 140) | 11 | 0.5 | 24 |
| Q-154 | lnaG;lnaC;lnaC;rA;rG;rA;rG;rA;rC;rU;rU;rC;rA;rG2p;rC2 p;rU2p (SEQ ID No. 139) | rA;rG;rG;rA;rG;rU;rG;rA;rC;rA;rC;rA;rU;rC;rU;rU;rG;rG;rC (SEQ ID No. 140) | 10 | 0.12 | 24 |
| Q-155 | lnaG;lnaC;lnaC;rA;rG;rA;rG;rA;rC;rU;rU;rC;rA;rG2p;rC2 p;rU2p (SEQ ID No. 139) | mA;mG;rG;rA;rG;rU;rG;rA;rC;rA;rC;rA;rU;rC;rU;rU;rG;rG;rC (SEQ ID No. 140) | 22 | 2.5 | 24 |
| Q-156 | rG;rA;rG;rC;rC;rA;rC;rC;rU;rG;rA;rU;rC;rA;rG2p;rC2p;rU2p $ (SEQ ID No. 87216) | rA;rA;rU;rC;rA;rG;rG;rU;rG;rG;rC;rG;rC2p;rA2p;rC2p$ (SEQ ID No. 87217) | | | 0 |
| Q-157 | rG;rA;rA;rG;rA;rA;rA;rU;rU;rC;rC;rG;rC;rA;rA;dA;dA;dA;dT$ (SEQ ID No. 87185) | rU;rU;rU;rU;rG;rC;rG;rA;rA;rU;rU;rU;rU;rC;mUpeth;mUpeth;dC; dT$ (SEQ ID No. 87186) | 55 | | 16 |
| Q-158 | mGpeth;dA;dA;rG;rA;rA;rA;rA;rU;rU;rC;rC;rG;rC;rA;rA;rA;d T$ (SEQ ID No. 87185) | rU;rU;rU;rU;rG;rC;rG;rA;rA;rU;rU;rU;rU;rC;mUpeth;mUpeth;dC; dT$ (SEQ ID No. 87186) | 100 | | |
| Q-159 | rG;mA;rA;mG;rA;mA;rA;mA;rU;mU;rU;mU;rC;mC;rG;mC;rA;mA;r A$ (SEQ ID No. 87179) | rU;rU;rU;rU;rG;rC;rG;rA;rA;rU;rU;rU;rU;rC;mUpeth;mUpeth;dC; dT$ (SEQ ID No. 87186) | 38 | | 16 |
| Q-160 | rG;rA;rG;rA;rA;rA;rA;rU;rU;rC;rC;rG;rC;rA;rA;rA;rA;dT$ (SEQ ID No. 87185) | mUpeth;mUpeth;mUpeth;rU;rG;rC;rG;rA;rA;rU;rU;rU;rU;rU;rC; U;rC;dT$ (SEQ ID No. 87186) | 87 | | |
| Q-161 | mGpeth;dA;dA;rG;rA;rA;rA;rA;rU;rU;rC;rC;rG;rC;rA;rA;rA;d T$ (SEQ ID No. 87185) | mUpeth;mUpeth;mUpeth;rU;rG;rC;rG;rA;rA;rU;rU;rU;rU;rC;rU;r U;rC;dT$ (SEQ ID No. 87186) | 100 | | |
| Q-162 | rG;mA;rA;mG;rA;mA;rA;mA;rU;mU;rU;mU;rC;mC;rG;mC;rA;mA;r A$ (SEQ ID No. 87179) | mUpeth;mUpeth;mUpeth;rU;rG;rC;rG;rA;rA;rU;rU;rU;rU;rC;rU;r U;rC;rU;r (SEQ ID No. 87186) | 100 | | |

FIG. 23 Continued

| ID | Sense | AntiSense | Activity at 20nM (% of control) | IC50 (nM) | Stability in hum-serum |
|---|---|---|---|---|---|
| Q-163 | rG;rA;rG;rA;rA;rA;rU;rU;rC;rC;rG;rC;rA;dA;dA;dA;dT$ (SEQ ID No. 87185) | mU;rU;mU;rU;mG;rC;mG;rA;mA;rA;mA;rU;mU;rU;mU;rC;mU;rU;mC$ (SEQ ID No. 87180) | 17 | 0.19 | 16 |
| Q-164 | mCpeth;dA;dA;rG;rA;rA;rA;rA;rU;rU;rC;rC;rG;rC;rA;rA;rA;rA;d T$ (SEQ ID No. 87185) | mU;rU;mU;rU;mG;rC;mG;rA;mA;rA;mA;rU;mU;rU;mU;rC;mU;rU;mC$ (SEQ ID No. 87180) | 19 | 1.14 | 16 |
| Q-165 | rG;rA;rG;rA;rA;rA;rA;rU;rU;rC;rC;rG;rC;rA;LdA;LdA;rA (SEQ ID No. 87179) | rU;rU;rU;rU;rG;rC;rG;rA;rA;rA;rA;rU;rU;rU;rU;rC;rU;LdT;rC (SEQ ID No. 87180) | 91 | | 0 |
| Q-166 | rG;rA;rA;rG;rA;rA;rA;rA;rU;rU;rC;rC;rG;rC;rA;rA;rA;LdA;rA (SEQ ID No. 87179) | rU;rU;rU;rU;rG;rC;rG;rA;rA;rA;rA;rU;rU;rU;rU;rC;rU;LdT;rC (SEQ ID No. 87180) | 60 | | 0 |
| Q-167 | rG;rA;rA;rG;rA;rA;rA;rA;rU;rU;rC;rC;rG;rC;rA;rA;LdA;rA (SEQ ID No. 87179) | rU;rU;rU;rU;rG;rC;rG;rA;rA;rA;rA;rU;rU;rU;rU;rC;LdT;LdT;rC (SEQ ID No. 87180) | 78 | | 0 |
| Q-168 | rG;rA;rG;rA;rA;rA;rA;rU;rU;rC;rC;rG;rC;rA;LdA;LdA;rA (SEQ ID No. 87179) | rU;rU;rU;rU;rG;rC;rG;rA;rA;rA;rA;rU;rU;rU;rU;rC;LdT;LdT;rC (SEQ ID No. 87180) | 9 | | 0 |
| Q-169 | rG;rA;rC;rG;rU;rU;rC;rC;rU;rG;rC;rA;rC;rU;rC;rA;rA;LdG;LdA (SEQ ID No. 87218) | rU;rC;rU;rG;rA;rG;rU;rG;rC;rA;rG;rG;rA;rA;rC;rG;rU;LdC;rC (SEQ ID No. 87219) | 15 | | 1 |
| Q-170 | rG;rA;rC;rC;rU;rG;rC;rC;rU;rU;rU;rU;rA;rU;rU;rA;rU;LdC;LdA (SEQ ID No. 133) | rU;rG;rA;rU;rA;rA;rU;rA;rA;rA;rG;rG;rA;rG;rG;rU;rC;LdC;rC (SEQ ID No. 134) | 29 | | 0 |
| Q-171 | rA;rG;rU;rU;rG;rA;rU;rU;rU;rA;rU;rU;rU;rG;LdA;LdT (SEQ ID No. 211) | rA;rC;rA;rA;rA;rU;rA;rA;rA;rU;rC;rA;rA;rC;rU;rU;rG;rC;LdC;LdC (SEQ ID No. 212) | 39 | | 1 |
| Q-172 | rG;rA;rG;rU;rG;rU;rU;rC;rA;rU;rU;rU;rU;rC;rA;rU;LdG;LdT (SEQ ID No. 87220) | rA;rC;rA;rU;rG;rA;rA;rA;rA;rU;rG;rA;rA;rC;rA;rC;rU;rC;LdC;LdC (SEQ ID No. 87221) | 18 | | 1 |
| Q-173 | rG;rC;rA;rG;rG;rC;rC;rC;rA;rU;rU;rU;rA;rU;rU;rC;rA;LdG;LdT (SEQ ID No. 87222) | rA;rC;rU;rG;rA;rA;rU;rA;rA;rA;rU;rG;rG;rG;rC;rC;rU;rG;LdC (SEQ ID No. 87223) | 17 | | 0 |
| Q-174 | rG;rU;rG;rC;rC;rA;rU;rU;rA;rC;rA;rU;rA;rA;rA;rC;LdC;rA (SEQ ID No. 87224) | rU;rG;rG;rU;rU;rU;rA;rU;rG;rU;rA;rA;rU;rG;rG;rC;rA;LdC;rC (SEQ ID No. 87225) | 38 | | 0 |
| Q-175 | rC;rC;rC;rG;rG;rG;rC;rA;rC;rU;rA;rU;rG;rA;rC;rA;LdA;LdA (SEQ ID No. 87226) | rU;rU;rG;rU;rC;rA;rU;rA;rG;rU;rG;rC;rC;rC;rG;rG;LdG;rC (SEQ ID No. 87227) | 22 | | 0 |
| Q-176 | rC;rC;rC;rU;rU;rA;rA;rA;rC;rU;rA;rA;rC;rA;LdA;LdA (SEQ ID No. 87228) | rU;rU;rU;rG;rU;rA;rU;rA;rG;rU;rU;rU;rA;rA;rG;rG;LdG (SEQ ID No. 87229) | 19 | | 0 |
| Q-177 | rG;rC;rU;rU;rG;rU;rA;rU;rU;rU;rU;rA;LdA;LdA (SEQ ID No. 87230) | rU;rU;rU;rA;rA;rA;rA;rU;rA;rC;rA;rA;rG;rC;LdG (SEQ ID No. 87231) | 17 | | 0 |
| Q-178 | rG;rC;rC;rA;rA;rU;rG;rG;rU;rG;rK;rA;rC;rU;rC;LdC;LdT (SEQ ID No. 139) | rA;rG;rG;rA;rG;rU;rC;rA;rC;rA;rC;rC;rA;rU;rU;rG;rG;LdC (SEQ ID No. 140) | 10 | 0.375 | 10 |
| Q-179 | rG;rC;rC;rA;rC;rU;rU;rA;rA;rC;rU;rU;rG;rU;LdA;LdC (SEQ ID No. 235) | rG;rU;rA;rC;rA;rA;rG;rU;rU;rA;rA;rG;rU;rG;rG;LdC (SEQ ID No. 236) | 36 | | 0 |
| Q-180 | rU;rC;rC;rG;rU;rU;rG;rA;rU;rU;rG;rA;rC;LdA;LdA (SEQ ID No. 87232) | rU;rU;rG;rU;rC;rA;rA;rU;rC;rA;rA;rC;rG;rG;LdA (SEQ ID No. 87233) | 8 | | 1 |

FIG. 23 Continued

| ID | Sense | AntiSense | Activity at 20nM (% of control) | IC50 (nM) | Stability in hum-serum |
|---|---|---|---|---|---|
| Q-181 | rG;rA;rG;rA;rA;rA;rU;rU;rU;rC;rC;rG;rC;rG;rA;rA;3mA2p;3mA2p;mA$ (SEQ ID No. 87179) | rU;rU;rU;rG;rC;rG;rG;rA;rA;rA;rU;rU;rU;rC;3mU2p;3mU2p;3mU2p;mC$ (SEQ ID No. 87180) | 65 | | 3 |
| Q-182 | 3mG2p;3mA2p;3mA2p;rG;rA;rA;rA;rU;rU;rU;rC;rC;rG;rC;rA;rA;rA;rA$ (SEQ ID No. 87179) | rU;rU;rU;rG;rC;rG;rG;rA;rA;rA;rU;rU;rU;rC;3mU2p;3mU2p;mC$ (SEQ ID No. 87180) | 35 | 0.678 | 10 |
| Q-183 | rG;mA;rA;mG;rA;mA;rA;mU;rU;mC;rC;mG;rC;mA;rA;mA;rA$ (SEQ ID No. 87179) | rU;rU;rU;rG;rC;rG;rG;rA;rA;rA;rU;rU;rU;rC;3mU2p;3mU2p;mC$ (SEQ ID No. 87180) | 57 | | 10 |
| Q-184 | rG;rA;rA;rG;rA;rA;rA;rU;rU;rU;rC;rC;rG;rC;rA;3mA2p;3mA2p;mA$ (SEQ ID No. 87179) | 3mU2p;3mU2p;3mU2p;rU;rU;rC;rG;rG;rA;rA;rA;rU;rU;rU;rC$ (SEQ ID No. 87180) | 100 | | |
| Q-185 | 3mG2p;3mA2p;rG;rA;rA;rA;rU;rU;rU;rC;rC;rG;rC;rA;rA;rA$ (SEQ ID No. 87179) | 3mU2p;3mU2p;rU;rU;rG;rC;rG;rG;rA;rA;rA;rU;rU;rU;rC$ (SEQ ID No. 87180) | 100 | | |
| Q-186 | rG;mA;rA;mG;rA;mA;rA;mU;rU;mC;rC;mG;rC;mA;rA;mA;rA$ (SEQ ID No. 87179) | 3mU2p;3mU2p;rU;rU;rG;rC;rG;rG;rA;rA;rA;rU;rU;rU;rC$ (SEQ ID No. 87180) | 100 | | |
| Q-187 | rG;rA;rA;rG;rA;rA;rA;rU;rU;rU;rC;rC;rG;rC;rA;3mA2p;3mA2p;mA$ (SEQ ID No. 87179) | mU;rU;mU;rU;mG;rC;mG;rA;mA;rA;mU;rU;mU;rC;mU;rU;mC$ (SEQ ID No. 87180) | 26 | 0.394 | 10 |
| Q-188 | 3mG2p;3mA2p;rG;rA;rA;rA;rU;rU;rU;rC;rC;rG;rC;rA;rA;rA$ (SEQ ID No. 87179) | mU;rU;mU;rU;mG;rC;mG;rA;mA;rA;mU;rU;mU;rC;mU;rU;mC$ (SEQ ID No. 87180) | 16 | 1.114 | 10 |
| Q-189 | rG;rA;rA;rG;rA;rA;rA;rU;rU;rU;rC;rC;rG;rC;rA;rA;rA$ (SEQ ID No. 87179) | rU;rU;rU;rC;rG;rC;rG;rA;rA;rA;rU;rU;rU;rC;rU;rU;rC$ (SEQ ID No. 87180) | 4 | 0.372 | 8 |
| Q-190 | rA;rC;rC;rU;rG;rA;rA;rA;rC;rC;rU;rG;rA;LdA;LdT (SEQ ID No. 87234) | rA;rU;rU;rC;rC;rA;rG;rC;rA;rA;rU;rU;rC;rA;rG;LdT (SEQ ID No. 87235) | 4 | | 8 |
| Q-191 | rC;rC;rU;rG;rU;rG;rA;rA;rA;rC;rC;rU;rG;rA;LdA;LdT (SEQ ID No. 81956) | rA;rA;rG;rC;rA;rU;rU;rC;rU;rC;rA;rU;rC;rA;rG;LdG (SEQ ID No. 82284) | 32 | | 0 |
| Q-192 | rG;rG;rG;rC;rU;rA;rA;rG;rA;rA;LdA;LdT (SEQ ID No. 13905) | rU;rU;rC;rU;rC;rA;rU;rU;rA;rG;rC;rC;LdC (SEQ ID No. 14108) | 28 | | 0 |
| Q-193 | rG;rU;rG;rC;rC;rA;rA;rC;rC;rU;rG;rC;rA;rA;rG;LdC;LdT (SEQ ID No. 87216) | mA;mG;rC;rU;mG;rC;mA;rU;mC;rA;mG;rG;mC;rA;mC (SEQ ID No. 87217) | 94 | | 24 |
| Q-194 | rG;rU;rG;rC;rC;rU;rG;rA;rU;rG;rC;rA;rG;LdC;LdT (SEQ ID No. 87216) | mA;rG;mC;rU;mG;rC;mA;rU;rC;mA;rG;mG;rC;mA;mC (SEQ ID No. 87217) | 20 | 1.567 | 24 |
| Q-195 | mG;mU;rG;rC;rC;rA;rA;rC;rC;rU;rG;rA;rU;rG;LdC;LdT (SEQ ID No. 87216) | mA;mG;rC;rU;mG;rC;mA;rU;rC;rA;rG;rG;rC;rA;LdC (SEQ ID No. 87217) | 96 | | |
| Q-196 | mG;mU;mG;mC;mC;mA;rA;rC;mC;mU;mG;rA;rU;rG;rC2p;rU2p (SEQ ID No. 87216) | rA;rG;rC;rU;rG;rC;rA;rU;rC;rA;rG;rG;rC;rA;mC (SEQ ID No. 87217) | 49 | | |
| Q-197 | mG;mU;mG;mC;mC;mA;rA;rC;mC;mU;mG;rA;rU;rG;rC2p;rU2p (SEQ ID No. 87216) | mA;mG;rC;rU;mG;rC;mA;rU;rC;rA;rG;rG;rC;rA;LdC (SEQ ID No. 87217) | 114 | | |
| Q-198 | rG;rU;rG;rC;rC;rU;rG;rA;rU;rG;rC;rA;rG;rC2p;rU2p (SEQ ID No. 87216) | mA;rG;mC;rU;mG;rC;mA;rU;mC;rA;mG;rG;mC;rA;mC (SEQ ID No. 87217) | 88 | 0.359 | 10 |

FIG. 23 Continued

| ID | Sense | AntiSense | Activity at 20nM (% of control) | IC50 (nM) | Stability in human serum |
|---|---|---|---|---|---|
| Q-199 | mG;mU;mG;mC;mC;rA;rA;rC;rC;rU;rG;rA;rU;rG;rC;rU;rG;rC;rU (SEQ ID No. 87216) | rA;rG;rC;rU;rG;rC;rA;rU;rC;rA;rG;rU;rU;rG;rG;rU;rU;rG;mC;mA;mC (SEQ ID No. 87217) | 58 | | |
| Q-200 | rG;rU;rG;rC;rC;rA;rA;rC;rC;rA;rU;rG;rA;rU;rG;rC;rA;rG;LdC;LdT (SEQ ID No. 87216) | rA;rG;rC;rU;rG;rC;rA;rU;rC;rA;rG;rU;rU;rG;rG;rU;rU;rG;rC;rA;LdC (SEQ ID No. 87217) | 42 | | |
| Q-201 | mG;mU;mG;mC;mC;rA;rA;rC;rC;rA;rU;rG;rA;rU;rG;rC;rA;rG;LdC;LdT (SEQ ID No. 87216) | rA;rG;rC;rU;rG;rC;rA;rU;rC;rA;rG;rU;rU;rG;rG;rU;rU;rG;mC;mA;mC (SEQ ID No. 87217) | 37 | 5.097 | 10 |
| Q-202 | rG;rA;rG;rA;rG;rA;rA;rA;rA;rU;rU;rU;rC;rG;rC;rA;rA;LdA;LdA (SEQ ID No. 87179) | rU;rU;rU;rU;rG;rC;rG;rA;rA;rA;rU;rU;rU;rC;rU;rU;rC;rU;rU;LdC (SEQ ID No. 87180) | | | |
| Q-203 | LdG;LdA;rA;rG;rA;rA;rA;rA;rU;rU;rU;rC;rG;rC;rA;rA;rA;rA (SEQ ID No. 87179) | rU;rU;rU;rU;rG;rC;rG;rA;rA;rA;rU;rU;rU;rC;rU;rU;rC;rU;rU;LdC (SEQ ID No. 87180) | | | |
| Q-204 | LdG;LdA;rA;rG;rA;rA;rA;rA;rU;rU;rU;rC;rG;rC;rA;rA;rA;LdA;LdA (SEQ ID No. 87179) | rU;rU;rU;rU;rG;rC;rG;rA;rA;rA;rU;rU;rU;rC;rU;rU;rC;rU;rU;LdC (SEQ ID No. 87180) | | | |
| Q-205 | rG;rA;rA;rG;rA;rA;rA;rA;rU;rU;rU;rU;rC;rG;rC;rA;rA;LdA;LdA (SEQ ID No. 87179) | mU;rU;mU;mG;rC;mG;rA;mA;rA;mA;rU;mU;rU;mC;rU;mU;rC;rU;mU;rU;mC (SEQ ID No. 87180) | | | |
| Q-206 | LdG;LdA;rA;rG;rA;rA;rA;rA;rU;rU;rU;rC;rG;rC;rA;rA;rA;rA (SEQ ID No. 87179) | mU;mU;mU;mG;rC;mG;rA;mA;rA;mA;rU;mU;rU;mC;rU;mU;rC;rU;mU;rU;mC (SEQ ID No. 87180) | | | |
| Q-207 | LdG;LdA;rA;rG;rA;rA;rA;rA;rU;rU;rU;rC;rG;rC;rA;rA;rA;LdA;LdA (SEQ ID No. 87179) | mU;mU;mU;mG;rC;mG;rA;mA;rA;mA;rU;mU;rU;mC;rU;mU;rC;rU;mU;rU;mC (SEQ ID No. 87180) | | | |
| Q-208 | rG;rA;rA;rG;rA;rA;rA;rA;rU;rU;rU;rC;rG;rC;rA;rA;rA;rA;LdA (SEQ ID No. 87179) | rU;rU;rU;rU;rG;rC;rG;rA;rA;rA;rU;rU;rU;rC;rU;rU;rC;rU;rU;LdC (SEQ ID No. 87180) | 52 | | 0 |
| Q-209 | rG;rA;rA;rG;rA;rA;rA;rA;rU;rU;rU;rC;rG;rC;rA;rA;rA;LdA (SEQ ID No. 87179) | rU;rU;rU;rU;rG;rC;rG;rA;rA;rA;rU;rU;rU;rC;rU;rU;rC;rU;LdT;LdC (SEQ ID No. 87180) | 73 | | 0 |
| Q-210 | rG;rA;rA;rG;rA;rA;rA;rA;rU;rU;rU;rC;rG;rC;rA;rA;rA;rA;LdA (SEQ ID No. 87179) | rU;rU;rU;rU;rG;rC;rG;rA;rA;rA;rU;rU;rU;rC;rU;rU;rC;LdT;LdT;LdC (SEQ ID No. 87180) | 85 | | 0 |
| Q-211 | rG;rA;rA;rG;rA;rA;rA;rA;rU;rU;rU;rC;rG;rC;rA;rA;rA;LdA;LdA (SEQ ID No. 87179) | rU;rU;rU;rU;rG;rC;rG;rA;rA;rA;rU;rU;rU;rC;rU;rU;rC;rU;rU;LdC (SEQ ID No. 87180) | 50 | | 3 |
| Q-212 | rG;rA;rA;rG;rA;rA;rA;rA;rU;rU;rU;rC;rG;rC;rA;rA;rA;LdA;LdA (SEQ ID No. 87179) | rU;rU;rU;rU;rG;rC;rG;rA;rA;rA;rU;rU;rU;rC;rU;rU;rC;rU;LdU;LdC (SEQ ID No. 87180) | 82 | | 0 |
| Q-213 | rG;rA;rA;rG;rA;rA;rA;rA;rU;rU;rU;rC;rG;rC;rA;rA;rA;LdA;LdA (SEQ ID No. 87179) | rU;rU;rU;rU;rG;rC;rG;rA;rA;rA;rU;rU;rU;rC;rU;rU;rC;LdT;LdT;LdC (SEQ ID No. 87180) | 100 | | 0 |
| Q-214 | rG;rA;rA;rG;rA;rA;rA;rA;rU;rU;rU;rC;rG;rC;rA;rA;LdA;LdA (SEQ ID No. 87179) | rU;rU;rU;rU;rG;rC;rG;rA;rA;rA;rU;rU;rU;rC;rU;rU;rC;LdT;LdT;LdC (SEQ ID No. 87180) | 62 | | 3 |
| Q-215 | rG;rA;rA;rG;rA;rA;rA;rA;rU;rU;rU;rC;rG;rC;rA;rA;LdA;LdA (SEQ ID No. 87179) | rU;rU;rU;rU;rG;rC;rG;rA;rA;rA;rU;rU;rU;rC;rU;rU;rC;rU;LdT;LdC (SEQ ID No. 87180) | 90 | | 0.5 |
| Q-216 | rG;rA;rA;rG;rA;rA;rA;rA;rU;rU;rU;rC;rG;rC;rA;rA;LdA;LdA (SEQ ID No. 87179) | rU;rU;rU;rU;rG;rC;rG;rA;rA;rA;rU;rU;rU;rC;rU;rU;rC;LdT;LdT;LdC (SEQ ID No. 87180) | 90 | | 0 |

FIG. 23 Continued

| ID | Sense | AntiSense | Activity at 20nM (% of control) | IC50 (nM) | Stability in human serum |
|---|---|---|---|---|---|
| Q-217 | rG;rA;rG;rA;rA;rA;rU;rU;rC;rG;rC;rA;rA;LdA (SEQ ID No. 87179) | mU;rU;mU;rU;mG;rC;mG;mA;rA;mA;rU;mU;rC;mU;rU;mC (SEQ ID No. 87180) | 21 | | 24 |
| Q-218 | rG;rA;rA;rG;rA;rA;rA;rU;rU;rC;rG;rC;rA;rA;LdA;LdA (SEQ ID No. 87179) | mU;rU;mU;rU;mG;rC;mG;mA;rA;mA;rU;mU;rC;mU;rU;mC (SEQ ID No. 87180) | 24 | | 24 |
| Q-219 | rG;rA;rA;rG;rA;rA;rA;rU;rU;rC;rG;rC;rA;LdA;LdA;LdA (SEQ ID No. 87179) | mU;rU;mU;rU;mG;rC;mG;mA;rA;mA;rU;mU;rC;mU;rU;mC (SEQ ID No. 87180) | 13 | | 24 |
| Q-220 | rC;rA;rG;rC;rC;rA;rA;rG;rU;rG;rU;rG;rC;rC;rC;rU2p;rC2p;rA2p (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 53 | | 24 |
| Q-221 | mC;mA;mG;mC;mC;mA;rG;rA;rA;rU;rG;rU;rG;rC;rC;rC;rU2p;rC2p;rA2p (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 53 | | 24 |
| Q-222 | mC;mA;mG;mC;mC;mA;rG;rA;rA;rU;rG;rU;rG;rC;rC;rC;rU;rC;rA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 48 | | 10 |
| Q-223 | mC;mA;mG;mC;mC;mA;rG;rA;rA;rU;rG;rU;rG;rC;rC;rC;rU;rC;rC;LdT;LdC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 31 | | 24 |
| Q-224 | mC;mA;mG;mC;mC;mA;rG;rA;rA;rU;rG;rU;rG;rC;rC;rC;rU;LdC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 34 | | 24 |
| Q-225 | mC;mA;mG;mC;mC;mA;rG;rA;rA;rU;rG;rU;rG;rC;rC;rC;rU;rC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 33 | | 24 |
| Q-226 | rC;rA;rG;rC;rC;rA;rA;rU;rG;rU;rG;rC;rC;rC;rU;rC;rC;rU;LdC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 50 | | 24 |
| Q-227 | rC;rA;rG;rC;rC;rA;rA;rU;rG;rU;rG;rC;rC;rC;rU;rC;rC;rU;LdC;rU;L (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 52 | | 24 |
| Q-228 | rC;rA;rG;rC;rC;rA;rA;rU;rG;rU;rG;rC;rC;rC;rU;rC;rC;rU;rC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 37 | | 24 |
| Q-229 | mC;rA;rG;rC;rC;rA;rA;rU;rG;rU;rG;rC;rC;rC;rU;rC;rC;rU;LdC;LdA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 32 | | 24 |
| Q-230 | rC;rA;rG;rC;rC;rA;rA;rU;rG;rU;rG;rC;rC;rC;rU;rC;rC;rU;LdC;rA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 26 | | 24 |
| Q-231 | rC;rA;rG;rC;rC;rA;rA;rU;rG;rU;rG;rC;rC;rC;rU;rC;rC;rU;LdC;LdT;LdC;rA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 100 | | 24 |
| Q-232 | mC;rA;rG;mC;rC;mA;rC;mA;rA;mU;rG;mU;rG;rA;mA;rC;mU;rC;mC;rU;mC;rA (SEQ ID No. 38078) | mU;rG;mA;rG;mG;rA;mG;rU;mU;rC;mC;rA;mU;rC;rA;mU;rC;rU;mG;rG;mC;rU;mG (SEQ ID No. 39666) | 73 | | 24 |
| Q-233 | rG;rG;rA;rA;rG;rA;rA;rA;rU;rU;rC;rG;rC;rG;rC;rA;rA;rA;LdA (SEQ ID No. 87181) | rU;rU;rU;rU;rG;rC;rG;rC;rG;rA;rA;rU;rU;rU;rC;rU;rU;rC;rC;LdG (SEQ ID No. 87182) | 3 | | 1 |
| Q-234 | LdG;LdG;rA;rA;rG;rA;rA;rA;rU;rU;rC;rG;rC;rG;rC;rA;rA;rA (SEQ ID No. 87181) | rU;rU;rU;rU;rG;rC;rG;rC;rG;rA;rA;rU;rU;rU;rC;rU;rU;rC;rC;LdG (SEQ ID No. 87182) | 5 | | 1 |

FIG. 23 Continued

| ID | Sense | AntiSense | Activity at 20nM (% of control) | IC50 (nM) | Stability in human serum |
|---|---|---|---|---|---|
| Q-235 | LdG;LdG;rA;rA;rG;rA;rA;rG;rA;rU;rU;rG;rC;rG;rC;rG;rC;rA;rA;LdA;LdA (SEQ ID No. 87181) | rU;rU;rU;rG;rU;rG;rC;rG;rC;rG;rA;rA;rU;rU;rC;rU;rU;rC;rU;rU;rC;Ld C (SEQ ID No. 87182) | 4 | | 1 |
| Q-236 | rG;rG;rA;rA;rG;rA;rA;rG;rA;rA;rU;rU;rC;rG;rC;rG;rC;rG;mC;mA;m A;mA;mA (SEQ ID No. 87181) | rU;rU;rU;rG;rU;rG;rC;rG;rC;rG;rA;LdA;rU;rU;rC;rU;rU;rC;rU;mC;mU; mC;mC (SEQ ID No. 87182) | 53 | | 3 |
| Q-237 | rG;rG;rA;rA;rG;rA;rA;rG;rA;rA;rU;rU;rC;rG;rC;rG;rC;rG;mC;mA;m A;mA;mA (SEQ ID No. 87181) | rU;rU;rU;rG;rU;rG;rC;rG;rC;rG;rA;rA;LdA;rU;rU;rC;rU;rU;rC;mU;mC; mC;mC (SEQ ID No. 87182) | 42 | | 1 |
| Q-238 | rG;rA;rA;rG;rA;rA;rG;rA;rA;rU;rU;rU;rC;rC;rG;mC;mA;mA;mA (SEQ ID No. 87179) | rU;rU;rU;rG;rC;rG;rC;rG;rA;LdA;rA;rU;rU;rC;rU;mU;mU;mU;mU;mC (SEQ ID No. 87180) | 69 | | 6 |
| Q-239 | rG;rA;rA;rG;rA;rA;rG;rA;rA;rU;rU;rU;rC;rC;rG;mC;mA;mA;mA;mA (SEQ ID No. 87179) | rU;rU;rU;rG;rC;rG;rC;rG;rA;LdA;LdA;rU;rU;rU;rU;rU;mU;mU;mU;mC (SEQ ID No. 87180) | 71 | | 0 |
| Q-240 | rG;rA;rA;rG;rA;rA;rG;rA;rA;rU;rU;rU;rU;rC;rC;rG;mC;mA;mA;mA;mA (SEQ ID No. 87179) | rU;rU;rU;rG;rC;rG;rC;rG;rA;rA;LdA;rU;rU;rU;rU;mU;mU;mU;mU;mC (SEQ ID No. 87180) | 100 | | 0 |
| Q-241 | rG;rC;rC;rA;rG;rA;rU;rG;rU;rG;rA;rC;rU;rC2p;rC2p;rC2p;rU2p;rU2p (SEQ ID No. 139) | mA;rG;mG;rA;mG;rA;mU;rC;mC;rA;mC;rA;mU;rC;mG;rG;mC (SEQ ID No. 140) | 11 | 2.45 | 24 |
| Q-242 | mG;mC;mA;mG;rA;rA;rG;rU;rG;rU;rG;rA;rA;rC;rA;rA;rC;rU (SEQ ID No. 139) | mA;rG;mG;rA;mG;rA;mU;rC;mC;rA;mC;rA;mU;rC;mG;rG;mC (SEQ ID No. 140) | 17 | 2 | 24 |
| Q-243 | mG;mC;mC;mA;mG;rA;rA;rG;rU;rG;rU;rG;rA;rC;rU;rC;rU (SEQ ID No. 139) | mA;rG;mG;rA;mG;rA;mU;rC;mC;rA;mC;rA;mU;rC;mG;rG;mC (SEQ ID No. 140) | 17 | 8.8 | 24 |
| Q-244 | mG;mC;mC;mA;mG;rA;rA;rU;rG;rU;rG;rA;rC;rU;LdC;LdC;L dT (SEQ ID No. 139) | mA;rG;mG;rA;mG;rA;mU;rC;mC;rA;mU;rC;rA;mU;rC;mG;rG;mC (SEQ ID No. 140) | 9 | 2.56 | 24 |
| Q-245 | mG;mC;mC;mA;mG;rA;rA;rG;rU;rG;rU;rG;rA;rC;rU;LdC;LdC;LdT (SEQ ID No. 139) | mA;rG;mG;rA;mG;rA;mU;rC;mC;rA;mC;rA;mU;rC;mG;rG;mC (SEQ ID No. 140) | 3 | 1.6 | 24 |
| Q-246 | mG;mC;mC;mA;mG;rA;rA;rG;rU;rG;rU;rG;rA;rA;rC;rU;LdC;LdC;LdT (SEQ ID No. 139) | mA;rG;mG;rA;mG;rA;mU;rC;mC;rA;mC;rA;mU;rC;mG;rG;mC (SEQ ID No. 140) | 6 | 1.13 | 24 |
| Q-247 | rG;rC;rC;rA;rG;rA;rA;rG;rU;rG;rA;rA;rC;rU;rC;LdC;LdT (SEQ ID No. 139) | mA;rG;mG;rA;mG;rA;mU;rC;mC;rA;mC;rA;mU;rC;mG;rG;mC (SEQ ID No. 140) | 10 | 1.3 | 24 |
| Q-248 | rG;rC;rC;rA;rG;rA;rA;rG;rU;rG;rU;rG;rA;rC;rU;rC;rC;LdT (SEQ ID No. 139) | mA;rG;mG;rA;mG;rA;mU;rC;mC;rA;mC;rA;mU;rC;mG;rG;mC (SEQ ID No. 140) | 4 | 2.38 | 24 |
| Q-249 | rG;rC;rC;rA;rG;rA;rA;rG;rU;rG;rU;rG;rA;rC;rU;rC;rC;LdT (SEQ ID No. 139) | mA;rG;mG;rA;mG;rA;mU;rC;mC;rA;mC;rA;mU;rC;mG;rG;mC (SEQ ID No. 140) | 8 | 0.78 | 24 |
| Q-250 | mG;mC;mC;rA;rG;rA;rA;rG;rU;rG;rU;rG;rA;rC;rU;rC;LdT (SEQ ID No. 139) | mA;rG;mG;rA;mG;rA;mU;rC;mC;rA;mC;rA;mU;rC;mG;rG;mC (SEQ ID No. 140) | 7 | | 24 |
| Q-251 | rG;rC;rC;rA;rG;rA;rA;rU;rG;rU;rG;rA;rC;rU;rC;LdC;rU (SEQ ID No. 139) | mA;rG;mG;rA;mG;rA;mU;rC;mC;rA;mC;rA;mU;rC;mG;rG;mC (SEQ ID No. 140) | 6 | 0.46 | 24 |
| Q-252 | rG;rC;rC;rA;rG;rA;rU;rG;rU;rG;rA;rC;rU;LdC;LdC;rU (SEQ ID No. 139) | mA;rG;mG;rA;mG;rA;mU;rC;mC;rA;mC;rA;mU;rC;mG;rG;mC (SEQ ID No. 140) | 18 | 2.48 | 24 |

FIG. 23 Continued

| ID | Sense | AntiSense | Activity at 20nM (% of control) | IC50 (nM) | Stability in ham-serum |
|---|---|---|---|---|---|
| Q-253 | rG;rC;rC;rA;rG;rA;rG;rU;rG;rA;rA;rA;rC;rU2p;rC2p;rC;rU (SEQ ID No. 139) | mA;rG;mG;rA;mG;rU;rU;rC;mC;rA;mC;rA;mU;rU;mC;rU;mG;rG;mC (SEQ ID No. 140) | 15 | 3.78 | 24 |
| Q-254 | rG;mC;rC;mA;rG;mA;rG;mU;rG;mA;rA;mA;rC;mU;rC;mC;rU (SEQ ID No. 139) | mA;rG;mG;rA;mG;rU;mU;rC;mC;rA;mC;rA;mU;rU;mC;rU;mG;rG;mC (SEQ ID No. 140) | 10 | | 24 |
| Q-255 | rG;mC;rC;mA;rG;mA;rA;mA;rG;mA;rA;mA;rC;mU;rC;mC;rU$ (SEQ ID No. 139) | mA;rG;mG;rA;mG;rU;mU;rC;mC;rA;mC;rA;mU;rU;mC;rU;mG;rG;mC (SEQ ID No. 140) | 19 | | |
| Q-256 | rG;rC;rC;rA;rG;rA;rG;rU;rG;rA;rA;rA;rC;rU;rC2p;rC2p;rU$ (SEQ ID No. 139) | mA;rG;mG;rA;mG;rU;mU;rC;mC;rA;mC;rA;mU;rU;mC;rU;mG;rG;mC (SEQ ID No. 140) | 16 | | |
| Q-257 | rG;rC;rC;rA;rG;rA;rG;rU;rG;rA;rA;rA;rC;rU;rC2p;rC2p;rU (SEQ ID No. 139) | mA;rG;mG;rA;mG;rU;mU;rC;mC;rA;mC;rA;mU;rU;mC;rU;mG;rG;mC (SEQ ID No. 140) | 6 | 1.1 | 16 |
| Q-258 | rG;rC;rC;rA;rG;rA;rG;rU;rG;rA;rA;rA;rC;rU;rC2p;rC2p;rU2p (SEQ ID No. 139) | mA;rG;mG;rA;mG;rU;mU;rC;mC;rA;mC;rA;mU;rU;mC;rU;mG;rG;mC (SEQ ID No. 140) | 15 | | |
| Q-259 | rG;rC;rC;rA;rG;rA;rG;rU;rG;rA;rA;rA;rC;rU;rC;LdC;LdT (SEQ ID No. 139) | mA;rG;mG;rA;mG;rU;mU;rC;mC;rA;mC;rA;mU;rU;mC;rU;mG;rG;mC (SEQ ID No. 140) | 5 | | |
| Q-260 | rG;rC;rC;rA;rG;rA;rG;rU;rG;rA;rA;rA;rC;rU;rC;LdC;LdT$ (SEQ ID No. 139) | mA;rG;mG;rA;mG;rU;mU;rC;mC;rA;mC;rA;mU;rU;mC;rU;mG;rG;mC (SEQ ID No. 140) | 6 | | |
| Q-261 | rG;mC;rC;mA;rG;mA;rG;mU;rG;mA;rA;mA;rC;mU;rC;mC;rU (SEQ ID No. 139) | mA;rG;mG;rA;mG;rU;mU;rC;mC;rA;mC;rA;mU;rU;mC;rU;mG;rG;mC$ (SEQ ID No. 140) | 90 | | |
| Q-262 | rG;mC;rC;mA;rG;mA;rA;mA;rG;mU;rG;mU;rG;mA;rA;mA;rC;mU;rC;mC;rU$ (SEQ ID No. 139) | mA;rG;mG;rA;mG;rU;mU;rC;mC;rA;mC;rA;mU;rU;mC;rU;mG;rG;mC$ (SEQ ID No. 140) | 110 | | |
| Q-263 | rG;rC;rC;rA;rG;rA;rG;rU;rG;rA;rA;rA;rC;rU;rC2p;rC2p;rU$ (SEQ ID No. 139) | mA;rG;mG;rA;mG;rU;mU;rC;mC;rA;mC;rA;mU;rU;mC;rU;mG;rG;mC$ (SEQ ID No. 140) | 36 | | |
| Q-264 | rG;rC;rC;rA;rG;rA;rG;rU;rG;rA;rA;rA;rC;rU;rC2p;rC2p;rU (SEQ ID No. 139) | mA;rG;mG;rA;mG;rU;mU;rC;mC;rA;mC;rA;mU;rU;mC;rU;mG;rG;mC$ (SEQ ID No. 140) | 15 | | |
| Q-265 | rG;rC;rC;rA;rG;rA;rG;rU;rG;rA;rA;rA;rC;rU;rC2p;rC2p;rU2p (SEQ ID No. 139) | mA;rG;mG;rA;mG;rU;mU;rC;mC;rA;mC;rA;mU;rU;mC;rU;mG;rG;mC$ (SEQ ID No. 140) | 23 | | |
| Q-266 | rG;rC;rC;rA;rG;rA;rG;rU;rG;rA;rA;rA;rC;rU;rC;LdC;LdT (SEQ ID No. 139) | mA;rG;mG;rA;mG;rU;mU;rC;mC;rA;mC;rA;mU;rU;mC;rU;mG;rG;mC$ (SEQ ID No. 140) | 6 | | |
| Q-267 | rG;rC;rC;rA;rG;rA;rG;rU;rG;rA;rA;rA;rC;rU;rC;LdC;LdT$ (SEQ ID No. 139) | mA;rG;mG;rA;mG;rU;mU;rC;mC;rA;mC;rA;mU;rU;mC;rU;mG;rG;mC$ (SEQ ID No. 140) | 20 | | |
| Q-268 | rG;rA;rA;rU;rU;rG;rU;rG;rA;rA;rC;rU;rC;rU;rA2p;rA2p;rC$ (SEQ ID No. 2449) | mG;rU;mU;rG;mA;rG;mA;rG;mU;rU;rC;mC;rA;mC;rA;mC;rA;mU;rU;mC (SEQ ID No. 2949) | 18 | 1.176 | 3 |
| Q-269 | rG;rA;rA;rU;rG;rU;rG;rA;rA;rC;rU;rC;rU;rA2p;rA2p;rC (SEQ ID No. 2449) | mG;rU;mU;rG;mA;rG;mA;rG;mU;rU;rC;mC;rA;mC;rA;mC;rA;mU;rU;mC (SEQ ID No. 2949) | 10 | 0.263 | 8 |
| Q-270 | mG;mA;mA;mU;mG;rU;rG;rA;rA;rC;rU;rC;rU;rA2p;rA2p;rC2p (SEQ ID No. 2449) | mG;rU;mU;rG;mA;rG;mA;rG;mU;rU;rC;mC;rA;mC;rA;mC;rA;mU;rU;mC (SEQ ID No. 2949) | 11 | 0.1 | 1 |

FIG. 23 Continued

| ID | Sense | AntiSense | Activity at 20nM (% of control) | IC50 (nM) | Stability in human serum |
|---|---|---|---|---|---|
| Q-271 | rG;rA;rA;rU;rG;rU;rG;rG;rA;rA;rC;rU;rC;rU;rC;rA;LdA;LdC (SEQ ID No. 2449) | mG;rU;mU;rG;mA;rG;mG;rA;mG;rU;rU;rC;mC;rA;mC;rA;mU;rU;mC (SEQ ID No. 2949) | 10 | 0.646 | 6 |
| Q-272 | rG;rA;rA;rU;rG;rU;rG;rG;rA;rA;rC;rU;rC;rU;rC;rA;LdA;LdC$ (SEQ ID No. 2449) | mG;rU;mU;rG;mA;rG;mG;rA;mG;rU;rU;rC;mC;rA;mC;rA;mU;rU;mC (SEQ ID No. 2949) | 11 | 0.174 | 6 |
| Q-273 | rG;rA;rA;mU;rG;mU;rG;mG;rA;mA;rC;mU;rC;mU;rC;rA;mA;rC (SEQ ID No. 2449) | mG;rU;mU;rG;mA;rG;mG;rA;mG;rU;rU;rC;mC;rA;mC;rA;mU;rU;mC$ (SEQ ID No. 2949) | 20 | | |
| Q-274 | rG;mA;rA;mU;rG;mU;rG;mG;rA;mA;rC;mU;rC;mU;rC;rA;mA;rC$ (SEQ ID No. 2449) | mG;rU;mU;rG;mA;rG;mG;rA;mG;rU;rU;rC;mC;rA;mC;rA;mU;rU;mC$ (SEQ ID No. 2949) | 44 | | |
| Q-275 | rG;rA;rA;rU;rG;rU;rG;rG;rA;rA;rC;rU;rC;rU;rC;rA;rA2p;rA2p;rC$ (SEQ ID No. 2449) | mG;rU;mU;rG;mA;rG;mG;rA;mG;rU;rU;rC;mC;rA;mC;rA;mU;rU;mC$ (SEQ ID No. 2949) | 88 | | |
| Q-276 | rG;rA;rA;rU;rG;rU;rG;rG;rA;rA;rC;rU;rC;rU;rC;rA2p;rA2p;rC (SEQ ID No. 2449) | mG;rU;mU;rG;mA;rG;mA;rG;mG;rA;mG;rU;rU;rC;mC;rA;mC;rA;mU;rU;mC$ (SEQ ID No. 2949) | 54 | | |
| Q-277 | rG;rA;rA;rU;rG;rU;rG;rG;rA;rA;rC;rU;rC;rU;rC;rA2p;rA2p;rC2p (SEQ ID No. 2449) | mG;rU;mU;rG;mA;rG;mG;rA;mG;rU;rU;rC;mC;rA;mC;rA;mU;rU;mC$ (SEQ ID No. 2949) | 46 | | |
| Q-278 | rG;rA;rA;rU;rG;rU;rG;rG;rA;rA;rC;rU;rC;rU;rC;rA;LdA;LdC (SEQ ID No. 2449) | mG;rU;mU;rG;mA;rG;mG;rA;mG;rU;rU;rC;mC;rA;mC;rA;mU;rU;mC$ (SEQ ID No. 2949) | 16 | 0.329 | 16 |
| Q-279 | rG;rA;rA;rU;rG;rU;rG;rG;rA;rA;rC;rU;rC;rU;rC;rA;LdA;LdC$ (SEQ ID No. 2449) | mG;rU;mU;rG;mA;rG;mG;rA;mG;rU;rU;rC;mC;rA;mC;rA;mU;rU;mC$ (SEQ ID No. 2949) | 28 | | |
| Q-280 | iB;mG;mA;mA;mG;mA;mA;mA;mG;mU;mC;mC;rG;rC;rA;rA;rA (SEQ ID No. 87179) | s;rU;rU;rU;rG;rC;rG;rA;rA;rA;rG;mA;rA;rU;mU;mU;mU;mC (SEQ ID No. 87180) | 10 | | |
| Q-281 | iB;rG;rA;rA;rG;rA;rA;rA;rG;rU;rU;rU;rC;rG;rC;rA;rA;rA (SEQ ID No. 87179) | s;mU;rU;mU;rU;mU;rG;rC;mG;rA;rA;rA;rG;mA;rA;rU;rU;rU;mC (SEQ ID No. 87180) | 4 | | |
| Q-282 | rG2p;rA2p;rA2p;rG;rA;rA;rA;rG;rU;rU;rU;rC;rG;rC;rA;rA;rA (SEQ ID No. 87179) | s;rU2p;rU2p;rU2p;rU;rG;rC;rG;rA;rA;rA;rG;rA;rA;rU;rU;rU;rC (SEQ ID No. 87180) | 24 | | |
| Q-283 | rG;rA;rA;rG;rA;rA;rA;rG;rU;rU;rU;rC;rG;rC;rA;rA2p;rA2p (SEQ ID No. 87179) | s;rU2p;rU2p;rU2p;rU;rG;rC;rG;rA;rA;rA;rG;rA;rA;rU;rU;rU;rC (SEQ ID No. 87180) | 63 | | |
| Q-284 | iB;rG;rA;rA;rG;rA;rA;rA;rG;rU;rU;rU;rC;rG;rC;rA;rA2p;rA2p (SEQ ID No. 87179) | s;rU;rU;rU;rU;rG;rC;rG;rA;rA;rA;rG;rA;rA;rU;rU;rU;rC;rU2p;rC2p (SEQ ID No. 87180) | 19 | | |
| Q-285 | rG;mC;rC;mA;rC;mU;rU;mA;rU;mG;rU;mA (SEQ ID No. 235) | mG;rU;mA;rA;mC;rA;mU;rA;mU;rU;mA;rA;mG;rU;mG;rG;mC (SEQ ID No. 236) | 6.5 | 1.12 | 0 |
| Q-286 | rG;mC;rC;mA;rC;mU;rU;mA;rU;mG;rU;mU;rA (SEQ ID No. 235) | mG;rU;mA;rA;mC;rA;mU;rA;mC;rA;mU;rA;mU;rU;mA;rA;mG;rU;mG;rG;mC (SEQ ID No. 236) | 5.1 | | 0 |
| Q-287 | rG;rC;rC;rA;rC;rU;rU;rA;rU;rG;rU;rA2p;rC$ (SEQ ID No. 235) | mG;rU;mA;rA;mC;rA;mU;rA;mC;rA;mU;rA;mU;rU;mA;rA;mG;rU;mG;rG;mC (SEQ ID No. 236) | 10 | | 1 |
| Q-288 | rG;rC;rC;rA;rC;rU;rU;rA;rU;rA;rU;rG;rU;rA2p;rC (SEQ ID No. 235) | mG;rU;mA;rA;mC;rA;mU;rA;mC;rA;mU;rA;mU;rU;mA;rA;mG;rU;mG;rG;mC (SEQ ID No. 236) | 8 | | 1 |

FIG. 23 Continued

| ID | Sense | AntiSense | Activity at 20nM (% of control) | IC50 (nM) | Stability in human serum |
|---|---|---|---|---|---|
| Q-289 | rG;rC;rC;rA;rC;rU;rA;rA;rU;rG;rU;rG;rU;rU2p;rA2p;rC2p (SEQ ID No. 235) | mG;rU;mA;rA;mC;rA;mU;rA;mC;rA;mU;rU;mA;rA;mG;rU;mG;mC (SEQ ID No. 236) | 8.8 | | 1 |
| Q-290 | rG;rC;rC;rA;rC;rU;rA;rA;rU;rG;rU;rG;rU;rU;LdA;LdC (SEQ ID No. 235) | mG;rU;mA;rA;mC;rA;mU;rA;mC;rA;mU;rU;mA;rA;mG;rU;mG;mC (SEQ ID No. 236) | 5.8 | | 1 |
| Q-291 | rG;rC;rC;rA;rC;rU;rA;rA;rU;rG;rU;rG;rU;rU;LdA;LdC$ (SEQ ID No. 235) | mG;rU;mA;rA;mC;rA;mU;rA;mC;rA;mU;rU;mA;rA;mG;rU;mG;mC (SEQ ID No. 236) | 4.9 | | 1 |
| Q-292 | rG;mC;rC;mA;rC;mU;rA;mA;rU;mG;rU;mG;rU;mU;rA; rC (SEQ ID No. 235) | mG;rU;mA;rA;mC;rA;mU;rA;mC;rA;mU;rU;mA;rA;mG;rU;mG;mC$ (SEQ ID No. 236) | 6.7 | | 0 |
| Q-293 | rG;mC;rC;mA;rC;mU;rA;mA;rU;mG;rU;mG;rU;mU;rA; rC$ (SEQ ID No. 235) | mG;rU;mA;rA;mC;rA;mU;rA;mC;rA;mU;rU;mA;rA;mG;rU;mG;mC$ (SEQ ID No. 236) | 6.9 | | 0 |
| Q-294 | rG;rC;rC;rA;rC;rU;rA;rA;rU;rG;rU;rG;rU;rU2p;rA2p;rC$ (SEQ ID No. 235) | mG;rU;mA;rA;mC;rA;mU;rA;mC;rA;mU;rU;mA;rA;mG;rU;mG;mC$ (SEQ ID No. 236) | 26.5 | | 1 |
| Q-295 | rG;rC;rC;rA;rC;rU;rA;rA;rU;rG;rU;rG;rU;rU2p;rA2p;rC (SEQ ID No. 235) | mG;rU;mA;rA;mC;rA;mU;rA;mC;rA;mU;rU;mA;rA;mG;rU;mG;mC$ (SEQ ID No. 236) | 12.9 | | 1 |
| Q-296 | rG;rC;rC;rA;rC;rU;rA;rA;rU;rG;rU;rG;rU;rU2p;rA2p;rC2p (SEQ ID No. 235) | mG;rU;mA;rA;mC;rA;mU;rA;mC;rA;mU;rU;mA;rA;mG;rU;mG;mC$ (SEQ ID No. 236) | 14.5 | | 1 |
| Q-297 | rG;rC;rC;rA;rC;rU;rA;rA;rU;rG;rU;rG;rU;rU;LdA;LdC (SEQ ID No. 235) | mG;rU;mA;rA;mC;rA;mU;rA;mC;rA;mU;rU;mA;rA;mG;rU;mG;mC$ (SEQ ID No. 236) | 8.9 | | 1 |
| Q-298 | rG;rC;rC;rA;rC;rU;rA;rA;rU;rG;rU;rG;rU;rU;LdA;LdC$ (SEQ ID No. 235) | mG;rU;mA;rA;mC;rA;mU;rA;mC;rA;mU;rU;mA;rA;mG;rU;mG;mC$ (SEQ ID No. 236) | 11.9 | | 1 |
| Q-299 | rC;mG;rG;mA;rU;mU;rG;mA;rU;mG;rA;mC;rC;mA;rC;mA; rA (SEQ ID No. 13729) | mU;rU;mG;rU;mG;rU;mG;rU;mG;rC;mA;rU;mC;rA;mU;rC;mC;rC;mG (SEQ ID No. 13932) | 11 | | 6 |
| Q-300 | rC;mG;rG;mA;rU;mU;rG;mA;rU;mG;rA;mC;rC;mA;rC;mA; rA$ (SEQ ID No. 13729) | mU;rU;mG;rU;mG;rU;mG;rU;mG;rC;mA;rU;mC;rA;mU;rC;mC;rC;mG (SEQ ID No. 13932) | 4 | | 6 |
| Q-301 | rC;rG;rG;rA;rU;rU;rG;rA;rU;rG;rA;rC;rA;rC;rA;rC2p;rA2p;rA$ (SEQ ID No. 13729) | mU;rU;mG;rU;mG;rU;mG;rU;mG;rC;mA;rU;mC;rA;mU;rC;mC;rC;mG (SEQ ID No. 13932) | 3 | | 6 |
| Q-302 | rC;rG;rG;rA;rU;rU;rG;rA;rU;rG;rA;rC;rA;rC;rA;rC2p;rA2p;rA (SEQ ID No. 13729) | mU;rU;mG;rU;mG;rU;mG;rU;mG;rC;mA;rU;mC;rA;mU;rC;mC;rC;mG (SEQ ID No. 13932) | 2 | | 6 |
| Q-303 | rC;rG;rG;rA;rU;rU;rG;rA;rU;rG;rA;rC;rA;rC;rA;rC2p;rA2p;rA2p (SEQ ID No. 13729) | mU;rU;mG;rU;mG;rU;mG;rU;mG;rC;mA;rU;mC;rA;mU;rC;mC;rC;mG (SEQ ID No. 13932) | 2 | | 6 |
| Q-304 | rC;rG;rG;rA;rU;rU;rG;rA;rU;rG;rA;rC;rA;rC;rA;rC;LdA;LdA (SEQ ID No. 13729) | mU;rU;mG;rU;mG;rU;mG;rU;mG;rC;mA;rU;mC;rA;mU;rC;mC;rC;mG (SEQ ID No. 13932) | 2 | | 6 |
| Q-305 | rC;rG;rG;rA;rU;rU;rG;rA;rU;rG;rA;rC;rA;rC;rA;rC;LdA;LdA$ (SEQ ID No. 13729) | mU;rU;mG;rU;mG;rU;mG;rU;mG;rC;mA;rU;mC;rA;mU;rC;mC;rC;mG (SEQ ID No. 13932) | 2 | | 3 |
| Q-306 | rC;mG;rG;mA;rU;mU;rG;mA;rU;mG;rA;mC;rC;mA;rC;mA; rA (SEQ ID No. 13729) | mU;rU;mG;rU;mG;rU;mG;rU;mG;rC;mA;rU;mC;rA;mU;rC;mC;rC;mG$ (SEQ ID No. 13932) | 5 | | 6 |

FIG. 23 Continued

| ID | Sense | AntiSense | Activity at 20nM (% of control) | IC50 (aM) | Stability in human serum |
|---|---|---|---|---|---|
| Q-307 | rC;rG;rG;mA;rA;mU;rG;mA;rU;mG;mA;rU;mG;rA;mG;rC;mA;rC;mA;rC;mA;rA$ (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 5 | | 3 |
| Q-308 | rC;rG;rG;rA;rA;rU;rG;rA;rU;rG;rA;rU;rG;rA;rG;rC;rA;rC;rA;rC2p;rA2p;rA$ (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 5 | | 8 |
| Q-309 | rC;rG;rG;rA;rA;rU;rG;rA;rU;rG;rA;rU;rG;rA;rG;rC;rA;rC;rA;rC2p;rA2p;rA (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 3 | | 8 |
| Q-310 | rC;rG;rG;rA;rA;rU;rG;rA;rU;rG;rA;rU;rG;rA;rG;rC;rA;rC;rA;rC2p;rA2p;rU (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 2 | | 1 |
| Q-311 | rC;rG;rG;rA;rA;rU;rG;rA;rU;rG;rA;rU;rG;rC;rA;rC;rA;rC;LdA;LdA (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 2 | | 1 |
| Q-312 | rC;rG;rG;rA;rA;rU;rG;rA;rU;rG;rA;rU;rG;rC;rA;rC;rA;rC;LdA;LdA$ (SEQ ID No. 13729) | mU;rU;mG;rU;mG;rU;mG;rU;mG;rA;mU;rC;mA;rU;mC;rA;mU;rU;mC;rC;mG$ (SEQ ID No. 13932) | 3 | | 3 |
| Q-313 | rG;mA;rA;mG;rG;mA;rU;mC;rU;mC;mG;mA;rA;mU;rG;mA;rU (SEQ ID No. 13750) | mA;rU;mC;rA;mU;rU;mC;rA;mG;mA;rG;mA;rU;mC;mU;rU;mC (SEQ ID No. 13953) | 1.7 | | 24 |
| Q-314 | mA;rA;mG;rG;mA;rU;mC;rU;mC;mG;mA;rA;mU;rG;mA;rU$ (SEQ ID No. 13750) | mA;rU;mC;rA;mU;rU;mC;rA;mG;mA;rG;mA;rU;mC;mU;rU;mC (SEQ ID No. 13953) | 2.1 | | 24 |
| Q-315 | rG;rA;rA;rG;rG;rA;rU;rC;rU;rC;rG;rA;rA;rU;rG2p;rA2p;rU$ (SEQ ID No. 13750) | mA;rU;mC;rA;mU;rU;mC;rA;mG;mA;rG;mA;rU;mC;mU;rU;mC (SEQ ID No. 13953) | 3.4 | | 1 |
| Q-316 | rG;rA;rA;rG;rG;rA;rU;rC;rU;rC;rG;rA;rA;rU;rG2p;rA2p;rU (SEQ ID No. 13750) | mA;rU;mC;rA;mU;rU;mC;rA;mG;mA;rG;mA;rU;mC;mU;rU;mC (SEQ ID No. 13953) | 3.2 | | 10 |
| Q-317 | rG;rA;rA;rG;rG;rA;rU;rC;rU;rC;rG;rA;rA;rU;rG2p;rA2p;rU2p (SEQ ID No. 13750) | mA;rU;mC;rA;mU;rU;mC;rA;mG;mA;rG;mA;rU;mC;mU;rU;mC (SEQ ID No. 13953) | 3.2 | | 24 |
| Q-318 | rG;rA;rA;rG;rG;rA;rU;rC;rU;rC;rG;rA;rA;rU;LdA;LdT (SEQ ID No. 13750) | mA;rU;mC;rA;mU;rU;mC;rA;mG;mA;rG;mA;rU;mC;mU;rU;mC (SEQ ID No. 13953) | 2.2 | | 6 |
| Q-319 | rG;rA;rA;rG;rG;rA;rU;rC;rU;rC;rG;rA;rA;rU;rG;LdA;LdT$ (SEQ ID No. 13750) | mA;rU;mC;rA;mU;rU;mC;rA;mG;mA;rG;mA;rU;mC;mU;rU;mC (SEQ ID No. 13953) | 2.5 | | 6 |
| Q-320 | rG;mA;rA;mG;rG;mA;rU;mC;rU;mC;mG;mA;rA;mU;rG;mA;rU (SEQ ID No. 13750) | mA;rU;mC;rA;mU;rU;mC;rA;mG;mA;rG;mA;rU;mC;mU;rU;mC$ (SEQ ID No. 13953) | 3 | | 24 |
| Q-321 | rG;mA;rA;mG;rG;mA;rU;mC;rU;mC;mG;mA;rA;mU;rG;mA;rU$ (SEQ ID No. 13750) | mA;rU;mC;rA;mU;rU;mC;rA;mG;mA;rG;mA;rU;mC;mU;rU;mC$ (SEQ ID No. 13953) | 6 | | 24 |
| Q-322 | rG;rA;rA;rG;rA;rU;rC;rU;rC;rG;rA;rA;rU;rG2p;rA2p;rU$ (SEQ ID No. 13750) | mA;rU;mC;rA;mU;rU;mC;rA;mG;mA;rG;mA;rU;mC;mU;rU;mC (SEQ ID No. 13953) | 6 | | 10 |
| Q-323 | rG;rA;rA;rG;rG;rA;rU;rC;rU;rC;rG;rA;rA;rU;rG2p;rA2p;rU (SEQ ID No. 13750) | mA;rU;mC;rA;mU;rU;mC;rA;mG;mA;rG;mA;rU;mC;mU;rU;mC$ (SEQ ID No. 13953) | 4 | | 10 |
| Q-324 | rG;rA;rA;rG;rG;rA;rU;rC;rU;rC;rG;rA;rA;rU;rG2p;rA2p;rU2p (SEQ ID No. 13750) | mA;rU;mC;rA;mU;rU;mC;rA;mG;mA;rG;mA;rU;mC;mU;rU;mC$ (SEQ ID No. 13953) | 5 | | 16 |

FIG. 23 Continued

| ID | Sense | AntiSense | Activity at 20nM (% of control) | IC50 (nM) | Stability in human serum |
|---|---|---|---|---|---|
| Q-325 | rG;rA;rG;rA;rG;rA;rU;rC;rU;rC;rG;rA;rA;rU;rG;LdA;LdT (SEQ ID No. 13750) | mA;rU;mC;rA;mU;rU;mC;rC;mG;rA;mA;rU;mC;rC;mU;rU;mC$ (SEQ ID No. 13953) | 4 | | 3 |
| Q-326 | rG;rA;rA;rG;rG;rA;rU;rC;rU;rU;rC;rG;rA;rA;rU;rG;LdA;LdT$ (SEQ ID No. 13750) | mA;rU;mC;rA;mU;rU;mC;rC;mG;rA;mA;rU;mC;rC;mU;rU;mC$ (SEQ ID No. 13953) | 4 | | 10 |
| Q-327 | rU;mC;rG;mA;rC;mA;rG;mC;rC;mC;rU;mG;rA;mU;rA;mG;rU;mU;rU (SEQ ID No. 13798) | mA;rA;mA;rC;mU;rA;mU;rC;mA;rG;mG;rG;mC;rU;mG;rU;mC;rG;mA (SEQ ID No. 14001) | | | 24 |
| Q-328 | rU;mC;rG;mA;rC;mA;rG;mC;rC;mC;rU;mG;rA;mU;rA;mG;rU;mU;rU$ (SEQ ID No. 13798) | mA;rA;mA;rC;mU;rA;mU;rC;mA;rG;mG;rG;mC;rU;mG;rU;mC;rG;mA (SEQ ID No. 14001) | | | 24 |
| Q-329 | rU;rC;rG;rA;rC;rA;rG;rC;rC;rC;rU;rG;rA;rU;rA;rG;rU;rU;rU$ (SEQ ID No. 13798) | mA;rA;mA;rC;mU;rA;mU;rC;mA;rG;mG;rG;mC;rU;mG;rU;mC;rG;mA (SEQ ID No. 14001) | | | 0 |
| Q-330 | rU;rC;rG;rA;rC;rA;rG;rC;rC;rC;rU;rG;rA;rU;rA;rG;rU2p;rU2p;rU (SEQ ID No. 13798) | mA;rA;mA;rC;mU;rA;mU;rC;mA;rG;mG;rG;mC;rU;mG;rU;mC;rG;mA (SEQ ID No. 14001) | | | 0 |
| Q-331 | rU;rC;rG;rA;rC;rA;rG;rC;rC;rC;rU;rG;rA;rU;rA;rG;rU2p;rU2p;rU2p (SEQ ID No. 13798) | mA;rA;mA;rC;mU;rA;mU;rC;mA;rG;mG;rG;mC;rU;mG;rU;mC;rG;mA (SEQ ID No. 14001) | | | 0 |
| Q-332 | rU;rC;rG;rA;rC;rA;rG;rC;rC;rC;rU;rG;rA;rU;rA;rG;rU;LdT;LdT (SEQ ID No. 13798) | mA;rA;mA;rC;mU;rA;mU;rC;mA;rG;mG;rG;mC;rU;mG;rU;mC;rG;mA (SEQ ID No. 14001) | | | 0 |
| Q-333 | rU;rC;rG;rA;rC;rA;rG;rC;rC;rC;rU;rG;rA;rU;rA;rG;rU;LdT;LdT$ (SEQ ID No. 13798) | mA;rA;mA;rC;mU;rA;mU;rC;mA;rG;mG;rG;mC;rU;mG;rU;mC;rG;mA (SEQ ID No. 14001) | | | 24 |
| Q-334 | rU;mC;rG;mA;rC;mA;rG;mC;rC;mC;rU;mG;rA;mU;rA;mG;rU;mU;rU (SEQ ID No. 13798) | mA;rA;mA;rC;mU;rA;mU;rC;mA;rG;mG;rG;mC;rU;mG;rU;mC;rG;mA$ (SEQ ID No. 14001) | | | 24 |
| Q-335 | rU;mC;rG;mA;rC;mA;rG;mC;rC;mC;rU;mG;rA;mU;rA;mG;rU;mU;rU$ (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-336 | rU;rC;rG;rA;rC;rA;rG;rC;rC;rC;rU;rG;rA;rU;rA;rG;rU2p;rU2p;rU$ (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-337 | rU;rC;rG;rA;rC;rA;rG;rC;rC;rC;rU;rG;rA;rU;rA;rG;rU2p;rU2p;rU (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-338 | rU;rC;rG;rA;rC;rA;rG;rC;rC;rC;rU;rG;rA;rU;rA;rG;rU2p;rU2p;rU2p (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-339 | rU;rC;rG;rA;rC;rA;rG;rC;rC;rC;rU;rG;rA;rU;rA;rG;rU;LdT;LdT (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-340 | rU;rC;rG;rA;rC;rA;rG;rC;rC;rC;rU;rG;rA;rU;rA;rG;rU;LdT;LdT$ (SEQ ID No. 13798) | mA;rA;mA;rC;mU;rA;mU;rC;mA;rG;mG;rG;mC;rU;mG;rU;mC;rG;mA$ (SEQ ID No. 14001) | | | 0 |
| Q-341 | rC;mU;rA;mC;rA;mG;rA;mA;rC;mA;rC;mA;rA;rC;mC;rA;mA;rA;mA;r A (SEQ ID No. 2210) | mU;rU;mU;rU;mU;rG;mG;rU;mU;rG;rU;mG;rU;mU;rC;mU;rG;mU;rA;mG (SEQ ID No. 2710) | 11 | | 24 |
| Q-342 | rC;mU;rA;mC;rA;mG;rA;mA;rC;mA;rC;mA;rA;mC;mC;rA;mA;rA;mA;r A$ (SEQ ID No. 2210) | mU;rU;mU;rU;mU;rG;mG;rU;mU;rG;rU;mG;rU;mU;rC;mU;rG;mU;rA;mG (SEQ ID No. 2710) | 10 | | 24 |

FIG. 23 Continued

| ID | Sense | AntiSense | Activity at 20nM (% of control) | IC50 (nM) | Stability in human serum |
|---|---|---|---|---|---|
| Q-343 | rC;rU;rA;rC;rA;rG;rA;rA;rC;rA;rA;rA;rC;rA;rA;rA2p;rA2p;rA$ (SEQ ID No. 2210) | mU;rU;mU;rU;mU;rG;mG;rU;mU;rU;mU;rC;mU;rG;mU;rA;mG (SEQ ID No. 2710) | 14 | | 1 |
| Q-344 | rC;rU;rA;rC;rA;rG;rA;rA;rC;rA;rA;rA;rC;rA;rA;rA2p;rA2p;rA (SEQ ID No. 2210) | mU;rU;mU;rU;mU;rG;mG;rU;mU;rU;mU;rC;mU;rG;mU;rA;mG (SEQ ID No. 2710) | 11 | | 1 |
| Q-345 | rC;rU;rA;rC;rA;rG;rA;rA;rC;rA;rA;rA;rC;rA;rA;rA2p;rA2p;rA2p (SEQ ID No. 2210) | mU;rU;mU;rU;mU;rG;mG;rU;mU;rU;mU;rC;mU;rG;mU;rA;mG (SEQ ID No. 2710) | 8 | | 1 |
| Q-346 | rC;rU;rA;rC;rA;rG;rA;rA;rC;rA;rA;rA;rC;rA;rA;rA;LdA;LdA (SEQ ID No. 2210) | mU;rU;mU;rU;mU;rG;mG;rU;mU;rU;mU;rC;mU;rG;mU;rA;mG (SEQ ID No. 2710) | 13 | | 1 |
| Q-347 | rC;rU;rA;rC;rA;rG;rA;rA;rC;rA;rA;rA;rC;rA;rA;rA;LdA;LdA$ (SEQ ID No. 2210) | mU;rU;mU;rU;mU;rG;mG;rU;mU;rU;mU;rC;mU;rG;mU;rA;mG$ (SEQ ID No. 2710) | 11 | | 1 |
| Q-348 | rC;mU;rA;mC;rA;mG;rA;mA;rC;rA;mA;rA;mC;rA;mA;rA (SEQ ID No. 2210) | mU;rU;mU;rU;mU;rG;mG;rU;mU;rU;mU;rC;mU;rG;mU;rA;mG$ (SEQ ID No. 2710) | 5 | | 24 |
| Q-349 | rC;mU;rA;mC;rA;mG;rA;mA;rC;rA;mA;rA;mC;rA;mA;rA$ (SEQ ID No. 2210) | mU;rU;mU;rU;mU;rG;mG;rU;mU;rU;mU;rC;mU;rG;mU;rA;mG$ (SEQ ID No. 2710) | 6 | | 24 |
| Q-350 | rC;rU;rA;rC;rA;rG;rA;rA;rC;rA;rA;rA;rC;rA;rA;rA;rA2p;rA2p;rA$ (SEQ ID No. 2210) | mU;rU;mU;rU;mU;rG;mG;rU;mU;rU;mU;rC;mU;rG;mU;rA;mG$ (SEQ ID No. 2710) | 16 | | 0 |
| Q-351 | rC;rU;rA;rC;rA;rG;rA;rA;rC;rA;rA;rA;rC;rA;rA;rA;rA2p;rA2p;rA (SEQ ID No. 2210) | mU;rU;mU;rU;mU;rG;mG;rU;mU;rU;mU;rC;mU;rG;mU;rA;mG$ (SEQ ID No. 2710) | 12 | | 0 |
| Q-352 | rC;rU;rA;rC;rA;rG;rA;rA;rC;rA;rA;rA;rC;rA;rA;rA;rA2p;rA2p;rA2p (SEQ ID No. 2210) | mU;rU;mU;rU;mU;rG;mG;rU;mU;rU;mU;rC;mU;rG;mU;rA;mG$ (SEQ ID No. 2710) | 11 | | 0 |
| Q-353 | rC;rU;rA;rC;rA;rG;rA;rA;rC;rA;rA;rA;rC;rA;rA;rA;LdA;LdA (SEQ ID No. 2210) | mU;rU;mU;rU;mU;rG;mG;rU;mU;rU;mU;rC;mU;rG;mU;rA;mG$ (SEQ ID No. 2710) | 14 | | 1 |
| Q-354 | rC;rU;rA;rC;rA;rG;rA;rA;rC;rA;rA;rA;rC;rA;rA;rA;LdA;LdA$ (SEQ ID No. 2210) | mU;rU;mU;rU;mU;rG;mG;rU;mU;rU;mU;rC;mU;rG;mU;rA;mG$ (SEQ ID No. 2710) | 12 | | 1 |
| Q-355 | rG;mG;rA;mU;rU;rC;mA;rU;mG;rC;mA;rU;mG;rC;mA;rU;mG;rC;mA; rA (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 39 | | 10 |
| Q-356 | rG;mG;rA;mU;rC;mA;rU;mG;rU;mA;rA;mG;rU;mA;rU;mG;rC;mA; rA$ (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 25 | | 10 |
| Q-357 | rG;rG;rA;rU;rC;rA;rU;rG;rU;rA;rU;rA;rU;rU;rC;rC2p;rU;rC2p;rA2p;rA$ (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 100 | | 0 |
| Q-358 | rG;rG;rA;rU;rC;rA;rU;rG;rU;rA;rU;rA;rU;rU;rC;rC2p;rU;rC2p;rA2p;rA (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 100 | | 0 |
| Q-359 | rG;rG;rA;rU;rC;rA;rU;rG;rU;rA;rU;rA;rU;rU;rC;rC2p;rU;rC2p;rA2p;rA2p (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 100 | | 0 |
| Q-360 | rG;rG;rA;rU;rC;rA;rU;rG;rU;rA;rU;rA;rU;rU;rC;rC;LdA;LdA (SEQ ID No. 2101) | mU;rU;mU;rU;mG;rA;mG;rC;mA;rU;mG;rA;mU;rC;mA;rU;mG;rA;mU;rC;mC (SEQ ID No. 2601) | 91 | | 1 |

FIG. 23 Continued

| ID | Sense | AntiSense | Activity at 20nM (% of control) | IC50 (nM) | Stability in human serum |
|---|---|---|---|---|---|
| Q-361 | rG;rG;rU;rC;rA;rU;rG;rU;rA;rA;rA;rU;rG;rU;rC;LdA;LdA$ (SEQ ID No. 2101) | mU;rU;mG;rA;mG;rC;mA;rU;mU;rU;mA;rC;mA;rU;mG;rA;mU;rC;mC (SEQ ID No. 2601) | 68 | | 0 |
| Q-362 | rG;mG;rA;mU;rC;mA;rU;mG;rU;mA;rA;mA;rU;mG;rC;mU;rC;mA;rA (SEQ ID No. 2101) | mU;rU;mG;rA;mG;rC;mA;rU;mU;rU;mA;rC;mA;rU;mG;rA;mU;rC;mC$ (SEQ ID No. 2601) | 32 | | 10 |
| Q-363 | rG;mG;rA;mU;rC;mA;rU;mG;rU;mA;rA;mA;rU;mG;rC;mU;rC;mA;rA$ (SEQ ID No. 2101) | mU;rU;mG;rA;mG;rC;mA;rU;mU;rU;mA;rC;mA;rU;mG;rA;mU;rC;mC$ (SEQ ID No. 2601) | 45 | | 10 |
| Q-364 | rG;rG;rA;rU;rC;rA;rU;rG;rU;rA;rA;rA;rU;rG;rC;rU;rC;C2p;rA$ (SEQ ID No. 2101) | mU;rU;mG;rA;mG;rC;mA;rU;mU;rU;mA;rC;mA;rU;mG;rA;mU;rC;mC$ (SEQ ID No. 2601) | 100 | | 0 |
| Q-365 | rG;rG;rA;rU;rC;rA;rU;rG;rU;rA;rA;rA;rU;rG;rC;rU;rC;C2p;rA2p;rA (SEQ ID No. 2101) | mU;rU;mG;rA;mG;rC;mA;rU;mU;rU;mA;rC;mA;rU;mG;rA;mU;rC;mC$ (SEQ ID No. 2601) | 67 | | 0 |
| Q-366 | rG;rG;rA;rU;rC;rA;rU;rG;rU;rA;rA;rA;rU;rG;rC;rU;rC;C2p;rA2p;rA2p (SEQ ID No. 2101) | mU;rU;mG;rA;mG;rC;mA;rU;mU;rU;mA;rC;mA;rU;mG;rA;mU;rC;mC$ (SEQ ID No. 2601) | 73 | | 0 |
| Q-367 | rG;rG;rA;rU;rC;rA;rU;rG;rU;rA;rA;rA;rU;rG;rC;rU;rC;LdA (SEQ ID No. 2101) | mU;rU;mG;rA;mG;rC;mA;rU;mU;rU;mA;rC;mA;rU;mG;rA;mU;rC;mC$ (SEQ ID No. 2601) | 88 | | 1 |
| Q-368 | rG;rG;rA;rU;rC;rA;rU;rG;rU;rA;rA;rA;rU;rG;rC;rU;rC;LdA;LdA (SEQ ID No. 2101) | mU;rU;mG;rA;mG;rC;mA;rU;mU;rU;mA;rC;mA;rU;mG;rA;mU;rC;mC$ (SEQ ID No. 2601) | 71 | | 0.5 |
| Q-369 | rG;rA;rG;rU;rC;rC;rU;rG;rC;rA;rU;rU;rU;rG;rA2p;rA2p$ (SEQ ID No. 211) | mU;rU;mC;rA;mA;rA;mU;rG;mC;rA;mG;rG;mA;rC;mU;rC;mC$ (SEQ ID No. 212) | 52 | | 0 |
| Q-370 | rG;rA;rG;rU;rC;rC;rU;rG;rC;rA;rU;rU;rU;rG;rA2p;rA2p;rA2p (SEQ ID No. 211) | mU;rU;mC;rA;mA;rA;mU;rG;mC;rA;mG;rG;mA;rC;mU;rC;mC$ (SEQ ID No. 212) | 55 | | 0 |
| Q-371 | rG;rA;rG;rU;rC;rC;rU;rG;rC;rA;rU;rU;rU;rG;LdA;LdA (SEQ ID No. 211) | mU;rU;mC;rA;mA;rA;mU;rG;mC;rA;mG;rG;mA;rC;mU;rC;mC$ (SEQ ID No. 212) | 40 | | 0 |
| Q-372 | rG;rA;rG;rU;rC;rC;rU;rG;rC;rA;rU;rU;rU;rG;LdA;LdA$ (SEQ ID No. 211) | mU;rU;mC;rA;mA;rA;mU;rG;mC;rA;mG;rG;mA;rC;mU;rC;mC$ (SEQ ID No. 212) | 40 | | 0 |
| Q-373 | mG;mA;mG;mU;mC;rC;rU;rG;rC;rA;rU;rU;rU;rG;LdA;LdA (SEQ ID No. 211) | mU;rU;mC;rA;mA;rA;mU;rG;mC;rA;mG;rG;mA;rC;mU;rC;mC$ (SEQ ID No. 212) | 53 | | 0 |
| Q-374 | mG;mA;mG;mU;mC;rC;rU;rG;rC;rA;rU;rU;rU;rG;LdA;LdA$ (SEQ ID No. 211) | mU;rU;mC;rA;mA;rA;mU;rG;mC;rA;mG;rG;mA;rC;mU;rC;mC$ (SEQ ID No. 212) | 39 | | 0 |
| Q-375 | rU;rC;rC;rC;rU;rG;rU;rU;rU;rG;rA;rU;rG;rA;rU;rC;rA2p;rA2p$ (SEQ ID No. 87232) | mU;rU;mG;rA;mU;rC;mA;rU;mC;rA;mA;rA;mC;rA;mG;rG;mA$ (SEQ ID No. 87233) | 12 | | 0 |
| Q-376 | rU;rC;rC;rC;rU;rG;rU;rU;rU;rG;rA;rU;rG;rA;rU;rC;rA2p (SEQ ID No. 87232) | mU;rU;mG;rA;mU;rC;mA;rU;mC;rA;mA;rA;mC;rA;mG;rG;mA$ (SEQ ID No. 87233) | 15 | | 8 |
| Q-377 | rU;rC;rC;rC;rU;rG;rU;rU;rU;rG;rA;rU;rG;rA;rU;rC;LdA;LdA (SEQ ID No. 87232) | mU;rU;mG;rA;mU;rC;mA;rU;mC;rA;mA;rA;mC;rA;mG;rG;mA$ (SEQ ID No. 87233) | 13 | | 0 |
| Q-378 | rU;rC;rC;rC;rU;rG;rU;rU;rU;rG;rA;rU;rG;rA;rU;rC;LdA;LdA$ (SEQ ID No. 87232) | mU;rU;mG;rA;mU;rC;mA;rU;mC;rA;mA;rA;mC;rA;mG;rG;mA$ (SEQ ID No. 87233) | 9 | | 0 |

FIG. 23 Continued

| ID | Sense | AntiSense | Activity at 20nM (% of control) | IC50 (nM) | Stability in human serum |
|---|---|---|---|---|---|
| Q-379 | rU;mC;mC;mC;mG;rU;rU;rU;rA;rA;rG;rA;rU;rG;rA;rC;LdA;Ld A (SEQ ID No. 87232) | mU;rU;mG;rU;rU;rC;mU;rA;mC;rA;mA;rA;mC;rA;mC;rG;mG;rG;mA$ (SEQ ID No. 87233) | 13 | | 1 |
| Q-380 | mU;mC;mC;mC;mG;rU;rU;rU;rG;rU;rG;rA;rA;rG;rA;rU;rG;rA;rC;LdA;Ld A$ (SEQ ID No. 87232) | mU;rU;mG;rU;rU;rC;mU;rA;mC;rA;mA;rA;mC;rA;mC;rG;mG;rG;mA$ (SEQ ID No. 87233) | 21 | | 1 |
| Q-381 | rU;rC;rC;rC;rG;rU;rU;rU;rG;rU;rG;rA;rU;rG;rA;dCpac;dApac;rA$ (SEQ ID No. 87232) | mU;rU;mG;rU;rU;rC;mU;rA;mC;rA;mA;rA;mC;rA;mC;rG;mG;rG;mA$ (SEQ ID No. 87233) | 5 | | 0 |
| Q-382 | dTpac;dCpac;rC;rC;rG;rU;rU;rU;rG;rU;rA;rG;rA;rU;rG;rA;rC;rA;rA (SEQ ID No. 87232) | mU;rU;mG;rU;rU;rC;mU;rA;mC;rA;mA;rA;mC;rA;mC;rG;mG;rG;mA$ (SEQ ID No. 87233) | 22 | | 0 |
| Q-383 | dTpac;dCpac;rC;rG;rU;rU;rU;rG;rU;rA;rG;rA;rU;rG;rG;rA;dCpac;d Apac;rA$ (SEQ ID No. 87232) | mU;rU;mG;rU;rU;rC;mU;rA;mC;rA;mA;rA;mC;rA;mC;rG;mG;rG;mA$ (SEQ ID No. 87233) | 8 | | 1 |
| Q-384 | rU;rC;rC;rC;rG;rU;rU;rU;rG;rU;rA;rG;rA;rU;rG;rA;dApac;dCpac;rA;rA$ (SEQ ID No. 87232) | mU;rU;mG;rU;rU;rC;mU;rA;mC;rA;mA;rA;mC;rA;mC;rG;mG;rG;mA$ (SEQ ID No. 87233) | 7 | | 1 |
| Q-385 | mU;mC;mC;mC;mG;rU;rU;rU;rG;rU;rA;rG;rA;rU;rG;rA;rC;rA;rA$ (SEQ ID No. 87232) | mU;rU;mG;rU;rU;rC;mU;rA;mC;rA;mA;rA;mC;rA;mC;rG;mG;rG;mA$ (SEQ ID No. 87233) | 9 | | 1 |
| Q-386 | rU;rC;rC;rC;rG;rU;rU;rU;rG;rU;rA;rG;rA;rU;rG;rA;rC;dApac;rA;rA$ (SEQ ID No. 87232) | mU;rU;mG;rU;rU;rC;mU;rA;mC;rA;mA;rA;mC;rA;mC;rG;mG;rG;mA$ (SEQ ID No. 87233) | 7 | | 1 |
| Q-387 | dTpac;dCpac;rC;rG;rU;rU;rU;rG;rU;rA;rG;rA;rU;rC;rA;dCpac;dApac;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 15 | | 0 |
| Q-388 | dTpac;dCpac;rC;rC;rG;rU;rG;rU;rA;rG;rA;rU;rG;rA;rC;rA;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 16 | | 1 |
| Q-389 | dTpac;dCpac;rC;rG;rU;rU;rU;rG;rU;rA;rG;rA;rU;rG;rA;dCpac;dApac;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 49 | | 0 |
| Q-390 | rU;rC;rC;rC;rG;rU;rU;rU;rG;rU;rA;rG;rA;rU;rG;dApac;dCpac;rA;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 25 | | 0 |
| Q-391 | rU;rC;rC;rC;rG;rU;rU;rG;rU;rA;rG;rA;rU;rG;rA;rC;dApac;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 49 | | 0 |
| Q-392 | rU;rC;rC;rC;rG;rU;rU;rU;rG;rU;rA;rG;rA;rC;dCpac;rA;rA$ (SEQ ID No. 87232) | rU;rU;rG;rU;rU;rC;rU;rA;rC;rA;rA;rA;rC;rA;rC;rG;dGpac;dGpac;rA$ (SEQ ID No. 87233) | 49 | | 1 |
| Q-393 | rG;rC;rC;rA;rG;rA;rA;rU;rG;rU;rG;dG;dA;dC;dT;dC;dC;dT$ (SEQ ID No. 139) | dA;dG;dG;dA;dG;dT;dT;dC;rC;rA;rC;rA;rU;rU;rC;rU;rG;rG;rC$ (SEQ ID No. 140) | 93 | | 10 |
| Q-394 | rG;rC;rC;rA;rG;rA;rA;rU;rG;rU;rG;rG;dA;dC;dT;dC;dC;dT$ (SEQ ID No. 139) | dA;dG;dG;dA;dG;dT;rC;rC;rA;rC;rA;rU;rU;rC;rU;rG;rG;rC$ (SEQ ID No. 140) | 121 | | 10 |
| Q-395 | rG;rC;rC;rA;rG;rA;rA;rU;rG;rU;rG;rG;rA;dC;dT;dC;dC;dT$ (SEQ ID No. 139) | dA;dG;dG;dA;dG;dT;dT;rC;rA;rC;rA;rU;rU;rC;rU;rG;rG;rC$ (SEQ ID No. 140) | 74 | | 10 |
| Q-396 | rG;rC;rC;rA;rG;rA;rA;rU;rG;rU;rG;rG;dA;dC;dC;dC;dT$ (SEQ ID No. 139) | dA;dG;dG;dA;dG;rU;rC;rC;rA;rC;rA;rU;rU;rC;rU;rG;rG;rC$ (SEQ ID No. 140) | 83 | | 10 |

FIG. 23 Continued

| ID | Sense | AntiSense | Activity at 20nM (% of control) | IC50 (nM) | Stability in human serum |
|---|---|---|---|---|---|
| Q-397 | rG;rC;rC;rA;rG;rA;rG;rU;rG;dA;dG;dA;dC;dT;dC;dC;dT$ (SEQ ID No. 139) | dA;dG;dG;dA;dG;rU;rC;rU;rC;rA;rC;rU;rC;rU;rG;dG;dG;dC$ (SEQ ID No. 140) | 85 | | 3 |
| Q-398 | rG;rC;rC;rA;rG;rA;rG;rU;rG;dA;dA;dG;dA;dC;dT;dC;dC;dT$ (SEQ ID No. 139) | dA;dG;dG;dA;dG;rU;rC;rU;rU;rC;rA;rC;rU;rC;rU;rG;rG;rC$ (SEQ ID No. 140) | 83 | | 16 |
| Q-399 | rG;rC;rC;rA;rG;rA;rG;rU;rG;dA;dA;dG;dA;dC;dT;dC;dC;dT$ (SEQ ID No. 139) | dA;dG;dG;dA;dG;dT;dT;rC;rU;rC;rA;rC;rU;rC;rU;rG;rG;rC$ (SEQ ID No. 140) | 127 | | 10 |
| Q-400 | rG;rC;rC;rA;rG;rA;rG;rU;rG;dA;dA;dG;dA;dC;dT;dC;dC;dT$ (SEQ ID No. 139) | dA;dG;dG;dA;dG;dT;rU;rC;rU;rC;rA;rC;rU;rC;rU;rG;rG;rC$ (SEQ ID No. 140) | 151 | | 10 |
| Q-401 | rG;rC;rC;rA;rG;rA;rG;rU;rG;dA;dA;dG;dA;dC;dT;dC;dC;dT$ (SEQ ID No. 139) | dA;dG;dG;dA;dG;rU;rC;rU;rC;rA;rC;rU;rC;rU;rG;rG;rC$ (SEQ ID No. 140) | 73 | | 10 |
| Q-402 | rG;rC;rC;rA;rG;rA;rG;rU;rG;rA;dA;dA;dC;dA;dC;dT;dC;dC;dT$ (SEQ ID No. 139) | dA;dG;dG;dA;dG;rU;rC;rU;rC;rA;rC;rU;rC;rU;dG;dG;dC$ (SEQ ID No. 140) | 27 | | 10 |
| Q-403 | rG;rC;rC;rA;rG;rA;rG;rU;rG;rA;dA;dG;dA;dC;dT;dC;dC;dT$ (SEQ ID No. 139) | dA;dG;dG;dA;dG;rU;rC;rU;rC;rA;rC;rU;rC;rU;rG;rG;rC$ (SEQ ID No. 140) | 35 | | 10 |
| Q-404 | rG;rC;rC;rA;rG;rA;rG;rU;rG;rA;rA;dG;dA;dC;dT;dC;dC;dT$ (SEQ ID No. 139) | dA;dG;dG;dA;dG;rU;rC;rU;rC;rA;rC;rU;rC;rU;rG;rG;rC$ (SEQ ID No. 140) | 15 | | 10 |
| Q-405 | rG;rC;rC;rA;rG;rA;rG;rU;rG;rA;rA;rG;dA;dC;dT;dC;dC;dT$ (SEQ ID No. 139) | dA;dG;dG;dA;dG;rU;rC;rU;rC;rA;rC;rU;rC;rU;rG;rG;rC$ (SEQ ID No. 140) | 23 | | 10 |
| Q-406 | rG;rC;rC;rA;rG;rA;rG;rU;rG;rA;rA;rG;rA;dC;dT;dC;dC;dT$ (SEQ ID No. 139) | dA;dG;dG;dA;dG;rU;rC;rU;rC;rA;rC;rU;rC;rU;rG;rG;rC$ (SEQ ID No. 140) | 21 | | 10 |
| Q-407 | rG;rC;rC;rA;rG;rA;rG;rU;rG;rA;rA;rG;rA;rC;dT;dC;dC;dT$ (SEQ ID No. 139) | dA;dG;dG;dA;dG;rU;rC;rU;rC;rA;rC;rU;rC;dT;dG;dG;dC$ (SEQ ID No. 140) | 28 | | 1 |
| Q-408 | dG;dC;dC;dA;dG;dA;dG;dA;rA;rU;rG;rC;rU;rC;rU$ (SEQ ID No. 139) | dA;dG;dG;dA;dG;rU;rU;rC;rU;rC;rA;rU;rU;rC;rU;rG;rG;rC$ (SEQ ID No. 140) | 39 | | 1 |
| Q-409 | dG;dC;dC;dC;dA;dG;dA;dG;dA;rA;rU;rG;rC;rU;rC;rU$ (SEQ ID No. 139) | dA;dG;dG;dA;dG;dT;dT;rC;rU;rC;rA;rC;rU;rC;rU;rG;rG;rC$ (SEQ ID No. 140) | 56 | | 0.5 |
| Q-410 | dG;dC;dC;dA;dG;dA;dG;dA;rA;rU;rG;rC;rU;rC;rU$ (SEQ ID No. 139) | dA;dG;dG;dA;dG;dT;rU;rC;rU;rC;rA;rC;rU;rC;rU;rG;rG;rC$ (SEQ ID No. 140) | 51 | | 10 |
| Q-411 | dG;dC;dC;dA;dG;dA;dG;dA;rA;rU;rG;rC;rU;rC;rU$ (SEQ ID No. 139) | dA;dG;dG;dA;dG;rU;rC;rU;rC;rA;rC;rU;rC;rU;rG;rG;rC$ (SEQ ID No. 140) | 50 | | 0 |
| Q-412 | dG;dC;dC;dA;dG;dA;dG;rA;rA;rU;rG;rC;rU;rC;rU$ (SEQ ID No. 139) | dA;dG;dG;dA;dG;dT;rA;rC;rU;rC;rA;rC;rU;rU;rG;rG;rC$ (SEQ ID No. 140) | 109 | | 3 |
| Q-413 | dG;dC;dC;dA;dG;dA;rG;rA;rA;rU;rG;rG;rA;dC;dT;dC;dC;dT$ (SEQ ID No. 139) | dA;dG;dG;dA;dG;dT;dT;rC;rU;rC;rA;rC;rU;rU;rG;rG;rC$ (SEQ ID No. 140) | 94 | | 0.5 |
| Q-414 | dG;dC;dC;dA;dG;dA;rG;rU;rG;rA;rA;dC;dA;dC;dT;dC;dC;dT$ (SEQ ID No. 139) | dA;dG;dG;dA;dG;dT;dT;rC;rU;rC;rA;rC;rU;rU;rC;rG;rG;rC$ (SEQ ID No. 140) | 118 | | 0.5 |

FIG. 23 Continued

| ID | Sense | AntiSense | Activity at 20nM (% of control) | IC50 (nM) | Stability in human serum |
|---|---|---|---|---|---|
| Q-415 | dG;dC;dC;dA;dG;dA;rA;rU;rG;rA;rU;rG;rA;dA;dC;dT;dC;dC;dT$ (SEQ ID No. 139) | dA;dG;dG;dA;dG;dT;rU;rC;rC;rA;rC;rA;rU;rC;rA;rU;rC;rU;rG;rG;rC$ (SEQ ID No. 140) | 100 | | 0 |
| Q-416 | dG;dC;dC;dC;dA;dG;dA;rA;rU;rG;rA;rU;rG;rA;dA;dC;dT;dC;dC;dT$ (SEQ ID No. 139) | dA;dG;dG;dA;dG;dG;rU;rU;rC;rC;rA;rC;rA;rU;rC;rA;rU;rC;rU;rG;rC$ (SEQ ID No. 140) | 73 | | 0 |
| Q-417 | dG;dC;dC;dC;dA;dG;dA;rA;rU;rG;rA;rU;rG;rA;dA;dC;dT;dC;dC;dT$ (SEQ ID No. 139) | dA;dG;dG;dA;dG;dG;rU;rU;rC;rC;rA;rC;rA;rU;rU;rC;dT;dG;dG;dC$ (SEQ ID No. 140) | 94 | | 10 |
| Q-418 | dG;dC;dC;dC;dA;dG;dA;rA;rU;rG;rA;rU;rG;rA;dA;dA;dC;dT;dC;dC;dT$ (SEQ ID No. 139) | dA;dG;dG;dA;dG;dG;dT;dC;dC;rA;rC;rA;rU;rC;rA;rU;rC;rU;rG;rG;rC$ (SEQ ID No. 140) | 122 | | 8 |
| Q-419 | dG;dC;dC;dC;dA;dG;dA;rA;rU;rG;rA;rU;rG;rG;dA;dA;dC;dT;dC;dC;dT$ (SEQ ID No. 139) | dA;dG;dG;dA;dG;dG;dT;dT;rC;rC;rA;rC;rA;rU;rC;rA;rU;rC;rU;rG;rG;rC$ (SEQ ID No. 140) | 76 | | 10 |
| Q-420 | dG;dC;dC;dC;dA;dG;dA;dG;rA;rA;rU;rG;rA;rU;rG;rG;dA;dA;dC;dT;dC;dC;dT$ (SEQ ID No. 139) | dA;dG;dG;dG;dG;dA;dT;rU;rC;rC;rA;rC;rA;rU;rC;rA;rU;rC;rU;rG;rG;rC$ (SEQ ID No. 140) | 106 | | 10 |
| Q-421 | dG;dC;dC;dC;dA;dG;rA;rA;rU;rG;rA;rU;rG;rA;dA;dA;dC;dT;dC;dC;dT$ (SEQ ID No. 139) | dA;dG;dG;dA;dG;dA;rU;rU;rC;rC;rA;rC;rA;rU;rC;rA;rU;rC;rU;rG;rG;rC$ (SEQ ID No. 140) | 109 | | 0 |
| Q-422 | dG;dC;dC;dC;dA;dG;dA;rA;rU;rG;rA;rU;rG;rA;dA;dA;dC;dT;dC;dC;dT$ (SEQ ID No. 139) | dA;dG;dG;dA;dG;dG;rU;rU;rU;rC;rC;rA;rC;rA;rU;rC;rA;rU;rC;rU;dT;dG;dG;dC$ (SEQ ID No. 140) | 134 | | 16 |
| Q-423 | enaT;rC;rC;rC;rU;rU;rU;rU;rG;rA;rU;rA;rG;rA;rC;rU;rG;rA;rC;rA;rA$ (SEQ ID No. 87232) | mU;rU;mG;rU;mC;rA;mU;rC;mU;rC;mU;rA;mC;rA;mA;rA;mC;rA;mC;rG;mG;rG$ (SEQ ID No. 87233) | 30 | | 0.5 |
| Q-424 | enaT;enaC;rC;rC;rG;rU;rU;rU;rU;rG;rA;rU;rA;rG;rA;rC;rU;rG;rA;rC;rA;rA$ (SEQ ID No. 87232) | mU;rU;mG;rU;mC;rA;mU;rC;mU;rC;mU;rA;mC;rA;mA;rA;mC;rA;mC;rG;mG;rG$ (SEQ ID No. 87233) | 36 | | 0.5 |
| Q-425 | enaT;enaC;enaC;rC;rG;rU;rU;rU;rU;rG;rA;rU;rA;rG;rA;rC;rU;rG;rA;rC;rA;r A$ (SEQ ID No. 87232) | mU;rU;mG;rU;mC;rA;mU;rC;mU;rC;mU;rA;mC;rA;mA;rA;mC;rA;mC;rG;mG;rG;mA$ (SEQ ID No. 87233) | 45 | | 0.5 |
| Q-426 | enaT;enaC;enaC;rC;rG;rU;rU;rU;rU;rG;rA;rU;rA;rG;rA;rU;rG;rA;rC;LdA;LdA$ (SEQ ID No. 87232) | mU;rU;mG;rU;mC;rA;mU;rC;mU;rC;mU;rA;mC;rA;mA;rA;mC;rA;mC;rG;mG;rG;mA$ (SEQ ID No. 87233) | 6 | | 0.5 |
| Q-427 | enaT;enaC;enaC;rC;rG;rU;rU;rU;rU;rG;rA;rU;rA;rG;rA;rU;rG;rA;LdC;Ld A;rA$ (SEQ ID No. 87232) | mU;rU;mG;rU;mC;rA;mU;rC;mU;rC;mU;rA;mC;rA;mA;rA;mC;rA;mC;rG;mG;rG;mA$ (SEQ ID No. 87233) | 24 | | 6 |
| Q-428 | enaT;enaC;enaC;rC;rG;rU;rU;rU;rU;rG;rU;rA;rG;rA;rU;rG;rA;rC2p; A2p;rA$ (SEQ ID No. 87232) | mU;rU;mG;rU;mC;rA;mU;rC;mU;rC;mU;rA;mC;rA;mA;rA;mC;rA;mC;rG;mG;rG;mA$ (SEQ ID No. 87233) | 11 | | 6 |
| Q-429 | enaT;enaC;enaC;rC;rG;rU;rU;rU;rU;rG;rU;rA;rG;rA;rU;rA;rC;rU;rG;rA2p;rC2p ;rA;rA$ (SEQ ID No. 87232) | mU;rU;mG;rU;mC;rA;mU;rC;mU;rC;mU;rA;mC;rA;mA;rA;mC;rA;mC;rG;mG;rG;mA$ (SEQ ID No. 87233) | 31 | | 6 |
| Q-430 | enaT;rC;rC;rC;rG;rU;rU;rU;rU;rG;rU;rA;rG;rA;rU;rG;rA;rC;rA;rA$ (SEQ ID No. 87232) | rU;rU;rG;rU;rC;rA;rU;rC;rU;rC;rU;rA;rC;rA;rA;rA;rC;rG;rG;enaG;enaA$ (SEQ ID No. 87233) | 41 | | 1 |
| Q-431 | enaT;enaC;rC;rC;rG;rU;rU;rU;rU;rG;rU;rA;rG;rA;rU;rG;rA;rC;rA;rA$ (SEQ ID No. 87232) | rU;rU;rG;rU;rC;rA;rU;rC;rU;rC;rU;rA;rA;rA;rA;rC;rG;enaG;enaA$ (SEQ ID No. 87233) | 35 | | 1 |
| Q-432 | enaT;enaC;enaC;rC;rG;rU;rU;rU;rU;rG;rU;rA;rG;rA;rU;rG;rA;rC;rA;r A$ (SEQ ID No. 87232) | rU;rU;rG;rU;rC;rA;rU;rC;rU;rC;rU;rA;rC;rA;rA;rA;rC;rG;enaG;enaA$ (SEQ ID No. 87233) | 50 | | 1 |

FIG. 23 Continued

| ID | Sense | AntiSense | Activity at 20 nM (% of control) | IC50 (nM) | Stability in human serum |
|---|---|---|---|---|---|
| Q-433 | enaT;enaC;enaC;rC;rG;rU;rU;rG;rU;rU;rA;rU;rA;rU;rG;rA;rU;rG;rA;rC;LdA;LdAS (SEQ ID No. 87232) | rU;rU;rG;rU;rC;rA;rU;rC;rU;rU;rA;rU;rA;rC;rA;rA;rC;rG;enaG;enaG;enaA$ (SEQ ID No. 87233) | 32 | | 1 |
| Q-434 | enaT;enaC;enaC;rC;rG;rU;rU;rG;rU;rU;rA;rU;rA;rU;rG;rA;rU;rG;rA;rU;rG;rA;rC;LdA;LdC;LdA;rA$ (SEQ ID No. 87232) | rU;rU;rG;rU;rC;rA;rU;rC;rU;rU;rA;rU;rA;rC;rA;rA;rC;rG;enaG;enaG;enaA$ (SEQ ID No. 87233) | 49 | | 0 |
| Q-435 | enaT;enaC;enaC;rC;rG;rU;rU;rG;rU;rU;rA;rU;rA;rU;rG;rA;rU;rG;rA;rC;rA;A2p;rA$ (SEQ ID No. 87232) | rU;rU;rG;rU;rC;rA;rU;rC;rU;rU;rA;rU;rA;rC;rA;rA;rC;rG;enaG;enaG;enaA$ (SEQ ID No. 87233) | 38 | | 1 |
| Q-436 | enaT;enaC;enaC;rC;rG;rU;rU;rG;rU;rU;rA;rU;rA;rU;rG;rA;rU;rG;rA2p;rC2p;rA;rA$ (SEQ ID No. 87232) | rU;rU;rG;rU;rC;rA;rU;rC;rU;rU;rA;rU;rA;rC;rA;rA;rC;rG;enaG;enaG;enaA$ (SEQ ID No. 87233) | 58 | | 1 |
| Q-437 | rG;LdC;rC;rA;rG;rA;rA;rU;rG;rU;rG;rA;rA;rA;rU;rC;rU;LdC;LdC;rU$ (SEQ ID No. 139) | mA;rG;mG;rA;mG;rU;mU;rC;mC;rA;mC;rA;mC;rA;mU;rU;mC;rU;mG;rG;mC$ (SEQ ID No. 140) | 45 | | |
| Q-438 | rG;LdC;rC;rA;rG;rA;rA;rU;rG;rU;rG;rA;rA;rA;rU;rC;rU;LdC;rU$ (SEQ ID No. 139) | mA;rG;mG;rA;mG;rU;mU;rC;mC;rA;mC;rA;mC;rA;mU;rU;mC;rU;mG;rG;mC$ (SEQ ID No. 140) | 13 | | |
| Q-439 | rG;rC;rC;rA;rG;rA;rA;rU;rG;rU;rG;rA;rA;rA;rU;rC;rU;rC;rU$ (SEQ ID No. 139) | mA;rG;mG;rA;mG;rU;mU;rC;mC;rA;mC;rA;mC;rA;mU;rU;mC;rU;mG;rG;mC$ (SEQ ID No. 140) | 8 | | |
| Q-440 | rG;rC;rC;rA;rG;rA;rA;rU;rG;rU;rG;rA;rA;rA;rU;rC;rU;LdC;LdC;rU$ (SEQ ID No. 139) | mA;rG;mG;rA;mG;rU;mU;rC;mC;rA;mC;rA;mC;rA;mU;rU;mC;rU;mG;rG;mC$ (SEQ ID No. 140) | 23 | | |
| Q-441 | rC;rC;rU;rG;rA;rG;rU;rG;rU;rG;rU;rU;rU;rC;rA;rA;rA;LdG;rA$ (SEQ ID No. 87236) | mU;rC;mU;rG;mU;rU;mU;rG;mA;rC;mA;rC;mU;rC;mA;rG;mG$ (SEQ ID No. 87237) | 8 | | |
| Q-442 | rC;rC;rU;rG;rA;rG;rU;rG;rU;rC;rA;rA;rC;LdG;LdG;rA$ (SEQ ID No. 87236) | mU;rC;mU;rG;mU;rU;mU;rG;mA;rC;mA;rC;mU;rC;mA;rG;mG$ (SEQ ID No. 87237) | 23 | | |
| Q-443 | rC;rC;rU;rG;rA;rG;rU;rG;rU;rC;rA;rA;rC;rA;LdA;rU$ (SEQ ID No. 87236) | mA;rU;mA;rU;mG;rG;mA;rG;mA;rG;mA;rC;rU;mU;rU;rG;mC;rC;mC$ (SEQ ID No. 87237) | 20 | | |
| Q-444 | rG;rG;rC;rA;rA;rA;rG;rU;rC;rU;rC;rU;rC;rC;rA;LdA;LdA;rU$ (SEQ ID No. 87236) | mA;rU;mA;rU;mG;rG;mA;rG;mA;rG;mA;rC;rU;mU;rU;rG;mC;rC;mC$ (SEQ ID No. 87237) | 41 | | |
| Q-445 | rG;rA;rA;rG;rA;rU;rC;rU;rU;rC;rG;rG;rA;rA;rU;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 10 | | |
| Q-446 | rG;rA;rA;rG;rA;rU;rC;rU;rU;rC;rG;rG;rA;rA;LdA;LdA;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 10 | | |
| Q-447 | lB;rG;rA;rA;rG;rA;rU;rC;rU;rU;rC;rG;rG;rA;rA;rU;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 10 | | |
| Q-448 | lB;rG;rA;rA;rG;rA;rU;rC;rU;rU;rC;rG;rG;rA;rA;LdA;LdA;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 46 | | |
| Q-449 | LdA;rG;rA;rA;rG;rA;rU;rC;rU;rU;rC;rG;rG;rA;rA;LdA;LdA;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 10 | | |
| Q-450 | LdA;rG;rA;rA;rG;rA;rU;rC;rU;rU;rC;rG;rG;rA;rdA;rA;rG;LdA;rU$ (SEQ ID No. 13750) | mA;rU;mC;rA;mU;rU;mC;rC;mG;rA;mA;rG;mA;rU;rC;mU;rU;rC$ (SEQ ID No. 13953) | 65 | | |

FIG. 23 Continued

| ID | Sense | AntiSense | Activity at 20nM (% of control) | IC50 (nM) | Stability in human serum |
|---|---|---|---|---|---|
| Q-451 | C6Np;rG;rA;rA;rG;rG;rA;rA;rU;rC;rU;rU;rC;rG;rA;rA;rU;rG;LdA;r US (SEQ ID No. 13750) | mA;rU;mC;rA;mU;rC;mG;rA;rA;mG;rA;mU;rC;mC;rU;mU;rC$ (SEQ ID No. 13953) | 8 | | |
| Q-452 | C6Np;rG;rA;rA;rG;rA;rG;rA;rU;rU;rC;rG;rG;rA;rA;LdA;LdA;rG;LdA;r US (SEQ ID No. 13750) | mA;rU;mC;rA;mU;rC;mG;rA;rA;mG;rA;rA;mC;rU;mU;rC$ (SEQ ID No. 13953) | 0 | | |
| Q-453 | rG;rA;rA;rG;rG;rA;rU;rC;rU;rU;rC;rG;rA;rA;rU;rG;LdA;rU$ (SEQ ID No. 13750) | mA;rU;mC;rA;mU;rC;mG;rA;rA;mG;rA;mU;rC;mC;rU;mU;rC$ (SEQ ID No. 13953) | 7 | | |
| Q-454 | rG;rA;rA;rG;rG;rA;rU;rU;rC;rG;rA;rA;LdA;LdA;rG;LdA;rU$ (SEQ ID No. 13750) | mA;rU;mC;rA;mU;rC;mG;rA;rA;mG;rA;rA;mC;rU;mU;rC$ (SEQ ID No. 13953) | 50 | | |
| Q-455 | iB;rG;rA;rA;rG;rG;rA;rU;rC;rU;rU;rC;rG;rA;rA;rU;rG;LdA;rU$ (SEQ ID No. 13750) | mA;rU;mC;rA;mU;rC;mG;rA;rA;mG;rA;mU;rC;mC;rU;mU;rC$ (SEQ ID No. 13953) | 6 | | |
| Q-456 | iB;rG;rA;rA;rG;rG;rA;rU;rU;rC;rG;rG;rA;rA;LdA;LdA;rG;LdA;rU$ (SEQ ID No. 13750) | mA;rU;mC;rA;mU;rC;mG;rA;rA;mG;rA;rA;mC;rU;mU;rC$ (SEQ ID No. 13953) | 46 | | |
| Q-457 | LdA;rG;rA;rA;rG;rG;rA;rU;rC;rU;rU;rC;rG;rA;rA;rU;rG;LdA;rU$ (SEQ ID No. 13750) | mA;rU;mC;rA;mU;rC;mG;rA;rA;mG;rA;mU;rC;mC;rU;mU;rC$ (SEQ ID No. 13953) | 10 | | |
| Q-458 | LdA;rG;rA;rA;rG;rG;rA;rU;rU;rC;rG;rG;rA;rA;LdA;LdA;rG;LdA;r U$ (SEQ ID No. 13750) | mA;rU;mC;rA;mU;rC;mG;rA;rA;mG;rA;rA;mC;rU;mU;rC$ (SEQ ID No. 13953) | 65 | | |
| Q-459 | C6Np;rG;rA;rA;rG;rG;rA;rU;rC;rU;rU;rC;rG;rA;rA;rU;rG;LdA;rU$ (SEQ ID No. 13750) | mA;rU;mC;rA;mU;rC;mG;rA;rA;mG;rA;mU;rC;mC;rU;mU;rC$ (SEQ ID No. 13953) | 5 | | |
| Q-460 | C6Np;rG;rA;rA;rG;rA;rG;rA;rU;rU;rC;rG;rG;rA;rA;LdA;LdA;rG;LdA;r US (SEQ ID No. 13750) | mA;rU;mC;rA;mU;rC;mG;rA;rA;mG;rA;rA;mC;rU;mU;rC$ (SEQ ID No. 13953) | 62 | | |
| Q-461 | rC;rG;rU;rG;rA;rA;rC;rU;rU;rG;rG;rA;rA;rA;rA;rdT;rU;rG;LdA;rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 39 | | |
| Q-462 | rC;rG;rU;rG;rA;rA;rC;rU;rU;rG;rG;rA;rA;rA;rA;rdT;rU;rG;LdA;rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 75 | | |
| Q-463 | iB;rC;rG;rU;rG;rA;rA;rC;rU;rU;rG;rG;rA;rA;rA;rA;rdT;rU;rG;LdA;rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 70 | | |
| Q-464 | LdA;rC;rG;rU;rG;rA;rA;rC;rU;rU;rG;rG;rA;rA;rA;rA;rdT;LdA;rG;LdA;rA (SEQ ID No. 87239) | mU;rU;mC;rA;mA;rU;mU;mU;rU;rC;mA;rA;mG;rU;mU;rC;mA;rC;mG$ (SEQ ID No. 87239) | 58 | | |
| Q-465 | C6Np;rC;rG;rU;rG;rA;rA;rC;rA;rU;rU;rG;rG;rA;rA;rA;rA;rdT;rU;rG;LdA;rA $ (SEQ ID No. 87239) | mU;rU;mC;rA;mA;rU;mU;mU;rU;rC;mA;rA;mG;rU;mU;rC;mA;rC;mG$ (SEQ ID No. 87239) | 53 | | |
| Q-466 | C6Np;rC;rG;rU;rG;rA;rA;rC;rU;rU;rG;rG;rA;rA;rA;rA;rdT;rU;rG;LdA; rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 99 | | |
| Q-467 | rC;LdA;rU;rG;rA;rA;rC;rU;rU;rG;rG;rA;rA;rA;rA;rdT;rU;rG;LdA;rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 80 | | |
| Q-468 | rC;LdA;rU;rG;rA;rA;rC;rU;rU;rG;rG;rA;rA;rA;rA;rdT;LdA;rG;LdA;rA$ (SEQ ID No. 87239) | mU;rU;mC;rA;mA;rU;mU;mU;rU;rC;mA;rA;mG;rU;mU;rC;mA;rC;mG$ (SEQ ID No. 87239) | 121 | | |

FIG. 23 Continued

| ID | Sense | AntiSense | Activity at 20nM (% of control) | IC50 (nM) | Stability in human serum |
|---|---|---|---|---|---|
| Q-469 | rC;rG;rU;rG;rA;rA;rC;rU;rG;rA;rA;rA;dT;rU;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-470 | rC;rG;rU;rG;rA;rA;rC;rU;rG;rA;rA;rA;dT;LdA;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-471 | iB;rC;rG;rU;rG;rA;rA;rC;rU;rA;rA;rA;dT;rU;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-472 | LdA;rC;rG;rU;rG;rA;rA;rC;rU;rG;rA;rA;rA;dT;LdA;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-473 | C6Np;rC;rG;rU;rG;rA;rA;rC;rU;rG;rA;rA;rA;dT;rU;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-474 | C6Np;rC;rG;rU;rG;rA;rA;rC;rU;rG;rA;rA;rA;dT;LdA;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-475 | rC;LdA;rU;rG;rA;rC;rU;rG;rU;rU;rG;rA;rA;rA;dT;rU;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-476 | rC;LdA;rU;rG;rA;rC;rU;rG;rU;rU;rG;rA;rA;rA;dT;LdA;rG;LdA;rA$ (SEQ ID No. 87238) | rU;mU;rC;mA;rA;mU;rC;rC;mA;rA;mG;rU;mU;rC;mA;rC;mG$ (SEQ ID No. 87239) | | | |
| Q-477 | rG;rC;rC;rA;rG;rU;rG;rA;rA;rA;rC;rA;dC;rU;rC;LdC;rU$ (SEQ ID No. 139) | mA;rG;mG;rA;mG;rU;mU;rC;rA;mU;rC;mC;rU;mG;rG;mC$ (SEQ ID No. 140) | 13 | | |
| Q-478 | rG;rC;rC;rA;rG;rU;rG;rA;rA;rA;rC;rA;dC;LdC;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 35 | | |
| Q-479 | iB;rC;rC;rA;rG;rU;rG;rA;rA;rA;rC;rA;dC;rU;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 18 | | |
| Q-480 | LdC;rG;rC;rC;rA;rG;rA;rU;rU;rG;rG;rA;dC;LdC;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 33 | | |
| Q-481 | C6Np;rG;rC;rC;rA;rG;rU;rG;rA;rA;rA;rC;rA;dC;rU;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 14 | | |
| Q-482 | C6Np;rG;rC;rC;rA;rG;rU;rG;rA;rA;rA;rC;rA;dC;LdC;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 40 | | |
| Q-483 | rG;LdC;rC;rA;rG;rA;rG;rA;rA;rU;rG;rA;dC;rU;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 17 | | |
| Q-484 | rG;LdC;rC;rA;rG;rA;rG;rA;rA;rU;rG;rA;dC;LdC;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 76 | | |
| Q-485 | rG;rC;rC;rA;rG;rA;rG;rA;rA;rU;rG;rA;dC;rU;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 13 | | |
| Q-486 | rG;rC;rC;rA;rG;rA;rG;rA;rA;rU;rG;rA;dC;LdC;rC;LdC;rU$ (SEQ ID No. 139) | mA;rG;mG;rA;mG;rU;mU;rC;rA;mC;rA;mU;rC;mC;rU;mG;rG;mC$ (SEQ ID No. 140) | 42 | | |

FIG. 23 Continued

| ID | Sense | AntiSense | Activity at 20nM (% of control) | IC50 (nM) | Stability in human serum |
|---|---|---|---|---|---|
| Q-487 | iB;rG;rC;rC;rA;rG;rA;rA;rG;rU;rG;rA;rA;dC;rU;rC;LdC;rU$ (SEQ ID No. 139) | mA;rG;mG;rA;mG;rU;mU;rC;mC;rA;rA;rC;mA;rU;mU;rG;rG;mG;rC$ (SEQ ID No. 140) | 17 | | |
| Q-488 | LdC;rG;rC;rC;rA;rG;rA;rA;rG;rU;rG;rA;rA;dC;LdC;rC;LdC;rU$ (SEQ ID No. 139) | mA;rG;mG;rA;mG;rU;mU;rC;mC;rA;rC;mA;rU;mU;rG;rG;mG;rC$ (SEQ ID No. 140) | 39 | | |
| Q-489 | C6N;rG;rC;rC;rA;rG;rA;rA;rG;rU;rG;rG;rA;rA;dC;rU;rC;LdC;rC;LdC;rU$ (SEQ ID No. 139) | mA;rG;mG;rA;mG;rU;mU;rC;mC;rA;rC;mA;rU;mU;rG;rG;mG;rC$ (SEQ ID No. 140) | 11 | | |
| Q-490 | C6Np;rG;rC;rC;rA;rG;rA;rA;rG;rU;rG;rG;rA;rA;dC;rU;rC;LdC;rC;rU$ (SEQ ID No. 139) | mA;rG;mG;rA;mG;rU;mU;rC;mC;rA;rC;mA;rU;mU;rG;rG;mG;rC$ (SEQ ID No. 140) | 39 | | |
| Q-491 | rG;LdC;rC;rA;rG;rA;rA;rU;rG;rA;rA;dC;rU;rC;LdC;rU$ (SEQ ID No. 139) | mA;rG;mG;rA;mG;rU;mU;rC;mC;rA;rC;mA;rU;mU;rG;rG;mG;rC$ (SEQ ID No. 140) | 17 | | |
| Q-492 | rG;LdC;rC;rA;rG;rA;rA;rU;rG;rA;rA;dC;LdC;rC;LdC;rU$ (SEQ ID No. 139) | mA;rG;mG;rA;mG;rU;mU;rC;mC;rA;rC;mA;rU;mU;rG;rG;mG;rC$ (SEQ ID No. 140) | 94 | | |
| Q-493 | rG;rC;rC;rA;rG;rA;rA;rU;rG;rA;rA;rC;rU;rC;LdC;rU (SEQ ID No. 139) | rA;mG;rG;mA;rG;dB;mU;rC;rA;mC;rA;mC;rA;mU;rU;mC;rU;mG;rG;mC (SEQ ID No. 140) | | | |
| Q-494 | rG;rC;rC;rA;rG;rA;rA;rU;rG;rA;rA;rC;rU;rC;LdC;rU (SEQ ID No. 139) | rA;mG;rG;mA;rG;dB;mU;rC;rA;mC;rA;mU;rU;mC;rU;mG;rG (SEQ ID No. 140) | | | |
| Q-495 | rG;rC;rC;rA;rG;rA;rA;rU;rG;rA;rA;rC;rU;rC;LdC;rU (SEQ ID No. 139) | rA;mG;rG;mA;rG;mU;rU;mC;rC;rA;mC;rA;mU;rU;dB;rU;mG;rG;mC (SEQ ID No. 140) | | | |
| Q-496 | rG;rC;rC;rA;rG;rA;rA;rU;rG;rA;rA;rC;rU;rC;LdC;rU (SEQ ID No. 139) | rA;mG;rG;mA;rG;mU;rU;mC;rC;rA;mC;rA;mU;dB;mC;rU;mG;r G;mC (SEQ ID No. 140) | | | |
| Q-497 | rG;rC;rC;rA;rG;rA;rA;rU;rG;rA;rA;rC;rU;LdC;LdC;LdC (SEQ ID No. 139) | rA;mG;rG;mA;rG;mU;rU;mC;rC;rA;mC;rA;mU;rU;mC;rU;mG;rG (SEQ ID No. 140) | | | |
| Q-498 | rG;rC;rC;rA;rG;rA;rA;rU;rG;rA;rA;rC;rU;LdC;LdC;rU (SEQ ID No. 139) | rA;mG;rG;mA;rG;dB;mU;rC;rA;mC;rA;mU;rU;mC;rU;mG;rG (SEQ ID No. 140) | | | |
| Q-499 | rG;rC;rC;rA;rG;rA;rA;rU;rG;rA;rA;rC;rU;LdC;LdC (SEQ ID No. 139) | rA;mG;rG;mA;rG;mU;rU;mC;rC;rA;mC;rA;mU;rU;dB;rU;mG;rG (SEQ ID No. 140) | | | |
| Q-500 | rG;rC;rC;rA;rG;rA;rA;rU;rG;rA;rA;rC;rU;LdC;LdC (SEQ ID No. 139) | rA;mG;rG;mA;rG;mU;rU;mC;rC;rA;mC;rA;mU;dB;mC;rU;mG;r (SEQ ID No. 140) | | | |
| Q-501 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;mC;rA;mU;rU;mC;rU;mG;r G;mC (SEQ ID No. 140) | | | |
| Q-502 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;mC;rA;mU;rU;mC;rU;mG;r (SEQ ID No. 140) | | | |
| Q-503 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;mC;rA;mU;rU;dB;rU;mG;rG (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-504 | 5medG;rC;rC;rA;rG;rA;rA;rU;rG;rU;rG;rG;rA;rA;rC;rU;rC;LdC;rU (SEQ ID No. 139) | rA;mG;rG;mA;rG;mU;rC;rU;mC;rA;mC;rA;mU;rdB;mC;rU;mG;rG;mC (SEQ ID No. 140) | | | |
| Q-505 | 5medG;rC;rC;rA;rG;rA;rA;rU;rG;rU;rG;rG;rA;rA;rC;rU;LdC; LdC;rU (SEQ ID No. 139) | rA;mG;rG;mA;dB;mU;rC;mC;rA;mC;rA;mU;rU;mC;rU;mG;r G;mC (SEQ ID No. 140) | | | |
| Q-506 | 5medG;rC;rC;rA;rG;rA;rA;rU;rG;rU;rG;rG;rA;rA;rC;rU;LdC; LdC;rU (SEQ ID No. 139) | rA;mG;rG;mA;rG;dB;rU;mC;rA;mU;rA;mU;rU;mC;rU;mG;rG ;mC (SEQ ID No. 140) | | | |
| Q-507 | 5medG;rC;rC;rA;rG;rA;rA;rU;rG;rU;rG;rG;rA;rA;rC;rU;LdC; LdC;rU (SEQ ID No. 139) | rA;mG;rG;mA;rG;mU;rC;mC;rA;mC;rA;mU;rU;dB;rU;mG;rG ;mC (SEQ ID No. 140) | | | |
| Q-508 | 5medG;rC;rC;rA;rG;rA;rA;rU;rG;rU;rG;rG;rA;rA;rC;rU;LdC; LdC;rU (SEQ ID No. 139) | rA;mG;rG;mA;rG;mU;rU;mC;rA;mC;rA;mU;dB;mC;rU;mG;r G;mC (SEQ ID No. 140) | | | |
| Q-509 | iB;rG;rC;rC;rA;rG;rA;rA;rU;rG;rU;rG;rG;rA;rA;rC;rU;rC;LdC ;rU (SEQ ID No. 139) | rA;mG;rG;mA;dB;mU;rC;mC;rA;mC;rA;mU;rU;mC;rU;mG;r G;mC (SEQ ID No. 140) | | | |
| Q-510 | iB;rG;rC;rC;rA;rG;rA;rA;rU;rG;rU;rG;rG;rA;rA;rC;rU;rC;LdC ;rU (SEQ ID No. 139) | rA;mG;rG;mA;rG;dB;rU;mC;rA;mC;rA;mU;rU;mC;rU;mG;rG ;mC (SEQ ID No. 140) | | | |
| Q-511 | iB;rG;rC;rC;rA;rG;rA;rA;rU;rG;rU;rG;rG;rA;rA;rC;rU;rC;LdC ;rU (SEQ ID No. 139) | rA;mG;rG;mA;rG;mU;rC;mC;rA;mC;rA;mU;rU;dB;rU;mG;rG ;mC (SEQ ID No. 140) | | | |
| Q-512 | iB;rG;rC;rC;rA;rG;rA;rA;rU;rG;rU;rG;rG;rA;rA;rC;rU;rC;LdC ;rU (SEQ ID No. 139) | rA;mG;rG;mA;rG;mU;rU;mC;rA;mC;rA;mU;dB;mC;rU;mG;r G;mC (SEQ ID No. 140) | | | |
| Q-513 | iB;rG;rC;rC;rA;rG;rA;rA;rU;rG;rU;rG;rG;rA;rA;rC;rU;LdC;Ld C;rU (SEQ ID No. 139) | rA;mG;rG;mA;dB;mU;rC;mC;rA;mC;rA;mU;rU;mC;rU;mG;r G;mC (SEQ ID No. 140) | | | |
| Q-514 | iB;rG;rC;rC;rA;rG;rA;rA;rU;rG;rU;rG;rG;rA;rA;rC;rU;LdC;Ld C;rU (SEQ ID No. 139) | rA;mG;rG;mA;rG;dB;rU;mC;rA;mC;rA;mU;rU;mC;rU;mG;rG ;mC (SEQ ID No. 140) | | | |
| Q-515 | iB;rG;rC;rC;rA;rG;rA;rA;rU;rG;rU;rG;rG;rA;rA;rC;rU;LdC;Ld C;rU (SEQ ID No. 139) | rA;mG;rG;mA;rG;mU;rC;mC;rA;mC;rA;mU;rU;dB;rU;mG;rG ;mC (SEQ ID No. 140) | | | |
| Q-516 | iB;rG;rC;rC;rA;rG;rA;rA;rU;rG;rU;rG;rG;rA;rA;rC;rU;LdC;Ld C;rU (SEQ ID No. 139) | rA;mG;rG;mA;rG;mU;rU;mC;rA;mC;rA;mU;dB;mC;rU;mG;r G;mC (SEQ ID No. 140) | | | |
| Q-517 | iB;rC;rC;rA;rG;rA;rA;rU;rG;rU;rG;rG;rA;rA;rC;dB;dB;dB;dB (SEQ ID No. 139) | mA;mG;mG;rA;mG;rU;mU;rC;mC;rA;mU;rU;mC;rU;mG ;rG;mC (SEQ ID No. 140) | | | |
| Q-518 | iB;rC;rC;rA;rG;rA;rA;rU;rG;rU;rG;rG;rA;rA;rC;dB;dB;dB;dB (SEQ ID No. 139) | rA;mG;rG;mA;rG;mU;rU;rC;mC;rA;mC;rA;mU;rU;mC;rU;mG ;rG;mC (SEQ ID No. 140) | | | |
| Q-519 | 5medG;rC;rC;rA;rG;rA;rA;rU;rG;rU;rG;rG;rA;rA;rC;dB;dB; dB;dB (SEQ ID No. 139) | mA;mG;mA;mG;rU;mU;rC;mC;rA;mC;rA;mU;rU;rU;mC;rU;mG ;rG;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-520 | 5medG;rC;rC;rA;rG;rA;rA;rU;rG;rU;rG;rG;rA;rA;dB;dB;dB;dB;dB (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-521 | iB;dB;rC;rA;rG;rA;rA;rU;rG;rG;rA;rA;rC;rA;rC;rU;dB;dB;dB (SEQ ID No. 139) | mA;mG;mG;rA;mG;rU;mU;rC;mC;rA;mC;rA;mU;mC;rU;mC;rU;mG (SEQ ID No. 140) | | | |
| Q-522 | iB;dB;rC;rA;rG;rA;rA;rU;rG;rG;rA;rA;rC;rA;rC;rU;dB;dB;dB (SEQ ID No. 139) | rA;mG;rG;mA;rG;mU;rU;mC;mC;rA;mC;rA;mU;rU;mC;rU;mG;rG;mC (SEQ ID No. 140) | | | |
| Q-523 | iB;dB;dB;rA;rG;rA;rA;rU;rG;rG;rA;rA;rC;rU;dB;dB (SEQ ID No. 139) | mA;mG;mG;rA;mG;rU;mU;rC;mC;rA;mC;rA;mU;mC;rU;mC;rU;mG;rG;mC (SEQ ID No. 140) | | | |
| Q-524 | iB;dB;dB;rA;rA;rU;rG;rG;rA;rA;rC;rU;dB;dB;dB (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-525 | iB;dB;dB;rG;rA;rA;rU;rG;rG;rA;rA;rC;rA;rC;rU;rC;rC;dB (SEQ ID No. 139) | mA;mG;mG;rA;mG;rU;mU;rC;mC;rA;mC;rA;mU;mC;rU;mC;rU;mG;rG;mC (SEQ ID No. 140) | | | |
| Q-526 | iB;dB;dB;dB;rG;rA;rA;rA;rU;rC;rU;rC;dB (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-527 | iB;dB;dB;dB;rA;rA;rA;rU;rG;rU;rG;rA;rA;rC;rU;rC;rC;rU (SEQ ID No. 139) | mA;mG;mG;rA;mG;rU;mU;rC;mC;rA;mC;rA;mU;mC;rU;mC;rU;mG (SEQ ID No. 140) | | | |
| Q-528 | iB;dB;dB;dB;rA;rA;rA;rU;rG;rU;rG;rA;rA;rC;rU;rC;rC;rU (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-529 | 5medG;rC;rC;rA;rG;lnaA;rA;rU;rG;rU;rG;rA;lnaA;dB;dB;dB;dB;dB (SEQ ID No. 139) | mA;mG;mG;rA;mG;rU;mU;rC;mC;rA;mC;rA;mU;mC;rU;mC;rU;mG (SEQ ID No. 140) | | | |
| Q-530 | 5medG;rC;rC;rA;rG;lnaA;rA;rU;rG;rU;rG;rA;lnaA;dB;dB;dB;dB;dB (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-531 | iB;dB;dB;dB;dB;lnaA;rA;rU;rG;rU;rG;rA;lnaA;rC;rU;rC;rU (SEQ ID No. 139) | mA;mG;mG;rA;mG;rU;mU;rC;mC;rA;mC;rA;mU;mC;rU;mC;rU;mG (SEQ ID No. 140) | | | |
| Q-532 | iB;dB;dB;dB;dB;lnaA;rA;rU;rG;rU;rG;rA;lnaA;rC;rU;rC;rU (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-533 | iB;rG;rC;rC;rA;rG;rA;rA;rU;rG;rU;rG;rA;rA;rC;rU;rU;rC;LdC;rU (SEQ ID No. 139) | rA;mG;rG;mA;rA;rA;rU;mC;rC;rA;mC;rA;mU;rU;mC;rU;mG;rG;mC (SEQ ID No. 140) | | | |
| Q-534 | iB;rG;rC;rC;rA;rG;rA;rA;rU;rG;rU;rG;rA;rA;rU;rU;LdC;LdC;rU (SEQ ID No. 139) | rA;mG;rG;mA;rA;rA;mC;rU;mC;rC;rA;mC;rA;mU;rU;mC;rU;mG;rG;mC (SEQ ID No. 140) | | | |
| Q-535 | iB;rG;rC;rC;rA;rG;rA;rA;rU;rG;rG;rA;rG;rA;rG;rU;rC;LdC;rU (SEQ ID No. 139) | rA;mG;rG;mA;rG;mC;rU;mC;rU;mC;rC;rA;mC;rA;mU;rU;mC;rU;mG;rG;mC (SEQ ID No. 140) | | | |

FIG. 23 Continued

| ID | Sense | AntiSense | Activity at 20nM (% of control) | IC50 (aM) | Stability in human serum |
|---|---|---|---|---|---|
| Q-536 | iB;rG;rC;rC;;rA;rG;rA;;rA;rU;rG;rA;;rU;rG;rA;;rG;rC;rU;LdC;L dC;rU (SEQ ID No. 139) | rA;mG;rG;mA;rG;mC;rU;mC;rC;rA;mC;rA;mU;rU;mC;rU;mG;r G;mC (SEQ ID No. 140) | | | |
| Q-537 | iB;rG;rC;rC;;rA;rG;rG;rA;rU;rG;rA;;rA;rC;rA;rC;rU;LdC;rU (SEQ ID No. 139) | rA;mG;rG;mA;rG;mU;rU;mC;rC;;rA;mC;rA;mU;rC;mC;rU;mG;r G;mC (SEQ ID No. 140) | | | |
| Q-538 | iB;rG;rC;rC;;rA;rG;rA;;rU;rG;rA;;rA;rA;rC;rA;rC;rU;LdC;L dC;rU (SEQ ID No. 139) | rA;mG;rG;mA;rG;mU;rU;mC;rC;rA;mC;rA;mU;rC;mC;rU;mG;r G;mC (SEQ ID No. 140) | | | |
| Q-539 | rG;rC;rC;;rA;rG;rA;;rU;rG;rA;;rA;rA;rC;rU;rC;rU;LdC;rU (SEQ ID No. 139) | mA;mG;mG;rA;dB;rU;mU;rC;rA;mC;rA;mU;rC;mC;rU;mG;r G;mC (SEQ ID No. 140) | | | |
| Q-540 | rG;rC;rC;rA;rG;rA;rU;rG;rA;;rA;rA;rC;rU;rC;rU;LdC;r U (SEQ ID No. 139) | mA;mG;mG;rA;mG;dB;mU;rC;mC;rA;mC;rA;mU;rC;mC;rU;mG ;rG;mC (SEQ ID No. 140) | | | |
| Q-541 | rG;rC;rC;;rA;rG;rA;rU;rG;rA;rA;rA;rC;rU;rC;rU;LdC;r U (SEQ ID No. 139) | mA;mG;mG;rA;mG;rU;mU;rC;mC;rA;mC;rA;mU;rU;dB;rU;mG; rG;mC (SEQ ID No. 140) | | | |
| Q-542 | rG;rC;rC;;rA;rG;rA;rU;rG;rA;rA;rA;rC;rU;rC;rU;LdC;r U (SEQ ID No. 139) | mA;mG;mG;rA;mG;rU;mU;rC;mC;rA;mC;rA;mU;dB;mC;rU;mG ;rG;mC (SEQ ID No. 140) | | | |
| Q-543 | rG;rC;rC;;rA;rG;rA;rU;rG;rA;rA;rA;rC;rU;rC;rU;LdC;r U (SEQ ID No. 139) | rA;mG;mG;mA;dB;mU;mU;rC;mC;rA;mC;rA;mU;rC;mC;rU;mG;r G;mC (SEQ ID No. 140) | | | |
| Q-544 | rG;rC;rC;;rA;rG;rA;rU;rG;rA;;rA;rA;rC;rU;rC;rU;LdC;r U (SEQ ID No. 139) | mA;mG;rG;mA;mG;dB;mU;mU;rC;mC;rA;mC;rA;mU;rC;rU;mG;r G;mC (SEQ ID No. 140) | | | |
| Q-545 | rG;rC;rC;;rA;rG;rA;rU;rG;rA;rA;rA;rC;rU;rC;rU;LdC;r U (SEQ ID No. 139) | rA;mG;rG;mA;rG;mU;rU;mC;rC;rA;mC;rA;mU;mC;mU;dB;mU; rG;mC (SEQ ID No. 140) | | | |
| Q-546 | rG;rC;rC;;rA;rG;rA;rU;rG;rA;rA;rA;rC;rU;rC;rU;LdC;r U (SEQ ID No. 139) | mA;mG;mG;mG;rA;rG;mU;rU;mC;rC;rA;mC;rA;mU;mU;dB;mU; mG;rG;mC (SEQ ID No. 140) | | | |
| Q-547 | rG;rC;rC;;rA;rG;rA;rU;rG;rA;rA;rA;rC;rU;LdC;LdC; rU (SEQ ID No. 139) | mA;mG;mG;rA;dB;rU;mU;rC;mC;rA;mC;rA;mU;rU;dB;rU;mG; G;mC (SEQ ID No. 140) | | | |
| Q-548 | rG;rC;rC;;rA;rG;rA;rU;rG;rA;rA;rA;rC;rU;LdC;LdC; rU (SEQ ID No. 139) | mA;mG;mG;rA;mG;dB;mU;rC;mC;rA;mC;rA;mU;rC;mC;rU;mG; rG;mC (SEQ ID No. 140) | | | |
| Q-549 | rG;rC;rC;;rA;rG;rA;rU;rG;rA;rA;rA;rC;rU;LdC;LdC; rU (SEQ ID No. 139) | mA;mG;mG;rA;mG;rU;mU;rC;mC;rA;mC;rA;mU;rU;dB;rU;mG; rG;mC (SEQ ID No. 140) | | | |
| Q-550 | rG;rC;rC;;rA;rG;rA;rU;rG;rA;rA;rA;rC;rU;LdC;LdC; rU (SEQ ID No. 139) | mA;mG;mG;rA;mG;rU;mU;rC;mC;rA;mC;rA;mU;dB;mC;rU;mG; rG;mC (SEQ ID No. 140) | | | |
| Q-551 | rG;rC;rC;;rA;rU;rG;rA;rA;rC;rA;rC;rU;LdC;LdC; rU (SEQ ID No. 139) | rA;mG;rG;mA;dB;mU;mU;rC;mC;rA;mC;rA;mU;rC;mC;rU;mG;r G;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-552 | rG;rC;rC;rA;rG;rA;rA;rG;rA;rA;rU;rG;rG;rA;rA;rC;rU;LdC;LdC;rU (SEQ ID No. 139) | mA;mG;rG;mA;dB;rU;mU;rC;mC;rA;mC;rA;mU;rU;mC;rU;mG;rG;mC (SEQ ID No. 140) | | | |
| Q-553 | rG;rC;rC;rA;rG;rA;rA;rG;rA;rA;rU;rG;rG;rA;rA;rC;rU;LdC;LdC;rU (SEQ ID No. 139) | rA;mG;rG;mA;rG;mU;rU;mC;rC;rA;mC;rA;mU;rU;mC;rU;mG;rG;mC (SEQ ID No. 140) | | | |
| Q-554 | rG;rC;rC;rA;rG;rA;rA;rG;rA;rA;rU;rG;rG;rA;rA;rC;rU;LdC;LdC;rU (SEQ ID No. 139) | mA;mG;mG;rA;mG;rU;mC;mC;rA;mC;rA;mU;mU;dB;mU;mG;rG;mC (SEQ ID No. 140) | | | |
| Q-555 | 5medG;rC;rC;rA;rG;rA;rA;rG;rA;rA;rU;rG;rG;rA;rA;rC;rU;rC;L dC;rU (SEQ ID No. 139) | mA;mG;mG;rA;dB;rU;mU;rC;mC;rA;mC;rA;mU;rU;mC;rU;mG;rG;mC (SEQ ID No. 140) | | | |
| Q-556 | 5medG;rC;rC;rA;rG;rA;rA;rG;rA;rA;rU;rG;rG;rA;rA;rC;rU;rC;L dC;rU (SEQ ID No. 139) | mA;mG;mG;rA;mG;dB;mU;rC;mC;rA;mC;rA;mU;rU;mC;rU;mG;rG;mC (SEQ ID No. 140) | | | |
| Q-557 | 5medG;rC;rC;rA;rG;rA;rA;rG;rA;rA;rU;rG;rG;rA;rA;rC;rU;rC;L dC;rU (SEQ ID No. 139) | mA;mG;mG;rA;mG;rU;mU;rC;mC;rA;mC;rA;mU;rU;dB;rU;mG;rG;mC (SEQ ID No. 140) | | | |
| Q-558 | 5medG;rC;rC;rA;rG;rA;rA;rG;rA;rA;rU;rG;rG;rA;rA;rC;rU;rC;L dC;rU (SEQ ID No. 139) | mA;mG;mG;rA;mG;rU;rC;mC;rA;mC;rA;mU;dB;mC;rU;mG;rG;mC (SEQ ID No. 140) | | | |
| Q-559 | 5medG;rC;rC;rA;rG;rA;rA;rG;rA;rA;rU;rG;rG;rA;rA;rC;rU;rC;L dC;rU (SEQ ID No. 139) | rA;mG;mG;mA;dB;mU;mU;rC;mC;rA;mC;rA;mU;rU;mC;rU;mG;rG;mC (SEQ ID No. 140) | | | |
| Q-560 | 5medG;rC;rC;rA;rG;rA;rA;rG;rA;rA;rU;rG;rG;rA;rA;rC;rU;rC;L dC;rU (SEQ ID No. 139) | mA;mG;mG;mA;dB;mU;mU;rC;mC;rA;mC;rA;mU;rU;mC;rU;mG;rG;mC (SEQ ID No. 140) | | | |
| Q-561 | 5medG;rC;rC;rA;rG;rA;rA;rG;rA;rA;rU;rG;rG;rA;rA;rC;rU;rC;L dC;rU (SEQ ID No. 139) | rA;mG;mG;mA;mG;rU;mU;mC;mC;rA;mC;rA;mU;mU;dB;mU;mG;rG;mC (SEQ ID No. 140) | | | |
| Q-562 | 5medG;rC;rC;rA;rG;rA;rA;rG;rA;rA;rU;rG;rG;rA;rA;rC;rU;rC;L dC;rU (SEQ ID No. 139) | mA;mG;mG;rA;mG;rU;mU;rC;mC;rA;mU;mU;dB;mU;m G;rG;mC (SEQ ID No. 140) | | | |
| Q-563 | 5medG;rC;rC;rC;rA;rG;rA;rA;rG;rA;rA;rU;rG;rG;rA;rA;rC;rU;LdC; LdC;rU (SEQ ID No. 139) | mA;mG;mG;rA;mG;rA;dB;rU;mU;rC;mC;rA;mC;rA;mU;rU;mC;rU;mG;r G;mC (SEQ ID No. 140) | | | |
| Q-564 | 5medG;rC;rC;rC;rA;rG;rA;rA;rG;rA;rA;rU;rG;rG;rA;rA;rC;rU;LdC; LdC;rU (SEQ ID No. 139) | mA;mG;mG;rA;mG;rA;mG;dB;mU;rC;mC;rA;mC;rA;mU;rU;mC;rU;mG; rG;mC (SEQ ID No. 140) | | | |
| Q-565 | 5medG;rC;rC;rC;rA;rG;rA;rA;rG;rA;rA;rU;rG;rG;rA;rA;rC;rU;LdC; LdC;rU (SEQ ID No. 139) | mA;mG;mG;rA;mG;rA;mG;rU;mU;rC;mC;rA;mC;rA;mU;rU;rU;mC;rU;mG; rG;mC (SEQ ID No. 140) | | | |
| Q-566 | 5medG;rC;rC;rC;rA;rG;rA;rA;rG;rA;rA;rU;rG;rG;rA;rA;rC;rU;LdC; LdC;rU (SEQ ID No. 139) | mA;mG;mG;rA;mG;rA;mG;rU;mC;mC;rA;mC;rA;mU;rU;dB;mC;rU;mG; rG;mC (SEQ ID No. 140) | | | |
| Q-567 | 5medG;rC;rC;rC;rA;rG;rA;rA;rG;rA;rA;rU;rG;rG;rA;rA;rC;rU;LdC; LdC;rU (SEQ ID No. 139) | rA;mG;rG;mA;mG;mA;dB;mU;mU;rC;mC;rA;mC;rA;mU;mC;rU;mG;r G;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-568 | 5medG;rC;rC;rA;G;rA;rA;rU;rG;rG;rU;rG;rA;rA;rC;rU;LdC;LdC;rU (SEQ ID No. 139) | mA;mG;rG;mA;dB;mU;mU;rC;mC;rA;mC;rA;mU;rU;mC;rU;mG;rG;mC (SEQ ID No. 140) | | | |
| Q-569 | 5medG;rC;rC;rA;G;rA;rA;rU;rG;rG;rU;rG;rA;rA;rC;rU;LdC;LdC;rU (SEQ ID No. 139) | rA;mG;rG;mA;rG;mU;mU;rC;rC;rA;mC;rA;mU;mU;dB;mU;mG;rG;mC (SEQ ID No. 140) | | | |
| Q-570 | 5medG;rC;rC;rA;G;rA;rA;rU;rG;rG;rU;rG;rA;rA;rC;rU;LdC;LdC;rU (SEQ ID No. 139) | mA;mG;mG;rA;mG;rU;rU;rC;mC;rA;mC;rA;mU;mU;dB;mU;mG;rG;mC (SEQ ID No. 140) | | | |
| Q-571 | iB;rG;rC;rC;rA;rG;rA;rA;rU;rG;rG;rU;rG;rA;rA;rC;rU;rC;LdC;rU (SEQ ID No. 139) | mA;mG;mG;rA;dB;rU;mU;rC;mC;rA;mC;rA;mU;rU;mC;rU;mG;rG;mC (SEQ ID No. 140) | | | |
| Q-572 | iB;rG;rC;rC;rA;rG;rA;rA;rU;rG;rG;rU;rG;rA;rA;rC;rU;rC;LdC;rU (SEQ ID No. 139) | mA;mG;mG;rA;mG;dB;mU;rC;mU;rC;mC;rA;mC;rA;mU;rU;mC;rU;mG;rG;mC (SEQ ID No. 140) | | | |
| Q-573 | iB;rG;rC;rC;rA;rG;rA;rA;rU;rG;rG;rU;rG;rA;rA;rC;rU;rC;LdC;rU (SEQ ID No. 139) | mA;mG;mG;rA;mG;rU;mU;rC;mC;rA;mC;rA;mU;rU;dB;rU;mG;rG;mC (SEQ ID No. 140) | | | |
| Q-574 | iB;rG;rC;rC;rA;rG;rA;rA;rU;rG;rG;rU;rG;rA;rA;rC;rU;rC;LdC;rU (SEQ ID No. 139) | mA;mG;mG;rA;mG;rU;mU;rC;mC;rA;mC;rA;mU;mU;dB;mC;mU;rG;mC (SEQ ID No. 140) | | | |
| Q-575 | iB;rG;rC;rC;rA;rG;rA;rA;rU;rG;rG;rU;rG;rA;rA;rC;rU;rC;LdC;rU (SEQ ID No. 139) | rA;mG;rG;mA;dB;mU;mU;rC;mC;rA;mC;rA;mU;rU;mC;rU;mG;rG;mC (SEQ ID No. 140) | | | |
| Q-576 | iB;rG;rC;rC;rA;rG;rA;rA;rU;rG;rG;rU;rG;rA;rA;rC;rU;rC;LdC;rU (SEQ ID No. 139) | mA;mG;mG;rA;mA;dB;mU;mU;rC;mC;rA;mC;rA;mU;mU;dB;mU;mG;mC (SEQ ID No. 140) | | | |
| Q-577 | iB;rG;rC;rC;rA;rG;rA;rA;rU;rG;rG;rU;rG;rA;rA;rC;rU;rC;LdC;rU (SEQ ID No. 139) | rA;mG;rG;mA;rG;mU;mU;rC;mC;rA;mC;rA;mU;mU;dB;mU;mG;rG;mC (SEQ ID No. 140) | | | |
| Q-578 | iB;rG;rC;rC;rA;rG;rA;rA;rU;rG;rG;rU;rG;rA;rA;rC;rU;rC;LdC;rU (SEQ ID No. 139) | mA;mG;mG;rA;mG;rA;mG;rU;mU;rC;mC;rA;mC;rA;mU;mU;dB;mU;mG;mC (SEQ ID No. 140) | | | |
| Q-579 | iB;rG;rC;rC;rA;rG;rA;rA;rU;rG;rG;rU;rG;rA;rA;rC;rU;rC;LdC;Ld C;rU (SEQ ID No. 139) | mA;mG;mG;rA;dB;rU;mU;rC;mC;rA;mC;rA;mU;rU;mC;rU;mG;rG;mC (SEQ ID No. 140) | | | |
| Q-580 | iB;rG;rC;rC;rA;rG;rA;rA;rU;rG;rG;rU;rG;rA;rA;rC;rU;rC;LdC;Ld C;rU (SEQ ID No. 139) | mA;mG;mG;rA;mG;dB;mU;rC;mC;rA;mC;rA;mU;rU;mC;rU;mG;rG;mC (SEQ ID No. 140) | | | |
| Q-581 | iB;rG;rC;rC;rA;rG;rA;rA;rU;rG;rG;rU;rG;rA;rA;rC;rU;rC;LdC;Ld C;rU (SEQ ID No. 139) | mA;mG;mG;rA;mG;rU;mU;rC;mC;rA;mC;rA;mU;rU;dB;rU;mG;rG;mC (SEQ ID No. 140) | | | |
| Q-582 | iB;rG;rC;rC;rA;rG;rA;rA;rU;rG;rG;rU;rG;rA;rA;rC;rU;rC;LdC;Ld C;rU (SEQ ID No. 139) | mA;mG;mG;rA;mG;rU;mU;rC;mC;rA;mC;rA;mU;mU;dB;mC;mU;rG;mC (SEQ ID No. 140) | | | |
| Q-583 | iB;rG;rC;rC;rA;rG;rA;rA;rU;rG;rG;rU;rG;rA;rA;rC;rU;rC;LdC;Ld C;rU (SEQ ID No. 139) | rA;mG;mG;mA;dB;mU;mU;rC;mC;rA;mC;rA;mU;rU;mC;rU;mG;rG;mC (SEQ ID No. 140) | | | |

FIG. 23 Continued

| ID | Sense | AntiSense | Activity at 20 nM (% of control) | IC50 (nM) | Stability in human serum |
|---|---|---|---|---|---|
| Q-584 | iB;rG;rC;rC;rA;rG;rA;rA;rU;rG;rG;rA;rA;rC;rU;LdC;Ld C;rU (SEQ ID No. 139) | mA;mG;rG;mA;dB;mU;rU;rC;mC;rA;mC;rA;mU;rU;mC;rU;mG ;rG;mC (SEQ ID No. 140) | | | |
| Q-585 | iB;rG;rC;rC;rA;rG;rA;rA;rU;rG;rG;rA;rA;rC;rU;LdC;Ld C;rU (SEQ ID No. 139) | rA;mG;rG;mA;rG;mU;rU;mC;rC;rA;mC;rA;mU;mU;dB;mU;mG; rG;mC (SEQ ID No. 140) | | | |
| Q-586 | iB;rG;rC;rC;rA;rG;rA;rA;rU;rG;rG;rA;rA;rC;rU;LdC;Ld C;rU (SEQ ID No. 139) | mA;mG;mG;rA;mG;rU;mU;rC;mC;rA;mC;rA;mC;rA;mU;mU;dB;mU;m G;rG;mC (SEQ ID No. 140) | | | |
| Q-587 | rG;rC;rC;rA;rG;rA;rA;rU;rG;rG;rA;rA;rC;rU;rC;LdC;r U (SEQ ID No. 139) | rA;mG;rG;mA;rG;mU;dB;mC;rC;rA;mC;rA;mU;rU;mC;rU;mG;r G;mC (SEQ ID No. 140) | | | |
| Q-588 | rG;rC;rC;rA;rG;rA;rA;rU;rG;rG;rA;rA;rC;rU;rC;LdC;r U (SEQ ID No. 139) | rA;mG;rG;mA;rG;mU;rU;dB;rC;rA;mC;rA;mC;rA;mU;rU;mC;rU;mG;rG ;mC (SEQ ID No. 140) | | | |
| Q-589 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;dB;rA;mC;rA;mU;rU;mC;rU;mG;r G;mC (SEQ ID No. 140) | | | |
| Q-590 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;dB;mC;rA;mU;rU;mC;rU;mG;r G;mC (SEQ ID No. 140) | | | |
| Q-591 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;dB;rA;mU;rU;mC;rU;mG;r G;mC (SEQ ID No. 140) | | | |
| Q-592 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;mC;dB;mU;rU;mC;rU;mG;r G;mC (SEQ ID No. 140) | | | |
| Q-593 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;mC;rA;dB;rU;mC;rU;mG;r G;mC (SEQ ID No. 140) | | | |
| Q-594 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;dB;mC;rC;rA;mC;rA;mU;rU;mC;rU;mG;r G;mC (SEQ ID No. 140) | | | |
| Q-595 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;mC;rA;mU;rU;mC;rU;mG;r G;mC (SEQ ID No. 140) | | | |
| Q-596 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;dB;rA;mC;rA;mU;rU;mC;rU;mG;r G;mC (SEQ ID No. 140) | | | |
| Q-597 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;dB;mC;rA;mU;rU;mC;rU;mG;r G;mC (SEQ ID No. 140) | | | |
| Q-598 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;dB;rA;mU;rU;mC;rU;mG;r G;mC (SEQ ID No. 140) | | | |
| Q-599 | rG;rC;rC;rA;rG;rA;rA;rU;rG;rG;rA;rA;rC;rU;rC;LdC;r U (SEQ ID No. 139) | rA;mG;rG;mA;rG;mU;rU;mC;rC;rA;mC;dB;mU;rU;mC;rU;mG;r G;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-600 | rG;rC;rC;rA;rG;rA;rA;rU;rG;rA;rA;rC;rU;LdC;LdC;rU (SEQ ID No. 139) | rA;mG;rG;mA;rG;mU;rU;mC;rC;rA;mC;rA;dB;rU;mC;rU;mG;rG;mC (SEQ ID No. 140) | | | |
| Q-601 | 5medG;rC;rC;rA;rG;rA;rA;rU;rG;rA;rA;rC;rU;rC;L dC;rU (SEQ ID No. 139) | rA;mG;rG;mA;rG;mU;mU;dB;mC;rC;rA;mC;rA;mU;rU;mC;rU;mG;r G;mC (SEQ ID No. 140) | | | |
| Q-602 | 5medG;rC;rC;rA;rG;rA;rA;rU;rG;rA;rA;rC;rU;rC;L dC;rU (SEQ ID No. 139) | rA;mG;rG;mA;rG;mU;rU;dB;rC;rA;mC;rA;mU;rU;mC;rU;mG;rG;mC (SEQ ID No. 140) | | | |
| Q-603 | 5medG;rC;rC;rA;rG;rA;rA;rU;rG;rA;rA;rC;rU;rC;L dC;rU (SEQ ID No. 139) | rA;mG;rG;mA;rG;mU;rU;mC;dB;rA;mC;rA;mU;rU;mC;rU;mG;r G;mC (SEQ ID No. 140) | | | |
| Q-604 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;dB;mC;rA;mU;rU;mC;rU;mG;r G;mC (SEQ ID No. 140) | | | |
| Q-605 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;dB;rA;mU;rU;mC;rU;mG;rG;mC (SEQ ID No. 140) | | | |
| Q-606 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;mC;dB;mU;rU;mC;rU;mG;r G;mC (SEQ ID No. 140) | | | |
| Q-607 | 5medG;rC;rC;rA;rG;rA;rA;rU;rG;rA;rA;rC;rU;rC;L dC;rU (SEQ ID No. 139) | rA;mG;rG;mA;rG;mU;rU;mC;rC;rA;mC;rA;dB;rU;mC;rU;mG;rG;mC (SEQ ID No. 140) | | | |
| Q-608 | 5medG;rC;rC;rA;rG;rA;rA;rU;rG;rA;rA;rC;rU;LdC; LdC;rU (SEQ ID No. 139) | rA;mG;rG;mA;rG;mU;rU;mC;dB;mC;rA;mC;rA;mU;rU;mC;rU;mG;r G;mC (SEQ ID No. 140) | | | |
| Q-609 | 5medG;rC;rC;rA;rG;rA;rA;rU;rG;rA;rA;rC;rU;rC;U LdC; (SEQ ID No. 139) | rA;mG;rG;mA;rG;mU;rU;dB;rC;rA;mC;dB;rA;mC;rA;mU;rU;mC;rU;mG;rG;mC (SEQ ID No. 140) | | | |
| Q-610 | 5medG;rC;rC;rA;rG;rA;rA;rU;rG;rA;rA;rC;rU;rC;U LdC; (SEQ ID No. 139) | rA;mG;rG;mA;rG;mU;rU;mC;dB;rA;mC;dB;rA;mC;rA;mU;rU;mC;rU;mG;r G;mC (SEQ ID No. 140) | | | |
| Q-611 | 5medG;rC;rC;rA;rG;rA;rA;rU;rG;rA;rA;rC;rU;rC;U LdC; (SEQ ID No. 139) | rA;mG;rG;mA;rG;mU;rU;mC;rC;mC;rC;dB;mC;rA;mU;rU;mC;rU;mG;r G;mC (SEQ ID No. 140) | | | |
| Q-612 | 5medG;rC;rC;rA;rG;rA;rA;rU;rG;rU;rG;rA;rC;rU;LdC; LdC;rU (SEQ ID No. 139) | rA;mG;rG;mA;rG;mU;rU;mC;rC;rA;mC;rC;dB;rA;dB;rA;mU;rU;mC;rU;mG;rG;mC (SEQ ID No. 140) | | | |
| Q-613 | 5medG;rC;rC;rA;rG;rA;rA;rU;rG;rA;rA;rC;rU;rC;U LdC; (SEQ ID No. 139) | rA;mG;rG;mA;rG;mU;rU;mC;rC;rA;mC;rA;mC;dB;mU;rU;mC;rU;mG;r G;mC (SEQ ID No. 140) | | | |
| Q-614 | 5medG;rC;rC;rA;rG;rA;rA;rU;rG;rA;rA;rC;rU;rC;U LdC; (SEQ ID No. 139) | rA;mG;rG;mA;rG;mU;rU;mC;dB;mC;rA;mC;rC;rA;dB;rU;mC;rU;mG;r G;mC (SEQ ID No. 140) | | | |
| Q-615 | iB;rG;rC;rC;rA;rG;rA;rA;rU;rG;rA;rA;rC;rU;rC;LdC;rU (SEQ ID No. 139) | rA;mG;rG;mA;rG;mU;mU;dB;mC;rC;rA;mC;rA;mU;rU;mC;rU;mG;r G;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-616 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;dB;rC;rA;mC;rA;mU;rU;mC;rU;mG;rG;mC (SEQ ID No. 140) | | | |
| Q-617 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;dB;rA;mC;rA;mU;rU;mC;rU;mG;rG;mC (SEQ ID No. 140) | | | |
| Q-618 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;dB;rA;mU;rU;mC;rU;mG;rG;mC (SEQ ID No. 140) | | | |
| Q-619 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;dB;rA;mU;rU;mC;rU;mG;rG;mC (SEQ ID No. 140) | | | |
| Q-620 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;dB;mU;rU;mC;rU;mG;rG;mC (SEQ ID No. 140) | | | |
| Q-621 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;rA;dB;rU;mC;rU;mG;rG;mC (SEQ ID No. 140) | | | |
| Q-622 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;rA;mU;dB;mC;rU;mG;rG;mC (SEQ ID No. 140) | | | |
| Q-623 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;dB;rC;rA;mC;rA;mU;rU;mC;rU;mG;rG;mC (SEQ ID No. 140) | | | |
| Q-624 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;dB;mC;rA;mU;rU;mC;rU;mG;rG;mC (SEQ ID No. 140) | | | |
| Q-625 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;rC;dB;mC;rU;mG;rG;mC (SEQ ID No. 140) | | | |
| Q-626 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;dB;rA;mC;rA;dB;rU;mG;rG;mC (SEQ ID No. 140) | | | |
| Q-627 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;rC;rA;dB;rU;mG;rG;mC (SEQ ID No. 140) | | | |
| Q-628 | iB;rG;rC;rC;rA;rG;rA;rA;rU;rG;rG;rA;rA;rC;rU;rC;rU;LdC;rU (SEQ ID No. 139) | rA;mG;rG;mA;rG;mU;rU;mC;rC;rA;mC;rA;dB;rU;mC;rU;mG;rG;mC (SEQ ID No. 140) | | | |
| Q-629 | rG;rC;rC;rA;rG;rA;rA;rU;rG;rG;rA;rA;rC;rU;rC;rU;rU (SEQ ID No. 139) | rA;rG;rG;mA;rG;rU;rU;rC;rC;rA;rC;rA;rU;rU;rC;rU;rG;rG;rC (SEQ ID No. 140) | | | |
| Q-630 | rG;rC;rC;rA;rG;rA;rA;rU;rG;rG;rA;rA;rC;rU;rC;rU;rU (SEQ ID No. 139) | rA;mG;rG;mA;rG;mU;rU;dB;rC;rA;mC;rA;mU;rU;mC;rU;mG;rG;mC (SEQ ID No. 140) | | | |
| Q-631 | rG;rC;rC;rA;rG;rA;rA;rU;rG;rG;rA;rA;rC;rU;rC;rU;rU (SEQ ID No. 139) | rA;mG;rG;mA;rG;mU;rU;mC;rC;rA;mC;rA;mU;rU;mC;rU;mG;rG;mC (SEQ ID No. 140) | | | |

FIG. 23 Continued

| ID | Sense | AntiSense | Activity at 20nM (% of control) | IC50 (nM) | Stability in human serum |
|---|---|---|---|---|---|
| Q-632 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rA;mC;rA;mU;rU;dB;rU;mG;rG;mC (SEQ ID No. 140) | | | |
| Q-633 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rA;mC;rA;mU;dB;mC;rU;mG;rG;mC (SEQ ID No. 140) | | | |
| Q-634 | rG;rC;rC;rA;rG;rA;rA;rU;rG;rG;rA;rA;rC;rU;rC;rC;rU (SEQ ID No. 139) | rA;mG;rG;mA;rG;mU;rU;mC;dB;mC;rC;rA;mC;rA;mU;rU;mG;rG;mC (SEQ ID No. 140) | | | |
| Q-635 | rG;rC;rC;rA;rG;rA;rA;rU;rG;rG;rA;rA;rC;rU;rC;rC;rU (SEQ ID No. 139) | rA;mG;rG;mA;rG;mU;rU;dB;rC;rA;mC;rA;mU;rU;mC;rU;mG;rG;mC (SEQ ID No. 140) | | | |
| Q-636 | rG;rC;rC;rA;rG;rA;rA;rU;rG;rG;rA;rA;rC;rU;rC;rC;rU (SEQ ID No. 139) | rA;mG;rG;mA;rG;mU;rU;mC;mC;dB;rA;mC;rA;mU;rU;mC;rU;mG;rG;mC (SEQ ID No. 140) | | | |
| Q-637 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rC;dB;mC;rA;mU;rU;mC;rU;mG;rG;mC (SEQ ID No. 140) | | | |
| Q-638 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rA;dB;rA;mU;rU;mC;rU;mG;rG;mC (SEQ ID No. 140) | | | |
| Q-639 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rA;mC;dB;mU;rU;mC;rU;mG;rG;mC (SEQ ID No. 140) | | | |
| Q-640 | rG;rC;rC;rA;rG;rA;rA;rU;rG;rG;rA;rA;rC;rU;rC;rC;rU (SEQ ID No. 139) | rA;mG;rG;mA;rG;mU;rU;mC;rC;rA;mC;rA;dB;rU;mC;rU;mG;rG;mC (SEQ ID No. 140) | | | |
| Q-641 | rG;rC;rC;rA;rG;rA;rA;rU;rG;rG;rA;rA;rC;rU;rC;LdC;rU (SEQ ID No. 139) | rA;rG;rG;rA;rG;rU;rU;rC;rC;rA;rC;rA;rU;rU;rC;rU;rG;rG;rC (SEQ ID No. 140) | | | |
| Q-642 | rG;rC;rC;rA;rG;rA;rA;rU;rG;rG;rA;rA;rC;rU;rC;LdC;LdC;rU (SEQ ID No. 139) | rA;rG;rG;rA;rG;rU;rU;rC;rC;rA;rC;rA;rU;rU;rC;rU;rG;rG;rC (SEQ ID No. 140) | | | |
| Q-643 | 5medG;rC;rC;rA;rG;rA;rA;rU;rG;rA;rA;rC;rU;rC;L;dC;rU (SEQ ID No. 139) | rA;rG;rG;rA;rG;rU;rU;rC;rC;rA;rC;rA;rU;rU;rC;rU;rG;rG;rC (SEQ ID No. 140) | | | |
| Q-644 | 5medG;rC;rC;rA;rG;rA;rA;rU;rG;rG;rA;rA;rC;rU;rC;rU;LdC;LdC;rU (SEQ ID No. 139) | rA;rG;rG;rA;rG;rU;rU;rC;rC;rA;rC;rA;rU;rU;rC;rU;rG;rG;rC (SEQ ID No. 140) | | | |
| Q-645 | iB;rG;rC;rC;rA;rG;rA;rG;rA;rA;rU;rG;rG;rA;rA;rC;rU;rC;LdC;rU (SEQ ID No. 139) | rA;rG;rG;rA;rG;rU;rU;rC;rC;rA;rC;rA;rU;rU;rC;rU;rG;rG;rC (SEQ ID No. 140) | | | |
| Q-646 | iB;rG;rC;rC;rA;rG;rA;rA;rU;rG;rG;rA;rA;rC;rU;rC;rU;LdC;Ld;C;rU (SEQ ID No. 139) | rA;rG;rG;rA;rG;rU;rU;rC;rC;rA;rC;rA;rU;rU;rC;rU;rG;rG;rC (SEQ ID No. 140) | | | |

DOUBLE-STRANDED RNA DIRECTED TO CASP2 AND METHODS OF USE THEREOF

This application is a §371 national stage of PCT International Application No. PCT/IL2008/01197, filed Sep. 4, 2008, and claims the benefit of U.S. Provisional Applications Nos. 61/189,035, filed Aug. 15, 2008; 61/134,638, filed Jul. 10, 2008; 61/128,519, filed May 22, 2008; 61/010,040, filed Jan. 4, 2008; 61/003,535, filed Nov. 15, 2007; 61/000,664, filed Oct. 25, 2007; and 60/997,576, filed Oct. 3, 2007, the contents of all of which are hereby incorporated by reference into this application.

This application incorporates-by-reference nucleotide and/or amino acid sequences which are present in the file named "120520_2094_77602-A-PCT-US_Substitute_Sequence_Listing_NJC.txt," which is 15.9 megabytes in size, and which was created May 15, 2012, in the IBM-PCT machine format, having an operating system compatibility with MS-Windows, which is contained in the text file filed May 15, 2012 as part of this application.

Throughout this application various patent and scientific publications are cited. The disclosures for these publications in their entireties are hereby incorporated by reference into this application to more fully describe the state of the art to which this invention pertains.

FIELD OF THE INVENTION

The present invention relates to novel compounds, pharmaceutical compositions comprising same and methods of use thereof for the inhibition of certain mammalian genes including TP53BP2, LRDD, CYBA, CASP2, NOX3, HRK, RAC1, RHOA and DUOX1. The compounds and compositions are thus useful in the treatment of subjects suffering from diseases or conditions and or symptoms associated with such diseases or conditions in which gene expression has adverse consequences. In particular embodiments, the invention provides, compositions comprising same and methods of use thereof. The present invention also provides novel structural motifs useful in the preparation of chemically modified siRNA oligonucleotides, compositions comprising same and methods of use thereof.

BACKGROUND OF THE INVENTION siRNAs and RNA Interference

RNA interference (RNAi) is a phenomenon involving double-stranded (ds) RNA-dependent gene specific posttranscriptional silencing. Initial attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later, it was discovered that synthetic duplexes of 21 nucleotide RNAs could mediate gene specific RNAi in mammalian cells, without stimulating the generic antiviral defense mechanisms (see Elbashir et al. Nature 2001, 411:494-498 and Caplen et al. PNAS USA 2001, 98:9742-9747). As a result, small interfering RNAs (siRNAs) have become powerful tools in attempting to understand gene function.

RNA interference (RNAi) in mammals is mediated by small interfering RNAs (siRNAs) (Fire et al, Nature 1998, 391:806) or microRNAs (miRNAs) (Ambros, Nature 2004, 431(7006):350-355; Bartel, Cell 2004, 116(2): 281-97). The corresponding process in plants is commonly referred to as specific post-transcriptional gene silencing (PTGS) or RNA silencing and is also referred to as quelling in fungi.

An siRNA is a double-stranded RNA or modified RNA molecule which down-regulates or silences (prevents) the expression of a gene/mRNA of its endogenous (cellular) counterpart. The mechanism of RNA interference is detailed infra.

Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Nat. Med. 2005, 11(1):50-55). Recent reviews discussing siRNA therapeutics are available (Barik, et al., J. Mol. Med. 2005, 83:764-773; Dallas and Vlassov, Med. Sci. Monitor 2006, 12(4):RA67-74; Chakraborty, Current Drug Targets 2007, 8(3):469-82; Dykxhoorn et al., Gene Therapy 2006. 13:541-552).

Mucke (IDrugs 2007 10(1):37-41) presents a review of current therapeutics, including siRNA to various targets, for the treatment of ocular diseases, for example age related macular degeneration (AMD) and glaucoma.

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol. Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107, 094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl modifications. Holen et al (NAR. 2003, 31(9):2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the present invention offer an advantage in that they are non-toxic and are useful in the preparation of pharmaceutical compositions for treatment of various diseases.

Pro-Apoptotic Genes

Pro-apoptotic genes are generally defined as genes that play a role in apoptotic cell death. A non-limiting list of pro-apoptotic genes, useful in the present invention is as follows: tumor protein p53 binding protein 2 (TP53BP2); leucine-rich repeats and death domain containing (LRDD);

cytochrome b-245, alpha polypeptide (CYBA, p22phox); activating transcription factor 3 (ATF3); caspase 2, apoptosis-related cysteine peptidase (CASP2); NADPH oxidase 3 (NOX3); harakiri, BCL2 interacting protein (HRK, BID3); complement component 1, q subcomponent binding protein (C1QBP); BCL2/adenovirus E1B 19 kDa interacting protein 3 (BNIP3); mitogen-activated protein kinase 8 (MAPK8, JNK1); mitogen-activated protein kinase 14 (MAPK14, p38); ras-related C3 botulinum toxin substrate 1 (rho family, small GTP binding protein RAC1); glycogen synthase kinase 3 beta (GSK3B); purinergic receptor P2X, ligand-gated ion channel, 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2 (BMP2); gap junction protein, alpha 1, 43 kDa (connexin 43, GJA1); TYRO protein tyrosine kinase binding protein (TYROBP); connective tissue growth factor (CTGF); secreted phosphoprotein 1 (osteopontin, SPP1); ras homolog gene family, member A (RHOA); and dual oxidase 1 (DUOX1).

PCT Patent Application No. PCT/IL2007/001278 (PCT Publication No. WO 2008/050329) and U.S. Ser. No. 11/978,089 to the assignee of the present invention relate to inhibitors of the above-mentioned genes, and are incorporated by reference in their entirety.

Hearing Loss

Chemical-Induced Ototoxicity

The ototoxic effects of various therapeutic drugs on auditory cells and spiral ganglion neurons are often the factor limiting their therapeutic usefulness. Commonly used ototoxic drugs include the widely used chemotherapeutic agent cisplatin and its analogs, aminoglycoside antibiotics, e.g. gentamycin, quinine and its analogs, salicylate and its analogs, and loop-diuretics.

For example, antibacterial aminoglycosides such as gentamycin, streptomycin, kanamycin, tobramycin, and the like are known to have serious toxic side effects, particularly ototoxicity and nephrotoxicity, which reduce their value as therapeutic agents (see Goodman and Gilman's The Pharmacological Basis of Therapeutics, 6th ed., A. Goodman Gilman et al., eds; Macmillan Publishing Co., Inc., 1980. New York, pp. 1169-71). Thus, ototoxicity is a recognized dose-limiting side-effect of antibiotic administration. Studies have shown that from 4 to 15% of patients receiving one gram per day for greater than one week develop measurable hearing loss, which gradually worsens and can lead to permanent deafness if treatment continues.

Ototoxicity is also a serious dose-limiting side-effect for cisplatin, a platinum coordination complex that has proven effective on a variety of human cancers including testicular, ovarian, bladder, and head and neck cancer. Cisplatin (Platinol®) has been shown to damage auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects and can lead to tinnitus ("ringing in the ears") and temporary hearing loss. Moreover, if the drug is used at high doses for a prolonged time, chronic and irreversible hearing impairment can arise.

Without being bound by theory, cisplatin drugs and other potentially ototoxic drugs induce the ototoxic effects via apoptosis in inner ear tissue, particularly inner ear hair cells (Zhang et al., Neuroscience 2003, 120(1):191-205; Wang et al., 2003, J. Neuroscience, 23(24):8596-8607). Prolonged use of high doses of ototoxic drugs leads to persistent and irreversible hearing impairment. In mammals, auditory hair cells are produced only during embryonic development and do not regenerate if lost during postnatal life. Therefore, a loss of hair cells will result in profound and irreversible deafness.

Unfortunately, there are presently no effective therapies to treat the cochlea to reverse deafness. Thus, an effective therapy to prevent cell death of auditory hair cells would be of great therapeutic value. U.S. Ser. No. 11/655,610, assigned to the applicant of the present invention relates to methods for treating hearing impairment in a subject comprising administering to the subject a composition comprising an effective amount of a p53 polynucleotide inhibitor, and optionally an inhibitor of a pro-apoptotic gene.

Presbycusis

Another type of hearing loss is presbycusis, which is hearing loss that gradually occurs in aging individuals. About 30-35% of adults between the ages of 65 and 75 years and 40-50% of people 75 and older experience hearing loss. Accordingly, there exists a need for means to prevent, reduce or treat the incidence and/or severity of inner ear disorders and hearing impairments involving inner ear tissue, particularly inner ear hair cells.

Acoustic Trauma

Acoustic trauma is a type of hearing loss that is caused by prolonged exposure to loud noises. Without wishing to be bound to theory, exposure to loud noise causes the hair cells on the cochlea to become less sensitive. With more severe exposure, injury can proceed from a loss of adjacent supporting cells to complete disruption of the organ of Corti. Death of the sensory cell can lead to progressive Wallerian degeneration and loss of primary auditory nerve fibers.

Accordingly, there exists a need for means to prevent, reduce or treat the incidence and/or severity diseases or disorders resulting from chemical toxicity including inner ear disorders and hearing impairment, renal damage (nephrotoxicity) and neural damage (neurotoxicity).

Acute Renal Failure

Acute renal failure (ARF) is a clinical syndrome characterized by rapid deterioration of renal function that occurs within days. The principal feature of ARF is an abrupt decline in glomerular filtration rate (GFR), resulting in the retention of nitrogenous wastes (urea, creatinine). Worldwide, severe ARF occurs in about 170-200 persons per million annually. Today, there is no specific treatment for established ARF. Several drugs have been found to ameliorate toxic and ischemic experimental ARF in animal models, as manifested by lower serum creatinine levels, reduced histological damage and faster recovery of renal function. These include antioxidants, calcium channel blockers, diuretics, vasoactive substances, growth factors, anti-inflammatory agents and more. However, when these drugs were tested in clinical trials no benefit was shown and their use for treating ARF has not been approved.

In the majority of hospitalized ARF patients, ARF is caused by acute tubular necrosis (ATN), which results from ischemic and/or nephrotoxic insults. Renal hypoperfusion is caused by hypovolemic, cardiogenic and septic shock, by administration of vasoconstrictive drugs or renovascular injury. Nephrotoxins include exogenous toxins such as contrast media and aminoglycosides as well as endogenous toxin such as myoglobin. Recent studies suggest that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al. 1999, Science. 285(5434):1733-7; Supavekin et al. 2003, Kidney Int. 63(5):1714-24). In conclusion, there are no currently satisfactory modes of therapy for the prevention and/or treatment of acute renal failure, and there is a clear need to develop novel compounds for this purpose.

Renal Transplant

Delayed Graft Function

Delayed graft function (DGF) is the most common complication of the immediate postoperative period in renal transplantation and results in poor graft outcome (Moreso et al. Nephrol. Dial. Transplant. 1999. 14(4):930-35). Although the incidence and definition of DGF vary among transplant centers, the consequences are invariable and include prolonged hospital stay, additional invasive procedures, and additional cost to the patient and health-care system.

Acute Transplant Rejection

Graft rejection has been categorized into three subsets depending on the onset of graft destruction. Hyperacute rejection is the term applied to very early graft destruction, usually within the first 48 hours. Acute rejection has an onset of several days to months or even years after transplantation and can involve humoral and/or cellular mechanisms. Chronic rejection relates to chronic alloreactive immune response.

Glaucoma

Glaucoma is one of the leading causes of blindness in the world. It affects approximately 66.8 million people worldwide. At least 12,000 Americans are blinded by this disease each year (Kahn and Milton, Am J. Epidemiol. 1980, 111(6): 769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage. Mucke (IDrugs 2007, 10(1):37-41) reviews current therapeutics, including siRNA to various targets for the treatment of ocular diseases, for example, age-related macular degeneration (AMD) and glaucoma.

Acute Respiratory Distress Syndrome

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators which cause inflammation, hypoxemia and frequently result in failure of multiple organs. This condition is life threatening and often lethal, usually requiring mechanical ventilation and admission to an intensive care unit. A less severe form is called acute lung injury (ALI).

Ischemia-Reperfusion Injury Following Organ Transplantation

Ischemia reperfusion injury (IRI) is one of the leading causes of death in organ allograft recipients. Significant IRI occurs in every organ transplant from a deceased donor and in some from live donors. It contributes to increased acute rejection and impaired long-term allograft function. Lung transplantation, the only definitive therapy for many patients with end stage lung disease, has poor survival rates in all solid allograft recipients.

Acute Lung Transplant Rejection

Acute allograft rejection remains a significant problem in lung transplantation despite advances in immunosuppressive medication. Rejection, and ultimately early morbidity and mortality may result from ischemia-reperfusion (I/R) injury and hypoxic injury.

Spinal Cord Injury

Spinal cord injury, is a disturbance of the spinal cord that results in loss of sensation and/or mobility, also known as myelopathy. The two most common types of spinal cord injury are due to trauma and disease. Traumatic injuries are often due to automobile accidents, falls, gunshots diving accidents, and the like. Diseases that can affect the spinal cord include polio, spina bifida, tumors, and Friedreich's ataxia.

Pressure Sores

Pressure sores, often known as bedsores or pressure ulcers, are areas of damaged skin and tissue. With unrelieved pressure, tissue ischemia can develop resulting in the accumulation of metabolic waste in the interstitial tissue, resulting in anoxia and cellular death. This pressure-induced ischemia also leads to excessive tissue hypoxia, further promoting bacterial proliferation and tissue destruction.

Age-Related Macular Degeneration

The most common cause of decreased best-corrected vision in individuals over 65 years of age in the United States is the retinal disorder known as age-related macular degeneration (AMD). The area of the eye affected by AMD is the macula, a small area in the center of the retina, composed primarily of photoreceptor cells. As AMD progresses, the disease is characterized by loss of sharp, central vision. So-called "dry" AMD accounts for about 85%-90% of AMD patients and involves alterations in eye pigment distribution, loss of photoreceptors and diminished retinal function due to overall atrophy of cells. "Wet" AMD involves proliferation of abnormal choroidal vessels leading to clots or scars in the sub-retinal space. Thus, the onset of "wet" AMD occurs because of the formation of an abnormal choroidal neovascular network (choroidal neovascularization, CNV) beneath the neural retina. The newly formed blood vessels are excessively leaky, leading to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness (Hamdi & Kenney, Frontiers in Bioscience, e305-314, May 2003).

Diabetic Retinopathy

Diabetic retinopathy (DR) is recognized as a retinal vascular disorder exhibiting excess capillary permeability, vascular closure, and proliferation of new vessels. DR occurs in two stages: nonproliferative and proliferative. In the nonproliferative stage the disease is characterized by a loss of retinal capillary pericytes, thickening of the basement membrane and development of microaneurysms, dot-blot hemorrhages, and hard exudates. In the proliferative stage the disease is characterized by extensive neovascularization, vessel intrusion into the vitreous, bleeding and fibrosis with subsequent retinal traction, which leads to severe vision impairment. U.S. Pat. No. 6,740,738 and related patents and applications to the assignee of the present invention are directed to methods of inhibiting the RTP801 gene and protein, for treating, inter alia, retinopathy.

Oral Mucositis

Oral mucositis, also referred to as a stomatitis, is a common and debilitating side effect of chemotherapy and radiotherapy regimens, which manifests itself as erythema and painful ulcerative lesions of the mouth and throat. Routine activities such as eating, drinking, swallowing, and talking may be difficult or impossible for subjects with severe oral mucositis. Palliative therapy includes administration of analgesics and topical rinses.

Dry-Eye Syndrome

Dry eye syndrome is a common problem usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases.

Ischemic Ocular Conditions

Ischemic optic neuropathy (ION) includes a variety of disorders that produce ischemia to the optic nerve. By definition, ION is termed anterior if disc edema is present acutely, suggesting infarction of the portion of the optic nerve closest to the globe. ION also may be posterior, lying several centimeters behind the globe. Ischemic optic neuropathy usually occurs only in people older than 60 years of age. Most cases are nonarteritic and attributed to the effects of atherosclerosis, diabetes, or hypertension on optic nerve perfusion. Temporal arteritis causes about 5% of cases (arteritic ION).

Symptoms and signs are sudden, partial or complete vision loss, accompanied by swelling of the optic nerve head and often hemorrhage. Visual field defects may manifest as loss of half the visual field with a horizontal demarcation or as central or centrocecal (surrounding the natural blind spot) scotomata. Decreased vision is soon followed by pallor of the optic disk.

More effective therapies to treat the above mentioned diseases and disorders would be of great therapeutic value.

SUMMARY OF THE INVENTION

The present invention provides novel TP53BP2, LRDD, CYBA, CASP2, NOX3, HRK, RAC1, RHOA and DUOX1 siRNA, and novel chemically and or structurally modified siRNA compounds for the inhibition of gene expression in general and of mammalian genes TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1, RHOA, and DUOX1, in particular. (See Table A, infra, for genes' details).

Novel structures of double stranded oligonucleotides, having advantageous properties and which may be applied to siRNA to any target sequence, and in particular to the siRNA oligonucleotides disclosed herein, are further provided. The chemically modified siRNA motifs disclosed in the present invention are useful in the preparation of stable and active compounds useful in RNA interference (RNAi).

The present invention also provides pharmaceutical compositions comprising one or more such oligonucleotides. The present invention further relates to methods for treating or preventing the incidence or severity of a disease or condition in a subject in need thereof wherein the disease or condition and/or symptoms associated therewith is associated with expression of the target gene. In some embodiments the disease or condition is selected from the group consisting of hearing loss, acute renal failure (ARF), glaucoma, acute respiratory distress syndrome (ARDS) and other acute lung and respiratory injuries, ischemia-reperfusion injury following lung transplantation, ocular ischemic conditions, organ transplantation including lung, liver, heart, pancreas, and kidney transplantation, nephro- and neurotoxicity, spinal cord injury, pressure sores, age-related macular degeneration (AMD), dry eye syndrome, oral mucositis, ischemic ocular neuropathy (ION) and chronic obstructive pulmonary disease (COPD). Such methods involve administering to a mammal in need of such treatment a prophylactically or therapeutically effective amount of one or more such compounds, which inhibit or reduce expression or activity of at least one such gene.

Accordingly, in one aspect the present invention provides novel oligonucleotide sequences useful in inhibiting a gene selected from LRDD, CYBA, CASP2, NOX3, HRK, RAC1, RHOA, and DUOX1, whose mRNA polynucleotide sequences are set forth in SEQ ID NOS: 1-2, 3-5, 6, 10-11, 12, 13, 24-26, 46 and 47-48, respectively. Tables D (D1-D34) provide 19, 21 and 23-mer sense and corresponding antisense oligonucleotides of the present invention. In another aspect the present invention provides chemically and or structurally modified nucleic acid compounds useful in inhibiting gene expression in general or gene expression of a gene selected from TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1, RHOA, or DUOX1. In various embodiments the modified compound comprises an oligonucleotide sequence present in Tables B (B1-B74) and C (C1-C3), set forth in SEQ ID NOS:97-68654 (disclosed in U.S. Ser. No. 11/978,089 and PCT Patent Application No. PCT/IL 2007/001278, which are hereby incorporated by reference in their entirety).

In certain embodiments the chemically and or structurally modified siRNA compounds comprise an oligonucleotide sequence present in Tables D (D1-D34; SEQ ID NOS:68, 655-87,088).

In one aspect the present invention provides a compound having structure (A) set forth below:

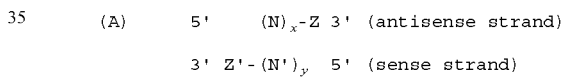

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein each of x and y is an integer between 18 and 40;

wherein each of Z and Z' may be present or absent, but if present is 1-5 consecutive nucleotides covalently attached at the 3' terminus of the strand in which it is present;

wherein the sequence of $(N)_x$ comprises one or more of the antisense sequences present in Tables D (D1-D34).

In certain embodiments (N)x and (N')y are fully complementary. In other embodiments (N)x and (N')y are substantially complementary. In certain embodiments (N)x is fully complementary to a target sequence. In other embodiments (N)x is substantially complementary to a target sequence. According to certain preferred embodiments the present invention provides an siRNA compound comprising one or more modified nucleotide, wherein the modified nucleotide possesses a modification in the sugar moiety, in the base moiety or in the internucleotide linkage moiety.

In one aspect the present invention provides a compound having Structure (IX) set forth below:

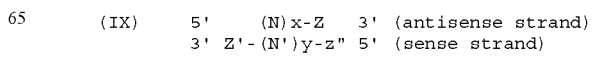

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N')y;
wherein x=18 to 27;
wherein y=18 to 27;
wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;
wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and
wherein the sequence of (N)x is substantially complementary to the sequence of (N')y; and the sequence of (N')y is substantially identical to the sequence of an mRNA encoded by a target gene.

In some embodiments x=y=19. In other embodiments x=y=23. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments of Structure (IX) (N)x comprises nine alternating modified ribonucleotides. In other embodiments of Structure (IX) (N)x comprises nine alternating modified ribonucleotides further comprising a 2'O modified nucleotide at position 2. In some embodiments (N)x comprises 2'O Me modified ribonucleotides at the odd numbered positions 1, 3, 5, 7, 9, 11, 13, 15, 17, 19. In other embodiments (N)x further comprises a 2'O Me modified ribonucleotide at one or both of positions 2 and 18. In yet other embodiments (N)x comprises 2'O Me modified ribonucleotides at positions 2, 4, 6, 8, 11, 13, 15, 17, 19.

In various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (X) set forth below:

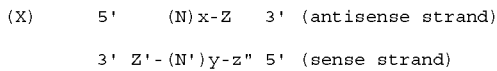

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of (N')y;
wherein x=18 to 27;
wherein y=18 to 27;
wherein (N)x comprises modified or unmodified ribonucleotides, and optionally at least one unconventional moiety;
wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and
wherein the sequence of (N)x is substantially complementary to the sequence of (N')y; and the sequence of (N')y is substantially identical to the sequence of an mRNA encoded by a target gene.

In some embodiments x=y=19. In other embodiments x=y=23. In some preferred embodiments (N)x comprises modified and unmodified ribonucleotides, and at least one unconventional moiety. In various embodiments (N)x comprises less than 15 consecutive nucleotides complementary to the mRNA.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety. In certain embodiments there are less than 15 base pairs between (N)x and (N')y.

In various embodiments of Structure (X) z" is present and is selected from an abasic ribose moiety, a deoxyribose moiety; an inverted abasic ribose moiety, a deoxyribose moiety; C6-amino-Pi; a mirror nucleotide.

In yet another aspect the present invention provides a compound having Structure (XI) set forth below:

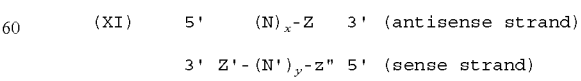

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present; wherein z" may be present or absent but if present is a capping moiety covalently attached at the 5' terminus of (N')y;
wherein x=18 to 27;
wherein y=18 to 27;
wherein (N)x comprises a combination of modified or unmodified ribonucleotides and unconventional moieties, any modified ribonucleotide having a 2'-O-methyl on its sugar;
wherein (N')y comprises modified or unmodified ribonucleotides and optionally an unconventional moiety, any modified ribonucleotide having a 2'OMe on its sugar;
wherein the sequence of (N)x is substantially complementary to the sequence of (N')y; and the sequence of (N')y is substantially identical to the sequence of an mRNA encoded by a target gene; and wherein there are less than 15 consecutive nucleotides complementary to the mRNA.

In some embodiments x=y=19. In other embodiments x=y=23. In some preferred embodiments the at least one preferred one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N)x comprises less than 15 consecutive nucleotides complementary to the mRNA. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

The Structure (IX), (X) and (XI) motifs is useful with any oligonucleotide pair (sense and antisense strands) to a mammalian or non-mammalian gene. In some embodiments the mammalian gene is a human gene. In various embodiments the mRNA of the human gene is set forth in one of SEQ ID NOS:1-41, 46-48.

In some embodiments the Structure (IX), (X) and (XI) motifs are used in combination with the oligonucleotide pairs presented in Tables B (B1-B74), C (C1-C3C4) and Tables D (D1-D34) (SEQ ID NOS:97-87,178).

In various embodiments the present invention provides an siRNA set forth in Structure (IV):

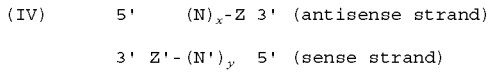

wherein each of N and N' is a nucleotide selected from an unmodified ribonucleotide, a modified ribonucleotide, an unmodified deoxyribonucleotide and a modified deoxyribonucleotide;
wherein each of (N)$_x$ and (N')$_y$ is an oligonucleotide in which each consecutive N or N' is joined to the next N or N' by a covalent bond;
wherein Z and Z' are absent;
wherein x=y=19;
wherein in (N')y the nucleotide in at least one of positions 15, 16, 17, 18 and 19 comprises a nucleotide selected from an abasic pseudo-nucleotide, a mirror nucleotide, a deoxyribonucleotide and a nucleotide joined to an adjacent nucleotide by a 2'-5' internucleotide bond;
wherein (N)x comprises alternating modified ribonucleotides and unmodified ribonucleotides each modified ribonucleotide being modified so as to have a 2'-O-methyl on its sugar and the ribonucleotide located at the middle position of (N)x being modified or unmodified, preferably unmodified; and wherein the sequence of (N)x is substantially complementary to the sequence of (N')y; and the sequence of (N')y is substantially identical to the mRNA of a target gene.

In some embodiments of Structure (IV), in (N')y the nucleotide in one or both of positions 17 and 18 comprises a modified nucleotide selected from an abasic pseudo-nucleotide, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic pseudo-nucleotide analog and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)X further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

Other embodiments of Structures (IV), (IX) and (X) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23 mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'O Me modifications on the antisense strand are similarly adjusted. In some embodiments (N)x comprises 2'O Me modified ribonucleotides at the odd numbered positions (5' to 3'; positions 1, 3, 5, 7, 9, 12, 14, 16, 18, 20 for the 21 mer oligonucleotide [nucleotide at position 11 unmodified] and 1, 3, 5, 7, 9, 11, 13, 15, 17, 19, 21, 23 for the 23 mer oligonucleotide [nucleotide at position 12 unmodified]. In other embodiments (N)x comprises 2'O Me modified ribonucleotides at positions 2, 4, 6, 8, 10, 12, 14, 16, 18, 20 [nucleotide at position 11 unmodified for the 21 mer oligonucleotide and at positions 2, 4, 6, 8, 10, 13, 15, 17, 19, 21, 23 for the 23 mer oligonucleotide [nucleotide at position 12 unmodified].

In some embodiments (N')y further comprises a 5' terminal cap nucleotide. In various embodiments the terminal cap moiety is selected from an abasic pseudo-nucleotide analog, an inverted abasic pseudo-nucleotide analog, an L-DNA nucleotide, and a C6-imine phosphate.

The Structure (IV) motif is useful with any oligonucleotide pair (sense and antisense strands) to a mammalian or non-mammalian gene. In some embodiments the mammalian gene is a human gene. In various embodiments the mRNA of the human gene is set forth in one of SEQ ID NOS:1-41, 46-48.

In some embodiments the Structure (IV) motif is used in combination with the oligonucleotide pairs presented in Tables B (B1-B74), C (C1-C3C4) and Tables D (D1-D34) (SEQ ID NOS:97-87,178)

In other embodiments the present invention provides a compound having Structure V set forth below:

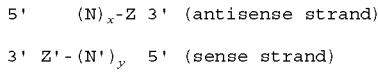

wherein each of N and N' is selected from a pseudo-nucleotide and a nucleotide;
wherein each nucleotide is selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein Z and Z' are absent;
wherein x=18 to 27;
wherein y=18 to 27;
wherein the sequence of (N)x is substantially complementary to the sequence of (N')y; and the sequence of (N')y is substantially identical to the mRNA of a target gene;
wherein at least one of N is selected from an abasic pseudo nucleotide, a non-pairing nucleotide analog and a nucleotide mismatch to the mRNA of a target gene in a position of (N)x such that (N)x comprises less than 15 consecutive nucleotides complementary to the mRNA of a target gene.

In other embodiments the present invention provides a double stranded compound having Structure (VI) set forth below:

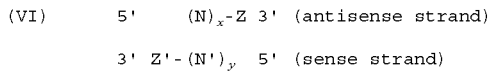

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein Z and Z' are absent;
wherein each of x and y is an integer between 18 and 40;
wherein the sequence of (N)x is substantially complementary to the sequence of (N')y; and the sequence of (N')y is substantially identical to the mRNA of a target gene;
wherein (N)x, (N')y or (N)x and (N')y comprise non base-pairing modified nucleotides such that (N)x and (N')y form less than 15 base pairs in the double stranded compound.

In other embodiments the present invention provides a compound having Structure (VII) set forth below:

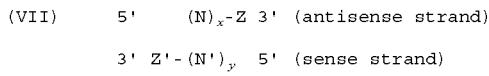

wherein each of N is a nucleotide selected from an unmodified ribonucleotide, a modified ribonucleotide, an unmodified deoxyribonucleotide and a modified deoxyribonucleotide;
wherein each of N' is a nucleotide analog selected from a six membered sugar nucleotide, seven membered sugar nucleotide, morpholino moiety, peptide nucleic acid and combinations thereof;
wherein each of $(N)_x$ and $(N')_y$ is an oligonucleotide in which each consecutive N or N' is joined to the next N or N' by a covalent bond;
wherein Z and Z' are absent;
wherein each of x and y is an integer between 18 and 40;
wherein the sequence of (N)x is substantially complementary to the sequence of (N')y; and the sequence of (N')y is substantially identical to the mRNA of a target gene.

In other embodiments the present invention provides a compound having Structure (VIII) set forth below:

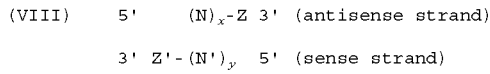

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein Z and Z' are absent;
wherein each of x and y is an integer between 18 and 40;
wherein one of N or N' in an internal position of (N)x or (N')y or one or more of N or N' at a terminal position of (N)x or (N')y comprises an abasic moiety or a 2' modified nucleotide;
wherein the sequence of (N)x is substantially complementary to the sequence of (N')y; and the sequence of (N')y is substantially identical to the mRNA of a target gene.

In some embodiments of Structures (V)-(VIII) (N)x comprises alternating modified ribonucleotides and unmodified ribonucleotides; each modified ribonucleotide being modified so as to have a 2'-O-methyl on its sugar. In some embodiments N located at the middle position of (N)x is unmodified.

In some embodiments of Structure (IV), in (N')y the nucleotide in one or both of positions 17 and 18 comprises a modified nucleotide selected from an abasic pseudo-nucleotide, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic pseudo-nucleotide analog.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments $(N)_x$ further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

Other embodiments of Structure (IV) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23 mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'O Me modifications on the antisense strand are similarly adjusted. In some embodiments (N)x comprises 2'O Me modified ribonucleotides at the odd numbered positions (5' to 3'; positions 1, 3, 5, 7, 9, 12, 14, 16, 18, 20 for the 21 mer oligonucleotide [nucleotide at position 11 unmodified] and 1, 3, 5, 7, 9, 11, 13, 15, 17, 19, 21, 23 for the 23 mer oligonucleotide [nucleotide at position 12 unmodified]. In other embodiments (N)x comprises 2'O Me modified ribonucleotides at positions 2, 4, 6, 8, 10, 12, 14, 16, 18, 20 [nucleotide at position 11 unmodified for the 21 mer oligonucleotide and at positions 2, 4, 6, 8, 10, 13, 15, 17, 19, 21, 23 for the 23 mer oligonucleotide [nucleotide at position 12 unmodified].

In some embodiments (N')y further comprises a 5' terminal cap nucleotide. In various embodiments the terminal cap moiety is selected from an abasic pseudo-nucleotide analog, an inverted abasic pseudo-nucleotide analog, an L-DNA nucleotide, and a C6-imine phosphate.

The Structure (IV) motif is useful with any oligonucleotide pair (sense and antisense strands) to a mammalian or non-mammalian gene. In some embodiments the mammalian gene is a human gene. In various embodiments the mRNA of the human gene is set forth in one of SEQ ID NOS:1-41, 46-48.

In some embodiments the Structure (IV) motif is used in combination with the oligonucleotide pairs presented in Tables B (B1-B74), C (C1-C4) and Tables D (D1-D34).

In a second aspect the present invention provides chemically and or structurally modified siRNA compounds based on Structures (C)-(H) and the related Structures (I)-(XI) disclosed herein. In various embodiments the siRNA compounds are based on one of a sense oligonucleotide and corresponding antisense oligonucleotide shown in Tables B (B1-B74), Tables C (C1-C4) and/or Tables D (D1-D34).

In another aspect the present invention provides a pharmaceutical composition comprising a modified or unmodified compound of the present invention, in an amount effective to inhibit human gene expression wherein the compound comprises an antisense sequence, (N)$_x$, present in Tables D (D1-D34); and a pharmaceutically acceptable carrier.

In yet another aspect the present invention provides a pharmaceutical composition comprising one or more modified compounds of the present invention, in an amount effective to inhibit human gene expression wherein the compound comprises an antisense sequence, (N)$_x$, present in Tables B (B1-B74) or Tables C (C1-C4) and/or Tables D (D1-D34); and a pharmaceutically acceptable carrier.

In another aspect, the present invention relates to a method for the treatment of a subject in need of treatment for a disease or disorder or symptoms associated with the disease or disorder, associated with the expression of a gene wherein the mRNA polynucleotide sequence of said gene is set forth in any one of SEQ ID NOS:1-41, 46-48 comprising administering to the subject an amount of an siRNA, according to the present invention, in a therapeutically effective dose so as to thereby treat the subject.

More specifically, the present invention provides methods and compositions useful in treating a subject suffering from acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation and including Delayed Graft Function (DGF) nephrotoxicity, spinal cord injury, pressure sores, dry eye syndrome, oral mucositis, ischemic ocular neuropathy (ION) and chronic obstructive pulmonary disease (COPD).

The methods of the invention comprise administering to the subject one or more siRNA compounds which inhibit expression of a gene wherein the mRNA polynucleotide sequence of said gene is set forth in any one of SEQ ID NOS:1-41, 46-48. The novel structures disclosed herein, when integrated into antisense and corresponding sense nucleic acid sequences to any target gene, provides siRNA compound useful in reducing expression of that target gene. The target gene is a mammalian or non-mammalian gene. In particular embodiments, the target gene is a mammalian gene having mRNA selected from any one of SEQ ID NOS:1-41, or 46-48.

The sense and corresponding antisense nucleotide sequences set forth in Tables B and C are disclosed in PCT publication no. WO2008/050329, to the assignee of the present invention, incorporated herein by reference in its entirety.

siRNA compounds wherein both the sequence and the modifications are known are excluded from the present invention.

BRIEF DESCRIPTION OF THE FIGURES

FIGS. 1A and 1B present 19-mer siRNA structures and experimental results obtained with 2'-O-methylated compounds of the present invention;

FIG. 2 shows examples of 23-mer siRNA compounds having alternating methylation pattern on both sense and antisense (AS) strands;

FIGS. 3A and 3B present 23-mer CASP2 siRNA structures comprising 2'-O-methylated monomers and experimental results obtained with those compounds;

FIGS. 5A and 5B present 23-mer CASP2 siRNA structures comprising 2'-O-methylated monomers and experimental results obtained with those compounds;

FIGS. 7A and 7B present 19-mer CASP2 siRNA structures comprising 2'5' bridged nucleotides and experimental results obtained using those compounds;

FIGS. 8A and 8B present 19-mer REDD2 and QM5 siRNA structures, respectfully, comprising 2'5' bridged nucleotides.

FIGS. 9A and 9B present 19-mer QM5 siRNA structures, comprising combination of 2'5' bridged nucleotides (stars) and 2'-O methoxyribonucleotides (bold, underlined)

FIGS. 10A and 10B present 19-mer QM5 siRNA structures, comprising combination of 2'5' bridged nucleotides (stars) and 2'-O methoxyribonucleotides (bold, underlined) and experimental results using those compounds.

FIGS. 11A and 11B present 23-mer CASP2 siRNA structures, comprising combination of 2'5' bridged nucleotides (stars) and 2'-O methoxyribonucleotides (bold, underlined) and experimental results using those compounds;

FIGS. 12A and 12B present 23-mer CASP2 siRNA structures, comprising 2'5' bridged nucleotides (stars) and experimental results using those compounds;

FIG. 13A shows QM5 siRNA structures, comprising L-DNA nucleotides; FIG. 13C shows serum stability and FIG. 13D shows the IC50 value of an siRNA comprising L-DNA nucleotides compared to an siRNA comprising an alternating 2' methoxy pattern;

FIG. 14A shows QM5 siRNA structures, comprising LNA nucleotides.

FIGS. 17A-17C show examples of siRNA compounds comprising combinations of modifications;

FIG. 18 depicts RNA/DNA chimeric oligonucleotides;

FIGS. 19A-19E show examples of oligonucleotides comprising L-DNA motifs, alone or in combination with additional modifications;

FIG. 20 depicts additional oligonucleotide structures useful in the preparation of duplex compounds according to the present invention;

FIG. 21 examples of non-base-pairing nucleotide monomers which are used in the various structures detailed herein;

FIG. 23 provides a table of compounds useful in RNAi comprising sequences and structural motifs according to the present invention.

DETAILED DESCRIPTION OF THE INVENTION

Figure 1B:
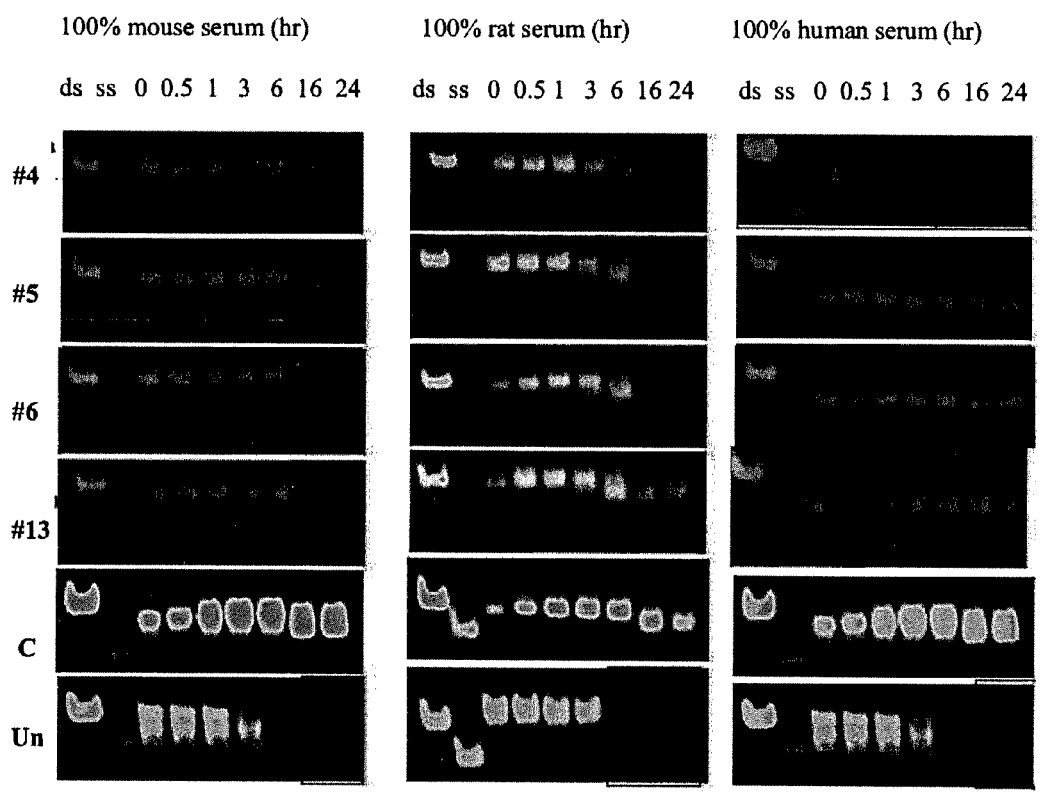

The present invention relates generally to compounds which down-regulate expression of various genes, particularly to novel small interfering RNAs (siRNAs), and to the use of these novel siRNAs in the treatment of a subject suffering from various medical conditions.

Accordingly, in one aspect the present invention provides novel oligonucleotide sequences useful in inhibiting a gene selected from LRDD, CYBA, CASP2, NOX3, HRK, RAC1, RHOA, and DUOX1, whose mRNA polynucleotide sequences are set forth in SEQ ID NOS: 1-2, 3-5, 6, 10-11, 12, 13, 24-26, 46 and 47-48, respectively. The oligonucleotide sequences are presented in Tables D (D1-D34) wherein a sense strand is paired with a complementary antisense strand. Novel structural motifs, useful in the preparation of siRNA to any target gene, are also provided. Lists of preferred siRNA to be used in the present invention are provided in Tables B (B1-B74), C (C1-C4) and D (D1-D34). For each gene there is a separate table of 19-mer, 21-mer and 23-mer sequences, which are prioritized based on their score in the proprietary algorithm as the best sequences for targeting the human gene expression.

Molecules and compositions, which inhibit the genes of the invention, are discussed herein at length, and any of said molecules and/or compositions may be beneficially employed in the treatment of a subject suffering from any of said conditions.

The siRNA compounds of the present invention possess structures and modifications which may for example increase activity, increase stability, and or minimize toxicity; the novel modifications of the siRNAs of the present invention are beneficially applied to double stranded RNA useful in preventing or attenuating target gene expression, in particular the target genes discussed herein.

Details of certain target genes and preferred indications are presented in Table A, hereinbelow.

TABLE A

Target genes of the present invention

| No. | Gene | Full name and Human Gene ID | Preferred diseases/ conditions |
|---|---|---|---|
| 1 | TP53BP2 | tumor protein p53 binding protein, 2<br>gi\|112799848\|ref\|NM_001031685.2 (SEQ ID NO: 1)<br>gi\|112799845\|ref\|NM_005426.2 (SEQ ID NO: 2): | ARF, nephrotoxicity, glaucoma, dry eye, ION, DGF, kidney transplantation, hearing loss, acoustic trauma, oral mucositis |
| 2 | LRDD | leucine-rich repeats and death domain containing<br>gi\|61742781\|ref\|NM_018494.3 (SEQ ID NO: 3)<br>gi\|61742783\|ref\|NM_145886.2 (SEQ ID NO: 4)<br>gi\|61742785\|ref\|NM_145887.2 (SEQ ID NO: 5) | ARF, glaucoma, hearing loss, SCI, oral mucositis; dry eye, kidney or lung transplantation, ION, ischemic-reperfusion lung injury |
| 3 | CYBA | cytochrome b-245, alpha polypeptide<br>gi\|68509913\|ref\|NM_000101.2\| (SEQ ID NO: 6) | ARF, ARDS, hearing loss, SCI, glaucoma, kidney transplantation, lung transplantation and ischemic-reperfusion lung injury, ION |
| 4 | ATF3 | activating transcription factor 3<br>gi\|95102484\|ref\|NM_001030287.2\| (SEQ ID NO: 7)<br>gi\|71902534\|ref\|NM_001674.2\| (SEQ ID NO: 8)<br>gi\|95102480\|ref\|NM_004024.4\| (SEQ ID NO: 9) | ARF, glaucoma, hearing loss, SCI, oral mucositis |
| 5 | CASP2 | caspase 2, apoptosis-related cysteine peptidase<br>gi\|39995058\|ref\|NM_032982.2 (SEQ ID NO: 10)<br>gi\|39995060\|ref\|NM_032983.2 (SEQ ID NO: 11) | ARF, glaucoma, hearing loss, SCI, dry eye, kidney transplantation, lung transplantation and ischemic-reperfusion lung injury, oral mucositis, ION |
| 6 | NOX3 | NADPH oxidase 3<br>Gi\|11136625\|ref\|NM_015718.1 (SEQ ID NO: 12) | Hearing loss, acoustic trauma |
| 7 | HRK | harakiri<br>gi\|4504492\|ref\|NM_003806.1 (SEQ ID NO: 13) | ARF, glaucoma, hearing loss, SCI, ARDS, ION |
| 8 | C1QBP | complement component 1, q subcomponent binding protein<br>gi\|28872801\|ref\|NM_001212.3 (SEQ ID NO: 14) | ARF, COPD, hearing loss, spinal-cord injury, pressure sores |

TABLE A-continued

Target genes of the present invention

| No. | Gene | Full name and Human Gene ID | Preferred diseases/ conditions |
|---|---|---|---|
| 9 | BNIP3 | BCL2/adenovirus E1B 19 kDa interacting protein 3 Gi\|7669480\|ref\|NM_004052.2 (SEQ ID NO: 15) | ARF, glaucoma, hearing loss, acoustic trauma, ION, SCI, ARDS, COPD, transplantation (lung) and ischemic-reperfusion lung injury, |
| 10 | MAPK8 | mitogen-activated protein kinase 8 gi\|20986493\|ref\|NM_002750.2 (SEQ ID NO: 16) gi\|20986522\|ref\|NM_139049.1 (SEQ ID NO: 17) gi\|20986518\|ref\|NM_139046.1 (SEQ ID NO: 18) gi\|20986520\|ref\|NM_139047.1 (SEQ ID NO: 19) | ARF, glaucoma, hearing loss, SCI, ARDS |
| 11 | MAPK14 | mitogen-activated protein kinase 14 gi\|20986511\|ref\|NM_139012.1 (SEQ ID NO: 20) gi\|20986515\|ref\|NM_139014.1 (SEQ ID NO: 21) gi\|4503068\|ref\|NM_001315.1 (SEQ ID NO: 22) gi\|20986513\|ref\|NM_139013.1 (SEQ ID NO: 23) | ARF, glaucoma, hearing loss, SCI, ARDS |
| 12 | Rac1 | ras-related C3 botulinum toxin substrate 1 (rho family, small GTP binding protein) gi\|38505164\|ref\|NM_198829.1 (SEQ ID NO: 24) gi\|156071511\|ref\|NM_018890.3 (SEQ ID NO: 25) gi\|156071503\|ref\|NM_006908.4 (SEQ ID NO: 26) | ARF, glaucoma, hearing loss, acoustic trauma, SCI, ARDS, AMD, pressure sores, lung transplantation and ischemic-reperfusion lung injury |
| 13 | GSK3B | glycogen synthase kinase 3 beta gi\|21361339\|ref\|NM_002093.2 (SEQ ID NO: 27) | ARF, hearing loss, SCI, COPD, pressure sores, ARDS, transplantation |
| 14 | P2RX7 | purinergic receptor P2X, ligand-gated ion channel, 7 gi\|34335273\|ref\|NM_002562.4 (SEQ ID NO: 28) | ARF, hearing loss, SCI, COPD, pressure sores, ARDS, transplantation |
| 15 | TRPM2 | transient receptor potential cation channel, subfamily M, member 2 gi\|67906811\|ref\|NM_001001188.3 (SEQ ID NO: 29) gi\|67906812\|ref\|NM_003307.3 (SEQ ID NO: 30) | ARF, hearing loss, SCI, COPD, pressure sores, ARDS, transplantation |
| 16 | PARG | poly (ADP-ribose) glycohydrolase gi\|70610135\|ref\|NM_003631.2 (SEQ ID NO: 31) | ARF, hearing loss, SCI, COPD, pressure sores, ARDS, transplantation |
| 17 | CD38 | CD38 molecule Gi\|38454325\|ref\|NM_001775.2 (SEQ ID NO: 32) | ARF, hearing loss, SCI, COPD, pressure sores |
| 18 | STEAP4 | STEAP family member 4 Gi\|13375867\|ref\|NM_024636.1 (SEQ ID NO: 33) | ARF, hearing loss, SCI, COPD, pressure sores |
| 19 | BMP2 | bone morphogenetic protein 2 gi\|80861484\|ref\|NM_001200.2 (SEQ ID NO: 34) | ARF, hearing loss, SCI, COPD, pressure sores |
| 20 | GJA1 | gap junction protein, alpha 1, 43 kDa gi\|4755136\|ref\|NM_000165.2 (SEQ ID NO: 35) | ARF, hearing loss, SCI, COPD, pressure sores |
| 21 | TYROBP | TYRO protein tyrosine kinase binding protein gi\|38157998\|ref\|NM_003332.2 (SEQ ID NO: 36) gi\|38158004\|ref\|NM_198125.1 (SEQ ID NO: 37) | ARF, hearing loss, SCI, COPD, pressure sores |
| 22 | CTGF | connective tissue growth factor gi\|4503122\|ref\|NM_001901.1 (SEQ ID NO: 38) | ARF, hearing loss, SCI, COPD |
| 23 | SPP1 | secreted phosphoprotein 1 gi\|91206461\|ref\|NM_001040058.1 (SEQ ID NO: 39) gi\|38146097\|ref\|NM_000582.2 (SEQ ID NO: 40) gi\|91598938\|ref\|NM_001040060.1 (SEQ ID NO: 41) | ARF, glaucoma, ARDS, osteoarthritis |
| 24 | RTN4R | reticulon 4 receptor gi\|47519383\|ref\|NM_023004.5 (SEQ ID NO: 42) | SCI |
| 25 | ANXA2 | annexin A2 gi\|50845387\|ref\|NM_001002858.1\| (SEQ ID NO: 43) gi\|50845389\|ref\|NM_004039.2\| (SEQ ID NO: 44) gi\|50845385\|ref\|NM_001002857.1 (SEQ ID NO: 45) | ARF, hearing loss, SCI, COPD |
| 26 | RHOA | ras homolog gene family member A gi\|50593005\|ref\|NM_001664.2 (SEQ ID NO: 46) | SCI, glaucoma, ION |
| 27 | DUOX1 | dual oxidase 1 gi\|28872749\|ref\|NM_017434.3 (SEQ ID NO: 47) gi\|28872750\|ref\|NM_175940.1 (SEQ ID NO: 48) | ARDS, COPD |

ARDS: acute respiratory distress syndrome;
AMD: age-related macular degeneration;
COPD: Chronic obstructive pulmonary disease;
ARF: acute renal failure;
SCI: spinal cord injury;
ION: ischemic ocular neuropathy.

Table A provides the gi (GeneInfo identifier) and accession numbers for polynucleotide sequences of the mRNA set forth as SEQ ID NOS:1-48. The corresponding polypeptides are set forth in SEQ ID NOS:49-96. The genes listed in Table A, supra, are described in more detail as follows:

(1) Tumor Protein p53 Binding Protein, 2 (TP53BP2):

Gene aliases: BBP; 53BP2; ASPP2; p53BP2; PPP1R13A, AI746547, X98550

This gene encodes a member of the ASPP (apoptosis-stimulating protein of p53) family of p53 interacting proteins. The corresponding protein contains four ankyrin repeats and an SH3 domain involved in protein-protein interactions. It is localized to the perinuclear region of the cytoplasm, and regulates apoptosis and cell growth through interactions with other regulatory molecules including members of the p53 family. Multiple transcript variants encoding different isoforms have been found for this gene. The polynucleotide sequences of human TP53BP2 mRNA transcriptional variants 1 and 2 are SEQ ID NOS:1 and 2, respectively, and the corresponding polypeptide sequence are set forth in SEQ ID NOS:49-50, respectively.

(2) Leucine-Rich Repeats and Death Domain Containing (LRDD)

Gene aliases: PIDD; MGC16925; DKFZp434D229, 1200011D09Rik, AU042446

The protein encoded by this gene contains a leucine-rich repeat and a death domain (LRDD). This protein has been shown to interact with other death domain proteins, such as Fas (TNFRSF6)-associated via death domain (FADD) and MAP-kinase activating death domain-containing protein (MADD), and thus may function as an adaptor protein in cell death-related signaling processes. The expression of the mouse counterpart of this gene has been found to be positively regulated by the tumor suppressor p53 and to induce cell apoptosis in response to DNA damage, which suggests a role for this gene as an effector of p53-dependent apoptosis. Three alternatively spliced transcript variants encoding distinct isoforms have been reported. The polynucleotide sequence of human LRDD transcriptional variants 2, 1 and 3 are set forth in SEQ ID NOS: 3-5, respectively, and the corresponding polypeptide sequence are set forth in SEQ ID NOS:51-53, respectively.

International Patent Publication WO 01/18037 discloses the LRDD polynucleotide and polypeptide sequences. International Patent Publication WO 03/087368 teaches compositions and methods for inhibiting genes.

(3) Cytochrome b-245, Alpha Polypeptide (CYBA)

Gene aliases: cytochrome b light chain; cytochrome b(558) alpha-subunit; cytochrome b, alpha polypeptide; flavocytochrome b-558 alpha polypeptide; p22-phox.

Cytochrome b is comprised of a light chain (alpha) and a heavy chain (beta). This gene encodes the light, alpha subunit which has been proposed as a primary component of the microbicidal oxidase system of phagocytes. Mutations in this gene are associated with autosomal recessive chronic granulomatous disease (CGD) characterized by the failure of activated phagocytes to generate superoxide, which is important for the microbicidal activity of these cells. The polynucleotide sequence of human CYBA mRNA is set forth in SEQ ID NO:6, and the corresponding polypeptide sequence is set forth in SEQ ID NO:54. International Patent Publication WO 2005/103297 teaches modulation of p22phox activity.

(4) Activating Transcription Factor 3 (ATF3)

Gene aliases: ATF3deltaZip2; ATF3deltaZip2c; ATF3deltaZip3, LRG-21, LRF-1

ATF3 is a member of the mammalian activation transcription factor/cAMP responsive element-binding (CREB) protein family of transcription factors. Multiple transcript variants encoding two different isoforms have been found for this gene. The longer isoform represses rather than activates transcription from promoters with ATF binding elements. The shorter isoform (deltaZip2) lacks the leucine zipper protein-dimerization motif and does not bind to DNA, and it stimulates transcription presumably by sequestering inhibitory co-factors away from the promoter. It is possible that alternative splicing may be physiologically important in the regulation of target genes. The polynucleotide sequences of human ATF3 transcriptional variants 3, 1 and 2 are set forth in SEQ ID NOS: 7-9, respectively, and the corresponding polypeptide sequences are set forth in SEQ ID NOS:55-57, respectively.

US Patent Publication No. 2003/0125277 teaches antisense to ATF3. International Patent Publication No. WO 2005/103297 relates to the methods of treating neuronal disease.

(5) Caspase 2, Apoptosis-Related Cysteine Peptidase (Neural Precursor Cell Expressed, Developmentally Down-Regulated 2 (CASP2)

Gene aliases: CASP-2, ICH-1L, ICH-1L/1S, ICH1, NEDD2; ICH-1 protease; NEDD2 apoptosis regulatory gene; Caspase 2, apoptosis-related cysteine protease.

This gene encodes a protein, which is a member of the cysteine-aspartic acid protease (caspase) family. Sequential activation of caspases plays a central role in the execution-phase of cell apoptosis. Caspases exist as inactive proenzymes, which undergo proteolytic processing at conserved aspartic residues to produce two subunits, large and small, that dimerize to form the active enzyme. The proteolytic cleavage of this protein is induced by a variety of apoptotic stimuli. Alternative splicing of this gene results in multiple transcript variants that encode different isoforms. The polynucleotide sequences of human CASP2 transcriptional variants 1 and 3 are set forth in SEQ ID NOS:10-11, respectively, and the corresponding polypeptide sequences are set forth in SEQ ID NOS:58-59, respectively.

U.S. Pat. No. 6,083,735 relates to the alternative splicing products of Casp2. U.S. Pat. Nos. 5,929,042 and 7,223,856 disclose specific Casp2 antisense compounds for the treatment of neurodegenerative disorders. International Patent Publication WO 02/024720 teaches Casp2 antisense. International Patent Publications WO 02/034201 discloses methods of treating diabetic retinopathy; WO 03/05821 relates to the inhibition of apoptosis related genes; WO 2004/009797 teaches Casp2 antisense; and WO 2004/103389 relates to methods for preventing cell death.

(6) NADPH Oxidase 3 (NOX3)

Gene aliases: GP91-3, MGC124289, het, nmf250; NADPH oxidase catalytic subunit-like 3, NADPH oxidase 1; head-tilt NADPH oxidases, such as NOX3, are plasma membrane-associated enzymes found in many cell types. They catalyze the production of superoxide by a 1-electron reduction of oxygen, using NADPH as the electron donor. The polynucleotide sequence of human NOX3 mRNA is set forth in SEQ ID NO:12, and the corresponding polypeptide sequence is set forth in SEQ ID NO:60.

International Patent Publication No. WO 2005/119251 relates to a method of treating hearing loss.

(7) Harakiri, BCL2 Interacting Protein (Contains Only BH3 Domain) (HRK)

Gene aliases: DP5, Bid3; BCL2-interacting protein; activator of apoptosis Hrk; BH3 interacting (with BCL2 family) domain, apoptosis agonist.

As an activator of apoptosis, Hrk regulates apoptosis through interaction with death-repressor proteins Bcl-2 and Bcl-X(L). The HRK protein lacks significant homology to other BCL2 family members except for an 8-amino acid region that was similar to the BCL2 homology domain-3 (BH3) motif of BIK. HRK interacts with BCL2 and BCLXL via the BH3 domain, but not with the death-promoting BCL2-related proteins BAX, BAK, or BCLXS. HRK localizes to membranes of intracellular organelles in a pattern similar to that previously reported for BCL2 and BCLXL. The polynucleotide sequence of human HRK mRNA is set forth in SEQ ID NO: 13 and the corresponding polypeptide sequence is set forth in SEQ ID NO. 61.

(8) Complement Component 1, q Subcomponent Binding Protein (C1QBP)

Gene aliases: GC1QBP, HABP1, SF2p32, gC1Q-R, gC1qR, p32, RP23-83I13.1, AA407365, AA986492, D11Wsu182e, MGC91723; C1q globular domain-binding protein; hyaluronan-binding protein 1; splicing factor SF2-associated protein.

The human complement subcomponent C1q associates with C1r and C1s in order to yield the first component of the serum complement system. The protein encoded by this gene is known to bind to the globular heads of C1q molecules and inhibit C1 activation. This protein has also been identified as the p32 subunit of pre-mRNA splicing factor SF2, as well as a hyaluronic acid-binding protein. The polynucleotide sequence of human C1QBP mRNA is set forth in SEQ ID NO: 14 and the corresponding polypeptide sequence is set forth in SEQ ID NO:62.

(9) BCL2/Adenovirus E1B 19 kDa Interacting Protein 3 (BNIP3)

Gene aliases: NIP3, MGC93043; BCL2/adenovirus E1B 19 kD-interacting protein 3, BCL2/adenovirus E1B 19 kDa-interacting protein 3 nuclear gene for mitochondrial product.

This gene is a member of the BCL2/adenovirus E1B 19 kd-interacting protein (BNIP) family. It interacts with the E1B 19 kDa protein, which is responsible for the protection of virally-induced cell death, as well as E1B 19 kDa-like sequences of BCL2, also an apoptotic protector. This gene contains a BH3 domain and a transmembrane domain, which have been associated with pro-apoptotic function. The dimeric mitochondrial protein encoded by this gene is known to induce apoptosis, even in the presence of BCL2. The polynucleotide sequence of human BNIP3 mRNA is set forth in SEQ ID NO:15 and the corresponding polypeptide sequence is set forth in SEQ ID NO:63.

U.S. Pat. No. 5,858,678 relates to the BNIP3 polynucleotide and polypeptide sequences. International Patent Publication No. WO 2004/009780 discloses methods of preventing ischemia induced cell damage.

(10) Mitogen-Activated Protein Kinase 8 (MAPK8)

Gene aliases: JNK; JNK1; PRKM8; SAPK1; JNK1A2; JNK21B1/2; JNK1 alpha protein kinase; JNK1 beta protein kinase; c-Jun N-terminal kinase 1; mitogen-activated protein Kinase 8 Transcript Variant 2; Protein Kinase JNK1; Stress-Activated Protein Kinase JNK1.

The protein encoded by this gene is a member of the MAP kinase family. MAP kinases act as an integration point for multiple biochemical signals, and are involved in a wide variety of cellular processes such as proliferation, differentiation, transcription regulation and development. This kinase is activated by various cell stimuli, and targets specific transcription factors, and thus mediates immediate-early gene expression in response to cell stimuli. The activation of this kinase by tumor-necrosis factor alpha (TNF-α) is found to be required for TNF-α induced apoptosis. This kinase is also involved in UV radiation induced apoptosis, which is thought to be related to cytochrome c-mediated cell death pathway. Studies of the mouse counterpart of this gene suggested its role in T cell proliferation, apoptosis and differentiation. Four alternatively spliced transcript variants encoding distinct isoforms have been reported. The polynucleotide sequence of MAPK8 transcriptional variants 2, 1, 3 and 4 are set forth in SEQ ID NOS:16-19, respectively, and the corresponding polypeptide sequences are set forth in SEQ ID NO:64-67.

International Patent Publication WO 99/09214 and U.S. Pat. No. 5,877,309 disclose antisense to JNK family members.

(11) Mitogen-Activated Protein Kinase 14 (MAPK14)

Gene aliases: CSBP1; CSBP2; CSPB1; EXIP; Mxi2; PRKM14; PRKM15; RK; SAPK2A; p38; p38ALPHA; MGC102436; p38MAPK; CSBP; Exip; Hog; MGC105413; p38Hog; Csaids binding protein; MAP kinase Mxi2; MAX-interacting protein 2; cytokine suppressive anti-inflammatory drug binding protein; p38 MAP kinase; p38 mitogen activated protein kinase; p38alpha Exip; stress-activated protein kinase 2A, tRNA synthetase cofactor p38.

The protein encoded by this gene is a member of the MAP kinase family, which act as an integration point for multiple biochemical signals, and are involved in a wide variety of cellular processes such as proliferation, differentiation, transcription regulation and development. This kinase is activated by various environmental stresses and proinflammatory cytokines. The activation requires its phosphorylation by MAP kinase kinases (MKKs), or its autophosphorylation triggered by its interaction with MAP3K7IP1/TAB1 protein. The substrates of this kinase include transcription regulator ATF2, MEF2C, and MAX, cell cycle regulator CDC25B, and tumor suppressor p53, which suggest its role in stress related transcription and cell cycle regulation, as well as in genotoxic stress response. Four alternatively spliced transcript variants of this gene encoding distinct isoforms have been reported. The polynucleotide sequence of human MAPK14 transcriptional variants 2, 4, 1 and 3 are set forth in SEQ ID NOS:20-23, respectively and the corresponding polypeptide sequences are set forth in SEQ ID NO:68-71.

International Patent Publications WO 2000/59919 and WO 2005/016947 and U.S. Pat. Nos. 6,140,124 and 6,448,079 teach antisense inhibition of p38.

(12) Ras-Related C3 Botulinum Toxin Substrate 1 (rho Family, Small GTP Binding Protein Rac1; RAC1)

Gene aliases: MGC111543, MIG5, TC-25, p21-Rac1; migration-inducing gene 5; migration-inducing protein 5; ras-related C3 botulinum toxin substrate 1; rho family, small GTP binding protein Rac1, ras-related C3 botulinum toxin substrate 1 (rho family small GTP binding protein Rac1)

The protein encoded by this gene is a GTPase, which belongs to the RAS superfamily of small GTP-binding proteins. Members of this superfamily regulate a diverse array of cellular events, including the control of cell growth, cytoskeletal reorganization, and the activation of protein kinases. Several alternatively spliced transcript variants of this gene have been described, but the full-length nature of some of these variants has not been determined. The polynucleotide sequences of human RAC1 transcriptional variants 1c, 1b and 1 are set forth in SEQ ID NOS:24-26, respectively and the corresponding polypeptide sequences are set forth in SEQ ID NO:72-74.

U.S. Pat. No. 6,180,597 relates to rho GTPase inhibitors that increase endothelial cell nitric oxide synthase levels. International Patent Publication WO 01/15739 teaches antisense modulation of Rho family members. International Patent Publication WO 2004/042052 teaches methods of suppressing TNF-α secretion.

(13) Glycogen Synthase Kinase 3 Beta (GSK3B)

Gene aliases: 7330414F15Rik, 8430431H08Rik, C86142, GSK-3, GSK-3beta, GSK3

Glycogen synthase kinase-3 (GSK3) is a proline-directed serine-threonine kinase that was initially identified as a phosphorylating and inactivating glycogen synthase. Two isoforms, alpha (GSK3A; MIM 606784) and beta, show a high degree of amino acid homology (Stambolic and Woodgett, Biochem J. 1994 303(Pt 3):701-4). GSK3B is involved in energy metabolism, neuronal cell development, and body pattern formation (Plyte et al., Biochim Biophys Acta. 1992. 1114(2-3):147-62). The polynucleotide sequence of human GSK3B mRNA is set forth in SEQ ID NO:27, and the corresponding polypeptide sequence is set forth in SEQ ID NO:75.

U.S. Pat. No. 6,323,029 relates to antisense inhibition of GSK3B.

(14) Purinergic Receptor P2X, Ligand-Gated Ion Channel, 7 (P2RX7)

Gene aliases: MGC20089, P2X7, AI467586; ATP receptor; P2X purinoceptor 7; P2X7 receptor; P2Z receptor; purinergic receptor P2X7.

The product of this gene belongs to the family of purinoceptors for ATP. This receptor functions as a ligand-gated ion channel and is responsible for ATP-dependent lysis of macrophages through the formation of membrane pores permeable to large molecules. Activation of this nuclear receptor by ATP in the cytoplasm may be a mechanism by which cellular activity can be coupled to changes in gene expression. Multiple alternatively spliced variants which would encode different isoforms have been identified although some fit nonsense-mediated decay (NMD) criteria. The polynucleotide sequence of human P2RX7 mRNA is set forth in SEQ ID NO:28 and the corresponding polypeptide sequence is set forth in SEQ ID NO:76.

(15) Transient Receptor Potential Cation Channel, Subfamily M, Member 2 (TRPM2)

Gene aliases: EREG1, KNP3, LTRPC2, MGC133383, NUDT9H, NUDT9L1, TRPC7, 9830168K16Rik, C79133, Trp7, Trrp7; estrogen responsive element associated gene 1; long transient receptor potential channel 2; transient receptor potential channel 7, transient receptor potential cation channel, subfamily M, member 2 (Trpm2); transient receptor potential channel 7; transient receptor protein 7.

The protein encoded by this gene is a calcium-permeable cation channel that is regulated by free intracellular ADP-ribose. The encoded protein is activated by oxidative stress and confers susceptibility to cell death. The polynucleotide sequences of the human TRPM2 is set forth in SEQ ID NO:29 and the corresponding polypeptide sequences is set forth in SEQ ID NO:77. (Two transcript variants encoding different isoforms S and L had been found for this gene. The S variant (SEQ ID NO:30) was removed by NCBI since it contains a sequencing error and does not exist).

(16) Poly (ADP-ribose) Glycohydrolase (PARG)

Gene aliases: PARG99; poly(ADP-ribose) glycohydrolase

PARG is the major enzyme responsible for the catabolism of poly(ADP-ribose), a reversible covalent-modifier of chromosomal proteins. The protein is found in many tissues and may be subject to proteolysis generating smaller, active products. The polynucleotide sequence of human PARG mRNA is set forth in SEQ ID NO:31, and the corresponding polypeptide sequence is set forth in SEQ ID NO:79.

(17) CD38 Molecule (CD38)

Gene aliases: T10, Cd38-rs1; ADP-ribosyl cyclase/cyclic ADP-ribose hydrolase; CD38 antigen; CD38 antigen (p45); cyclic ADP-ribose hydrolase.

CD38 is a novel multifunctional ectoenzyme widely expressed in cells and tissues; especially in leukocytes. CD38 also functions in cell adhesion, signal transduction and calcium signaling. The polynucleotide sequence of human CD38 mRNA is set forth in SEQ ID NO: 32, and the corresponding polypeptide sequences are set forth in SEQ ID NO:80.

(18) STEAP Family Member 4 (STEAP4)

Gene aliases: DKFZp666D049, FLJ23153, STAMP2, TIARP, TNFAIP9, 1110021O17Rik, AI481214, dudulin 4; six transmembrane prostate protein 2; tumor necrosis factor, alpha-induced protein 9; tumor necrosis-alpha-induced adipose-related protein, TNF α-induced adipose-related protein; tumor necrosis factor, alpha-induced protein 9.

A membrane protein induced by TNF-α and IL-6 in adipose tissues. Both IL-6 and TNF-α were shown to be unregulated in a spinal cord injury model (Ahn, et al., BBRC 2006 348(2):560-70) and are thought to promote apoptotic events. The polynucleotide sequence of human STEAP4 mRNA is set forth in SEQ ID NO:33, and the corresponding polypeptide sequence is set forth in SEQ ID NO:81.

(19) Bone Morphogenetic Protein 2 (BMP2)

Gene aliases: BMP2A, AI467020, BC069214CR618407, M22489

The protein encoded by this gene belongs to the transforming growth factor-beta (TGFB) superfamily. The encoded protein acts as a disulfide-linked homodimer and induces bone and cartilage formation. The polynucleotide sequence of human BMP2 mRNA is set forth in SEQ ID NO:34, and the corresponding polypeptide sequence is set forth in SEQ ID NO:82.

International Patent Publication No. WO 2005/041857, coassigned to the assignee of the present application, relates to BMP inhibition for the treatment of ischemia and neurological disease.

(20) Gap Junction Protein, Alpha 1, 43 kDa (Connexin 43, GJA1)

Gene aliases: CX43, DFNB38, GJAL, ODD, ODDD, ODOD, SDTY3, MGC93610, AU042049, AW546267, Cnx43, Cx43alpha1, Gja-1, Npm1, gap junction protein, alpha-like; oculodentodigital dysplasia (syndactyly type III), gap junction protein alpha 1 43 kD; gap junction protein, alpha 1, 43 kD, alpha 1 connexin.

Gap junction protein, alpha 1 is a member of the connexin gene family of proteins and is a component of gap junctions in the heart, and is believed to have a crucial role in the synchronized contraction of the heart and in embryonic development. Connexin 43 is targeted by several protein kinases that regulate myocardial cell-cell coupling. A related intron-less connexin 43 pseudogene, GJA1P, has been mapped to chromosome 5. The polynucleotide sequence of human GJA1 mRNA is set forth in SEQ ID NO:35, and the corresponding polypeptide sequence is set forth in SEQ ID NO:83.

U.S. Pat. No. 7,098,190 teaches antisense compounds for treating, inter alia, wounds and spinal cord injury.

(21) TYRO Protein Tyrosine Kinase Binding Protein (TYROBP)

Gene aliases: DAP12, KARAP, PLOSL, Ly83; DNAX-activation protein 12; killer activating receptor associated protein.

This gene encodes a transmembrane signaling polypeptide that contains an immunoreceptor tyrosine-based activation motif (ITAM) in its cytoplasmic domain. The protein may associate with the killer-cell inhibitory receptor (KIR) family of membrane glycoproteins and may act as an activating signal transduction element. This protein may bind zeta-chain (TCR) associated protein kinase 70 kDa (ZAP-70) and spleen tyrosine kinase (SYK) and play a role in signal transduction, bone modeling, brain myelination, and inflammation. Mutations within the gene have been associated with polycystic lipomembranous osteodysplasia with sclerosing leukoencephalopathy (PLOSL), also known as Nasu-Hakola disease. Its putative receptor, triggering receptor expressed on myeloid cells 2 (TREM2), also causes PLOSL. Two alternative transcript variants encoding distinct isoforms have been identified for this gene. Other alternative splice variants have been described, but their full-length nature has not been determined. The polynucleotide sequences of human TYROBP transcriptional variants 1 and 2 are set forth in SEQ ID NO:36-37, respectively, and the corresponding polypeptide sequences are set forth in SEQ ID NO:84-85.

(22) Connective Tissue Growth Factor (CTGF)

Gene aliases: CCN2, HCS24, IGFBP8, MGC102839, NOV2, CTGRP, Fisp12, Hcs24, fisp-12; hypertrophic chondrocyte-specific protein 24; insulin-like growth factor-binding protein 8, FISP-12 protein; fibroblast inducible secreted protein; fibroblast inducible secreted protein; hypertrophic chondrocyte-specific gene product 24.

A major connective tissue mitoattractant secreted by vascular endothelial cells. Promotes proliferation and differentiation of chondrocytes. The polynucleotide sequence of human CTGF mRNA is set forth in SEQ ID NO:38 and the corresponding polypeptide sequence is set forth in SEQ ID NO:86.

(23) Secreted Phosphoprotein 1 (SPP1)

Gene aliases: AA960535, AI790405, Apl-1, BNSP, BSPI, Bsp, ETA-1, Eta, OP, Opn, Opnl, Ric, Spp-1, minopontin, OSP; 44 kDa bone phosphoprotein; 44 kDa bone phosphoprotein; bone sialoprotein I; osteopontin, early T-lymphocyte activation 1.

SSP1 is a secreted protein which acts as a cytokine involved in enhancing production of interferon-γ and interleukin-12 and reducing production of interleukin-10, essential in the pathway that leads to type I immunity. The polynucleotide sequences of human SPP1 transcriptional variants 1, 2 and 3 are set forth in SEQ ID NOS:39-41, respectively and the corresponding polypeptide sequences are set forth in SEQ ID NOS:87-89.

U.S. Pat. No. 6,458,590 and US Patent Publication Nos. 2004/0142865 and 2006/0252684 relate to inhibition of osteopontin.

(24) Reticulon 4 Receptor (RTN4R)

Gene aliases: NGR, NOGOR, NgR1; Nogo-66 receptor; UNQ330/PRO526; nogo receptor; reticulon 4 receptor precursor.

This gene encodes the receptor for reticulon 4, oligodendrocyte myelin glycoprotein and myelin-associated glycoprotein. This receptor mediates axonal growth inhibition and may play a role in regulating axonal regeneration and plasticity in the adult central nervous system. The polynucleotide sequence of human RTN4R mRNA is set forth in SEQ ID NO:42 and the corresponding polypeptide sequence is set forth in SEQ ID NO:90.

(25) Annexin A2 (ANXA2)

Gene aliases: ANX2, ANX2L4, CAL1H, LIP2, LPC2, LPC2D, P36, PAP-IV; annexin calpactin I heavy polypeptide; chromobindin 8; lipocortin II; placental anticoagulant protein IV.

This gene encodes a member of the annexin family. Members of this calcium-dependent phospholipid-binding protein family play a role in the regulation of cellular growth and in signal transduction pathways. This protein functions as an autocrine factor, which heightens osteoclast formation and bone resorption. This gene has three pseudogenes located on chromosomes 4, 9 and 10, respectively. Multiple alternatively spliced transcript variants encoding different isoforms have been found for this gene. The polynucleotide sequences of human ANXA2 transcriptional variants 1, 3 and 2 are set forth in SEQ ID NOS:43-45 and the corresponding polypeptide sequences are set forth in SEQ ID NOS:91-93.

(26) ras Homolog Gene Family, Member A (RHOA)

Gene Aliases: ARH12, ARHA, RHO12, RHOH12, Aplysia ras-related homolog 12; oncogene RHO H12; small GTP binding protein RhoA.

RHOA is a small GTPase protein known to regulate the actin cytoskeleton in the formation of stress fibers. It acts upon the effector proteins: Rho kinase (ROCK) culminating in the inhibition of axonal regeneration. In vitro studies using the Rho-A antagonist C3 transferase enhances axonal growth on myelin substrates while in vivo studies have not been effective. The polynucleotide sequence of human RHOA mRNA is set forth in SEQ ID NO:46 and the corresponding polypeptide sequence is set forth in SEQ ID NO:94.

(27) Dual Oxidase 1 (DUOX1)

Gene Aliases: LNOX1, MGC138840, MGC138841, NOXEF1, THOX1, NADPH thyroid oxidase 1; flavoprotein NADPH oxidase; nicotinamide adenine dinucleotide phosphate oxidase.

The protein encoded by this gene is a glycoprotein and a member of the NADPH oxidase family. The synthesis of thyroid hormone is catalyzed by a protein complex located at the apical membrane of thyroid follicular cells. This complex contains an iodide transporter, thyroperoxidase, and a peroxide generating system that includes this encoded protein and DUOX2. This protein has both a peroxidase homology domain and a gp91phox domain. Two alternatively spliced transcript variants encoding the same protein have been described for this gene. The polynucleotide sequence of human DUOX1 transcriptional variants 1 and 2 are set forth in SEQ ID NOS:47-48, respectively and the corresponding polypeptide sequences are set forth in SEQ ID NOS:95-96.

A "pro-apoptotic polypeptide" refers to a polypeptide encoded by any of the above listed genes, including splice variants, isoforms, orthologs, or paralogs and the like.

According to one aspect the present invention provides inhibitory oligonucleotide compounds comprising unmodified and modified nucleotides. The compound comprises at least one modified nucleotide selected from the group consisting of a sugar modification, a base modification and an internucleotide linkage modification and may contain DNA, and modified nucleotides such as LNA (locked nucleic acid) including ENA (ethylene-bridged nucleic acid; PNA (peptide nucleic acid); arabinoside; PACE (phosphonoacetate and derivatives thereof), mirror nucleotide, or nucleotides with a 6 member sugar analog (eg. hexose or morpholino).

In one embodiment the compound comprises a 2' modification on the sugar moiety of at least one ribonucleotide ("2' sugar modification"). In certain embodiments the compound comprises 2'O-alkyl or 2'-fluoro or 2'O-allyl or any other 2' sugar modification, optionally on alternate positions. A preferred 2' modification is 2' O-methyl (2' methoxy, 2'OMe).

Other stabilizing modifications are also possible (eg. modified nucleotides added to a 3' or 5' terminus of an oligomer). In some embodiments the backbone of the oligonucleotides is modified and comprises phosphate-D-ribose entities but may also contain thiophosphate-D-ribose entities, phosphodiester L-ribose entities, triester, thioate, 2'-5' bridged backbone (also may be referred to as 5'-2'), PACE modified internucleotide linkage or any other type of modification.

Other modifications include additions to the 5' and/or 3' termini of the oligonucleotides. Such terminal modifications may be lipids, peptides, sugars or other molecules.

The present invention also relates to compounds which down-regulate expression of various genes, particularly to novel small interfering RNAs (siRNAs), and to the use of these novel siRNAs in the treatment of various diseases and medical conditions. Particular diseases and conditions to be treated are acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, ocular ischemic conditions, organ transplantation nephrotoxicity, spinal cord injury, pressure sores, dry eye syndrome, oral mucositis, ION and chronic obstructive pulmonary disease (COPD).

Lists of preferred siRNA to be used in the present invention are provided in Tables B (B1-B74), Tables C (C1-C4) and Tables D (D1-D34). For each gene there is a separate list of 19-mer, 21-mer and 23-mer sequences, which are prioritized based on their score in the proprietary algorithm as the best sequences for targeting the human gene expression. The 21- or 23-mer siRNA sequences are also generated by 5' and/or 3' extension of the 19-mer sequences disclosed herein. Such extension is preferably complementary to the corresponding mRNA sequence. Certain 23-mer oligomers were devised by this method where the order of the prioritization is the order of the corresponding 19-mer.

Structural Motifs

According to the present invention the siRNA compounds are chemically and or structurally modified according to one of the following modifications set forth in Structures (A)-(H) or as tandem siRNA or RNAstar.

In one aspect the present invention provides a compound set forth as Structure (A):

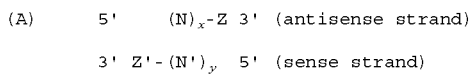

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present; and
wherein the sequence of $(N)_x$ is set forth in any one of Tables D (D1-D34); and with the proviso that each of (N)x and (N')y does not comprise more than 50% unmodified deoxyribonucleotide or modified deoxyribonucleotide.

The presently preferred antisense sequences are novel siRNA compounds directed to TP53BP2, LRDD, CYBA, CASP2, NOX3, HRK, RAC1, RHOA and DUOX1, whose mRNA polynucleotide sequences are set forth in SEQ ID NOS:1-2, 3-5, 6, 10-11, 12, 13, 24-26, 46 and 47-48, respectively.

In certain embodiments the present invention provides a compound having structure B (structures having alternating 2'-O-methyl modification in both strands for Tables D):

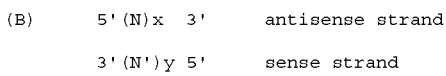

wherein each of $(N)_x$ and $(N')_y$ is an oligomer in which each consecutive N or N' is an unmodified ribonucleotide or a modified ribonucleotide joined to the next N or N' by a covalent bond;
wherein each of x and y=19, 21 or 23 and $(N)_x$ and $(N')_y$ are fully complementary
wherein alternating ribonucleotides in each of $(N)_x$ and $(N')_y$ are modified to result in a 2'-O-methyl modification in the sugar residue of the ribonucleotides;
wherein the sequence of $(N')_y$ is a sequence complementary to (N)x; and wherein the sequence of $(N)_x$ is present in any one of Tables D.

In some embodiments each of $(N)_x$ and $(N')_y$ is independently phosphorylated or non-phosphorylated at the 3' and 5' termini.

In certain embodiments of the invention, alternating ribonucleotides are modified in both the antisense and the sense strands of the compound.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N')_y$ is modified.

In particular embodiments, when x and y=19, the siRNA is modified such that a 2'-O-methyl (2'-OMe) group is present on the first, third, fifth, seventh, ninth, eleventh, thirteenth, fifteenth, seventeenth and nineteenth nucleotide of the antisense strand $(N)_x$, and whereby the very same modification, i.e. a 2'-OMe group, is present at the second, fourth, sixth, eighth, tenth, twelfth, fourteenth, sixteenth and eighteenth nucleotide of the sense strand $(N')_y$. In various embodiments these particular siRNA compounds are blunt ended at both termini.

New Structures C-H for siRNA

The following structural motifs are useful in designing siRNA compounds.

In some embodiments, the present invention provides a compound having Structure (C):

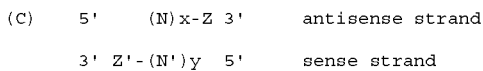

wherein each of N and N' is a nucleotide independently selected from an unmodified ribonucleotide, a modified ribonucleotide, an unmodified deoxyribonucleotide and a modified deoxyribonucleotide;
wherein each of (N)x and (N')y is an oligomer in which each consecutive nucleotide is joined to the next nucleotide by a covalent bond and each of x and y is an integer between 18 and 40;
wherein in (N)x the nucleotides are unmodified or (N)x comprises alternating modified ribonucleotides and unmodified ribonucleotides; each modified ribonucleotide being modified so as to have a 2'-O-methyl on its sugar and the ribonucleotide located at the middle position of (N)x being modified or unmodified preferably unmodified;
wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;

wherein if more than one nucleotide is modified in (N')y, the modified nucleotides may be consecutive;

wherein each of Z and Z' may be present or absent, but if present is 1-5 deoxyribonucleotides covalently attached at the 3' terminus of any oligomer to which it is attached;

wherein the sequence of $(N')_y$ comprises a sequence substantially complementary to (N)x; and wherein the sequence of $(N)_x$ comprises an antisense sequence substantially complementary to about 18 to about 40 consecutive ribonucleotides in the mRNA transcribed from a gene.

In certain embodiments the sequence of $(N)_x$ is present in any one of Tables A-D.

In particular embodiments, x=y=19 and in (N)x each modified ribonucleotide is modified so as to have a 2'-O-methyl on its sugar and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 5. In other embodiments, (N)x comprises 2'O Me modified ribonucleotides at positions 2, 4, 8, 11, 13, 15, 17 and 19 and may further comprise at least one abasic or inverted abasic pseudo-nucleotide for example in position 6. In other embodiments, (N)x comprises 2'O Me modified ribonucleotides at positions 2, 4, 6, 8, 11, 13, 17 and 19 and may further comprise at least one abasic or inverted abasic pseudo-nucleotide for example in position 15. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 14. In other embodiments, (N)x comprises 2'O Me modified ribonucleotides at positions 1, 2, 3, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 1, 2, 3, 5, 7, 9, 11, 13, 15, 17 and 19 and may further comprise at least one abasic or inverted abasic pseudo-nucleotide for example in position 6. In other embodiments, (N)x comprises 2'O Me modified ribonucleotides at positions 1, 2, 3, 5, 7, 9, 11, 13, 17 and 19 and may further comprise at least one abasic or inverted abasic pseudo-nucleotide for example in position 15. In other embodiments, (N)x comprises 2'O Me modified ribonucleotides at positions 1, 2, 3, 5, 7, 9, 11, 13, 15, 17 and 19 and may further comprise at least one abasic or inverted abasic pseudo-nucleotide for example in position 14. In other embodiments, (N)x comprises 2'O Me modified ribonucleotides at positions 2, 4, 6, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 1, 2, 4, 6, 7, 9, 11, 13, 15, 17 and 19 and may further comprise at least one abasic or inverted abasic pseudo-nucleotide for example in position 5. In other embodiments, (N)x comprises 2'O Me modified ribonucleotides at positions 2, 4, 6, 8, 11, 13, 14, 16, 17 and 19 and may further comprise at least one abasic or inverted abasic pseudo-nucleotide for example in position 15. In other embodiments, (N)x comprises 2'O Me modified ribonucleotides at positions 1, 2, 3, 5, 7, 9, 11, 13, 14, 16, 17 and 19 and may further comprise at least one abasic or inverted abasic pseudo-nucleotide for example in position 15.

In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 7. In other embodiments, (N)x comprises 2'O Me modified ribonucleotides at positions 2, 4, 6, 11, 13, 15, 17 and 19 and may further comprise at least one abasic or inverted abasic pseudo-nucleotide for example in position 8. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 9. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 10. In other embodiments, (N)x comprises 2'O Me modified ribonucleotides at positions 2, 4, 6, 8, 13, 15, 17 and 19 and may further comprise at least one abasic or inverted abasic pseudo-nucleotide for example in position 11. In other embodiments, (N)x comprises 2'O Me modified ribonucleotides at positions 2, 4, 6, 8, 11, 13, 15, 17 and 19 and may further comprise at least one abasic or inverted abasic pseudo-nucleotide for example in position 12. In other embodiments, (N)x comprises 2'O Me modified ribonucleotides at positions 2, 4, 6, 8, 11, 15, 17 and 19 and may further comprise at least one abasic or inverted abasic pseudo-nucleotide for example in position 13. In yet other embodiments (N)x comprises at least one nucleotide mismatch relative to the target gene. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be modified with 2'-O-methyl on its sugar. In another preferred embodiment, in (N)x the nucleotides alternate between 2'-O-methyl modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl modifications.

In certain preferred embodiments of Structure C, x=y=19 and in (N')y, at least one position comprises an abasic or inverted abasic pseudo-nucleotide, preferably five positions comprises an abasic or inverted abasic pseudo-nucleotides. In various embodiments, the following positions comprise an abasic or inverted abasic: positions 1 and 16-19, positions 15-19, positions 1-2 and 17-19, positions 1-3 and 18-19, positions 1-4 and 19 and positions 1-5. (N')y may further comprise at least one LNA nucleotide.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond.

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic pseudo-nucleotide as an overhang.

In yet other embodiments (N')y comprises at least one nucleotide mismatch relative to the target gene. In certain preferred embodiments, (N')y comprises a single nucleotide mismatch on position 6, 14, or 15.

In yet other embodiments (N')y comprises a DNA at position 15 and L-DNA at one or both of positions 17 and 18. In that structure, position 2 may further comprise an L-DNA or an abasic pseudo-nucleotide.

Other embodiments of Structure C are envisaged in wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mers.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16, 17, 18, 16-17, 17-18, or 16-18. In certain embodiments (N')y comprises 2'-5' internucleotide bonds at positions 16, 17, 18, 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently minor nucleotides. In some embodiments the minor nucleotide is an L-ribonucleotide. In other embodiments the minor nucleotide is an L-deoxyribonucleotide. The minor nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one series of preferred embodiments, three, four or five consecutive nucleotides at the 5' terminus of (N')y comprise the 2'-OMe modification. In another preferred embodiment, three consecutive nucleotides at the 3' terminus of (N')y comprise the 2'-O-methyl modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O, 4'-C-ethylene-bridged nucleic acid (ENA) is a species of LNA (see below).

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'-O-methyl sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides. Examples of PACE nucleotides and analogs are disclosed in U.S. Pat. Nos. 6,693,187 and 7,067,641 both incorporated by reference.

In additional embodiments, the present invention provides a compound having Structure (D):

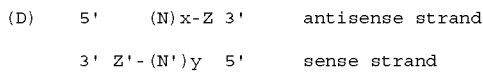

wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and
wherein the sequence of (N)x comprises an antisense sequence having substantial identity to about 18 to about 40 consecutive ribonucleotides in the mRNA transcribed from a gene.

In certain embodiments the sequence of (N)x and the complementary (N')y are present in any one of Tables A-D.

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D) 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide. In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one preferred embodiment of Structure (D), five consecutive nucleotides at the 5' terminus of (N')y comprise the 2'-O-methyl modification and five consecutive nucleotides at the 3' terminus of (N')x comprise the 2'-O-methyl modification. In another preferred embodiment of Structure (D), ten consecutive nucleotides at the 5' terminus of (N')y comprise the 2'-O-methyl modification and five consecutive nucleotides at the 3' terminus of (N')x comprise the 2'-O-methyl modification. In another preferred embodiment of Structure (D), thirteen consecutive nucleotides at the 5' terminus of (N')y comprise the 2'-O-methyl modification and five consecutive nucleotides at the 3' terminus of (N')x comprise the 2'-O-methyl modification.

In some embodiments of Structure (D), in (N')y 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'-O-methyl modification and two consecutive nucleotides at the 3' terminus of (N')y are L-DNA. In addition, the compound may further comprise five consecutive 2'-O-methyl modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E):

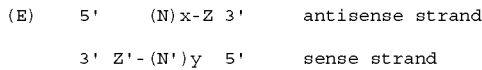

wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and
wherein the sequence of $(N)_x$ comprises an antisense sequence having substantial identity to about 18 to about 40 consecutive ribonucleotides in the mRNA transcribed from a gene.

In certain embodiments the sequence of $(N)_x$ and the complementary (N')y are present in any one of Tables A-D.

In certain preferred embodiments the ultimate nucleotide at the 5' terminus of (N)x is unmodified.

According to various embodiments of Structure (E) 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3° terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (E), in (N')y 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by a P-alkoxy backbone modification or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F):

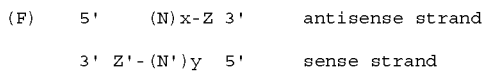

wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')$_y$ is a sequence substantially complementary to (N)x; and
wherein the sequence of (N)$_x$ comprises an antisense sequence having substantial identity to about 18 to about 40 consecutive ribonucleotides in the mRNA transcribed from a gene.

In certain embodiments the sequence of (N)$_x$ and the complementary (N')y are present in any one of Tables A-D.

In some embodiments of Structure (F), x=y=19 or x=y=23; (N')y comprises unmodified ribonucleotides in which two consecutive nucleotides at the 3' terminus comprises two consecutive mirror deoxyribonucleotides; and (N)x comprises unmodified ribonucleotides in which one nucleotide at the 3' terminus comprises a mirror deoxyribonucleotide (set forth as Structure III).

According to various embodiments of Structure (F) 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of (N')x are joined by two 2'-5' phosphodiester bonds.

According to various embodiments of Structure (F), 2, 3, 4, 5, 6, 7, 8, 9, 10, 11, 12, 13 or 14 consecutive nucleotides independently beginning at the ultimate or penultimate position of the 3' termini of (N)x and (N')y are independently mirror nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O, 4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (G):

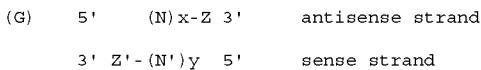

(G)  5'   (N)x-Z 3'      antisense strand
     3' Z'-(N')y 5'      sense strand wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;
wherein for (N)x the modified nucleotide is preferably at penultimate position of the 5' terminal;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')$_y$ is a sequence substantially complementary to (N)x; and
wherein the sequence of (N)$_x$ comprises an antisense sequence having substantial identity to about 18 to about 40 consecutive ribonucleotides in the mRNA transcribed from a gene.

In certain embodiments the sequence of (N)$_x$ and the complementary (N')y are present in any one of Tables A-D.

In some embodiments of Structure (G), x=y=19 or x=y=23.

According to various embodiments of Structure (G) 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably starting at the penultimate position of the 5' terminal.

According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably starting at the penultimate position of the 5' terminal.

In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'-O-methyl modification and one ribonucleotide at the 5' penultimate position of (N')x comprises a 2'-O-methyl modification. In another preferred embodiment of Structure (G), five consecutive ribonucleotides at the 5' terminus of (N')y comprise a 2'-O-methyl modification and two consecutive ribonucleotides at the 5' terminal position of (N')x comprise a 2'-O-methyl modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O, 4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H):

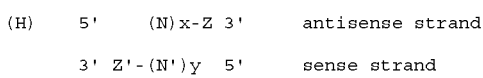

(H)  5'   (N)x-Z 3'      antisense strand
     3' Z'-(N')y 5'      sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence having substantial identity to about 18 to about 40 consecutive ribonucleotides in the mRNA transcribed from a gene.

In certain embodiments the sequence of $(N)_x$ and the complementary (N')y are present in any one of Tables A-D.

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises the presence of an amino, a fluoro, an alkoxy or an alkyl moiety. In certain embodiments the 2' sugar modification comprises a methoxy moiety (2'-OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a 2'-5' phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions 9-11 of (N')y comprise 2'-O-methyl modification and five consecutive ribonucleotides at the 3' terminal position of (N')x comprise 2'-O-methyl modification.

For all the above Structures (A)-(H), in various embodiments x=y and each of x and y is 19, 20, 21, 22 or 23. In certain embodiments, x=y=19. In yet other embodiments x=y=23. In additional embodiments the compound comprises modified ribonucleotides in alternating positions wherein each N at the 5' and 3' termini of (N)x are modified in their sugar residues and the middle ribonucleotide is not modified, e.g. ribonucleotide in position 10 in a 19-mer strand, position 11 in a 21 mer and position 12 in a 23-mer strand.

In some embodiments where x=y=21 or x=y=23 the position of modifications in the 19 mer are adjusted for the 21 and 23 mers with the proviso that the middle nucleotide of the antisense strand is preferably not modified.

In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

In certain embodiments for all the above-mentioned Structures, the compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Preferred locked nucleic acids are 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, 9 or more deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N or N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Said triple-stranded oligonucleotide may be an oligoribonucleotide having the general structure:

```
5' Oligo1 (sense)      LINKER A Oligo2 (sense)       3'
3' Oligo1 (antisense)  LINKER B Oligo3 (sense)       5'
3' Oligo3 (antisense)  LINKER C Oligo2 (antisense)   5'
or
5' Oligo1 (sense)      LINKER A Oligo2 (antisense)   3'
3' Oligo1 (antisense)  LINKER B Oligo3 (sense)       5'
3' Oligo3 (antisense)  LINKER C Oligo2 (sense)       5'
or
5' Oligo1 (sense)      LINKER A Oligo3 (antisense)   3'
3' Oligo1 (antisense)  LINKER B Oligo2 (sense)       5'
5' Oligo3 (sense)      LINKER C Oligo2 (antisense)   3'
``` wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Thus, a triple-armed structure is formed, wherein each arm comprises a sense strand and substantially complementary antisense strand (i.e. Oligo1 antisense base pairs to Oligo1 sense etc.). The triple armed structure may be triple stranded, whereby each arm possesses base pairing.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting certain target genes than the similar but non-gapped molecules. This may also be the case for nicked molecules.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N or N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

A "pro-apoptotic polypeptide" refers to a polypeptide encoded by any of the above listed genes, including splice variants, isoforms, orthologs, or paralogs and the like.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including siRNA, shRNA, miRNA and ribozymes. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the target of their corresponding genes. The terms "mRNA polynucleotide sequence" and mRNA are used interchangeably.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

The present invention provides methods and compositions for inhibiting expression of a target gene in vivo. In general, the method includes administering oligoribonucleotides, in particular small interfering RNAs (i.e., siRNAs) or a nucleic acid material that can produce siRNA in a cell, to target an mRNA set forth in any one of SEQ ID NOS:1-41, 46-48; in an amount sufficient to down-regulate expression of a target gene by an RNA interference mechanism. In particular, the method is useful for inhibiting expression of the gene for treatment of a subject suffering from a disease related to expression of that gene. In accordance with the present invention, the siRNA molecules or inhibitors of the target gene are used as drugs to treat various pathologies.

"Nucleotide" is meant to encompass deoxyribonucleotides and ribonucleotides, which may be natural or synthetic, and be modified or unmodified. Modifications include changes and substitutions to the sugar moiety, the base moiety and/or the internucleotide linkages.

All analogs of, or modifications to, a nucleotide/oligonucleotide may be employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Figure 22:
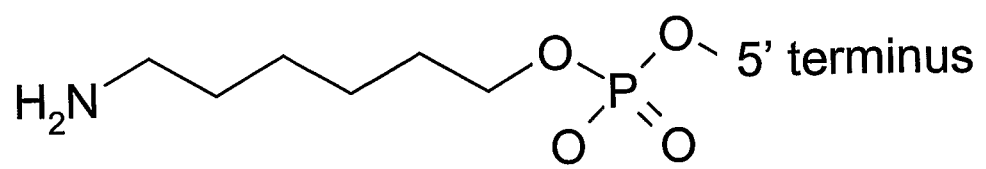
FIG. 22 provides an image of the chemical structure of the C6-amino-phosphate (C6-amino-Pi) moiety useful as a 5' cap structure in the present invention.

Certain preferred capping moieties are abasic ribose or abasic deoxyribose moieties; inverted abasic ribose or abasic deoxyribose moieties; C6-amino-Pi; a mirror nucleotide including L-DNA and L-RNA. FIG. 22 shows the chemical structure of a C6-amino phosphate 5' capping moiety and its attachment point to the 5' terminal (N').

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. Abasic pseudo-nucleotides are encompassed by the present invention, as well as molecules comprising alternating RNA and DNA nucleotides. A nucleotide monomer comprising a modified base, including abasic pseudo-nucleotide monomers, may be substituted for one or more ribonucleotides of the oligonucleotide. An abasic pseudo-nucleotide monomer may be included at the one or more of the terminal positions or as a 5' terminal cap. A 5' terminal cap may also be selected from an inverted abasic pseudo-nucleotide analog, an L-DNA nucleotide, and a C6-imine phosphate.

In addition, analogues of polynucleotides are prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA comprises with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, locked nucleic acid (LNA), glycol nucleic acid (GNA), threose nucleic acid (TNA), arabinoside; altritol (ANA) and other 6-membered sugars including morpholinos, and cyclohexinyls.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in International Patent Publication No. WO 2004/083430. Six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides comprising 6-membered ring nucleotide analogs including hexitol and altritol nucleotide monomers are disclosed in International patent application publication No. WO 2006/047842.

The compounds of the present invention are synthesized using one or more inverted nucleotides, for example inverted thymidine or inverted adenine (for example see Takei, et al., 2002. JBC 277(26):23800-06.

In the context of the present invention, a "mirror" nucleotide (also referred to as a spiegelmer), is a nucleotide analog with reverse chirality to the naturally occurring or commonly employed nucleotide, i.e., a mirror image of the naturally occurring or commonly employed nucleotide. The mirror nucleotide is a ribonucleotide (L-RNA) or a deoxyribonucleotide (L-DNA) and may further comprise at least one sugar or base modification and/or a backbone modification, such as a phosphorothioate or phosphonate moiety. U.S. Pat. No. 6,602,858 discloses nucleic acid catalysts comprising at least one L-nucleotide substitution.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

Oligonucleotides

Tables B (B1-B74), Tables C (C1-C4) and Tables D (D1-D34) comprise nucleic acid sequences of sense and corresponding antisense oligomers, useful in preparing siRNA compounds. The compounds are used as chemically and or structurally modified compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud & Leirdal, Met. Mol. Biol. 2004, 252:457-69; Levenkova et al., Bioinform. 2004, 20(3):430-2; Ui-Tei et al., NAR. 2004, 32(3):936-48. For examples of the use and production of modified siRNA see for example Braasch et al., Biochem. 2003, 42(26):7967-75; Chiu et al., RNA. 2003, 9(9):1034-48; PCT Publication Nos. WO 2004/015107 and WO 02/44321 and U.S. Pat. Nos. 5,898,031 and 6,107,094.

The present invention provides double-stranded oligonucleotides (e.g. siRNAs), which down-regulate the expression of a desired gene. An siRNA of the invention is a duplex oligoribonucleotide in which the sense strand is derived from the mRNA sequence of the desired gene, and the antisense strand is at least substantially complementary to the sense strand. In general, some deviation from the target mRNA sequence is tolerated without compromising the siRNA activity (see e.g. Czauderna et al., NAR. 2003, 31(11):2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

In some embodiments an oligonucleotide pair selected from Tables D (D1-D34) comprises modified siRNA, having one or more of any of the modifications disclosed herein. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid which is mRNA transcribed from a target gene, and the second strand comprises a ribonucleotide sequence at least partially complementary to the first strand and wherein said first strand and or said second strand comprises a plurality of groups of modified ribonucleotides, optionally having a modification at the 2'-position of the sugar moiety whereby within each strand each group of modified ribonucleotides is flanked on one or both sides by a group of flanking nucleotides, optionally ribonucleotides, whereby each ribonucleotide forming the group of flanking ribonucleotides is selected from an unmodified ribonucleotide or a ribonucleotide having a modification different from the modification of the groups of modified ribonucleotides.

In some embodiments the group of modified ribonucleotides and/or the group of flanking nucleotides comprises a number of ribonucleotides selected from the group consisting of an integer from 1 to 12. Accordingly, the group thus comprises one nucleotide, two nucleotides, three nucleotides, four nucleotides, five nucleotides, six nucleotides, seven nucleotides, eight nucleotides, nine nucleotides, ten nucleotides, eleven nucleotides or twelve nucleotides.

The groups of modified nucleotides and flanking nucleotides may be organized in a pattern on one or both of the strands. In some embodiments the antisense and sense strands comprise alternating unmodified and 2' sugar modified ribonucleotides. In some preferred embodiments the middle ribonucleotide in the antisense strand is an unmodified nucleotide. For example, in a 19-oligomer antisense strand, ribonucleotide at position 10 is unmodified; in a 21-oligomer antisense strand, the ribonucleotide at position 11 is unmodified; and in a 23-oligomer antisense strand, ribonucleotide at position 12 is unmodified. The modifications or pattern of modification, if any, of the siRNA must be planned to allow for this. In an even-numbered oligomer, e.g. a 22 mer, the middle nucleotide may be at position 11 or 12.

Possible modifications on the 2' moiety of the sugar residue include amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; amino alkylamino; polyalkylamino or substituted silyl, as, among others, described in European patents EP 0 586 520 B1 or EP 0 618 925 B1. One or more deoxyribonucleotides are also tolerated in the compounds of the present invention. As used herein, in the description of any strategy for the design of molecules, RNAi or any embodiment of RNAi disclosed herein, the term "end modification" means a chemical entity added to the terminal 5' or 3' nucleotide of the sense and/or antisense strand. Examples for such end modifications include, but are not limited to, 3' or 5' phosphate, inverted abasic, abasic, amino, fluoro, chloro, bromo, CN, $CF_3$, methoxy, imidazolyl, carboxylate, phosphothioate, $C_1$ to $C_{22}$ and lower alkyl, lipids, sugars and polyaminoacids (i.e. peptides), substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1.

In some embodiments the siRNA is blunt ended, i.e. Z and Z' are absent, on one or both ends. More specifically, the siRNA may be blunt ended on the end defined by the 5'-terminus of the first strand and the 3'-terminus of the second strand, and/or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides.

In certain embodiments the complementarity between said first strand and the target nucleic acid may be perfect. In some embodiments, the strands are substantially complementary, i.e. having one, two or up to five mismatches between said first strand and the target mRNA or between the first and the second strands. Substantially complementary refers to complementarity of greater than about 70%, and less than 100% to another sequence. For example in a duplex region consisting of 19 base pairs one mismatch results in 94.7% complementarity, two mismatches results in about 89.5% complementarity, 3 mismatches results in about 84.2% complementarity, 4 mismatches results in about 79% complementarity and 5 mismatches results in about 74% complementarity, rendering the duplex region substantially complementary. Accordingly, substantially identical refers to identity of greater than about 70%, to another sequence.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 2-100 nucleobases, preferably about 2 to about 30 nucleobases.

In preferred embodiments of the compounds of the invention having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

According to one preferred embodiment of the invention, the antisense and the sense strands of the oligonucleotide/siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence disclosed herein are prepared having any of the modifications/structures disclosed herein. The combination of sequence plus structure is novel and is useful used in the treatment of the conditions disclosed herein.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different oligonucleotides/siRNAs.

The invention further provides a pharmaceutical composition comprising at least one compound of the invention covalently or non-covalently bound to one or more compounds of the invention in an amount effective to inhibit one or more genes as disclosed above; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to down-regulate expression in a cell of a target gene, the compound comprising a sequence substantially complementary to the sequence of $(N)_x$. In certain embodiments, the target gene is a viral, bacterial or mammalian gene. In various embodiments the target gene is a mammalian gene, preferably a human gene.

Additionally, the invention provides a method of inhibiting the expression of a target gene, by at least 50% as compared to a control, comprising contacting an mRNA transcript of the target gene with one or more of the compounds of the invention. In some embodiments an active siRNA compound inhibits gene expression at a level of at least 50%, 60% or 70% as compared to control. In certain preferred embodiments inhibition is at a level of at least 75%, 80% or 90% as compared to control. In some embodiments the target gene is a pro-apoptotic gene as disclosed herein.

In one embodiment the oligoribonucleotide is inhibiting one or more of the pro-apoptotic genes of the present invention, whereby the inhibition is selected from the group comprising inhibition of gene function, inhibition of polypeptide and inhibition of mRNA expression.

In one embodiment the compound inhibits expression of a polypeptide encoded by a target gene whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In additional embodiments the invention provides a method of treating a subject suffering from a disease accompanied by an elevated level of the pro-apoptotic genes of the present invention, the method comprising administering to the subject a compound of the invention in a therapeutically effective dose thereby treating the subject.

More particularly, the invention provides an oligoribonucleotide wherein one strand comprises consecutive nucleotides having, from 5' to 3', the sequence set forth in Table B or a homolog thereof wherein in up to two of the ribonucleotides do not base pair with the ribonucleotide in the complementary strand Additionally, further nucleic acids according to the present invention comprise at least 14 contiguous nucleotides of any one of the polynucleotides oligomers set forth in Table B (Tables B1-B74) and more preferably 14 contiguous nucleotide base pairs at any end of the double-stranded structure comprised of the first strand and second strand as described above.

Delivery

The siRNA molecules of the present invention may be delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome or lipofectin formulations and the like and are prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660.

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 mg/kg to about 20-100 mg/kg body weight per day, preferably about 0.01 mg to about 2-10 mg/kg body weight per day, in a regimen of one dose per day or twice or three or more times per day for a period of 1-4 weeks or longer.

The compounds of the present invention are administered by any of the conventional routes of administration. It should be noted that the compound is administered as the compound, per se, or as pharmaceutically acceptable salt and is administered alone or as an active ingredient in combination with pharmaceutically acceptable carriers, solvents, diluents, excipients, adjuvants and vehicles. The compounds are administered orally, topically, subcutaneously or parenterally including intravenous, intraarterial, intramuscular, intraperitoneally, and intranasal, inhalation, transtympanic administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration.

In addition, in certain embodiments the compositions for use in the novel treatments of the present invention may be formed as aerosols, for example for intranasal administration.

In certain embodiments, oral compositions (such as tablets, suspensions, solutions) may be effective for local delivery to the oral cavity such as oral composition suitable for mouthwash for the treatment of oral mucositis.

In preferred embodiments the subject being treated is a warm-blooded animal and, in particular, mammals including human.

In an additional embodiment, the modification is a modification of the phosphate moiety, whereby the modified phosphate moiety is selected from the group comprising phosphorothioate or lack of a phosphate group.

The molecules of the present invention may comprise siRNAs, synthetic siRNAs, synthetic shRNAs, in addition to other nucleic acid sequences or molecules which encode such molecules or other inhibitory nucleotide molecules.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety. This kind of compound is, inter alia, described in Sternberger, M., et al., (2002). Antisense Nucleic Acid Drug Dev, 12, 131-43. siNA compounds are described in international patent application WO 03/070918.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, are incorporated into the molecules of the present invention to form additional novel molecules, and are employed in the treatment of the diseases or disorders described herein.

In particular, it is envisaged that a long oligonucleotide (typically about 80-500 nucleotides in length) comprising one or more stem and loop structures, where stem regions comprise the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide is termed a tandem shRNA construct. It is envisaged that this long oligonucleotide is a single stranded oligonucleotide comprising one or more stem and loop structures, wherein each stem region comprises a sense and corresponding antisense siRNA sequence. Any molecules, such as, for example, antisense DNA molecules which comprise the inhibitory sequences disclosed herein (with the appropriate nucleic acid modifications) are particularly desirable and may be used in the same capacity as their corresponding RNAs/siRNAs for all uses and methods disclosed herein.

In addition, analogs of polynucleotides can be prepared wherein the structure of the nucleotide is fundamentally altered and that are better suited as therapeutic or experimental reagents. An example of a nucleotide analog is a peptide nucleic acid (PNA) wherein the deoxyribose (or ribose) phosphate backbone in DNA (or RNA comprises a polyamide backbone which is similar to that found in peptides. PNA analogs have been shown to be resistant to degradation by enzymes and to have extended, lives in vivo and in vitro. Further, PNAs have been shown to bind stronger to a complementary DNA sequence than a DNA molecule. This observation is attributed to the lack of charge repulsion between the PNA strand and the DNA strand. Other modified monomers useful in synthesizing the oligonucleotides include moieties having polymer backbones, cyclic backbones, or acyclic backbones.

Methods of Treatment

In another aspect, the present invention relates to a method for the treatment of a subject in need of treatment for a disease or disorder associated with the abnormal expression of a target gene the proapoptotic genes of Table A, comprising administering to the subject an amount of an inhibitor which reduces or inhibits expression of these genes.

In preferred embodiments the subject being treated is a warm-blooded animal and, in particular, mammals including human.

The methods of the invention comprise administering to the subject one or more inhibitory compounds which down-regulate expression of the proapoptotic genes of Table A; and in particular siRNA in a therapeutically effective dose so as to thereby treat the subject.

The term "treatment" refers to both therapeutic treatment and prophylactic or preventative measures, wherein the object is to prevent or slow down (lessen) a disorder as listed herein. Those in need of treatment include those already experiencing the disease or condition, those prone to having the disease or condition, and those in which the disease or condition is to be prevented. The compounds of the invention are administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of the pro-apoptotic genes of the invention particularly to novel small interfering RNAs (siRNAs), in the treatment of the following diseases or conditions in which inhibition of the expression of the pro-apoptotic genes is beneficial: hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation which includes DGF; spinal cord injury, pressure sores, age-related macular degeneration (AMD), dry eye syndrome, ocular ischemic conditions including ION and AION; oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Methods, molecules and compositions which inhibit the pro-apoptotic genes of the invention are discussed herein at length, and any of said molecules and/or compositions may be beneficially employed in the treatment of a subject suffering from any of said conditions.

The present invention also provides for a process of preparing a pharmaceutical composition, which comprises:
  providing one or more compounds of the invention; and
  admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Synthesis of Modified Compounds

The compounds of the present invention can be synthesized by any of the methods that are well known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., J. Am. Chem. Soc., 1987, 109:7845; Scaringe et al., NAR, 1990, 18:5433; Wincott et al., NAR 1995, 23:2677-2684; and Wincott et al., Methods Mol. Bio., 1997, 74:59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., Science 1992, 256:9923; International Patent Publication No. WO 93/23569; Shabarova et al., NAR 1991, 19:4247; Bellon et al., Nucleosides & Nucleotides, 1997, 16:951; Bellon et al., Bioconjugate Chem 1997, 8:204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker is selected from a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from Tables B (B1-B74), Tables C (C1-C4) and Tables D (D1-D34).

Thus, the siRNA molecules may be covalently or non-covalently bound or joined by a linker to form a tandem siRNA compound. Such tandem siRNA compounds comprising two siRNA sequences are typically about 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Synthetic modified tandem molecule are also considered to be a part of the present invention. A tandem compound comprising two or more siRNAs sequences of the invention is envisaged.

siRNA molecules that target the pro-apoptotic genes of the invention may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of said additional gene(s) will likely have an additive or synergistic effect for treatment of the diseases disclosed herein.

Additionally, the pro-apoptotic siRNA disclosed herein or any nucleic acid molecule comprising or encoding such siRNA may optionally be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any pro-apoptotic siRNA.

The compounds of the present invention are delivered for example as double stranded compounds, as double stranded hairpin compounds or as tandem compounds. It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide is termed a tandem shRNA construct. It is envisaged that this long oligonucleotide is a single stranded oligonucleotide comprising one or more stem and loop structures, wherein each stem region comprises a sense and corresponding antisense siRNA sequence of the pro-apoptotic genes of the invention. In particular, it is envisaged that this oligonucleotide comprises sense and antisense siRNA sequences as depicted in Tables B-D (B1-B74; C1-C4, D1-D34) set forth in SEQ ID NOS:97-87,178.

RNA Interference

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818): 363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol. Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, *A Practical Guide to Molecular Cloning*, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Cell Culture

HeLa cells (American Type Culture Collection) were cultured as described in Czauderna, et al. (NAR, 2003. 31:670-82). Human keratinocytes were cultured at 37° C. in Dulbecco's modified Eagle medium (DMEM) containing 10% FCS. The mouse cell line, B16V (American Type Culture Collection), was cultured at 37° C. in Dulbecco's modified Eagle medium (DMEM) containing 10% FCS. Culture conditions were as described in (Methods Find Exp Clin Pharmacol. 1997 May; 19(4):231-9).

In each case, the cells were subject to the experiments as described herein at a density of about 50,000 cells per well and the double-stranded nucleic acid according to the present invention was added at 20 nM, whereby the double-stranded nucleic acid was complexed using 1 μg/ml of a proprietary lipid as described below.

Induction of Hypoxia-Like Conditions

The cells were treated with $CoCl_2$ for inducing a hypoxia-like condition as follows: siRNA transfections were carried out in 10-cm plates (30-50% confluency) as described by Czauderna et al., 2003; Kretschmer et al., 2003. Briefly, siRNA were transfected by adding a preformed 10× concentrated complex of GB and lipid in serum-free medium to cells in complete medium. The total transfection volume was 10 ml. The final lipid concentration was 1.0 μg/ml; the final siRNA concentration was 20 nM unless otherwise stated. Induction of the hypoxic responses was carried out by adding $CoCl_2$ (100 μM) directly to the tissue culture medium 24 h before lysis.

Preparation of Cell Extracts and Immuno Blotting

The preparation of cell extracts and immuno blot analysis were carried out essentially as described (Klippel et al. Mol Cell Biol, 1998. 18:5699-711; Klippel, A., et al., Mol Cell Biol, 1996. 16:4117-27).

Example 1

In Vitro Testing of siRNA Compounds

About 1.5-2×10$^5$ tested cells (HeLa cells and/or 293T cells for siRNA targeting human genes and NRK52 cells and/or NMUMG cells for siRNA targeting the rat/mouse gene) were seeded per well in 6 wells plate (70-80% confluent).

24 hour later, cells were transfected with siRNA compounds using the Lipofectamine™ 2000 reagent (Invitrogen) at final concentrations of 5 nM or 20 nM. The cells were incubated at 37° C. in a CO2 incubator for 72 h.

As positive control for transfection PTEN-Cy3 labeled siRNA compounds were used. An additional positive control used was a blunt-ended 19-mer siRNA, i.e. x=y=19 wherein Z and Z' are both absent. This siRNA was non-phosphorylated and had alternating ribonucleotides modified at the 2' position of the sugar residue in both the antisense and the sense strands, wherein the moiety at the 2' position is methoxy (2'-O-methyl) and wherein the ribonucleotides at the 5' and 3' termini of the antisense strand are modified in their sugar residues, and the ribonucleotides at the 5' and 3' termini of the sense strand are unmodified in their sugar residues.

As negative control for siRNA activity GFP siRNA compounds were used.

At 72 h after transfection cells were harvested and RNA was extracted from cells. Transfection efficiency was tested by fluorescent microscopy.

The percent of inhibition of gene expression using specific preferred siRNA structures was determined using qPCR analysis of a target gene in cells expressing the endogenous gene.

In general, the siRNAs having specific sequences that were selected for in vitro testing were specific for human and a second species such as rat or rabbit genes. Similar results are obtained using siRNAs having these RNA sequences and modified as described herein. Similar results of reduced expression of specific genes are obtained with other siRNA oligomers, the sequences of which are listed in Tables B (B1-B74), Tables C (C1-C4) and Tables D (D1-D34). The siRNA oligomers of Tables B are set forth in SEQ ID NOS: 97-68654 (disclosed in U.S. Ser. No. 11/978,089 and PCT Patent Application No. PCT/IL 2007/001278, which are hereby incorporated by reference in their entirety).

Tables C1, C2, C3 and C4 below disclose preferred siRNA sequences, all of which siRNAs were found active in the above assay (Tables C1, C3 and C4-19mer siRNA molecules; Table C2-23mer siRNA molecules). In general, the siRNAs having specific sequences that were selected for in vitro testing were specific for both human and the rat/rabbit genes. Similar results are obtained using siRNAs having these RNA sequences and modified as described herein. Similar results of reduced expression of specific genes are obtained with other siRNAs, the sequences of which are listed in Tables B (B1-B74), Tables C (C1-C4) and Tables D (D1-D34).

TABLE C1

Preferred 19-mer siRNA sequences.

| Target gene | Cell line* | siRNA tested | Sequence |
|---|---|---|---|
| TP53BP2 | 293T | TP53BP2_1<br>SEQ ID NOS: 97-98 | SS: GAGGGUGAAAUUCAACCCC<br>AS: GGGGUUGAAUUUCACCCUC |
| TP53BP2 | 293T | TP53BP2_2<br>SEQ ID NOS: 99-100 | SS: CACCCAGAGAACAUUUAUU<br>AS: AAUAAAUGUUCUCUGGGUG |
| TP53BP2 | 293T | TP53BP2_3<br>SEQ ID NOS: 101-102 | SS: GGGUGAAAUUCAACCCCCU<br>AS: AGGGGGUUGAAUUUCACCC |

TABLE C1-continued

Preferred 19-mer siRNA sequences.

| Target gene | Cell line* | siRNA tested | Sequence |
|---|---|---|---|
| TP53BP2 | 293T | TP53BP2_4<br>SEQ ID No. 103-104 | SS: AGGGUGAAAUUCAACCCCC<br>AS: GGGGGUUGAAUUUCACCCU |
| TP53BP2 | 293T | TP53BP2_5<br>SEQ ID NOS: 105-106 | SS: AGGGAGUGUUUGAAUAAGC<br>AS: GCUUAUUCAAACACUCCCU |
| TP53BP2 | 293T | TP53BP2_6<br>SEQ ID NOS: 107-108 | SS: ACCCAGAGAACAUUUAUUC<br>AS: GAAUAAAUGUUCUCUGGGU |
| TP53BP2 | 293T | TP53BP2_8<br>SEQ ID NOS: 109-110 | SS: CGCUGAGGGAGAAAGAGAA<br>AS: UUCUCUUUCUCCCUCAGCG |
| LRDD | PC-3 | LRDD_1<br>SEQ ID NOS: 111-112 | SS: CGCACCUGAAGAAUGUGAA<br>AS: UUCACAUUCUUCAGGUGCG |
| LRDD | PC-3 | LRDD_2<br>SEQ ID NOS: 113-114 | SS: GUCUUCUACUCGCACCUGA<br>AS: UCAGGUGCGAGUAGAAGAC |
| LRDD | PC-3 | LRDD_3<br>SEQ ID NOS: 115-116 | SS: GACUGUUCCUGACCUCAGA<br>AS: UCUGAGGUCAGGAACAGUC |
| LRDD | PC-3 | LRDD_5<br>SEQ ID NOS: 117-118 | SS: ACCUCAGAUUUGGACAGCU<br>AS: AGCUGUCCAAAUCUGAGGU |
| CYBA | MDA-MB-4 | CYBA_15<br>SEQ ID NOS: 119-120 | SS: UGGGGACAGAAGUACAUGA<br>AS: UCAUGUACUUCUGUCCCCA |
| CYBA | MDA-MB-4 | CYBA_16<br>SEQ ID NOS: 121-122 | SS: GGGCCCUUUACCAGGAAUU<br>AS: AAUUCCUGGUAAAGGGCCC |
| CYBA | MDA-MB-4 | CYBA_17<br>SEQ ID NOS: 123-124 | SS: CCCUUUACCAGGAAUUACU<br>AS: AGUAAUUCCUGGUAAAGGG |
| ATF3 | 293T | ATF3_2<br>SEQ ID NOS: 125-126 | SS: GAAGGAACAUUGCAGAGCU<br>AS: AGCUCUGCAAUGUUCCUUC |
| ATF3 | 293T | ATF3_3<br>SEQ ID NOS: 127-128 | SS: ACAGAUAAAGAAGGAACA<br>AS: UGUUCCUUCUUUUAUCUGU |
| ATF3 | 293T | ATF3_4<br>SEQ ID NOS: 129-130 | SS: AUCCUAGUAUUCCUAACCU<br>AS: AGGUUAGGAAUACUAGGAU |
| ATF3 | 293T | ATF3_5<br>SEQ ID NOS: 131-132 | SS: AUCCCAGUAUUCCUAGCCU<br>AS: AGGCUAGGAAUACUGGGAU |
| CASP2 | HeLa- | CASP2_1<br>SEQ ID NOS: 133-134 | SS: GCACUCCUGAAUUUUAUCA<br>AS: UGAUAAAAUUCAGGAGUGC |
| CASP2 | HeLa- | CASP2_2<br>SEQ ID NOS: 135-136 | SS: GCACAGGAAAUGCAAGAGA<br>AS: UCUCUUGCAUUUCCUGUGC |
| CASP2 | HeLa- | CASP2_3<br>SEQ ID NOS: 137-138 | SS: GGGCUUGUGAUAUGCACGU<br>AS: ACGUGCAUAUCACAAGCCC |
| CASP2 | HeLa- | CASP2_4<br>SEQ ID NOS: 139-140 | SS: GCCAGAAUGUGGAACUCCU<br>AS: AGGAGUUCCACAUUCUGGC |
| NOX3 | 293 | NOX_4<br>SEQ ID NOS: 141-142 | SS: UCCUGGAACUUCACAUGAA<br>AS: UUCAUGUGAAGUUCCAGGA |
| NOX3 | 293 | NOX_5<br>SEQ ID NOS: 143-144 | SS: GGUGUUCAUUUCUAUUACA<br>AS: UGUAAUAGAAAUGAACACC |
| NOX3 | 293 | NOX_6<br>SEQ ID NOS: 145-146 | SS: ACACACACCAUGUUUUCAU<br>AS: AUGAAAACAUGGUGUGUGU |
| NOX3 | 293 | NOX_7<br>SEQ ID NOS: 147-148 | SS: GGUACACACACCAUGUUUU<br>AS: AAAACAUGGUGUGUGUACC |
| NOX3 | 293 | NOX_8<br>SEQ ID NOS: 149-150 | SS: CACUUUCUGAGUUAUCAUA<br>AS: UAUGAUAACUCAGAAAGUG |
| NOX3 | 293 | NOX_9<br>SEQ ID NOS: 151-152 | SS: CUGAAAUCUAUAUGGUACA<br>AS: UGUACCAUAUAGAUUUCAG |

TABLE C1-continued

Preferred 19-mer siRNA sequences.

| Target gene | Cell line* | siRNA tested | Sequence |
|---|---|---|---|
| NOX3 | 293 | NOX_10<br>SEQ ID NOS:153-154 | SS:CUGGCGAUUUCAACAAGAA<br>AS:UUCUUGUUGAAAUCGCCAG |
| NOX3 | 293 | NOX_11<br>SEQ ID NOS: 155-156 | SS:UCUGGCGAUUUCAACAAGA<br>AS:UCUUGUUGAAAUCGCCAGA |
| HRK | MDA-MB-468 | HRK_1<br>SEQ ID NOS: 157-158 | SS:CCCCAAUGCUAUUUACAUA<br>AS:UAUGUAAAUAGCAUUGGGG |
| HRK | MDA-MB-468 | HRK_2<br>SEQ ID NOS: 159-160 | SS:AUGCUAUUUACAUACAGCU<br>AS:AGCUGUAUGUAAAUAGCAU |
| CIQBP | HeLa- | CIQBP_1<br>SEQ ID NOS: 161-162 | SS:CCCCAAUGCUAUUUACAUA<br>AS:UAUGUAAAUAGCAUUGGGG |
| CIQBP | HeLa- | CIQBP_2<br>SEQ ID NOS: 163-164 | SS:AUGCUAUUUACAUACAGCU<br>AS:AGCUGUAUGUAAAUAGCAU |
| CIQBP | HeLa- | CIQBP_3<br>SEQ ID NOS: 165-166 | SS:GAGCCUGAACUGACAUCAA<br>AS:UUGAUGUCAGUUCAGGCUC |
| BNIP3 | 293T | BNIP3_1<br>SEQ ID NOS: 167-168 | SS:GAGACAUGGAAAAAAUACU<br>AS:AGUAUUUUUUCCAUGUCUC |
| BNIP3 | 293T | BN1P3_2<br>SEQ ID NOS: 169-170 | SS:GACAUGGAAAAAAUACUGC<br>AS:GCAGUAUUUUUUCCAUGUC |
| BNIP3 | 293T | BNIP3_3<br>SEQ ID NOS: 171-172 | SS:ACCCUCAGCAUGAGGAACA<br>AS:UGUUCCUCAUGCUGAGGGU |
| BNIP3 | 293T | BNIP3_4<br>SEQ ID NOS: 173-174 | SS:GAAAAACUCAGAUUGGAUA<br>AS:UAUCCAAUCUGAGUUUUUC |
| BNIP3 | 293T | BNIP3_11<br>SEQ ID NOS: 175-176 | SS:CUGCAUUGGUGAAUUUAAU<br>AS:AUUAAAUUCACCAAUGCAG |
| BNIP3 | 293T | BNIP3_12<br>SEQ ID NOS: 177-178 | SS:CAGGUUGUCUACUAAAGAA<br>AS:UUCUUUAGUAGACAACCUG |
| BNIP3 | 293T | BNIP3_13<br>SEQ ID NOS: 179-180 | SS:GCCUUAUAUAUCACACUAU<br>AS:AUAGUGUGAUAUAUAAGGC |
| BNIP3 | 293T | BNIP3_15<br>SEQ ID NOS: 181-182 | SS:GGAAUUAAGUCUCCGAUUA<br>AS:UAAUCGGAGACUUAAUUCC |
| BNIP3 | 293T | BN1P3_22<br>SEQ ID NOS: 183-184 | SS:AGGUUGUCUACUAAAGAAA<br>AS:UUUCUUUAGUAGACAACCU |
| BNIP3 | 293T | BNIP3_23<br>SEQ ID NOS: 185-186 | SS:GAGAAAAACAGCUCACAGU<br>AS:ACUGUGAGCUGUUUUUCUC |
| BNIP3 | 293T | BNIP3_24<br>SEQ ID NOS: 187-188 | SS:CCAAGAUAGAGCUACAAAC<br>AS:GUUUGUAGCUCUAUCUUGG |
| BNIP3 | 293T | BN1P3_25<br>SEQ ID NOS: 189-190 | SS:CACUCUGCAUUGGUGAAUU<br>AS:AAUUCACCAAUGCAGAGUG |
| BNIP3 | 293T | BN1P3_26<br>SEQ ID NOS: 191-192 | SS:CCUUAAUUCAGCUGAAGUA<br>AS:UACUUCAGCUGAAUUAAGG |
| BNIP3 | 293T | BNIP3_27<br>SEQ ID NOS: 193-194 | SS:GUUCAACUUUUGUGUGCUU<br>AS:AAGCACACAAAAGUUGAAC |
| BNIP3 | 293T | BNIP3_28<br>SEQ ID NOS: 195-196 | SS:UCCUUUGUGUUCAACUUUU<br>AS:AAAAGUUGAACACAAAGGA |
| MAPK8 | 293T | MAPK8_1<br>SEQ ID NOS: 197-198 | SS:ACCACAGAAAUCCCUAGAA<br>AS:UUCUAGGGAUUUCUGUGGU |
| MAPK8 | 293T | MAPK8_2<br>SEQ ID NOS: 199-200 | SS:GCCGACCAUUUCAGAAUCA<br>AS:UGAUUCUGAAAUGGUCGGC |
| MAPK8 | 293T | MAPK8_3<br>SEQ ID NOS: 201-202 | SS:GGACUUACGUUGAAAACAG<br>AS:CUGUUUUCAACGUAAGUCC |

TABLE C1-continued

Preferred 19-mer siRNA sequences.

| Target gene | Cell line* | siRNA tested | Sequence |
|---|---|---|---|
| MAPK8 | 293T | MAPK8_4<br>SEQ ID NOS: 203-204 | SS:UGGAUGCAAAUCUUUGCCA<br>AS:UGGCAAAGAUUUGCAUCCA |
| MAPK14 | A431 | MAPK14_1<br>SEQ ID NOS: 205-2-6 | SS:GACCAUUUCAGUCCAUCAU<br>AS:AUGAUGGACUGAAAUGGUC |
| MAPK14 | A431 | MAPK14_2<br>SEQ ID NOS: 207-208 | SS:GAGGUCUAAAGUAUAUACA<br>AS:UGUAUAUACUUUAGACCUC |
| MAPK14 | A431 | MAPK14_3<br>SEQ ID NOS: 209-210 | SS:GUGCUGCUUUUGACACAAA<br>AS:UUUGUGUCAAAAGCAGCAC |
| RAC-1 | 293T | RAC1_1<br>SEQ ID NOS: 211-212 | SS:UUGGUGCUGUAAAAUACCU<br>AS:AGGUAUUUUACAGCACCAA |
| RAC-1 | 293T | RAC1_2<br>SEQ ID NOS: 213-214 | SS:GAGUCCUGCAUCAUUUGAA<br>AS:UUCAAAUGAUGCAGGACUC |
| RAC-1 | 293T | RAC1_3<br>SEQ ID NOS: 215-216 | SS:GAUGUGUUCUUAAUUUGCU<br>AS:AGCAAAUUAAGAACACAUC |
| BMP2 | Hela | BMP2_5<br>SEQ ID NOS: 217-218 | SS:GUCAAGCCAAACACAAACA<br>AS:UGUUUGUGUUUGGCUUGAC |
| SPP1 | HEPG2 | SPP1_1<br>SEQ ID NOS: 219-220 | SS:GUCCAGCAAUUAAUAAAAC<br>AS:GUUUUAUUAAUUGCUGGAC |
| SPP1 | HEPG2 | SPP1_2<br>SEQ ID NOS: 221-222 | SS:GUGCCAUACCAGUUAAACA<br>AS:UGUUUAACUGGUAUGGCAC |
| SPP1 | HEPG2 | SPP1_3<br>SEQ ID NOS: 223-224 | SS:GCAAAAUGAAAGAGAACAU<br>AS:AUGUUCUCUUUCAUUUUGC |
| SPP1 | HEPG2 | SPP1_5<br>SEQ ID NOS: 225-226 | SS:GCAUUUCUCAUGAAUUAGA<br>AS:UCUAAUUCAUGAGAAAUGC |
| SPP1 | HEPG2 | SPP1_6<br>SEQ ID NOS: 227-228 | SS:CCGCAUUUCUCAUGAAUUA<br>AS:UAAUUCAUGAGAAAUGCGG |
| RHOA | 293T-human | RHOA_1<br>SEQ ID NOS: 229-230 | SS:GUACCAGUUAAUUUUUCCA<br>AS:UGGAAAAAUUAACUGGUAC |
| RHOA | 293T-human | RHOA_2<br>SEQ ID NOS: 231-232 | SS:UAGAAAACAUCCCAGAAAA<br>AS:UUUUCUGGGAUGUUUUCUA |
| RHOA | 293T-human | RHOA_3<br>SEQ ID NOS: 233-234 | SS:ACCAGUUAAUUUUUCCAAC<br>AS:GUUGGAAAAAUUAACUGGU |
| RHOA | 293T-human | RHOA_4<br>SEQ ID NOS: 235-236 | SS:GCCACUUAAUGUAUGUUAC<br>AS:GUAACAUACAUUAAGUGGC |
| RHOA | 293T-human | RHOA_5<br>SEQ ID NOS: 237-238 | SS:GGGCAGUUUUUGAAAAUG<br>AS:CAUUUUCAAAAACUGCCC |
| RHOA | 293T-human | RHOA_6<br>SEQ ID NOS: 239-240 | SS:GGCUAAGUAAAUAGGAAUU<br>AS:AAUUCCUAUUUACUUAGCC |
| RHOA | 293T-human | RHOA_7<br>SEQ ID NOS: 241-242 | SS:CCUGUGGAAAGACAUGCUU<br>AS:AAGCAUGUCUUUCCACAGG |
| RHOA | 293T-human | RHOA_8<br>SEQ ID NOS: 243-244 | SS:GUGCUCUUUUCUCCCUCACU<br>AS:AGUGAGGGAGAAAAGAGCAC |
| RHOA | 293T-human | RHOA_9<br>SEQ ID NOS: 245-246 | SS:GGGCUAAGUAAAUAGGAAU<br>AS:AUUCCUAUUUACUUAGCCC |
| RHOA | 293T-human | RHOA_10<br>SEQ ID NOS: 247-248 | SS:GUGGGCAGUUUUUUGAAAA<br>AS:UUUUCAAAAAACUGCCCAC |
| RHOA | 293T-human | RHOA_11<br>SEQ ID NOS: 249-250 | SS:GGUGCCUUGUCUUGUGAAA<br>AS:UUUCACAAGACAAGGCACC |
| RHOA | 293T-human | RHOA_12<br>SEQ ID NOS: 251-252 | SS:CCCAAGUUCAUGCAGCUGU<br>AS:ACAGCUGCAUGAACUUGGG |

TABLE C1-continued

Preferred 19-mer siRNA sequences.

| Target gene | Cell line* | siRNA tested | Sequence |
|---|---|---|---|
| RHOA | 293T-human | RHOA_13<br>SEQ ID NOS: 253-254 | SS:GGCACUCAGUCUCUCUUCU<br>AS:AGAAGAGAGACUGAGUGCC |
| RHOA | 293T-human | RHOA_14<br>SEQ ID NOS: 255-256 | SS:CACUUUGGAAGAUGGCAUA<br>AS:UAUGCCAUCUUCCAAAGUG |
| Duox1 | exogenous expression | Duox1_1<br>SEQ ID NOS: 257-258 | SS:GAGAGAAGUUCCAACGCAG<br>AS:CUGCGUUGGAACUUCUCUC |
| Duox1 | exogenous expression | Duox1_2<br>SEQ ID NOS: 259-260 | SS:CGAGAGAAGUUCCAACGCA<br>AS:UGCGUUGGAACUUCUCUCG |
| Duox1 | exogenous expression | Duox1_3<br>SEQ ID NOS: 261-262 | SS:ACCGAGAGAAGUUCCAACG<br>AS:CGUUGGAACUUCUCUCGGU |
| Duox1 | exogenous expression | Duox1_4<br>SEQ ID NOS: 263-264 | SS:AGAUCCCAAGGAGUAUGA<br>AS:UCAUACUCCUUGGGGAUCU |
| Duox1 | exogenous expression | Duox1_6<br>SEQ ID NOS: 265-266 | SS:UUGCCUCCAUCCUCAAAGA<br>AS:UCUUUGAGGAUGGAGGCAA |

TABLE C2

Preferred 23-mer siRNA sequences.

| Target gene | Cell line | siRNA tested | Sequence |
|---|---|---|---|
| CASP2 | HeLa- | CASP2_1-1<br>SEQ ID No. 267-268 | SS:CCUUGCACUCCUGAAUUUUAUCA<br>AS:UGAUAAAAUUCAGGAGUGCAAGG |
| CASP2 | HeLa- | CASP2_1-2<br>SEQ ID No. 269-270 | SS:CUUGCACUCCUGAAUUUUAUCAA<br>AS:UUGAUAAAAUUCAGGAGUGCAAG |
| CASP2 | HeLa- | CASP2_1-3<br>SEQ ID No. 271-272 | SS:UUGCACUCCUGAAUUUUAUCAAA<br>AS:UUUGAUAAAAUUCAGGAGUGCAA |
| CASP2 | HeLa- | CASP2_1-4<br>SEQ ID No. 273-274 | SS:UGCACUCCUGAAUUUUAUCAAAC<br>AS:GUUUGAUAAAAUUCAGGAGUGCA |
| CASP2 | HeLa- | CASP2_1-5<br>SEQ ID No. 275-276 | SS:GCACUCCUGAAUUUUAUCAAACA<br>AS:UGUUUGAUAAAAUUCAGGAGUGC |

TABLE C3

Additional preferred 19-mer siRNA sequences.

| Target gene | Cell line* | siRNA tested | Sequence |
|---|---|---|---|
| P2RX7 | Nalm6 | P2RX7_6<br>SEQ ID NOS: 50971-50972 | SS:CCGAGAAACAGGCGAUAAU<br>AS:AUUAUCGCCUGUUUCUCGG |
| P2RX7 | Nalm6 | P2RX7_7<br>SEQ ID NOS: 50973-50974 | SS:CCAGACGCCAUUUAAAAGU<br>AS:ACUUUUAAAUGGCGUCUGG |
| P2RX7 | Nalm6 | P2RX7_8<br>SEQ ID NOS: 50975-50976 | SS:GUGGCUCUGAUUGCUUUAU<br>AS:AUAAAGCAAUCAGAGCCAC |
| P2RX7 | Nalm6 | P2RX7_9<br>SEQ ID NOS: 50977-50978 | SS:CCAAAGGGAAAUAUGCUUU<br>AS:AAAGCAUAUUUCCCUUUGG |
| P2RX7 | Nalm6 | P2RX7_10<br>SEQ ID NOS: 50979-50980 | SS:CACAACUACACCACGAGAA<br>AS:UUCUCGUGGUGUAGUUGUG |
| TRPM2 | Nalm6 | TRPM2_5<br>SEQ ID NOS: 50981-50982 | SS:GACAAUGCCUGGAUCGAGA<br>AS:UCUCGAUCCAGGCAUUGUC |

TABLE C3-continued

Additional preferred 19-mer siRNA sequences.

| Target gene | Cell line* | siRNA tested | Sequence |
|---|---|---|---|
| TRPM2 | Nalm6 | TRPM2_6<br>SEQ ID NOS: 50983-50984 | SS:CCAAGAACUUCAACAUGAA<br>AS:UUCAUGUUGAAGUUCUUGG |
| PARG | Nalm6 | PARG_2<br>SEQ ID NOS: 50985-50986 | SS:GACAGAGUCUUGAAGAUUU<br>AS:AAAUCUUCAAGACUCUGUC |
| PARG | Nalm6 | PARG_3<br>SEQ ID NOS: 50987-50988 | SS:GUGGCAUAUUCUAAGAAAU<br>AS:AUUUCUUAGAAUAUGCCAC |
| PARG | Nalm6 | PARG_5<br>SEQ ID NOS: 50989-50990 | SS:CCCAGACAUUAACUUCAAU<br>AS:AUUGAAGUUAAUGUCUGGG |
| CD38 | Nalm6 | CD38_5 | SS:GGGUGCAUUUAUUUCAAAA |

TABLE C4

Additional preferred 19-mer siRNA sequences.

| Target gene | siRNA | SEQ ID NOS: | SS (Sense strand 5'>3')<br>AS (antisense strand 5'>3') |
|---|---|---|---|
| HRK | HRK_7 | SEQ ID NOS: 87089-87090 | CGAUCGUAGAAACACAGAA<br>UUCUGUGUUUCUACGAUCG |
| HRK | HRK_8 | SEQ ID NOS: 87091-87092 | AGGCGGAACUUGUAGGAAC<br>GUUCCUACAAGUUCCGCCU |
| HRK | HRK_9 | SEQ ID NOS: 87093-87094 | CCUGGAGCGAUCGUAGAAA<br>UUUCUACGAUCGCUCCAGG |
| HRK | HRK_10 | SEQ ID NOS: 87095-87096 | CUGGAGCGAUCGUAGAAAC<br>GUUUCUACGAUCGCUCCAG |
| HRK | HRK_11 | SEQ ID NOS: 87097-87098 | CCUUGGAGAAAGCUGGUUC<br>GAACCAGCUUUCUCCAAGG |
| HRK | HRK_12 | SEQ ID NOS: 87099-87100 | UGGAAAUCCAGCUGCAGAA<br>UUCUGCAGCUGGAUUUCCA |
| RAC1 | RAC1_9 | SEQ ID NOS: 87101-87102 | GGGAUGAUAAAGACACGAU<br>AUCGUGUCUUUAUCAUCCC |
| RAC1 | RAC1_10 | SEQ ID NOS: 87103-87104 | GUCUUCUUGAUUUGCUUUU<br>AAAAGCAAAUCAAGAAGAC |
| RAC1 | RAC1_11 | SEQ ID NOS: 87105-87106 | CCAAUACUGACCCUCUUUA<br>UAAAGAGGGUCAGUAUUGG |
| RAC1 | RAC1_12 | SEQ ID NOS: 87107-87108 | CCUUCUAAAGCCUUAUUU<br>AAAUAAGGCUUUAGAAGG |
| RAC1 | RAC1_13 | SEQ ID NOS: 87109-18110 | GGAGAUUGGUGCUGUAAAA<br>UUUUACAGCACCAAUCUCC |
| RAC1 | RAC1_14 | SEQ ID NOS: 87111-87112 | GGGCAUUUAAUUCAUCUUU<br>AAAGAUGAAUUAAAUGCCC |
| RAC1 | RAC1_15 | SEQ ID NOS: 87113-87114 | CGAGUUUUCUGACCAGCUU<br>AAGCUGGUCAGAAAACUCG |
| RAC1 | RAC1_16 | SEQ ID NOS: 87115-87116 | GCAGAAUUGUGGAGUGUUU<br>AAACACUCCACAAUUCUGC |
| RAC1 | RAC1_17 | SEQ ID NOS: 87117-87118 | GGUGUAAAAUCAUGUGUUU<br>AACACAUGAUUUUUACACC |
| STEAP4 | STEAP4_3 | SEQ ID NOS: 87119-87120 | GUGAUUCCUAUUCGAUAUU<br>AAUAUCGAAUAGGAAUCAC |
| RHOA | RHOA_15 | SEQ ID NOS: 87121-87122 | GGCCUUUUUCAUUUAUCUA<br>UAGAUAAAUGAAAAAGGCC |

TABLE C4-continued

Additional preferred 19-mer siRNA sequences.

| Target gene | siRNA | SEQ ID NOS: | SS (Sense strand 5'>3') AS (antisense strand 5'>3') |
|---|---|---|---|
| RHOA | RHOA_16 | SEQ ID NOS: 87123-87124 | UGAGAGAGGUUUUUGAAAU<br>AUUUCAAAAACCUCUCUCA |
| RHOA | RHOA_17 | SEQ ID NOS: 87125-87126 | GGUGGGCAGUUUUUUGAAA<br>UUUCAAAAAACUGCCCACC |
| RHOA | RHOA_18 | SEQ ID NOS: 87127-87128 | CAGAAAAGCCCAAGUUCAU<br>AUGAACUUGGGCUUUUCUG |
| RHOA | RHOA_19 | SEQ ID NOS: 87129-87130 | CUAAUACUGUCAUCCUCAA<br>UUGAGGAUGACAGUAUUAG |
| RHOA | RHOA_20 | SEQ ID NOS: 87131-87132 | GCUAGACGUGGGAAGAAAA<br>UUUUCUUCCCACGUCUAGC |
| RHOA | RHOA_21 | SEQ ID NOS: 87133-87134 | CAACUACUAAUAGAAUAAA<br>UUUAUUCUAUUAGUAGUUG |
| RHOA | RHOA_22 | SEQ ID NOS: 87135-87136 | GUGUAUUGGUUUUUUAAAA<br>UUUUAAAAAACCAAUACAC |
| RHOA | RHOA_23 | SEQ ID NOS: 87137-87138 | CGGAAUGAUGAGCACACAA<br>UUGUGUGCUCAUCAUUCCG |
| RHOA | RHOA_24 | SEQ ID NOS: 87139-87140 | GAAGGAUCUUCGGAAUGAU<br>AUCAUUCCGAAGAUCCUUC |
| RHOA | RHOA_25 | SEQ ID NOS: 87141-87142 | CCAGCUGACUAAACUUUUU<br>AAAAAGUUUAGUCAGCUGG |
| RHOA | RHOA_26 | SEQ ID NOS: 87143-87144 | UCGGAAUGAUGAGCACACA<br>UGUGUGCUCAUCAUUCCGA |
| RHOA | RHOA_27 | SEQ ID NOS: 87145-87146 | AGUCAGAUGGAAAAUUCAU<br>AUGAAUUUUCCAUCUGACU |
| RHOA | RHOA_28 | SEQ ID NOS: 87147-87148 | GUCAGAUGGAAAAUUCAUU<br>AAUGAAUUUUCCAUCUGAC |
| RHOA | RHOA_29 | SEQ ID NOS: 87149-87150 | UCGACAGCCCUGAUAGUUU<br>AAACUAUCAGGGCUGUCGA |
| RHOA | RHOA_30 | SEQ ID NOS: 87151-87152 | GCUGUGGCAGAGUUACAGU<br>ACUGUAACUCUGCCACAGC |
| CASP2 | CASP2_16 | SEQ ID NOS: 87153-87154 | GGAUCAUGUAAAUGCUCAA<br>UUGAGCAUUUACAUGAUCC |
| CASP2 | CASP2_18 | SEQ ID NOS: 87155-87156 | CCCUUACUAUUCCCACUUU<br>AAAGUGGGAAUAGUAAGGG |
| CASP2 | CASP2_19 | SEQ ID NOS: 87157-87158 | CCUGACAAGUGAAGUUGUA<br>UACAACUUCACUUGUCAGG |
| CASP2 | CASP2_20 | SEQ ID NOS: 87159-17160 | CCUUAUUGAUCUUUGCCCA<br>UGGGCAAAGAUCAAUAAGG |
| CASP2 | CASP2_21 | SEQ ID NOS: 87161-87162 | CAGGAAUGUUUCAGCUGCA<br>UGCAGCUGAAACAUUCCUG |
| CASP2 | CASP2_22 | SEQ ID NOS: 98162-87164 | GACUGCACAGGAAAUGCAA<br>UUGCAUUUCCUGUGCAGUC |
| CASP2 | CASP2_23 | SEQ ID NOS: 87165-87166 | CUACAGAACAAACCAAAAA<br>UUUUUGGUUUGUUCUGUAG |
| CASP2 | CASP2_25 | SEQ ID NOS: 87167-87168 | GAAUGUGGAACUCCUCAAC<br>GUUGAGGAGUUCCACAUUC |
| CASP2 | CASP2_26 | SEQ ID NOS: 87169-87170 | UCUUCAAGCUUUUGGGCUA<br>UAGCCCAAAAGCUUGAAGA |
| CASP2 | CASP2_27 | SEQ ID NOS: 87171-87172 | GAACAAACCAAAAAUGUUC<br>GAACAUUUUUGGUUUGUUC |

TABLE C4-continued

Additional preferred 19-mer siRNA sequences.

| Target gene | siRNA | SEQ ID NOS: | SS (Sense strand 5'>3')<br>AS (antisense strand 5'>3') |
|---|---|---|---|
| CASP2 | CASP2_37 | SEQ ID NOS: 87173-87174 | CAGAAUGUGGAACUCCUCA<br>UGAGGAGUUCCACAUUCUG |
| CASP2 | CASP2_38 | SEQ ID NOS: 87175-87176 | CAGAACAAACCAAAAAUGU<br>ACAUUUUUGGUUUGUUCUG |
| CASP2 | CASP2_39 | SEQ ID NOS: 87177-87178 | CAGAAUUUUGCACAGUUAC<br>GUAACUGUGCAAAAUUCUG |

Examples of some of the activity and or stability of compounds comprising an antisense sequence and sense sequence according to tables C1-C4 and structural modifications are shown in FIG. 23.

Example 2

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine). Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Testing an active siRNA compound was performed using an animal model for ischemia-reperfusion-induced ARF. Protection Against Ischemia-Reperfusion Induced ARF Ischemia-reperfusion injury was induced in rats following 45 minutes bilateral kidney arterial clamp and subsequent release of the clamp to allow reperfusion. The rats were sacrificed seven days following the reperfusion. 12 mg/kg of Casp2_4 siRNA compound (Casp2_4: Sense sequence: GCCAGAAUGUGGAACUCCU, SEQ ID NO:139; Antisense sequence: AGGAGUUCCACAUUCUGGC, SEQ ID NO:140) were injected into the jugular vein 4 hours following the clamp. ARF progression was monitored by measurement of serum creatinine levels before (day 0) and 1 day, 3 days, 5 days and 7 days post surgery. At the end of the experiment, the rats were perfused via an indwelling femoral line with warm PBS followed by 4% paraformaldehyde. The left kidneys were surgically removed and stored in 4% paraformaldehyde for subsequent histological analysis. Acute renal failure is frequently defined as an acute increase of the serum creatinine level from baseline. An increase of at least 0.5 mg per dL or 44.2 μmol per L of serum creatinine is considered as an indication for acute renal failure. Serum creatinine was measured at time zero before the surgery and 1 day, 3 days, 5 days and 7 days post ARF surgery.

A particularly preferred compound for the treatment and prevention of ARF which was used in this experiment is a CASP2_4 siRNA compound according to an embodiment of structure (IV) wherein (N')y (sense strand) comprises L-DNA at position 18 (results presented in the table headed "Group 2" below) or wherein (N')y (sense strand) comprises L-DNA at positions 17 and 18 (results presented in the table headed "Group 3" below), and wherein (N)x (antisense strand) comprises alternating modified and unmodified ribonucleotides wherein the modified ribonucleotides comprise a 2' OMe modification. The results using placebo is presented in the table headed "Group 1" below. The siRNA compound may further comprise a DNA nucleotide at position 15 and or an L-DNA nucleotide at position 2 in (N')y. As revealed from the results below, the Casp2_4 siRNA compound administered 4 hours following the clamp reduced the elevation in creatinine levels 1 and 3 days following the ischemia-reperfusion injury. Administration of the siRNA compound prior to the clamp is found to be protective as well against ischemia reperfusion.

Group 1: Creatinine levels (mg per dL) in serum in animals injected with placebo 4 hours post clamp.

| Animal No. | Body Weight before experiment (g) | Day 0 | Day 1 | Day 3 | Day 5 | Day 7 | Body Weight post experiment (g) |
|---|---|---|---|---|---|---|---|
| 1 | 286 | 0.2 | 3.8 | 1.9 | 0.9 | 0.1 | 265 |
| 2 | 294 | 0.3 | 4.9 | 2.4 | 0.7 | 0.4 | 271 |
| 3 | 281 | 0.3 | 3.9 | 2.0 | 0.6 | 0.5 | 252 |
| 4 | 273 | 0.1 | 4.5 | 1.8 | 0.7 | 0.5 | 255 |
| 5 | 264 | 0.1 | 4.0 | 1.9 | 0.6 | 0.2 | 247 |
| 6 | 287 | 0.2 | 4.0 | 2.0 | 1.0 | 0.5 | 269 |
| Mean | 281 | 0.2 | 4.2 | 2.0 | 0.7 | 0.4 | 260 |

Group 2: Creatinine levels in serum in animals treated with CASP2_4 siRNA (L-DNA at position 18 of the sense strand, 12 mg/kg) injected 4 hours post clamp.

| Animal No. | Body Weight before experiment (g) | Day 0 | Day 1 | Day 3 | Day 5 | Day 7 | Body Weight post experiment (g) |
|---|---|---|---|---|---|---|---|
| 1 | 290 | 0.2 | 1.9 | 1.1 | 0.8 | 0.7 | 276 |
| 2 | 303 | 0.1 | 3.4 | 1.4 | 0.9 | 0.8 | 282 |
| 3 | 298 | 0.3 | 4.0 | 1.6 | 0.9 | 0.8 | 238 |
| 4 | 310 | 0.3 | 2.0 | 1.2 | 0.5 | 0.4 | 296 |
| 5 | 288 | 0.1 | 1.8 | 1.1 | 0.7 | 0.8 | 269 |
| 6 | 293 | 0.3 | 1.9 | 1.0 | 0.7 | 0.8 | 261 |
| Mean | 297 | 0.2 | 2.5 | 1.2 | 0.8 | 0.7 | 270 |

Group 3: Creatinine levels in serum in animals treated with CASP2_4 siRNA (L-DNA at positions 17 and 18 of the sense strand, 12 mg/kg) injected 4 hours post clamp.

| Animal No. | Body Weight before experiment (g) | Day 0 | Day 1 | Day 3 | Day 5 | Day 7 | Body Weight post experiment (g) |
|---|---|---|---|---|---|---|---|
| 1 | 311 | 0.3 | 2.9 | 1.1 | 0.8 | 0.6 | 288 |
| 2 | 304 | 0.2 | 2.0 | 0.9 | 0.4 | 0.4 | 271 |
| 3 | 303 | 0.4 | 3.5 | 2.1 | 1.0 | 0.6 | 282 |
| 4 | 301 | 0.4 | 3.6 | 1.7 | 1.1 | 0.6 | 280 |
| 5 | 296 | 0.3 | 3.1 | 1.5 | 1.2 | 0.5 | 276 |
| 6 | 294 | 0.4 | 2.5 | 1.3 | 1.0 | 0.5 | 284 |
| Mean | 281 | 0.3 | 2.9 | 1.4 | 0.9 | 0.5 | 280 | siRNA compounds from Tables B (B1-B74), Tables C (C1-C4) and Tables D (D1-D34) in particular siRNAs directed to specific proapoptotic genes of Table A, in particular to genes TP53BP2, LRDD, CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and SPP1) are tested in the above model system and found to be protective against ischemia reperfusion.

Example 3

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA compounds) for treating pressure sore, ulcers and similar wounds is performed in the mouse model as described in Reid et al., J. Surg. Res. 116:172-180, 2004.

An additional rabbit model is described by Mustoe et al, JCI, 1991. 87(2):694-703; Aim and Mustoe, Ann P1 Surg, 1991. 24(1):17-23, and is used for testing the siRNA compounds of the invention. siRNA according to Tables B (B1-B74), Tables C (C1-C4) and Tables D (D1-D34). and specifically compounds directed to genes CIQBP, RAC1, GSK3B, P2RX7, TRPM2, PARG, CD38, STEAP4, BMP2, CX43, or TYROBP are tested in animal models where it is shown that these siRNA compounds treat and prevent pressure sores and ulcers.

Example 4

Model Systems of Chronic Obstructive Pulmonary Disease (COPD)

Chronic obstructive pulmonary disease (COPD) is characterized mainly by emphysema, which is permanent destruction of peripheral air spaces, distal to terminal bronchioles. Emphysema is also characterized by accumulation of inflammatory cells such as macrophages and neutrophils in bronchioles and alveolar structures. Emphysema and chronic bronchitis may occur as part of COPD or independently.

Testing the active inhibitors of the invention (such as siRNA) for treating COPD/emphysema/chronic bronchitis is performed in animal models such as those disclosed as follows:

Starcher and Williams, 1989. Lab. Animals, 23:234-240; Peng, et al., 2004; Am J Respir Crit. Care Med, 169:1245-1251; Jeyaseelan et al., 2004. Infect. Immunol, 72: 7247-56. Additional models are described in PCT patent publication WO 2006/023544 assigned to the assignee of the present application, which is hereby incorporated by reference into this application.

siRNA according to Tables B (B1-B74), Tables C (C1-C4) and Tables D (D1-D34), and in particular to siRNA to genes CIQBP, BNIP3, GSK3B, P2RX7, TRPM2, PARG, CD38, STEAP4, BMP2, CX43, TYROBP, CTGF, and DUOX1 are tested in these animal models, which show that these siRNA compounds may treat and/or prevent emphysema, chronic bronchitis and COPD.

Example 5

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Uptake of siRNA Molecules into Neurons Following Injection into Injured Spinal-Cord:

The uptake of Cy3 labeled siRNA (injected into the injured cord) in different types of cells is examined following spinal cord contusion and in uninjured rats. Sagittal cryosections are produced and immunostaining using four different groups of antibodies is performed in order to determine whether uptake has occurred in neurons, astroglia, oligdendroglia and/or macrophages/microglia. Markers for neurons include NeuN, or GAP43; markers for astroglia and potential neural stem cells include GFAP, nestin or vimentin; markers for oligdendroglia include NG2 or APC; markers for macrophages/microglia include ED1 or Iba-1 (Hasegawa et al., 2005. Exp Neurol 193:394-410).

Rats are injected with two different doses of Cy3 labeled siRNA (1 µg/µl, 10 µg/µl) and are left for 1 and 3 days before sacrifice. Histological analyses indicate that many long filamentous profiles take up the labeled siRNA as well as other processes and cell bodies. Immunostaining with antibodies to MAP2 identifies uptake of label into dendrites and into cell bodies of neurons including motorneurons. Staining with other antibodies specific to astrocytes or macrophages reveals lower uptake of Cy3 labeled siRNA as compared to neurons. These results indicate that siRNA molecules injected to the injured spinal-cord will reach the cell body and dendrites of neurons including motorneurons.

siRNA compounds according to Tables B (B1-B74), Tables C (C1-C4) and Tables D (D1-D34) and in particular siRNA directed to genes LRDD, CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and RHOA are tested in this animal model, which show that these siRNA compounds promote functional recovery following spinal cord injury and thus may be used to treat spinal cord injury.

Example 6

Model Systems of Glaucoma

Testing the active inhibitors of the invention (such as siRNA) for treating or preventing glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).

siRNA according to Tables B (B1-B74), Tables C (C1-C4) and Tables D (D1-D34) in particular to genes TP53BP2, LRDD, CYBA, ATF3, CASP2, HRK, BNIP3, MAPK8, MAPK14, RAC1, and RHOA are tested in this animal model which show that these siRNA compounds treat and/or prevent glaucoma.

Example 6A

Model Systems of Ischemic Optic Neuropathy (ION)

An animal model for Ischemic optic neuropathy was established in adults Wistar rats using a protocol of optic nerve crush injury. Seven days prior to the optic nerve crush, the retinal ganglion cells (RGC) were selectively labelled by application of the retrograde tracer FluoroGold (2%, Fluorochrome, Englewood, Colo.) to the superior colliculus. The tracer was transported by retrograde transport along RGC axons resulting in complete and specific labelling of all RGCs within 1 week post injection of the fluorescent tracer. The animals were subjected to the optic nerve crush injury 7 days post retrograde tracing. The orbital optic nerve was exposed through a supraorbital approach and all axons in the optic nerve were transected by crushing with forceps for 10 seconds, 2 mm from the lamina cribrosa. A single dose of 20 µg/5 µl of PBS of the Casp2_4 siRNA compound was microinjected into the vitreous body 2 mm anterior to the nerve head, using a glass micropipette at the time of the optic nerve crush (Casp2_4: Sense sequence: GCCAGAAUGUG-GAACUCCU, SEQ ID NO:139; Antisense sequence: AGGAGUUCCACAUUCUGGC, SEQ ID NO:140; sense strand comprises L-DNA at positions 17 and 18 and antisense strand comprises alternating modified and unmodified ribonucleotides wherein the modified ribonucleotides comprise a 2' OMe modification). The survival of RGCs was determined 7 days following the optic nerve crush by counting FluoroGold-labelled RGCs on flat-mounted retinas. The experimental animals were perfused transcardially with 4% paraformaldehyde at 1 week after the optic nerve crash. Both retinas were dissected out, fixed for an additional 30 min and flat-mounted on a glass slide for ganglion cell layer quantification. The number of fluorescent RGCs was counted in 16 distinct areas in each retina and the percent of survival of the RGCs was determined compared to samples obtained from rats which did not undergo optic nerve crush injury at all or samples obtained from rats which were injected with PBS, control siRNA or GFP siRNA along with the optic nerve crush injury. Microglia cells that may have incorporated FluoroGold after phagocytosis of dying RGCs were distinguished by their characteristic morphology and excluded from quantitative analyses. The results demonstrated in the table below revealed more than two fold increase in the % of survival of RGC in animals treated with the Casp2_4 compound compared to non-relevant siRNA compound.

| Quantification of RGC survival: | | | | |
|---|---|---|---|---|
| N = 4 retinas/treatment | PBS | siGFP | Casp2_4 siRNA | Control siRNA |
| % of survival of RGC | 25.52577 | 26.12142 | 59.04197 | 25.44345 |
| SD | 1.408675 | 1.07731 | 1.13383 | 1.19296 |

Similar results are obtained using another model of optic nerve axotomy where the entire population of RGCs are axotomized by transecting the optic nerve close to the eye. (Cheng L, Sapieha P, Kittlerova P, Hauswirth W W, Di Polo A. TrkB Gene Transfer Protects Retinal Ganglion Cells from Axotomy-Induced Death In Vivo. *J. Neurosci.* May 15, 2002 2002; 22:3977-3986).

Example 7

Model Systems of Ischemia/Reperfusion Injury Following Lung Transplantation in Rats Testing the active inhibitors of the invention (such as siRNA) for treating or preventing ischemia/reperfusion injury or hypoxic injury following lung transplantation is done in one or more of the experimental animal models, for example as described by Mizobuchi et al., 2004. J. Heart Lung Transplant, 23:889-93; Huang, et al., 1995. J. Heart Lung Transplant. 14: S49; Matsumura, et al., 1995. Transplantation 59: 1509-1517; Wilkes, et al., 1999. Transplantation 67:890-896; Naka, et al., 1996. Circulation Research, 79: 773-783.

siRNA according to Tables B (B1-B74), Tables C (C1-C4) and Tables D (D1-D34) and in particular to TP53BP2, LRDD, CYBA, CASP2, BNIP3, RAC1, and DUOX1 are tested in these animal models, which show that these siRNA compounds treat and/or prevent ischemia-reperfusion injury following lung transplantation and thus may be used in conjunction with transplant surgery.

Example 8

Model Systems of Acute Respiratory Distress Syndrome

Testing the active inhibitors of the invention (such as siRNA) for treating acute respiratory distress syndrome is done in the animal model as described by Chen et al (J Biomed Sci. 2003; 10(6 Pt 1):588-92. siRNA compounds according to Tables B (B1-B74), Tables C (C1-C4) and Tables D (D1-D34) in particular to genes CYBA, HRK, BNIP3, MAPK8, MAPK14, RAC1, GSK3B, P2RX7, TRPM2, PARG, SPP1, and DUOX1 are tested in this animal model which shows that these siRNAs treat and/or prevent acute respiratory distress syndrome and thus may be used to treat this condition.

Example 9

Model Systems of Hearing Loss Conditions (i) Distribution of Cy3-PTEN siRNA in the Cochlea Following Local Application to the Round Window of the Ear A solution of 1 µg/100 µl of Cy3-PTEN siRNA (total of 0.3-0.4 µg) PBS is applied to the round window of chinchillas.

The Cy3-labelled cells within the treated cochlea are analyzed 24-48 hours post siRNA round window application after sacrifice of the chinchillas. The pattern of labeling within the cochlea is similar following 24 h and 48 h and includes labeling in the basal turn of cochlea, in the middle turn of cochlea and in the apical turn of cochlea. Application of Cy3-PTEN siRNA onto scala tympani reveals labeling mainly in the basal turn of the cochlea and the middle turn of the cochlea. The Cy3 signal persists to up to 15 days after the application of the Cy3-PTEN siRNA. The siRNA compounds of the invention are tested in this animal model which shows that there is significant penetration of these siRNA compounds to the basal, middle and apical turns of the cochlea, and that these compounds may be used in the treatment of hearing loss.

(ii) Chinchilla Model of Carboplatin-Induced or Cisplatin-Induced Cochlea Hair Cell Death Chinchillas are pre-treated by direct administration of specific siRNA in saline to the left ear of each animal. Saline is given to the right ear of each animal as placebo. Two days following the administration of the specific siRNA compounds of the invention, the animals are treated with carboplatin (75 mg/kg ip) or cisplatin (intraperitoneal infusion of 13 mg/kg over 30 minutes). After sacrifice of the chinchillas (two weeks post carboplatin treatment) the % of dead cells of inner hair cells (IHC) and outer hair cells (OHC) is calculated in the left ear (siRNA treated) and in the right ear (saline treated). It is calculated that the % of dead cells of inner hair cells (IHC) and outer hair cells (OHC) is lower in the left ear (siRNA treated) than in the right ear (saline treated).

(iii) Chinchilla Model of Acoustic-Induced Cochlea Hair Cell Death

The activity of specific siRNA in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 μg of siRNA in ~10 μL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the level of inner and outer hair cell loss is determined in the siRNA-treated and the control ear.

siRNA molecules according to Tables B (B1-B74), Tables C (C1-C4) and Tables D (D1-D34) in particular to genes TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, and CTGF are tested in this animal model which shows that the thresholds in the siRNA-treated ear are lower (better) than in the untreated (saline) ear. In addition, the amount of inner and outer hair cell loss is lower in the siRNA-treated ear than in the control ear.

Example 10

Animal Models of Osteoarthritis (OA)

Collagen induced arthritis (CIA): CIA in mice is described in Trentham et al. (1977. J. Exp. Med. 146: 857-868). Adjuvant-induced arthritis (AA):AA is described in Kong et al., (1999. Nature, 402:304-308). A menisectomy model is described in Han et al., (1999. Nagoya J Med Sci 62(3-4): 115-26).

The effect of different siRNA inhibitors, such as siRNA to SSP1, on different parameters related to OA such as chondrocyte proliferation, terminal differentiation and development of arthritis, is evaluated using one or more of the above models, in addition to in vitro models known in the art. siRNA compounds directed to specific proapoptotic genes of Table A, in particular to SSP1, are tested in these animal models which show that these siRNAs treat and/or prevent OA and thus may be used to treat this condition.

Example 11

Rat Model Systems for Transplantation-Associated Acute Kidney Injury

Warm ischemia—In test rats a left nephrectomy is performed, followed by auto transplantation that results in a warm kidney graft preservation period of 45 minutes. Following auto transplantation, a right nephrectomy is performed on the same animal. Chemically modified siRNA to a target is administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Cold ischemia—A left nephrectomy is performed on a donor animal, followed by a cold preservation (on ice) of the harvested kidney for a period of 5 hours. At the end of this period, the recipient rat will undergo a bilateral nephrectomy, followed by transplantation of the cold-preserved kidney graft. The total warm ischemia time (including surgical procedure) is about 30 minutes. Chemically modified siRNA is administered intravenously via the femoral vein, either to the donor animal prior to the kidney harvest ("pre"), or to the recipient animal 15 minutes ("post 15 min") or 4 hours (post 4 hrs) post-transplantation.

To assess the efficacy of siRNA in improvement of post-transplantation renal function, serum creatinine levels are measured on days 1, 2, and 7 post-transplantation in both warm and cold ischemia models.

Example 12

Generation of Sequences for Active siRNA Compounds to Pro-Apoptotic Genes and Production of the siRNAs Using proprietary algorithms and the known sequence of any gene, optionally the pro-apoptotic genes disclosed herein, the sequences of many potential siRNAs were generated. In addition to the algorithm, some of the 23-mer oligomer sequences were generated by 5' and/or 3' extension of the 19-mer sequences. The sequences that have been generated using this method are fully complementary to the corresponding mRNA sequence.

Tables B (B1-B74), Tables C (C1-C4) and Tables D (D1-D34) show siRNAs for the following pro-apoptotic genes: tumor protein p53 binding protein, 2 (TP53BP2); leucine-rich repeats and death domain containing (LRDD); cytochrome b-245, alpha polypeptide (CYBA); activating transcription factor 3 (ATF3); caspase 2, apoptosis-related cysteine peptidase (neural precursor cell expressed, developmentally down-regulated 2) (CASP2); NADPH oxidase 3 (NOX3); harakiri, BCL2 interacting protein (contains only BH3 domain) (HRK); complement component 1, q subcomponent binding protein (C1QBP); BCL2/adenovirus E1B 19 kDa interacting protein 3 (BNIP3); mitogen-activated protein kinase 8 (MAPK8); mitogen-activated protein kinase 14 (MAPK14); ras-related C3 botulinum toxin substrate 1 (rho family, small GTP binding protein Rac1); glycogen synthase kinase 3 beta (GSK3B); purinergic receptor P2X, ligand-gated ion channel, 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2-BMP2; gap junction protein, alpha 1, 43 kDa (connexin 43) (GJA1); TYRO protein tyrosine kinase binding protein (TYROBP); connective tissue growth factor (CTGF); secreted phosphoprotein 1 (osteopontin, SPP1); ras homolog gene family, member A (RHOA); dual oxidase 1 (DUOX1). For each gene there is a separate list of 19-mer, 21-mer and 23-mer siRNA sequences, which are prioritized based on their score in the proprietary algorithm as the best sequences for targeting human gene expression.

Example 13

Modified siRNA

Certain structural motifs useful in siRNA compounds have been tested and shown to be active and or stable. Structures C-H are shown to be active and or stable with any one of the sequences set forth in Tables B (B1-B74), Tables C (C1-C4) and Tables D (D1-D34).

Other active structures include siRNA having a structural motif according to Structures (IX)-(XI). Compounds comprising the sequences set forth in Tables B (B1-B74), Tables C (C1-C4) and Tables D (D1-D34) and the motifs set forth in Structures (I)-(XI) are shown in FIG. 23, herein.

In one example, a CASP2 siRNA where x=y=19 was tested with different structural motifs and compared for activity and stability. In the first compound (Casp2-i) the (N)x (antisense) consists of alternating 2'-OMe modified and unmodified ribonucleotides; three consecutive nucleotides at the 3' terminus of (N')y (sense strand) are joined by two 2'-5' phosphodiester bonds and three nucleotides at the 5' terminus of (N')y are LNA. In the second compound (Casp2-ii) (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA. In the third compound (Casp2-iii), in (N)x two consecutive nucleotides at the 5" terminus (the terminal and penultimate nucleotides) are 2'-OMe modified ribonucleotides and three consecutive nucleotides at the 3' terminus of (N')y are joined by two 2'-5' phosphodiester bonds and three consecutive nucleotides at the 5' terminus of (N')y are LNA. These molecules are shown herein below in Table E and their activity as denoted by a % inhibition in human HeLa cells and IC50 is presented in Table F. The compounds were shown to be active (>50% inhibition) in HeLa cells. The compounds were further tested for serum stability. Structure CASP2-i was stable for 24 hours in human serum. Casp2-ii and Casp2-iii showed stability over 24 hours, with a low level of degradation products identified. The oligomers are CASP2-based sequences that can be replaced by any sense and antisense pair or the sense and antisense pairs shown in Tables B (B1-B74), Tables C (C1-C4) or Tables D (D1-D34).

TABLE E

| Compound | | | SEQ ID No. |
|---|---|---|---|
| Casp2-i | SEN 5' | *gcc*AGAAUGUGGAACUC\*C\*U-3' | SEQ ID No: 139 |
| | AS-5'- | AGGAGUUCCACAUUCUGGC-3' | SEQ ID No: 140 |
| Casp2-ii | SEN 5' | *gcc*AGAAUGUGGAACUC\*C\*U-3' | SEQ ID No: 139 |
| | AS-5'- | AGGAGUUCCACAUUCUGGC-3' | SEQ ID No: 140 |
| Casp2-iii | SEN 5' | *gcc*AGAAUGUGGAACUC\*C\*U-3' | SEQ ID No: 139 |
| | AS-5'- | AGGAGUUCCACAUUCUGGC-3' | SEQ ID No: 140 |

\*: 2'5' bridge; italics: LNA, underlined: 2'OMe

TABLE F

| Compound | % inhibition 20 nM | % inhibition 5 nM | IC50 (nM) |
|---|---|---|---|
| Casp2-i | 89 | 81 | 0.50 |
| Casp2-ii | 90 | 87 | 0.12 |
| Casp2-iii | 78 | 55 | 2.58 |

Table G shows 19-mer and 23-mer siRNA compounds (rat p53) based on Structure (E) wherein the underlined nucleotides are L-DNA nucleotides. In those compounds each of (N)x and (N')y comprise unmodified ribonucleotides wherein the 3' penultimate nucleotide or two consecutive nucleotides at the 3' penultimate position is an L-DNA nucleotide. The oligomers are p53-based sequences that can be replaced by any sense and antisense pair or the sense and antisense pairs shown in Tables B (B1-B74), Tables C (C1-C4) or Tables D (D1-D34).

TABLE G

| _S1 | 5'-GAAGAAAAUUUCCGCA<u>AAA</u>-3' | AA | (L-DNA) | SEQ ID NO: 87179 |
|---|---|---|---|---|
| _AS1 | 5'-UUUUGCGGAAAUUUUCU<u>U</u>C-3' | U | (L-DNA) | SEQ ID NO: 87180 |
| _S2 | 5'-GAAGAAAAUUUCCGCAA<u>A</u>A-3' | A | (L-DNA) | SEQ ID NO: 87179 |
| _AS2 | 5'-UUUUGCGGAAAUUUUCU<u>U</u>C-3' | U | (L-DNA) | SEQ ID NO: 87180 |
| _S3 | 5'-GAAGAAAAUUUCCGCAA<u>A</u>A-3' | A | (L-DNA) | SEQ ID NO: 87179 |
| _AS3 | 5'-UUUUGCGGAAAUUUUC<u>UU</u>C-3' | UU | (L-DNA) | SEQ ID NO: 87180 |
| _S4 | 5'-GAAGAAAAUUUCCGCA<u>AAA</u>-3' | AA | (L-DNA) | SEQ ID NO: 87179 |
| _AS4 | 5'-UUUUGCGGAAAUUUUC<u>UU</u>C-3' | UU | (L-DNA) | SEQ ID NO: 87180 |

TABLE G-continued

| | | | | |
|---|---|---|---|---|
| _S5 | 5'-GGAAGAAGAAAAUUUCCGCAAAA-3' | AA | (L-DNA) | SEQ ID NO: 87181 |
| _AS5 | 5'-UUUUGCGGAAAUUUUCUUCUUCC-3 | C | (L-DNA) | SEQ ID NO: 87182 |
| _S6 | 5'-GGAAGAAGAAAAUUUCCGCAAAA-3' | A | (L-DNA) | SEQ ID NO: 87181 |
| _AS6 | 5'-UUUUGCGGAAAUUUUCUUCUUCC-3' | C | (L-DNA) | SEQ ID NO: 87182 |
| _S7 | 5'-GGAAGAAGAAAAUUUCCGCAAAA-3' | A | (L-DNA) | SEQ ID NO: 87181 |
| _AS7 | 5'-UUUUGCGGAAAUUUUCUUCUUCC-3' | UC | (L-DNA) | SEQ ID NO: 87182 |
| _S8 | 5'-GGAAGAAGAAAAUUUCCGCAAAA-3' | AA | (L-DNA) | SEQ ID NO: 87181 |
| _AS8 | 5'-UUUUGCGGAAAUUUUCUUCUUUCC-3 | UC | (L-DNA) | SEQ ID NO: 87182 |

Example 14

Experimental Results with 2'O-Methylated Structures of the Present Invention a) siRNAs (20 nM) directed against the p53 gene having the following structures, as shown in were tested in cells which express endogenous p53 for ability to inhibit gene expression.

Figures 4A, 4B:
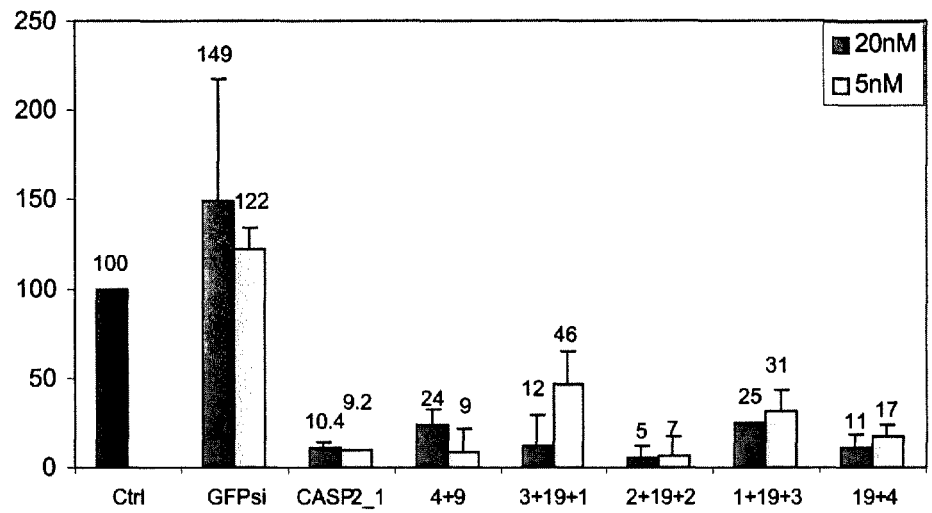
FIGS. 4A and 4B present 23-mer CASP2 siRNA structures comprising 2'-O-methylated monomers and experimental results obtained with those compounds.

FIG. 1A shows structures wherein 5=2'O-methylated riboUridine; 6=2'O-methylated riboAdenine; 7=2'O-methylated riboCytosine; and 8=2'O-methylated riboGuanine. Lower case letters refer to unmodified ribonucleotides.
Results
85-90% inhibition was observed following transfection of: structure Nos: #2; #4, #5, #6, #8 and #11.
75% inhibition was observed following transfection of structure No. #1.
60% inhibition was observed following transfection of: structure Nos: #3; #7, #10 and #12.
50% inhibition was observed following transfection of structure No. #9.
FIG. 1B presents the serum stability of some of the above structures, #4, #5, #8 and #11.
b) Further experimental results with 23-mer 2'O-Me structures of the present invention
siRNA compounds shown in FIG. 2, directed against p53 were tested in the above assay.
Nucleotides having a 2'-O-methyl modification are indicated by underlined capital letters.
90% inhibition or higher was achieved with structures #4, #5, #6, #8 and #11; 75% inhibition was achieved with structure #2.
c) siRNA compounds directed against CASP2, shown in FIG. 3A were tested in the above assay. Nucleotides having a 2'-O-methyl modification are indicated by underlined capital letters.
The activity results are presented in FIG. 3B; all the above molecules resulted in about 75-95% inhibition.
d) The siRNA compounds shown in FIG. 4A are directed against CASP2 and were tested in the above assay. Nucleotides having a 2'-O-methyl modification are indicated by underlined capital letters.
The results are presented in FIG. 4B; all the above molecules resulted in about 75-95% inhibition.
e) siRNA compounds directed against CASP2 and shown in FIG. 5A were tested in the above assay. The 2'-O-Me modified nucleotides are underlined capital letters.
The results are presented in FIG. 5B; all the above molecules resulted in about 75-90% inhibition.

Example 15

Figures 6A, 6B:
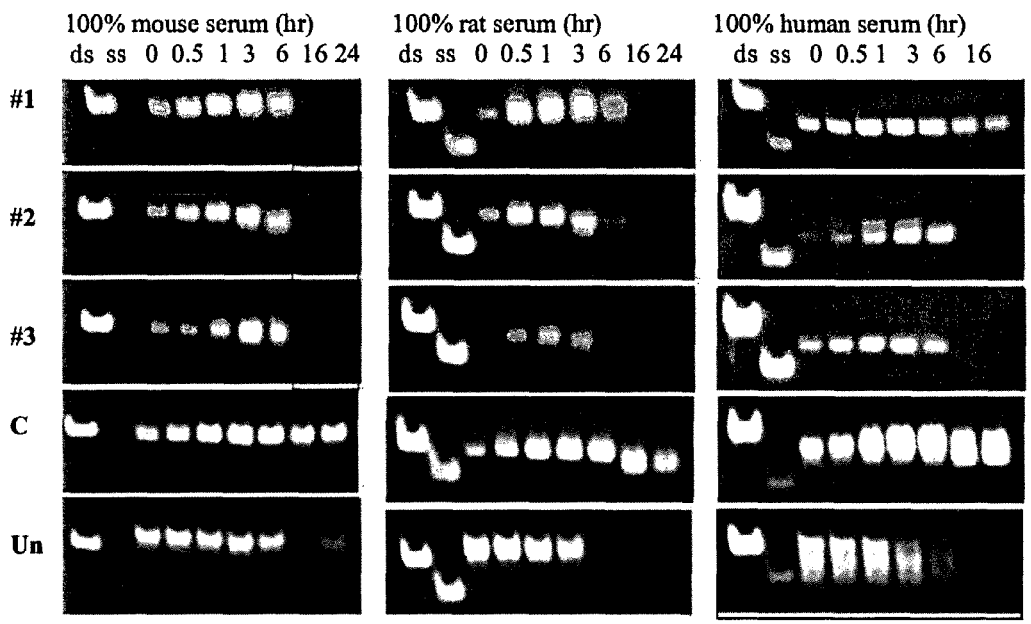
FIGS. 6A and 6B present 19-mer QM5 (targets p53) siRNA structures comprising 2'5' bridged nucleotides and experimental results obtained using those compounds.

Further Experimental Results with 2'-5' Bridged Structures a) siRNA compounds (20 nM) directed against the p53 gene having the structures shown in FIG. 6A were tested in cells which express endogenous p53 for ability to inhibit gene expression.

Figure 9C:
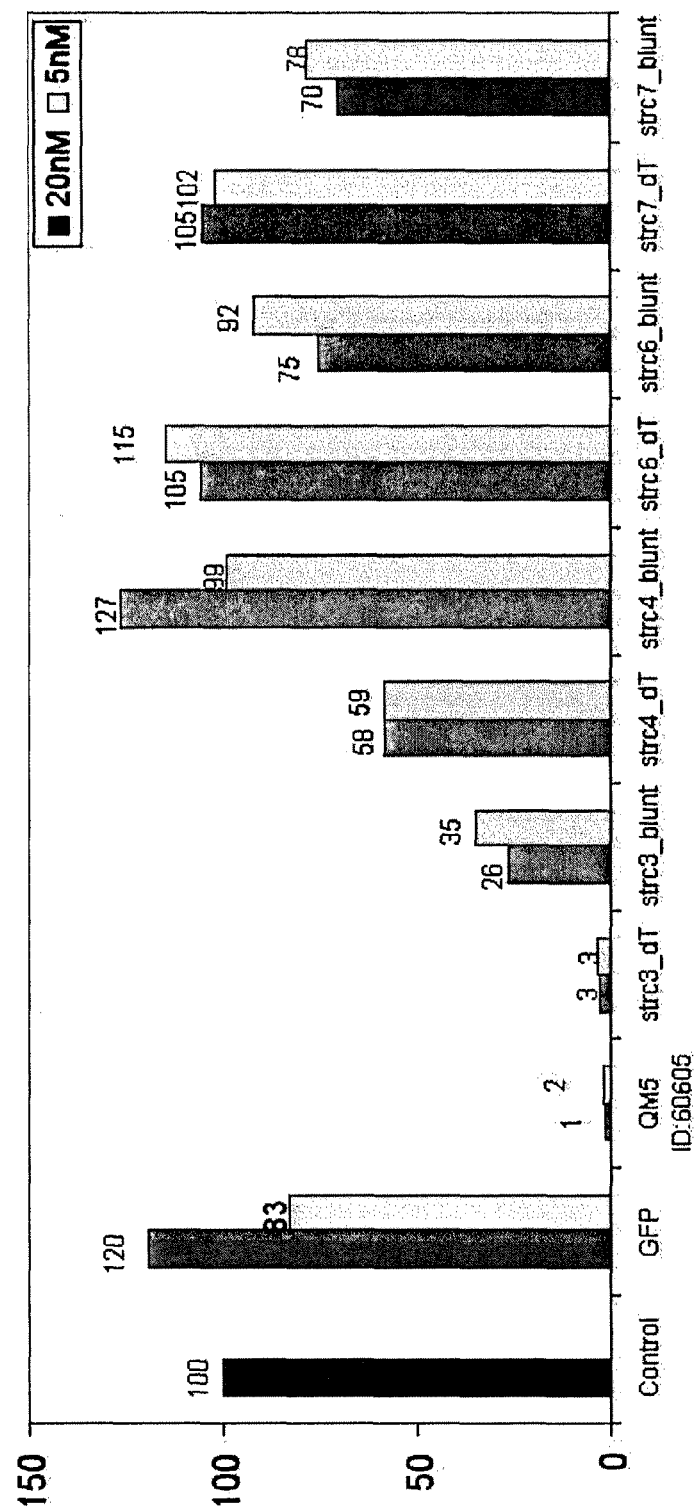
FIGS. 9C-9E show activity of those compounds.
Figure 9D:
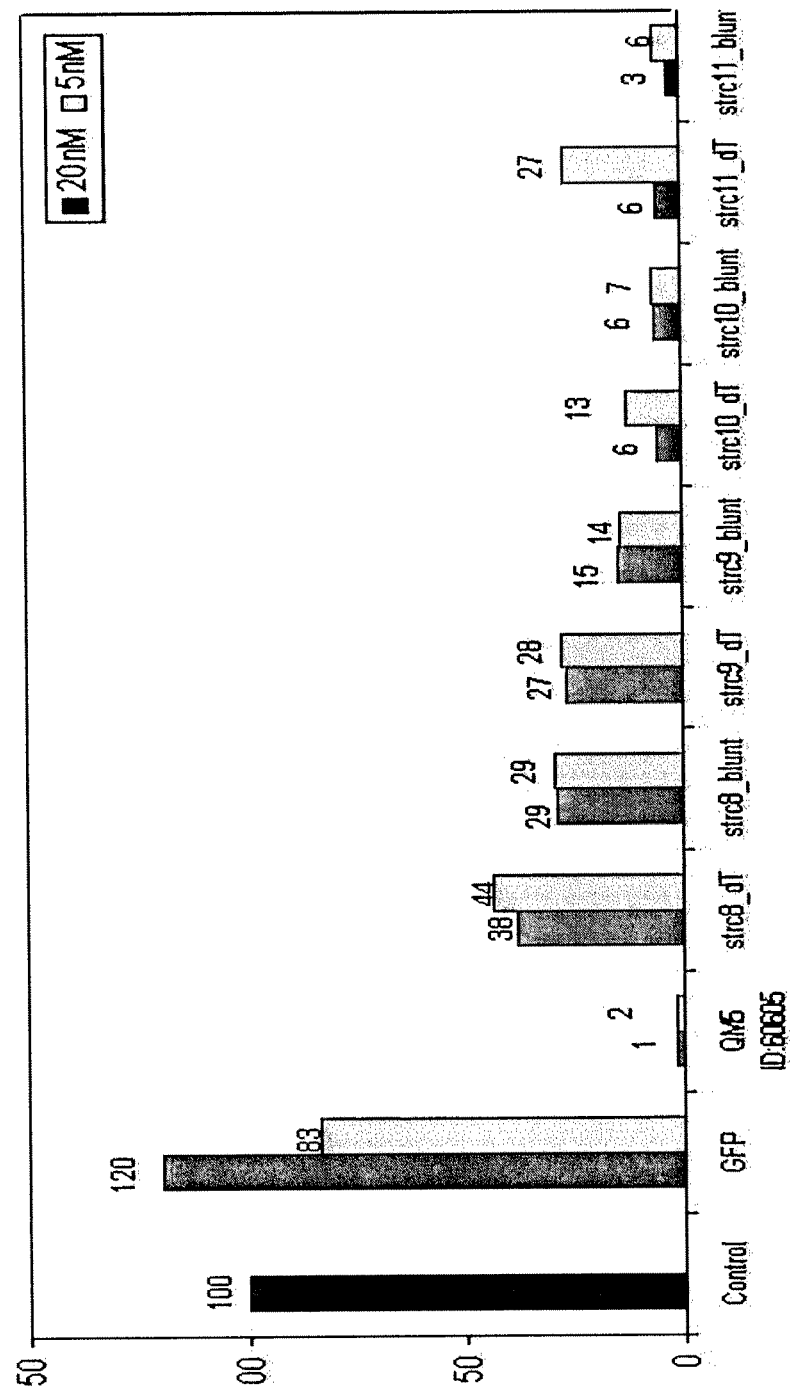
Figure 9E:
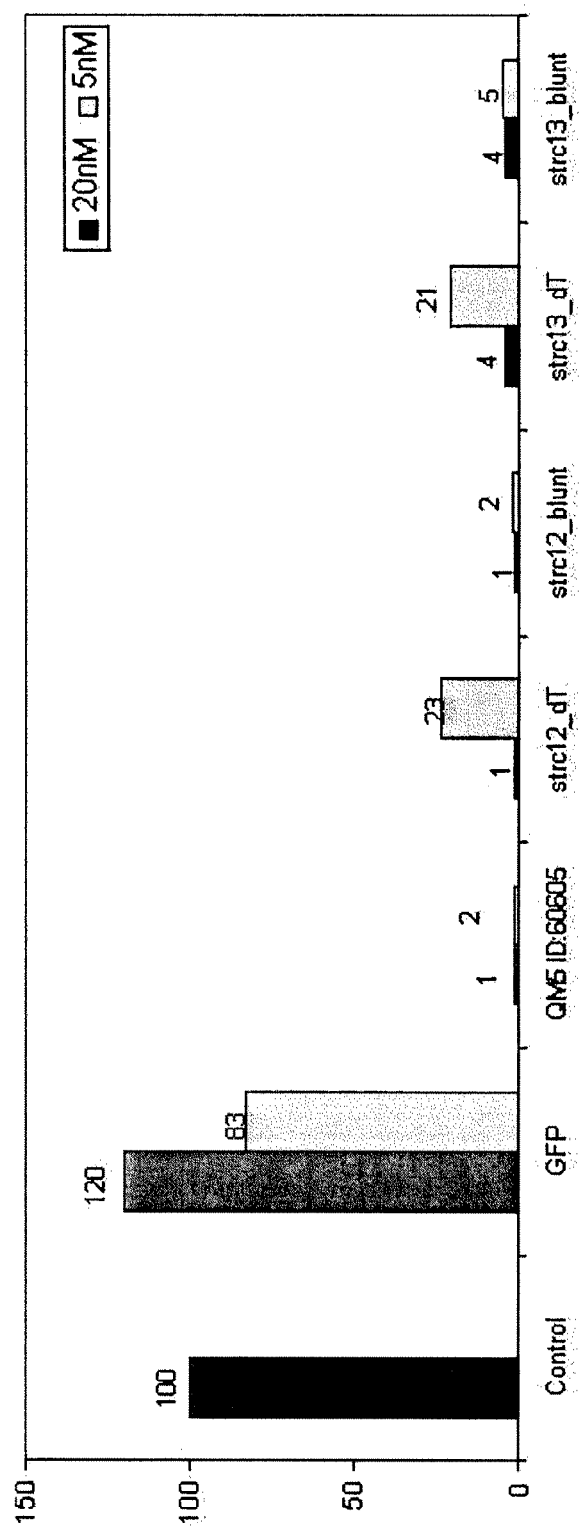

In FIG. 6A: 5=2'-5" bridged riboUridine; 6=2'-5" bridged riboAdenine; 7=2'-5" bridged riboCytosine; and 8=2'-5" bridged riboGuanine. Underlining indicates 2'-O-methylated nucleoside.
Results
90-95% inhibition was observed following transfection with structure Nos. 1-3, 10 and 12.
80-85% inhibition was observed following transfection with structures #4 and #15.
Other structures were less active. FIG. 6B presents the serum stability of some of the above structures. b) Results with 2'-5' structures relating to CASP2
siRNAs compounds directed against CASP2 and shown in FIG. 7A were tested in the above assay. Nucleotides linked by a 2'-5' bridge are indicated by an asterisk (*) between them.
The results are presented in FIG. 7B, and show that all 4 siRNAs against CASP2 were active and yielded 75-92% inhibition.
c) Results with 2'-5' structures relating to DDIT4 (REDD2)
siRNA compounds directed against DDIT4 and shown in FIG. 8A were tested in the above assay. Nucleotides linked by a 2'-5' bridge are indicated by an asterisk between them.
siRNA compounds 1 and 3 were active in the above assay and resulted in 60% inhibition of the endogenous gene.
d) Results with 2'-5' structures relating to QM5:
siRNA compounds directed against mouse p53 and shown in FIG. 8B were tested in the above assay. Nucleotides linked by a 2'-5' bridge are indicated by an asterisk between them.
Structures 1 and 3 results in 90-95% inhibition; structure 4 resulted in 70% inhibition and structure 2 resulted in about 50% inhibition.
e) Additional structures with 2'-5' and 2'-O-Methyl combination modifications
siRNA compounds directed against p53 (QM5 siRNA) and shown in FIGS. 9A-9B were tested in the above assay. Nucleotides linked by a 2'-5' bridge are indicated by an asterisk between them. The 2'-OMe modified nucleotides are underlined.
The results are shown in FIGS. 9C, 9D and 9E; many of the structures effect above 90% inhibition.

f) Additional 23-mer structures with 2'-5' and 2'-O-Methyl combination modifications siRNA compounds directed against p53 and shown in FIG. 10A were tested in the above assay. Nucleotides linked with a 2'-5' bridge are indicated by an asterisk between them. The 2'-O-Me modified nucleotides are underlined.

Figure 10C:
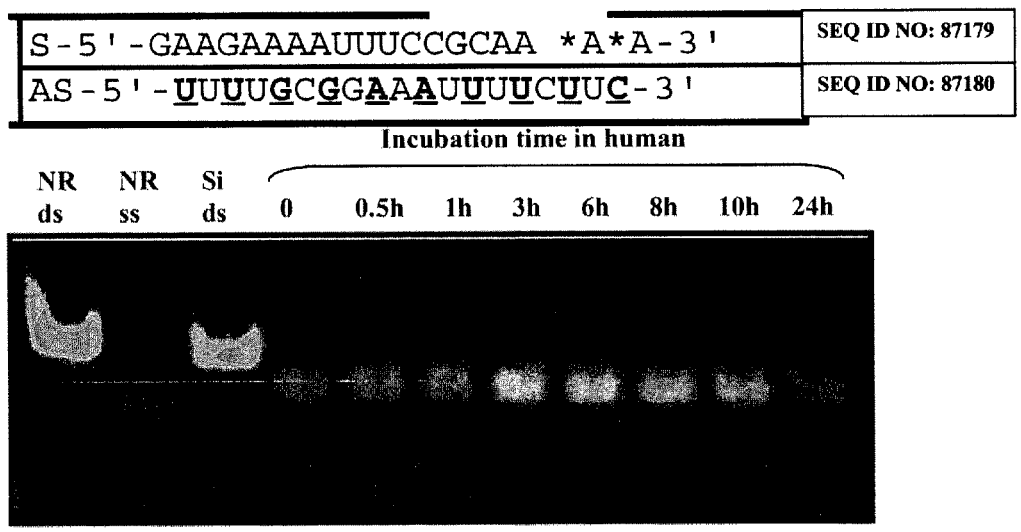
FIGS. 10C and 10D show serum stability results.
Figure 10D:
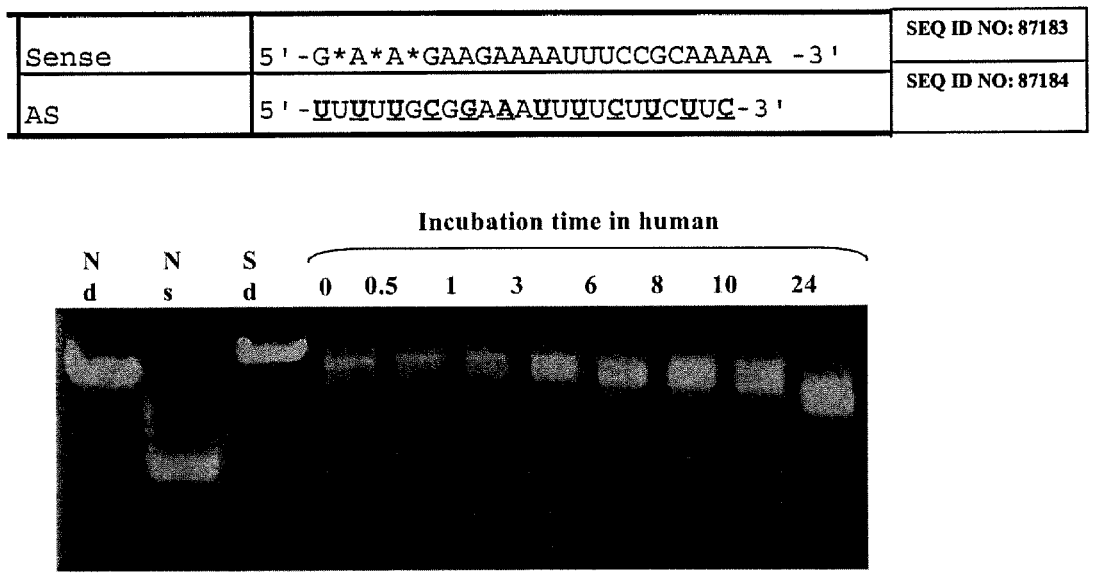

The results are presented in FIG. 10B. Structures 1-3 effected 80-95% inhibition. FIGS. 10C and 10D show serum stability results for structures having 2'5' linkages on the SS and an alternating methylation pattern on the AS.

g) siRNA compounds directed against CASP2 and shown in FIG. 11A were tested in the above assay. The 2'-OMe modified nucleotides are underlined and nucleotides linked by a 2'-5' bridge are indicated by an asterisk between them.

The results are presented in FIG. 11B, and indicate that structures 3-5 effect about 70-95% inhibition.

h) siRNA compounds directed against CASP2 and shown in FIG. 12A were tested in the above assay. Nucleotides linked by a 2'-5' bridge are indicated by an asterisk between them.

The results are presented in FIG. 12B, and indicate that structures 3-5 effect about 80-95% inhibition.

Example 16

Further Experimental Results with Mirror Nucleotide Containing Structures siRNA compounds (5 nM and 20 nM) directed against the p53 gene and having the structures as shown in FIG. 13A were tested in cells which express endogenous p53 for ability to inhibit gene expression.

Note that nucleotides which are underlined are mirror DNA nucleotides i.e. L-deoxyribonucleotides.

Results 80-95% inhibition was observed following transfection with structures 1-3, 10, 12 and 15. Structure 16, which comprises alternating nucleotides on both strands serves as positive control.

Figure 13B:
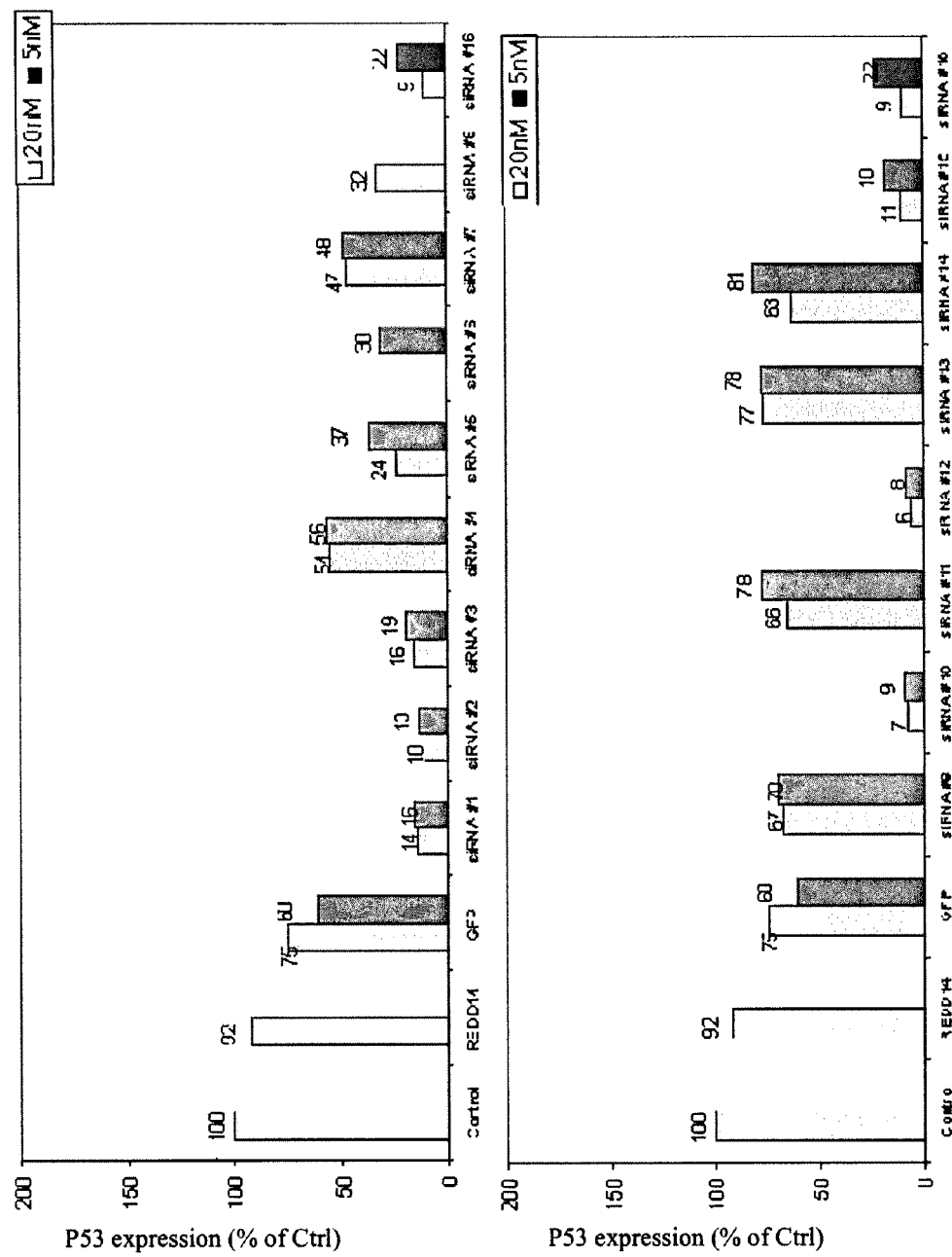
FIG. 13B shows experimental results using those compounds.

Other structures showed low to moderate activity. The results are presented in FIG. 13B. FIG. 13C shows serum stability of an siRNA compound which comprises L-DNA nucleotide monomers (covalently linked to adjacent nucleotide monomer). A further series of results in the activity assay with siRNA #1 demonstrated an IC50 of 0.09 nM. This level of activity is 2-fold greater than the same sequence with an alternating methylated structure on both strands, which had an IC50 of 0.23 nM (See FIG. 13D).

Example 17

Figure 14B:
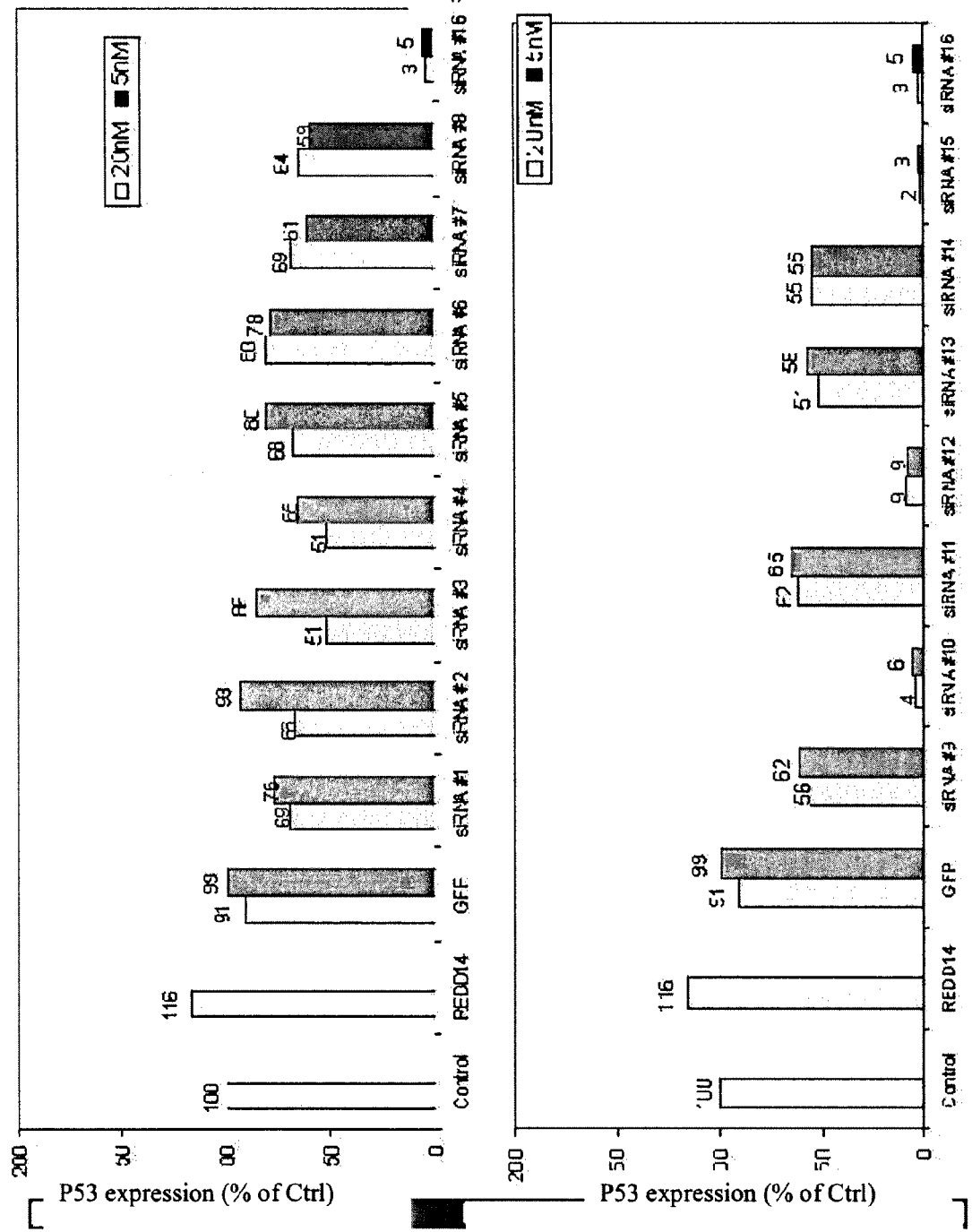
FIG. 14B shows experimental results using those compounds.

Further Experimental Results with LNA Containing Structures siRNA compounds (5 nM and 20 nM) directed against the p53 gene and having structures shown in FIG. 14A were tested in cells which express endogenous p53 for ability to inhibit gene expression. Note that underlining indicates an LNA nucleotide. The same assay presented in Example 1 was used.

Results 80-95% inhibition was observed following transfection with structures 10, 12 and 15.

Other structures showed low to moderate activity. The results are presented in FIG. 14B.

Example 18

Tandem and Star Structures

Figure 15:
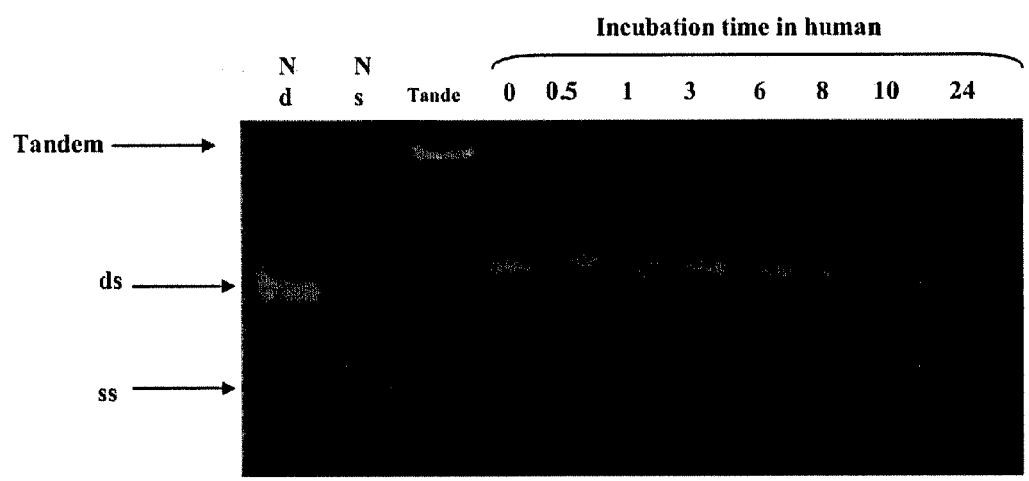
FIG. 15 shows an example of a tandem siRNA compound and serum stability results thereof.
Figure 16A:
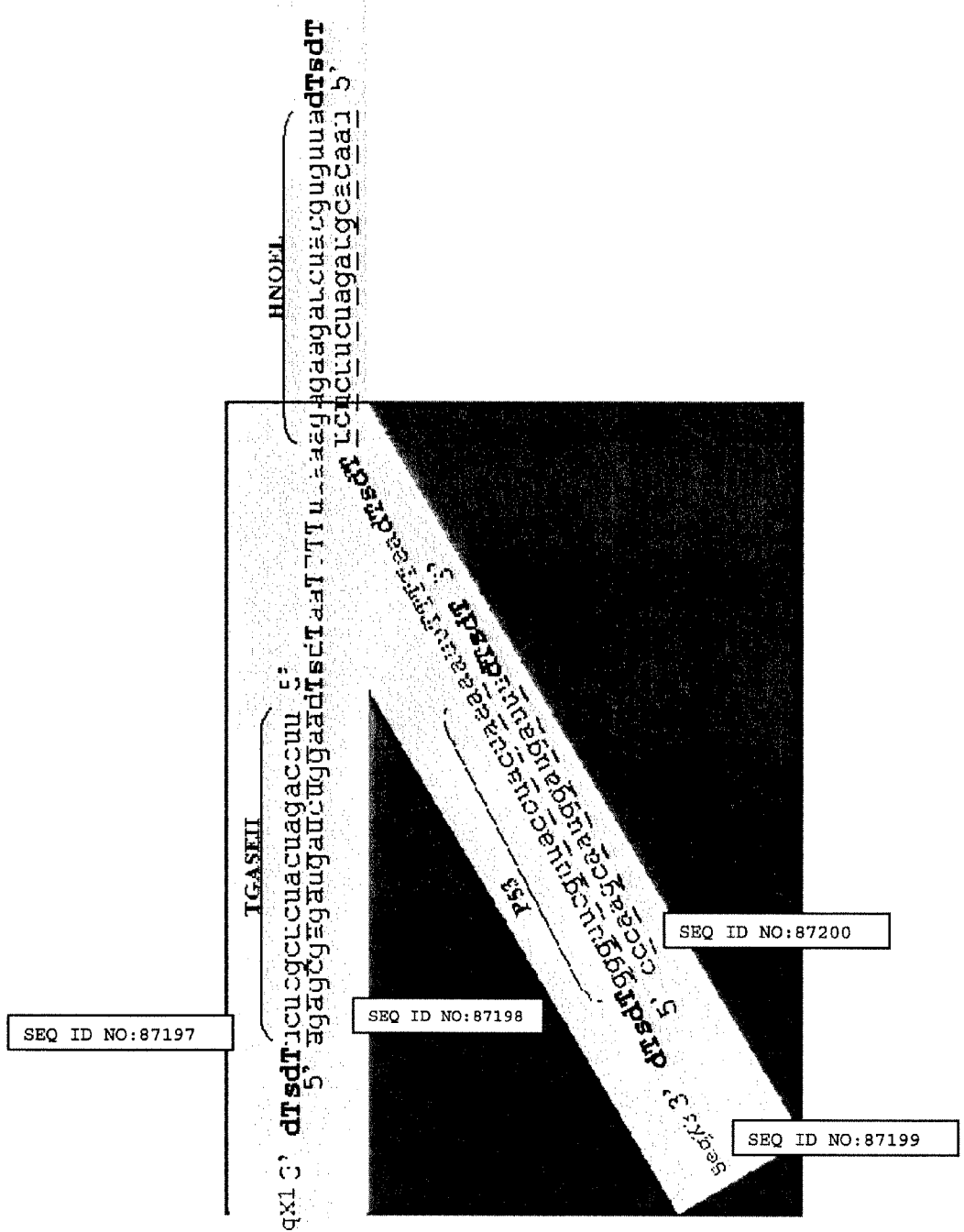
FIG. 16 shows an example of a star siRNA compound and serum stability results thereof.
Figure 16B:
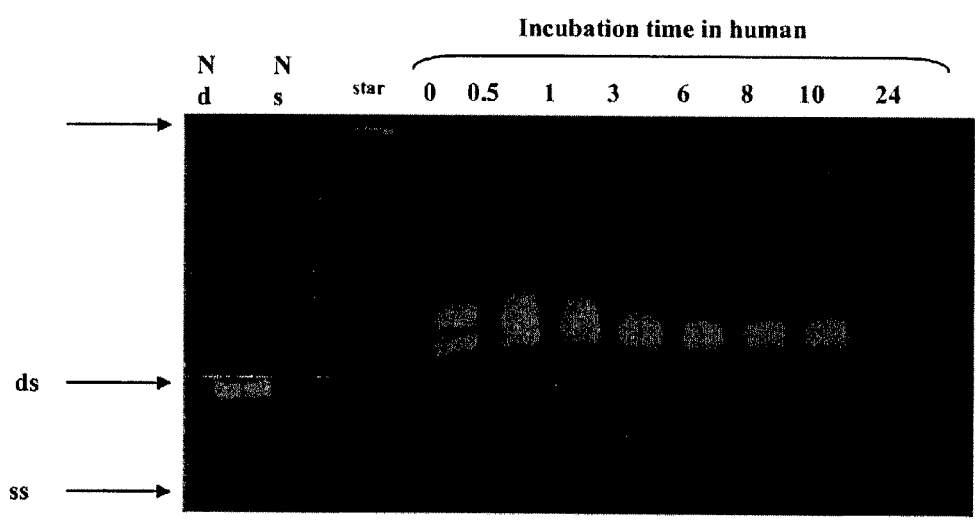

FIGS. 15 and 16 show examples and serum stability of tandem siRNA and "star" siRNA structures, respectively.

Example 19 siRNA Compounds Having Multiple Modification Types

FIGS. 17A-17C show p53 and CASP2 siRNA compounds, which comprise modified nucleotide monomers (covalently linked to adjacent nucleotide monomer) at various positions, and their activity, measured at 20 nM and showing % target gene knock down (KD). In FIG. 17A the bold underlined letters represent 2' methoxy modified nucleotides; the capital italicized letters represent nucleotides comprising 2'5' internucleotide linkages and a 3' methoxy modification. In FIG. 17B the bold underlined letters represent 2' methoxy modified nucleotides; the capital italicized letters represent nucleotides comprising P-ethoxy internucleotide linkages. In FIG. 17C the bold underlined letters represent 2' methoxy modified nucleotides; the capital italicized letters represent nucleotides comprising 2'5' internucleotide linkages, italics small letters represent L-DNA modified nucleotides and the small letters represent LNA (2'O-4'C) nucleotides.

Example 20

Deoxyribonucleotide Containing Structures

FIG. 18 show examples of CASP2_4 siRNA antisense strands (AS) and sense strands (S), which comprise DNA monomers at various positions (bolded and italicized letters and covalently linked to adjacent nucleotide monomer). siRNA compounds are synthesized by combining any sense strand with any of the antisense strands. In FIG. 18: 5=2'O methylated riboUridine; 6=2'O methylated riboAdenine; 7=2'O methylated riboCytosine; and 8=2'O methylated riboGuanine. FIGS. 19A-19E show examples of L-DNA motifs exemplified with the CASP2_4 and RhoA_24 sequences.

FIG. 19A shows two preferred double stranded duplexes targeting CASP2 useful in RNAi.

FIG. 19B shows CASP2_4 duplexes comprising L-DNA nucleotides (n=L-DNA (L-deoxyribonucleotide); N (underlined capital)-2'-OMe ribonucleotide; Lc—L-Deoxy cytidine 5'-overhang; ab—abasic pseudo deoxyribonucleotide analog.

FIG. 19C shows CASP2_4 SEN oligonucleotides comprising combinations of unmodified ribonucleotides, DNA nucleotides and L-DNA nucleotide analogs and CASP2_4 AS oligonucleotides comprising alternating unmodified and modified ribonucleotides, useful in preparing duplexes exhibiting RNAi activity.

FIG. 19D shows the activity and stability of CASP2_4 modified duplexes.

FIG. 19E shows certain duplex motifs exemplified with the RhoA_24 sequences, with and without the 3' phosphate at one or both 3' termini.

Example 21

Structures Containing Abasic, Inverted-Abasic, 2'O-Methyl, Mismatched Base Pairs and Other Modifications FIG. 20 describe such structures, which are effective in treating any of the conditions disclosed herein.

In FIGS. 20A-20G the legend of nucleotide analogs and pseudo nucleotides is as follows:

Underlined capital letter "N"—2'OMe ribonucleotide; "ab"—abasic pseudo nucleotide; I—inverted abasic pseudonucleotide; Italicized "5N"=5'OMe DNA, White capital "N"—LNA; italicized small case underlined n: L-DNA; strikethrough N— mismatches FIG. 20A: Set 1 shows AS strand comprising abasic mismatch to the target sequence; oligonucleotides lack 3' phosphate;

FIG. 20B: Set 2 shows oligonucleotides useful in preparing duplex compounds having less than 15 bp in the ds structure; oligonucleotides lack 3' phosphate;

FIG. 20C: Set 3 shows oligonucleotides having insertion of at least one mismatch to target sequence;

FIGS. 20D-20E: Sets 4 and 5 show AS strand comprising abasic pseudo nucleotide or nucleotides ("ab") paired with sense strands as in SET 1;

FIG. 20F: Set 6 shows AS strand comprising abasic pseudo nucleotide or nucleotides ("ab") paired with unmodified sense strands;

FIG. 20G: Set 7 shows unmodified AS strand paired with sense strands from SET1.

FIG. 21 shows examples of the base modifications in non-base pairing nucleotide analogs useful in preparing oligonucleotide having RNAi activity. (In the column showing the chemical structures, dR shows the point of attachment to the deoxyribose moiety; R shows the point of attachment to the ribose moiety).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08614309B2). An electronic copy of the "Sequence Listing" will also be available from the USPTO upon request and payment of the fee set forth in 37 CFR 1.19(b)(3).

What is claimed is:

1. A double-stranded RNA compound having the following structure:

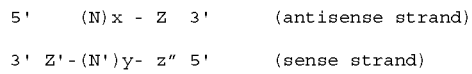

```
5'     (N)x - Z  3'         (antisense strand)

3' Z'-(N')y- z"  5'          (sense strand)
``` wherein each of N and N' is a modified or an unmodified ribonucleotide or is an unconventional moiety selected from the group consisting of a locked nucleic acid (LNA), a modified deoxyribonucleotide, an unmodified deoxyribonucleotide, a mirror nucleotide and a nucleotide joined to an adjacent nucleotide by a 2'-5' internucleotide phosphate bond;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent, but if present is a capping moiety covalently attached at the 5' terminus of (N')y;

wherein x=y=19;

wherein (N)x comprises at least five alternating 2'-O-methyl sugar modified ribonucleotides beginning at the 3' terminus and at least nine 2'-O-methyl sugar modified ribonucleotides in total, and each remaining N is an unmodified ribonucleotide or an unconventional moiety;

wherein in (N')y an unconventional moiety is present at one or more of positions 15, 16, 17 or 18;

an unconventional moiety may be present at one or more of positions 1, 2, 3 or 19; and an unmodified ribonucleotide is present at each remaining position;

wherein the sequence of (N)x is 5' AGGAGUUCCACA-UUCUGGC 3'(SEQ ID NO:140); and wherein the sequence of (N')y is 5' GCCAGAAUGUG-GAACUCCU 3' (SEQ ID NO:139);

or a pharmaceutical acceptable salt of such compound.

2. The double-stranded RNA compound according to claim 1, wherein at least one unconventional moiety in (N')y is a mirror nucleotide.

3. The double-stranded RNA compound according to claim 2, wherein the mirror nucleotide is present at position 17, position 18 or both positions 17 and 18.

4. The double-stranded RNA compound according to claim 1 or 3, wherein if an unconventional moiety is present at each of positions 1, 2, and 3 such unconventional moiety is LNA.

5. A composition comprising the double-stranded RNA compound according to claim 1, or a pharmaceutical acceptable salt of such compound; and a pharmaceutically acceptable carrier.

6. A method for treating a subject suffering from an ocular ischemic disease or condition, comprising administering to the subject the composition according to claim 5 in an amount effective to treat the subject.

7. The double-stranded RNA compound according to claim 1 or 3, wherein Z and Z' are absent.

8. The double-stranded RNA compound according to claim 1 or 3, wherein (N)x comprises 2'-O-methyl sugar modified ribonucleotides at positions 2, 4, 6, 8, 11, 13, 15, 17 and 19, and each remaining N is an unmodified ribonucleotide.

9. The double-stranded RNA compound according to claim 3, wherein the mirror nucleotide is present only at position 18.

10. The double-stranded RNA compound according to claim 1 or 3, wherein at least one of Z or Z' is present.

11. The double-stranded RNA compound according to claim 1 or 3, wherein (N)x comprises 2'-O-methyl sugar modified ribonucleotides at positions 1, 3, 5, 7, 9, 11, 13, 15, 17 and 19, and each remaining N is an unmodified ribonucleotide.

12. The double-stranded RNA compound according to claim 9, wherein the mirror nucleotide is L-DNA.

13. The double-stranded RNA compound according to claim 12, wherein the L-DNA is L-deoxycytidine.

14. The double-stranded RNA compound according to claim 1 or 13, wherein the covalent bond joining each consecutive N or N' is a phosphodiester bond.

15. The double-stranded RNA compound according to claim 3, wherein the mirror nucleotide is L-DNA.

16. The double-stranded RNA compound according to claim 1 or 13, wherein z" is present.

17. The double-stranded RNA compound according to claim 16, wherein z" is selected from the group consisting of an abasic ribose moiety, an abasic deoxyribose moiety, an inverted abasic ribose moiety, an inverted deoxyribose moiety, C6-amino-Pi and a mirror nucleotide.

18. The double-stranded RNA compound according to claim 17, wherein z" is an inverted abasic deoxyribose moiety.

19. The double-stranded RNA compound according to claim 1 or 13, wherein z" is absent.

20. The double-stranded RNA compound according to claim 1, having the following structure:

```
                                          (SEQ ID NO: 140)
5' AGGAGUUCCACAUUCUGGC 3'      (antisense strand)

(SEQ ID NO: 139)
3' UCCUCAAGGUGUAAGACCG-z" 5'   (sense strand)
``` wherein each of A, C, U and G is an unmodified ribonucleotide, a 2'-O-methyl sugar modified ribonucleotide or a mirror nucleotide;
wherein each of A, C, U and G is joined to the next A, C, U or G by a phosphodiester bond;
wherein z" is present and is an inverted abasic deoxyribose moiety; and
wherein the antisense strand comprises 2'-O-methyl sugar modified ribonucleotides at positions 2, 4, 6, 8, 11, 13, 15, 17 and 19.

21. The double-stranded RNA compound according to claim 1,
wherein the sense strand comprises an L-deoxycytidine mirror nucleotide at position 18 and each remaining ribonucleotide is an unmodified ribonucleotide.

22. A composition comprising the double-stranded RNA compound according to claim 20 or 21; and a pharmaceutically acceptable carrier.

23. A method for treating a subject suffering from acute renal failure (ARF), comprising administering to the subject the composition according to claim 22 in an amount effective to treat the subject.

24. A method for treating a subject suffering from an ocular ischemic condition, comprising administering to the subject the composition according to claim 22 in an amount effective to treat the subject.

25. The method according to claim 24, wherein the ocular ischemic condition is ischemic ocular neuropathy (ION) or anterior ischemic optic neuropathy (AION).

26. The method according to claim 6, wherein the ocular ischemic disease or condition is ischemic ocular neuropathy (ION) or anterior ischemic optic neuropathy (AION).

27. The double-stranded RNA compound according to claim 17, wherein z" is a C6-amino-Pi.

28. The double-stranded RNA compound according to claim 1, wherein no unconventional moiety is present in (N)x.

29. The double-stranded RNA compound according to claim 1, wherein in (N')y an unconventional moiety present at position 15, 16, 17 or 18 is a mirror nucleotide or a nucleotide joined to an adjacent nucleotide by a 2'-5' internucleotide phosphate bond.

30. The double-stranded RNA compound according to claim 29, wherein the unconventional moiety at position 15, 16, 17 or 18 is a mirror nucleotide.

31. The double-stranded RNA compound according to claim 29, wherein the unconventional moiety at position 15, 16, 17 or 18 is a nucleotide joined to an adjacent nucleotide by a 2'-5' internucleotide phosphate bond.

32. The double-stranded RNA compound according to claim 31, wherein the 2'-5' internucleotide phosphate bond is a 2'-5' phosphodiester bond.

33. The double-stranded RNA compound according to claim 1 or 3, wherein an unconventional moiety is present at each of positions 1, 2, 3 and 19 in (N')y.

34. The double-stranded RNA compound according to claim 1 or 3, wherein if one or more unconventional moiety is present at position 1, 2 or 3, such unconventional moiety is LNA.

* * * * *